United States Patent
Krisky et al.

(10) Patent No.: US 10,799,560 B2
(45) Date of Patent: Oct. 13, 2020

(54) HSV VECTORS FOR DELIVERY OF NT3 AND TREATMENT OF CIPN

(71) Applicant: PeriphaGen, Inc., Pittsburgh, PA (US)

(72) Inventors: David M. Krisky, Pittsburgh, PA (US); James B. Wechuck, Pittsburgh, PA (US); James R. Goss, Pittsburgh, PA (US)

(73) Assignee: Periphagen, Inc., Pittsburgh, PA (US)

( * ) Notice: Subject to any disclaimer, the term of this patent is extended or adjusted under 35 U.S.C. 154(b) by 163 days.

(21) Appl. No.: 16/088,408

(22) PCT Filed: Mar. 24, 2017

(86) PCT No.: PCT/US2017/024083
§ 371 (c)(1),
(2) Date: Sep. 25, 2018

(87) PCT Pub. No.: WO2017/165806
PCT Pub. Date: Sep. 28, 2017

(65) Prior Publication Data
US 2020/0206314 A1 Jul. 2, 2020

Related U.S. Application Data

(60) Provisional application No. 62/313,399, filed on Mar. 25, 2016.

(51) Int. Cl.
| | |
|---|---|
| *A61K 48/00* | (2006.01) |
| *C07K 16/00* | (2006.01) |
| *C07K 14/435* | (2006.01) |
| *A61K 38/00* | (2006.01) |
| *C07H 21/04* | (2006.01) |
| *A61K 38/18* | (2006.01) |
| *C12N 7/00* | (2006.01) |
| *C12N 15/86* | (2006.01) |
| *A61P 25/02* | (2006.01) |

(52) U.S. Cl.
CPC ............ *A61K 38/185* (2013.01); *A61P 25/02* (2018.01); *C12N 7/00* (2013.01); *C12N 15/86* (2013.01); *A61K 48/00* (2013.01); *C12N 2710/16621* (2013.01); *C12N 2710/16643* (2013.01); *C12N 2710/16662* (2013.01); *C12N 2830/008* (2013.01)

(58) Field of Classification Search
CPC .. A61K 2300/00; A61K 39/395; A61K 48/00; C12N 15/86; A61P 35/00
See application file for complete search history.

(56) References Cited

U.S. PATENT DOCUMENTS

| | | |
|---|---|---|
| 5,763,217 A | 6/1998 | Cynader et al. |
| 5,849,571 A | 12/1998 | Glorioso et al. |
| 5,879,934 A | 3/1999 | DeLuca |
| 2001/0026799 A1 | 10/2001 | DeLuca |
| 2002/0098170 A1 | 7/2002 | Wechsler et al. |
| 2005/0092374 A1 | 5/2005 | Kim et al. |
| 2009/0156638 A1 | 6/2009 | Khanna |
| 2014/0363469 A1 | 12/2014 | Meyers et al. |

FOREIGN PATENT DOCUMENTS

| | | | |
|---|---|---|---|
| WO | WO 98/015637 | | 4/1998 |
| WO | WO2005092374 | * | 10/2005 |
| WO | WO-2017/165806 A1 | | 9/2017 |
| WO | WO-2017/165813 A1 | | 9/2017 |

OTHER PUBLICATIONS

Accession No. I3TCD6, Transcriptional Regulator ICP4 [Human Alphaherpesvirus 1], 1 pages, Sep. 5, 2012 [Retrieved Jul. 10, 2017] URL: <https://www.ncbi.nlm.nih.gov/protein/388524993?report=genbank&log$=prottop&blast_rank=1 &Rid=PCWCCB3C014>.
International Search Report for PCT/US2017/024083, 4 pages (dated Jul. 13, 2017).
International Search Report for PCT/US2017/024092, 4 pages (dated Aug. 1, 2017).
Liu, M et al. ICP0 Antagonizes ICP4-Dependent Silencing of the Herpes Simplex Virus ICP0 Gene, PLoS One, 5(1): e8837 1-16 (2010).
Written Opinion for PCT/US2017/024083, 9 pages (dated Jul. 13, 2017).
Written Opinion for PCT/US2017/024092, 9 pages (dated Aug. 1, 2017).
Extended European Search Report dated Aug. 16, 2019 for Application No. EP 17771265.0.
Extended European Search Report dated Aug. 22, 2019 for Application No. EP 17771260.1.
Burton et al., Multiple applications for replication-defective herpes simplex virus vectors. Stem Cells. Jan. 2001;19(5):358-77.
Chattopadhyay et al., Long-term neuroprotection achieved with latency-associated promoter-driven herpes simplex virus gene transfer to the peripheral nervous system. Mol Ther. Aug. 2005;12(2):307-13.
Chattopadhyay et al., Protective effect of herpes simplex virus-mediated neurotrophin gene transfer in cisplatin neuropathy. Brain. Apr. 2004;127(4):929-39.
DeLuca et al., Isolation and characterization of deletion mutants of herpes simplex virus type 1 in the gene encoding immediate-early regulatory protein ICP4. J Virol. Nov. 1985;56(2):558-70.
Goss et al., Herpes simplex-mediated gene transfer of nerve growth factor protects against peripheral neuropathy in streptozotocin-induced diabetes in the mouse. Diabetes. Jul. 2002;51(7):2227-32.

(Continued)

*Primary Examiner* — Barry A Chestnut
(74) *Attorney, Agent, or Firm* — Wolf, Greenfield & Sacks, P.C.

(57) ABSTRACT

Disclosed herein are compositions and methods for treating neuropathy, embodiments, HSV vectors are provided comprising nucleic acid molecules encoding neurotrophins, such as neurotrophin 3 (NT3).

30 Claims, 124 Drawing Sheets

Specification includes a Sequence Listing.

(56) References Cited

OTHER PUBLICATIONS

Goss et al., PGN-503, a herpes simplex virus based vector expressing neurotrophin-3, prevents and reverses neuropathy in a mouse model of paclitaxel-induced peripheral neuropathy. Mol Ther. May 2016;24(Suppl. 1):S72.
MacDonald et al., Genome sequence of herpes simplex virus 1 strain McKrae. J Virol. Sep. 2012;86(17):7540-1.
Shepard et al., Activities of heterodimers composed of DNA-binding- and transactivation-deficient subunits of the herpes simplex virus regulatory protein ICP4. J Virol. Jan. 1991;65(1):299-307.
Wang et al., HSV-1 strain McKrae is more neuroinvasive than HSV-1 KOS after corneal or vaginal inoculation in mice. Virus Res. Jan. 20, 2013;173(2):436-40.
Watson et al., Sequence and comparative analysis of the genome of HSV-1 strain McKrae. Virology. Nov. 2012;433(2):528-37. Epub Sep. 25, 2012.
U.S. Appl. No. 16/088,393, filed Sep. 25, 2018, Krisky et al.
EP 17771265.0, Aug. 16, 2019, Extended European Search Report.
EP 17771260.1, Aug. 22, 2019, Extended European Search Report.

* cited by examiner

HSV McKrae strain nucleotide sequence (SEQ ID NO: 1)

Accession no. JQ730035.1

```
   1 gcagccggg ccccccgcgc gcgggcggc gcgcaaaaa ggcggcggc ggtccggcg
  61 gcgtgcgc gcgcggcgg cgtggggc ggggccgcgg gagcggggga ggagcccac
 121 ccacagacgg ggaggagcgg gggaggagcg ggggaggagc ggggaggag ccccacccac
 181 agacggggag gagcggggga ggagcggcca gaccccaaaa acggccccc cgaaacaca
 241 cccccggggg gtcgcgcgcg gccctttaaa gcgcggcggc gggcagcccg gccccccgc
 301 ggccgagct agcgagttag acaggaaagc actactcgcc tctgcacgca catgcttgcc
 361 tgtcaaactc taccacccg gcacgatctc tgtctccatg gcccgccgc gccgccatcg
 421 cggccccgc cgccccggc cgacgggcc cacgggcgcc gtcccaaccg cacagtccca
 481 ggtaacctcc acgccaact cggaacccgc ggtcaggagc gcgcccgcgg ccgccccgcc
 541 gccgccccc gcggtgggc ccccgcttc ttgttcgctg ctgctgcgcc agtggctcca
 601 cgttcccgag tccgcgtccg acgacgacga tgacgacgac tggccggaca gcccccgcc
 661 cgagccggcg ccagaggcc ggcccaccgc cgccgcccc cggcccggt ccccaccgcc
 721 cggcgtgggc ccggggggcg gggctgaccc ctcccacccc ccctcgcgcc ccttccgcct
 781 tccgccgcgc ctcgccctcc gcctgcgcgt caccgcggag cacctggcgc gcctgcgcct
 841 gcgacgcgcg gcgggggagg gggcgccgga gccccccgcg accccgcga ccccgcgac
 901 cccgcgacc ccgcgaccc ccgcgacccc cgcgaccccc gcgaccccg cgcggtgcg
 961 cttctcgcc cacgtccggg tcggccacct ggtggtctgg gcctcggccg cccgcctggc
1021 gggccgcggc tcgtgggtcc gcgagcgggc cgatcgggct cggttccggc gccgggtggc
1081 ggaggccgag gcggtcatcg ggcgtgcct ggggccgag gccgtgccc gggccctggc
1141 ccgggagcc ggccggcga actcggtcta acgttacacc cgaggcgcct gggtcttccg
1201 cggagctccc gggagctccg caccaagccg ctctccggag agacgatggc aggagccgcg
1261 catatatacg ctggagccg gtccgccccc aaggcgggcc cgcctcgggg gcgggactgg
1321 ccaatcggcg gcgccagcg cggcgggcc cggcaacca gcgtccgccg agtcttcggg
1381 gccggccca ttgggcggga gttaccgccc aatgggccgg gcgcccact tcccggtatg
1441 gtaattaaaa acttgcaaga ggccttgttc cgcttccgg tatggcaatt agaaactcat
1501 taatgggcgg cccggccgc ccttccgct tcggcaatt cccgcggccc ttaatgggca
```

FIGURE 16

```
1561 accccggtat tccgcgcctc ccgcgccgcg cgtaaccact ccsctgggt tccgggttat
1621 gctaattgct tttttggcgg aacacacgga ccctcgcgca ttggcccgcg ggtcgctcaa
1681 tgaacccgca ttggtccsct ggggttccgg gtatggtaat gagtttcttc gggaaggcgg
1741 gaagcccgg ggcaccgacg caggccaagc ccctgttgcg tcggcggag gggcatgcta
1801 atggggttct ttggggaca ccgggttggt ccsccaaatc ggggccggg ccgtgcatgc
1861 taatgatatt ctttggggc gccggttgg tccccgggga cgggccgcc ccgcggtggg
1921 cctgcctccc ctgggacgcg cggccatgg gggaatcgtc actgccgcc ctttggggag
1981 gggaaggcg tggggtataa gttagcccg gccgacggt ctggtcgcat ttgcacctcg
2041 gcactcggag cgagacgcag cagccaggca gactcggcc gccgcctctc cgcatcacca
2101 cagaagcccc gcctacgttg cgaccccag ggaccctccg tccgcgaccc tccagccgca
2161 tacgaccccc atggagcccc gccccggagc gagtaccgc cggcctgagg gccgccca
2221 gcgcgaggtg agggcgggg cgccatgtct ggggcgccat attgggggc gccatgttgg
2281 gggaccccg accttagcc tggaaccggc ccccatgttg ggggaccccc actcatacac
2341 gggagccggg cgccatgttg gggcgccatg ttaggggcg tggaaccccg tgacactata
2401 tatacaggga ccggggcgc catgttaggg ggcgcggaac cccctgaccc tatatataca
2461 gggaccgggg tcgccctgtt ggggtcgcc atgtgacccc ctgactttat atatacagac
2521 ccccaacaca tacacatggc ccctttgact cagacgcagg gccggggtc gccgtgggac
2581 cccctgactc atacacagag acacgccccc acaacaaaca cacagggacc ggggtcgccg
2641 tgttggggc gtggtcccca ctgactcata cgcaggcccc ccttactcac acgcatctag
2701 ggggtgggg aggagccgcc cgccatattt ggggacgcc gtgggaccc cgactccggt
2761 gcgtctggag gcgggagaa gagggaagaa gagggtcgg gatccaaagg acggaccag
2821 accacttttg gttgcagacc ccttcttccc ccctcttccg aggccagcag ggggcagga
2881 ctttgtgagg cgggggga gaggggaac tcgtgggcgc tgattgacgc gggaaatccc
2941 cccccattct tacccgcccc cctttttttcc ccttagcccg cccggatgt ctgggtgttt
3001 cccctgcgcc gagacctgcc ggacagcagc gactctgagg cggagaccga agtggggggg
3061 cggggggacg ccgaccacca tgacgacgac tccgcctccg aggcggacag cacggacacg
3121 gaactgttcg agacggggct gctgggccg cagggcgtgg atggggggc ggtctcgggg
3181 gggagccccc ccgcgagga agacccgcc agttgcgggg gcgcccccc tcgagaggac
```

FIGURE 16
(Continued)

```
3241 gggggagcg acgagggcga cgtgtgcgc gtgtgcacgg atgagatcgc gcccacctg
3301 cgctgcgaca ccttcccgtg catgcaccga ttctgcatcc cgtgcatgaa aacctggatg
3361 caattgcgca acacctgccc gctgtgcaac gccaagctgg tgtacctgat agtgggcgtg
3421 acgtccagcg ggtcgttcag caccatcccg atcgtgaacg accccagac ccgcatggag
3481 gccgaggagg ccgtcagggc gggcacggcc gtggacttta tctggacggg caatcagcgg
3541 ttcgtcccgc ggtacctgac cctggggggg cacacggtga gggccctgtc gcccacccac
3601 ccggagccca ccacggacga ggatgacgac gacctggacg acggtgaggc ggggggcggc
3661 aaggaccctg gggaggagg aggagggagg aatgggcggg cgggcgagga aaggggcgggc
3721 cggggagggg gcgtaacctg atcgcgcccc ccgttgtctc ttgcagcaga ctacgtccg
3781 cccgccccc gcggacgcc ccgtgccccc ccacgcagag gcaccgccgc gcccccgtg
3841 acgggcgggg cgtctaagc agccccag ccggcgcgg ctcggacagc gcccctcg
3901 gcgcccatcg ggccacacgg cagcagtaac accaacacca ccaccaacag cagcggcggc
3961 ggcggctccc gccagtcgcg agccgaggcg ccgcggggg cgtctggccc ctccggggg
4021 gttgggttg gggttggggt tgttgaagcg gaggcggggc ggccgagggg ccggacgggc
4081 cccctttgtca acagacccgc cccccttgca aacaacagag accccatagt gatcagcgac
4141 tccccccgg cctctcccca caggccccc gcggcgccca tgccaggctc cgcccccgc
4201 cccgggcccc ccgcgtcctc ggccgcgtcg ggacccgcgt gccccagcgc ggccgtggcc
4261 ccgtgcgtgc gagcgcagcc tcggggccc ggaccccgcg ccccggcccc cggggcggag
4321 ccggccgccc gccccgcgga cgcgcgccgt gtgcccagt cgcactcgtc cctggtcag
4381 gccgcaacc aagaacagag tctgtgccgg gcgcgtgcga cggtggcgcg cggctcgggg
4441 gggccggcg tggagggtgg gcacgggccc tcccgaggcc gcacccctc cggcgcgcc
4501 ccgctcctct ccgccgtctc tgtcgagcag gaggcggcgg tgcgtccgag gaagaggcgc
4561 gggtcgggcc aggaaaaccc ctcccccccag tccacgcgtc cccccctcgc gccggcaggg
4621 gccaagaggg cggcgacgca ccccccctcc gactcagggc cggggggcg cggccagggt
4681 gggccggga cccccctgac gtcctcggcg gcctccgcct cttcctcctc tgcctcttcc
4741 tcctcggccc cgacccccgc ggggggccgcc tcttccgccg ccggggccgc gtcctcctcc
4801 gcttccgcct cctcgggcgg ggccgtcggt gccctgggag ggagacaaga ggaaacctcc
4861 ctcggcccc gcgctgcttc tgggccgcgg gggcgagga agtgtcccg gaagacgcgc
```

FIGURE 16
(Continued)

```
4921 cacgcggaga attccggggc cgtccccgcg ggcggcctca cgcgctacct gcccatctcg
4981 ggggtctcta gcgtggtcgc cctgtcgcct tacgtgaaca agactatcac ggggactgc
5041 ctgcccatcc tggacatgga gacggggaac atggggcgt acgtggtcct ggtggaccag
5101 acgggaaaca tggcgacccg gctgcgggcc ggggtcccg gctggagccg ccgcaccctg
5161 ctccccgaga ccgcgggtaa ccacgtgatg ccccccgagt accgacggc cccgcgtcg
5221 gagtggaaca gcctctggat gaccccgtg gggaacatgc tgttcgacca gggcaccta
5281 gtgggcgccc tggacttccg cagcctgggg tctcggcacc cgtggtccgg ggagcagggg
5341 gcgtcgaccc gggacgaggg aaaacaataa gggacgccc ccgtgtttgt ggggagggg
5401 gtcgggtgct gggtggtctc tggccgcgcc cactacacca gccaatccgt gtcggggagg
5461 ggaaagtgaa agacacgggc accacacacc agcgggtctt tagtgttggc cctaataaaa
5521 aactcagggg atttttgctg tctattggga aataaaggtt tactttgta tcttttccct
5581 gtctgtgttg gatggatctt gggggtgcgt gggagtgggg gtgcgtggga gtggggtgc
5641 gtggagtgg gggtgcgtgg gagtgggggt gcgtgggagt gggggtgcgt gggagtgggg
5701 gtgcgtggga gtggggtgc gtgggagtgg gggtgcgtgg gagtggggt gcgtgggagt
5761 ggggtgcgt gggagtgggg gtgcgtggga gtggggtgc gtgggagtgg gggtgccatg
5821 ttgggcaggc tctggtgtta accacagagc cgcggcccgg gctgcctgac caccgatccc
5881 cgaaagcatc ctgccactgg catggagcca gaaccacagt gggctgggtg tgggtgttaa
5941 gtttccgcga gcgcctgccc gccgggactg acctggcctc tggccgccac aaagggcggg
6001 gggggggtta actacactat agggcaacaa aggacgggag gggtggcggg acggggcgcc
6061 caaaagggg tcggccacac cacagacgtg ggtgttgggg ggtggggcgg aggggtgggg
6121 gggagacaga aacaggaaca tagttagaaa acaagaatgc ggtgcagcca gagaatcaca
6181 ggagacgagg ggatgggcgt gttggttacc aacccacacc caggcatgct cggtggtatg
6241 aaggaggggg ggcggtgctt cttagagacc gccggggac gtgggggttgg tgtgcaaagg
6301 cacgcgcacc cgcgtcggcc aggtgggccg gtacccatc cccccctccc ccgacccttc
6361 cccccccgcg tgccagagat cacccccgtc cccggcacc agccactcct ccatatcctc
6421 gctttaggaa caacttgggg ggggggtac acacgcgccg tgcatttcct tccacaccc
6481 ccctccccg catcccccc cccaggcagt aagacccaag catagagagc caggcacaaa
6541 aacacaggcg gggtggaca catgccttct tggagtacgt gggtcattgg cgtgggggt
```

```
6601 tacagcgaca ccggccgacc ccctggcggt cttccagccg gccctagat aaggggcag
6661 ttggtggtcg gacgggtaag taacagagtc tgactaaggg tgggaggggg ggaaaagaac
6721 gggctggtgt gctgtaacac gagcccaccc gcgagtggcg tggccgacct tagcctctgg
6781 ggcgcccct gtcgtttggg tcccctcccc tctattgggg agaagcaggt gtctaaccta
6841 cctggaaacg cggcgtcttt gttgaacgac accgggcgc cctcgacgag tgggataacg
6901 ggggaggaag ggaggyagga gggtactggg ggtgaagaag gggggggga agaagcgaga
6961 acaggaaagg cgacggagcc cggcagaaca ccgaggaaaa aaaaaacaca gcgcatgcgc
7021 cggccgttg tggggcccg ggccggggcc ccttgggtcc gccggggccc cgggccgggc
7081 cgccacgggg gccggccgtt ggcggtaacc ccgattgttt atctcaggcc ccgggccggg
7141 aacccggaaa agcctccggg gggccttttt cgcgtcgcgt gccggcgagc gggcccggac
7201 ggggccggga ccgccgcggt cggggccccc tgtcccggg ccgtacgcgg ccttcgcccc
7261 gtgaggggcc gaacgaacga aacatcccgg cgacggaacg aaaaacaccc cagacgggtt
7321 taaaaacag aaaccgtaac ccccccacc cccgaaacgg ggaaaacaaa aaacagacca
7381 gcggccggcc ggccttaggg gggaggatgt cgccgaagcc ccttggccgc cccggctgca
7441 gggggaccg gagagccgcg gtaccggac gcgccggaa agtattgc accaccgcg
7501 atcggcacgg ccgcgcccc gctttataa aggctcagat gacgcagcaa aaacaggcca
7561 cagcaccacg tgggtaggtg atgtaatttt attttcctcg tctgcggcct aatggattc
7621 cgggcgcggt gccctgtct gcagagcact taacggattg atatctgcg ggcagcgcg
7681 ccttaatgg accggcgcgg ggcgggggc cggataccca cacgggcggg ggggtgtcga
7741 gggccgtctg ctggccgcg gccacataaa caatgactcg gggcctttct gcctctgccg
7801 cttgtgtgtg cgcgcgccgg ctctgcggtg tcggggcgg ctgcggcggc tgcgggcc
7861 gccgtgttcg gtatcggtag ccggccggcg ggtggactcg cgggggcg gagggtggaa
7921 ggcagggggg tgtaggatgg gtatcaggac ttccacttcc cgtccttcca tccccgttc
7981 ccctcggttg ttcctcgcct ccccaacac cccgccgctt tccgttgggg ttgttattgt
8041 tgtcgggatc gtgcggacg ggggtcgccg gggcagggc ggggcgggg gtgctcgtcg
8101 atcgacggg ctcagtgggg gcgtggggtg ggtgggaaaa ggcgaggaga ctggggtggg
8161 gggtgtcggg ggtggctgtt ttttgtggt tgttttttgt gtctgttccc gtccccgtc
8221 accccctcc ctccgtcccc ccgtcgcggg tgtttgtgtt tgtttattcc gacatcggtt
```

FIGURE 16
(Continued)

```
8281 tatttaaata aacacagccg ttatgcgtgt ctgttcttgc gtgtggctgg gggcttatat
8341 gtgggtccc ggggcggga tgggtttag cggcggggg cggcgcccg gacgggcgc
8401 tggagataac ggccccggg gaacggggga ccggggctgg gtctcccgcg gtgggtgggt
8461 gggcggcgt ggccgggcg ggccggccg ggtggcggg gtttggaaaa acgaggagga
8521 ggagaaggag gaggagggg ggggagacgg gggaaagca aggacacggc ccggggggg
8581 ggggagcgcg ggccggccg cttggcaacc ccctgtttc ttccggaaac caggcttgtg
8641 gcccaccg acatcacaag ggacctttg tcgggcctcc cgacgtacgc cgaggctatg
8701 tcggaccacc cccaaccta agagggagaa ggggagaggg gagaggggag aggggagagg
8761 ggagagggga ggagagggggg tatataaacc aacgaaaagc gcgggaacgg ggatacgggg
8821 cttgtgtggc acgacgtcgt ggttgtgtta ctgggcaaac acttggggac tgtaggtttc
8881 tgtggtgccg accctaggcg ctatggggat tttgggttgg gttgggctta ttgccgttgg
8941 ggttttgtgt gtgcgggggg gcttgcttc aacgaatat gttattcgga gtcgggtggc
9001 tcgagaggtg ggggatatat taaaggtgcc ttgtgtgccg ctcccgtctg acgatcttga
9061 ttggcgtac gagaccccct cggctataaa ctatgctttg atagacggta tattttgcg
9121 ttatcactgt cccggattgg acacggtctt gtgggatagg cacgccaga ggggcgtattg
9181 ggttaacccc ttttgtttg gggcgggttt tttggaggac ttgagtcatc ccgcgttccc
9241 tgccgacacc caggaaacag aaacgcgctt ggcctttat aaagagatac gcaggcgct
9301 ggacagtcgc aagcaggccg ccagccacac acctgtaag gctgggtgtg tgaactttga
9361 ctattcgcgc acccgccgct gtgtagggcg ccaggatttg ggacttacca acagaacgtc
9421 tggacggacc ccggttctgc cgtcggacga tgaagcgggc ctgcagccga agccctcac
9481 cacgccgtcg cccatcatcg ccacgtcgga ccccaccccg cgaggggacg ccgccacaaa
9541 aagcagacgc cgacgacccc attccggcg catctaatga tgcctcgacg gaaaaccgtc
9601 cgggtttggg gggcgaaccg gccgcctgtc gctcgtcagg gccggcgggc gctcctcgcc
9661 gccctagagg ctgtcccgct ggtgtgacgt tttcctcgtc cgcgccccc gacctccca
9721 tggatttaac aaacgggggg gtgtcgcctg cggcgaccct ggcgcctctg gactggacca
9781 cgtttcggcg tgtgttctg atcgacgacg cgtggcggcc cctgttggag cctgagctgg
9841 cgaaccctt aaccgccac ctcctggccg aatataatcg tcggtgccag accgaagagg
9901 tgctgcgcc gcgggaggat gtgttcgt ggactcgtta ttgcaccccc gacgaggtgc
```

FIGURE 16
(Continued)

```
 9961 gcgtggttat catggccag gacccatat accacctgg ccaggcgcac ggactgcgt
10021 ttagctgcg ccgaacgtg ccgcctccc cgagtcttcg gaatgtcttg gcggccgtca
10081 agaactgtta tcccgaggca ccgatgagcg gccacggttg cctggaaaag tgggcgcgg
10141 acggcgtcct gttactaaac acgaccctga ccgtcaagcg cggggcggcg ggtcccact
10201 ctagaatcgg ttggaccgc ttcgtgcg gagttatcg ccggttggct gcgcgccgcc
10261 ccggctggt gtttatgctc tgggcgcac atgcccagaa tgccatcagg ccggacctc
10321 gggtccattg cgtcctcaag ttttcgcacc cgtcgccct ctccaaggtt ccgttcggaa
10381 catgccagca tttcctcgtg gcgaatcgat atctcgagac ccggtcgatt tcacccatcg
10441 actggtcggt ttgaaaggca tcgacgtccg gggttttcgt ctgtgggggc ttttgggtat
10501 ttccgatgaa taaagacggt taatggttaa acctctggtc tcatacgggt cggtgatgtc
10561 gggcgtcggg ggagagggag ttccatctgc gcttgcgatt ctagctcgt ggggctggac
10621 gttcgacacg ccaaaccacg agtcaggat atcgccagat acgactcccg cagattccat
10681 tcgggggc gctgtggct cacctgacca acctttacac ggggcccgg aacggaggc
10741 cacagcgccg tcttctccc caacgcgcgc ggatgacggc ccgccctgta ccgacgggcc
10801 ctacgtgacg ttgataccc tgtttatggt gtcgtcgatc gacgaattag ggcgtcgcca
10861 gctcacggac accatccgca aggacctgcg gttgtcgctg gccaagttta gcattgcgtg
10921 caccaagacc tcctcgtttt cgggaaacgc ccggcgccac cacagacgcg gggcgttcca
10981 gcgcggcacg cgggcgccgc gcagcaacaa aagcttcag atgttgtgt tgtgcaaacg
11041 cgccacgcc gctcgagtgc gagagcagct tcgggtcgtt attcagtccc gcaagccgcg
11101 caagtattac acgcgatctt cggacgggcg gctctgcccc gccgtccccg tgttcgtcca
11161 cgagttcgtc tcgtccgagc caatgcgcct ccaccgagat aacgtcatgc tggcctggg
11221 ggccgagtaa ccgccccccc ccgcgccac cctcactgcc cgtcgcgcgt gtttgatgtt
11281 aataaataac acataaattt ggctggttgt ttgttgtctt taatggaccg ccgcagggg
11341 gggtggcatt tcagtgtcgg gtgacgagcg cgatccggcc gggatcctag gaccccaaaa
11401 gtttgtctgc gtattccagg gcggggtca gttgaatctc ccgcagcacc tctaccagca
11461 ggtccgcggt gggctggaga aactcggccg tcccggggca ggcggtcgtc gggagtggag
11521 gcgcggcgcc cacccgtgt gccgcgctg gcgtctcctc tgggggcgac ccgtaaatgg
11581 ttgcagtgat gtaaatggtg tccgcggtcc agaccacggt caaaatgccg gccgtggtgc
```

```
11641 tcgggcgct ttcgccgcgc gaggagctga cccaggagtc gaacggatac gcgtacatat
11701 gggcgtccca cccgcgttcg agcttctggt cgctgtccg gctataaag cggtaggcac
11761 aaaattcggc gcgacagtcg ataatcacca acagcccaat ggggtgtgc tggataacaa
11821 cgcctccgcg cggcaggcgg tcctggcgct cccggcccg taccataatc gcgcgggtgc
11881 cgtactcaaa aacatgcatc acctgcgcgg cgtcgggcag tgcgctggtc agcgaggcc
11941 tggcgtggca taggctatac gcgatggtcg tctgtggatt ggacatctcg cggtgggtag
12001 tgagtcccc gggccaggtt cggtagaact gtaaggggac ggcgggttaa tagacaatga
12061 ccacgttcgg atgcgcaga gcgatagta tgtgccact aatgacgtca tcgcgtcgt
12121 ggcgctccg gagcggattt aagttcatgc gaaggaattc ggaggaggtg gtgcgggaca
12181 tggccacgta cgcgctgttg aggcgcaggt tgccgggcgt aaagcagatg gcgaccttgt
12241 ccaggctaag gccctgggag cgcgtgatgg tcatggcaag cttggagctg atgccgtagt
12301 cggcgtttat ggccatggcc agctccgtag agtcaatgga ctcgacaaac tcgctgatgt
12361 tggtgttgac gacggacatg aagccgtgtt ggtcccgcaa gaccacgtaa ggcagggggg
12421 cctcttccag taactcggcc acgttggccg tcgcgtgccg cctccgcagc tcgtccgcaa
12481 aggcaaacac ccgtgcgtac gtgtatccca tgagcgtata attgtccgtc tgcagggcga
12541 cggacatcag cccccgcgc ggcgagccgg tcagcatctc gcagcccgg aagataacgt
12601 tgtccacgta cgtgctaaag ggggcgcctt caaatgcctc ccgaagagc tcttggagga
12661 ttaggaatct cccgaggaag gcctgttca gcagcgcaaa ctgggtgtga acggcggcgg
12721 tggtctccgg ttccccgggg gtgtagtggc agtaaaacac gtcgagctgt tgttcgtcca
12781 gcccgcgaa aataacgtcg aggtcgtcgt cgggaaaatc gtccgggccc ccgtcccgcg
12841 gcccccagttg cttaaaatca aacgcacgct cgccggggc gctgcgtcg gctattaccg
12901 acgcctgcgt cggcgccccc gaagatttgg ggcgcagaga cagaatctcc gccgttagtt
12961 ctcccatgcg ggcgtaggcg agggtcctct gggtcgcatc caggccgggg cgctgcagaa
13021 agttgtaaaa ggagataagc ccgctaaata tgagccgcga caggaacctg taggcaaact
13081 ccacgaagt ctccctaga gtctttacaa agctgtcgtc acgcaacact gcctcgaagg
13141 cccggaacgt ccgactaaac ccaaaaacca gtttcgcag gcgcgcggtc accgcgatct
13201 ggctgttgag gacgtaagtg acgtcgttgc ggggccacgac cagctgctgt ttgctgtgca
13261 cctgcagcg catgtgcccc gcgtcctggt cctggtctg cgagtagtcg gtgatgcggc
```

```
13321 tggcgttggc cgtgagccac ttttcaatag tcaggccggg ctggtgtgtc agccgtcggt
13381 attcgtcaaa ctccttgacc gacacgaacg taagcacggg gagggtgaac acgacgaact
13441 ccccctcacg ggtcaccttc aggtaggcgt ggagcttggc catgtacgcg ctcacctctt
13501 tgtgggagga gaacagccgc gtccagccgg ggaggttggc ggggttggtg atgtagcttt
13561 ccgggacgac gaagcgatcc acgaactgca tgtgctcctc ggtgatgggc aggcgtact
13621 ccagcacctt catgaggtta ccgaactgt gctcgacgca ccgtttgttg ttaataaaa
13681 tggcccagct atacgagagg cgggcgtact cgcgcagcgt ggggttgcag atgaggtacg
13741 tgagcacgtt ctcgctctgg cggacggaac accgcagttt ctggtgctcg aaggtcgact
13801 ccaggacgc cgtctgcgtc ggcgagccca cacaccaa cacgggccgc aggcgggccg
13861 catactgggg ggtgtggtac agggcgttaa tcatccacca gcaatacacc acggccgtga
13921 ggaggtgacg cccaaggagc ccggcctcgt ctatgacgat cacgttgctg cgggtaaagg
13981 ccggcagcgc cccgtgggtg gcgggggcca accgcgtcag ggcgcctcg gccaacccca
14041 gggtccgttc caggggcggcc agggcgcgaa actcgttccg cgactcctcg ccccggagg
14101 cggccaggc gcgcttcgtg aggtccaaaa tcaccctcca gtagtacgtc agatctcgtc
14161 gctgcaggtc ctccagcgag gcggggttgc tggtcagggt gtacgggtac tgtcccagtt
14221 gggcctggac gtgattcccg cgaaacccaa attcatgaaa gatggtgttg atgggtcggc
14281 tgagaaaggc gcccgagagt ttggggtaca tgttttgggt cgcaatgcgc gtggcgcccg
14341 tcaccacaca gtccaagacc tcgttgattg tctgcacgca cgtgctcttt cggagccag
14401 cgttgccggt gataagatac accgcgaacg gaaactccct gagggcagg cctgcggggg
14461 actgtaaggc cgccacgtcc cggaacgact gcagacgggg cacttgcgct ccgtcgagct
14521 gttgttgcga gagctctcgg atgcgcttaa ggattggctg caccccgtgc atagacgtaa
14581 aattttaaaaa ggcctcggcc ctccctggaa cggcggtcg gtccccggggt tgctgaaggt
14641 gggcggggc gggtctctgt ccgtctagct ggcgctcccc gccggccgcc gccatgaccg
14701 caccacgctc gcgggcccc actagcgtg cgcggggga cacggaagcg ctgtgctccc
14761 ccgaggacgg ctgggtaaag gttcaccca ccccggtac gatgctgttc cgtgagattc
14821 tccacgggca gctgggtat accgagggcc aggggtgta caacgtcgtc cggtccagcg
14881 aggcgaccac ccggcagctg caggcggcga tctttcacgc gctcctcaac gccaccactt
14941 accgggacct cgaggcggac tggctcggac acgtggcggc ccgaggtctg cagcccaaac
```

FIGURE 16
(Continued)

```
15001 ggctggttcg ccggtacagg aacgccggg aggcggatat cgccgggtg gccgagcgg
15061 tgttcgacac gtggcggaac acgcttagga cgacgctgct ggactttgcc cacgggtgg
15121 tcgcctgctt tgcgccgggc ggccgagcg gccgtcaag cttccccaaa tatatcgact
15181 ggctgacgtg cctggggctg gtcccatat tacgcaagcg acaagaaggg ggtgtgacgc
15241 agggtctgag ggcgtttctc aagcagcacc cgctgacccg ccagctggcc acggtcgcgg
15301 aggccgcgga gcgcgcaggc ccgggttttt ttgagctggc gctggccttc gactccacgc
15361 gcgtggcgga ctacgaccgc gtgtatatct actacaacca ccgccggggc gactggctcg
15421 tgcgagaccc catcagcggg cagcgcggag aatgtctggt gctgtggcct ccttgtgga
15481 ccggggacgg tctggtcttc gattcgcccg tccagcggct gtttccgag atcgtcgcgt
15541 gtcactccct ccgggaacac gcgcacgtct gcggctgcg caatacgcg tcgtcaagg
15601 tgatgctggg ggcaagagc gacagcgagc gggggtggc cggcgcgcg cgggtcgtta
15661 acaaggtgtt ggggaggac gacgagacca aggccgggtc ggccgcctca cgcctcgtgc
15721 ggcttatcat caacatgaag ggcatgcgcc acgtaggcga cattaacgac accgtgcgtg
15791 cctacctcga cgaggccggg gggcacctga tagacgcccc ggccgtcgac ggtaccctcc
15841 ctggattcgg caaggcgga aacagccgcg ggtctgcggg ccaggaccag gggggcggg
15901 cgccgcagct tgccaggcc ttccgcacgg ccgtggttaa caacatcaac ggcgtgttgg
15961 aggctatat aaataacctg tttggaacca tgagcgcct gcgcgagacc aacgcgggcc
16021 tggcgaccca attgcaggag cgcgaccgcg agctccggcg agcaacagcg ggggccctgg
16081 agcgccagca gcgcgcggcc gacctggcgg ccgagtccgt gaccggtgga tgcggcagcc
16141 gcctgcggg ggcggacctg ctccggccg actatgacat tatcgacgtc agcaagtcca
16201 tggacgacga catgtacgtc gccaacagct ttcagcaccc gtatatccct tcgtacgccc
16261 aggacctgga gcgcctgtcg cgcctctggg agcagagct ggtgcgctgt tttaaaattc
16321 tgtgtcaccg caacaaccag ggccaagaga cgtcgatctc gtactccagc ggggcgatcg
16381 ccgcattcgt cgcccctac tttgaggcag tgcttcaggc ccccgggta ggcgcccca
16441 tcacgggctc cgatgtcatc ctggggagg aggagttatg ggatgcggtg tttaagaaaa
16501 cctgctgca aacgtacctg acagacatcg cggccctgtt cgtcgcggac gtccagcacg
16561 cagcgctgcc gccgcccccc tccccggtcg gcgccgattt ccggcccggc gcgtcccgc
16621 gggcggtc cagatcgcgg tgccggaa gaactgcgcg aggcgaccg gaccagggcg
```

FIGURE 16
(Continued)

```
16681 ggggcatcgg gcaacgggat ggccgccgcg acggccgacg atgagggtc ggccgtcacc
16741 atcctcaagc aggccatcgc cggggaccgc agcctggtcg aggcggccga ggcgattagc
16801 cagcagacgc tgctccgcct ggcctgcgag gtgcgccagg tcggcgaccg ccagccgcgg
16861 tttaccgcca ccagcatcgc gcgcgtcgac gtcgcgcctg ggtgccggtt ggggttcgtt
16921 ctggacggga gtcccgagga cgcctatgtg acgtcggagg attacttaa ggctgctgc
16981 ggccagtcca gttatcgcgg cttcgcggtg gcggtcctga cggccaacga ggaccacgtg
17041 cacagcctgg ccgtgcccc cctcgtcctg ctgcaccggt tatccctgtt caacccagg
17101 gacctctgg actttgagct tgcctgtccg ctgatgtacc tggagaactg ccccgaagc
17161 cacgccaccc cgtcgacctt tgccaaggtt ctggcgtggc tcgggtcgc gggtcgccgc
17221 acgtcccat tcgaacgcgt tcgtgcctt ttcatccgca gttgccactg ggtcctaaac
17281 acactcatgt tcatggtgca cgtaaaaccg ttcgacgacg agttcgtcct gcccactgg
17341 tacatggcc ggtcctgct ggccaacaac ccgccccg ttctctcggc ccgttctgt
17401 gccaccga cgagctcctc attccggctg ccgggccgc ccccgctc cgactgcgtg
17461 gcctataacc ctgccgggat catggggagc tgctgggcgt cggaggaggt gcgcgcgcct
17521 ctggtctatt ggtggctttc ggagcccca aaacgacaga cgtcgtcgct gttttatcag
17581 ttttgttgaa ttttagtaaa taaacccggt tttgttttta tggcctcctg acggatgcgc
17641 gtgtccttac tccgttttgg tgggtgggtg gctgtgtatg gcgtcccatc tgtgcgggga
17701 ggggcaagt cggcacgtat tcgacagac tcaagcacac acggggagc gtcttggct
17761 cagggcaatg ttttattgg tcaaactcag gcaaacagaa acaacatctt gtcgtcaaag
17821 ggatacacaa acttccccc ctcgcccat actcccgcca gcaccccggt aaacaccaac
17881 tcaatctcgc gcaggattc gcgcaggtga tgagcgcagt ccagggggg gagcacaagg
17941 ggccgcggt atagatcgac ggggacgccg accgactccc cgctccggg acagacacgc
18001 acgacgcgcc gccagtagtg ctctgcgtcc aacaaggcgc cgcgcggaa ggcagtgggg
18061 ggcaagggt cgctggcctc aaggggggac accgaacga tccagtactc cgcgtccaac
18121 cgtttattaa acgcgtccaac gataaggcgg tcgcaggcgt actccataag gcccagggcc
18181 gtgagcgcgt cctcctccgg cacgcctgcc gttgtcaggc ccaggacccg tcgcagcgtg
18241 tcgcgtacga ccccggccgc cgtggtgtac gcgggcccgc ggagaggaaa tccccaaga
18301 tggtcagtgt tgtcgcggga gttccagaac cacactcccg cttggctcca ggcgacggcg
```

FIGURE 16
(Continued)

```
18361 tggggtgtaga cgccctcgag cgccaggcac agtgggtgcc gcagccgag gccgttggcc
18421 ataagcacgg ctcccacggc cgtctcgatg gcccgccggg cgtcctcgat caccccggaa
18481 gccgcatccg cgtcttgggg gtccacgtta aagacacccc agaacgcacc cccatcgccc
18541 ccgcagaccg cgaacttaac cgagctggcc gtctcctcaa tctgcaggca gacggcggcc
18601 atcacccgc ccaggagctg ccgcagcgca gggcaggcgt cgcacgtgtc cgggaccagg
18661 cgctcaaga cggcccccggc ccagggctct gagggagcgg ccaccaccag cgcgtccagt
18721 cttgctaggc ccgtccggcc gtggggttcc gccagcccgc tccccccgag gtcggccagg
18781 gccgcagga gctgggcgcg aagtccgggg aagcaaacc gcgccgtcca gacgggccg
18841 acggccgcgg gcgggtctaa cagttggatg attttagtgg cgggatgcca ccgcgccacc
18901 gcctcccgca ccgcgggcag gaggcatccg gctgccgccg aggccacgcc gggccaggct
18961 cgcgggggga ggacgaccct ggccccacc gcgggccagg ccccaggag cgggcgtaa
19021 gcggccgcgg cccgcgcac caggtcccgt gccgactcgg ccgtggccgg cacggtgaac
19081 gtgggccaac cggaaacc caggacggca aagtacggga cgggtccccc ccggacctca
19141 aactcgggcc ctagaaggc aaagacgggg gccagggccc cggggggcgg cgtggaccgtg
19201 gtatgcact gacggaaaag gcgacgagc gccggcgcgg agaacttctc gccggcgctt
19261 acaaagtagt cgtaatcgcg gggcagcagc acccgtgccg tgactcgttg cgggtgcacg
19321 cgtggccgca ggccccaactc gcacacctcg accaggtccc cgaacgctcc ctccttcttg
19381 atcggcggaa acgcaagagt ctggtattcg cgcgcaaata gcgcggttcc ggtggtgatg
19441 ttaacggtca gcgaagcggc ggacgcgcac tgggggtgt cgcgaatggc cgccaggcgc
19501 gcccaggcca gccgcgcgtc gggatgctcg gcaacgcgcg ccgccagggc catagggtcg
19561 atgtcaatgt tggcctccgc gaccaggaga gcggcgaag ggggggcggg cgggcccac
19621 gacgtctct caactttcac caccagtccc gtgcgtgggt ccgagccgat acgcagcggg
19681 gcgaacaggg ccaccggccc ggtctggcgc tccagggcg ccaggacgca cgcgtacagc
19741 gccgccaca gagtcgggtt ctccagggc tccagcgggg aggcggcgg cgtcgtcgcg
19801 gcgcgggcgg ccgccacgac ggcctggacg gagacgtccg cggagccgta gaaatcccgc
19861 agctccgtcg cggtgacgga gaccccgca aagcgcgcgc gaccctccc tgcggcgttg
19921 cgacatacaa aatacaccag ggcgtggaag tactcgcgag cgcggggggg cagccatacc
19981 gcgtaaaggg taatggcgct gacgctctcc tccaccaca cgatatctgc ggtgtccatc
```

FIGURE 16
(Continued)

```
20041 gcacggxccc taaggatcac gggcggtctg tgggtccxat gctgccgtgc ctggccgggc
20101 ccggcgggtc gcggaaaccg gtgacggggg ggggcggttt tggggttgg ggtgggggtg
20161 ggaaacggcc cgggtccggg ggccaacttg gccccctcggt gcgttccggc aacagcgccg
20221 cggtccgcg gacgactacg taccgaacga gtgcggtccc gagacttata gggtgctaaa
20281 gttcaccgcc ccctgcatca tgggccaggc ctcggtgggg agctccgaca gcgcgcctc
20341 caggatgatg tcagcgttgg ggttggcgct ggatgagtgc gtgcgcaaac agcgccccca
20401 cgcgggcacg cgtagcttga agcgcgcgcc cgcaaactcc cgcttgtggg ccataagcag
20461 ggcgtacagc tgcctgtggg tccggcaggc gctgtggtcg atgtggtggg cgtccaacaa
20521 cccacgatt gtctgtttgg tgaggttttt aacgcgcccc gcccgggaa acgtctgcgt
20581 gcttttggcc atctgcacgc caaacagttc gccccagatt atcttgaaca gcgccaccgc
20641 gtggtccgtc tcgctaacgg acccgcgcgg gggacagccg cttagggcgt cggcgacgcg
20701 cttgacggct tcctccgaga gcagaagtcc gtcggttacg ttacagtggc ccagttcgaa
20761 caccagctgc atgtagcggt cgtagtgggg ggtcagtagg tccagcacgt catcggggcc
20821 gaaggtcctc ccagatcccc cggccgccga gtcccaatgc aggcgcgcgg ccatggtgct
20881 gcacaggtac aacagctccc agacggggt tacgttcagg gtgggggca gggccacgag
20941 ctccagctct ccggtgacgt tgatcgtggg gatgacgccc gtggcgtagt ggtcatagat
21001 ccgccgaaat atggcgctgc tgcgggtggc catgggaacg cggagacagg cctccagcaa
21061 cgccaggtaa ataaacgcg tgcgtcccat caggctgttg aggttgcgca tgagcgcgac
21121 aatttccgcc ggcgcgacat cggaccggag gtattttcg acgaaaagac ccacctcctc
21181 cgtctggcg gcctgggccg gcagcgacgc ctcgggatcc cggcaccgca gctcccgtag
21241 atcgtgtgg gccctgaggg cgtcgaaatg tacgcccgc aaaaacagac agaagtcctt
21301 tggggtcagg gtatcgtcgt gtccccagaa gcgcacgcgt atgcagttta gggtcagcag
21361 catgtgaagg atgttaaggc tgtccgagag acacgccagc gtgcatctct caaagtagtg
21421 tttgtaacgg aattgttgt agatgcgtga ccccgcccc agcgacgtgt cgcatgccga
21481 cgcgtcacag cgcccttga acggcgaca cagcaggttt gtgactggg agaactgcgc
21541 gggccactgg ccgcaggaac tgaccacgtg gttcaggagc atgggcgtaa agacgggctc
21601 cgagcgcgcc ccggagccgt ccatgtaaat cagtagctcc cccttgcgga gggtgcgcac
21661 ccgtcccagg gactggtaca cggacaccat gtccggtccg tagttcatgg gtttcacgta
```

```
21721 ggcgaacatg ccatcaaagt gcagggatc gaagctgagg ccacggtta cgaccgtcgt
21781 gtatataacc acgcggtatt ggcccacgt ggtcacgtcc ccgagggggg tgagcgagtg
21841 aagcaacagc acgcggtccg taaactgacg gcagaaccgg gcacgatct ccgcgaagga
21901 gaccgtcgat gaaaaatgc agatgttatc gcccccgcca aggcgcgttt ccagctcccc
21961 aaagaacgtg gcccccgggg cgtccggaga ggcgtccgga gacgggccgc ttggcggccc
22021 ggcgggcgc agggcagcct gcaggagctc ggtcccaga cgcgggagaa acaggcaccg
22081 gcgcgtcgaa aacccgggca tggcgtactc gccgaccacc acatgcacgt tttttttcgcc
22141 ccggagaccg cacaggaagt ctaccaactg cgcgtggcg gtgcgtcca tggcgatgat
22201 ccgaggacag gtgcgcagca ggcgtagcat taacgcatcc acgcggccca gttgctgcat
22261 cgttggcgaa tagagctggc ccagcgtcga cataacctcg tccagaacga ggacgtcgta
22321 gttgttcaga aggtggggc ccacgcgatg aaggcttcc acctggacga taagtcggtg
22381 gaagggcgg tcgttcataa tgtaattggt ggatgagaag taggtgacaa agtcgaccag
22441 gcctgactca gcgaaccgcg tcgccagggt ctgggtaaaa ctccgacgac aggagacgac
22501 gagcacactc gtgtccggag agtggatcga ttcccgcagc cagcggatca gcgcggtagt
22561 tttttccgac cccattggcg cgcggaccac agtcacgcac ctggccgtcg ggcgctcgc
22621 gttggggaag gtgacgggtc cgtgctgctg ccgctcgatc gttgttttcg ggtgaacccg
22681 gggcaccat tcggccaaat ccccccgta caacatccgc gctagcgata cgctcgacgt
22741 gtactgttcg cactcgtcgt ccccaatggg acgcccggcc ccagaggat cccccgactc
22801 cgcgccccc acgaaaggca tgaccggggc gcggacggcg tggtgggtct ggtgtgtgca
22861 ggtggcgacg tttgtggtct ctgcggtctg cgtcacgggg cttctcgtcc tggcctctgt
22921 gttccgggca cggtttccct gcttttatga cacggcgagc tcttatgccg gggtgaactc
22981 cacggcgag gtgcgcgggg gtgtagccgt gcccctcagg ttggacacgc agagccttgt
23041 gggcacttat gtaatcacgg ccgtgttgtt gttggccgcg gccgtgtatg ccgtggtcgg
23101 cgccgtgacc tcccgctacg accgcgcct ggacgcggc gccgtctgg ctgcgcccg
23161 catggccatg acgcacgcca cgctgatcgc cggaaacgtc tgctcttggt tgctgcagat
23221 caccgtcctg ttgctggcc atcgcatcag ccagctggcc cacctggttt acgtcctgca
23281 cttgcgtgt ctggtgtatt ttgcggccca ttttgcacc agggggggtcc tgagcgggac
23341 gtatctgcgt caggtgcacg gctgatgga gccggcccg actcatcatc gcgtcgtcgg
```

FIGURE 16
(Continued)

```
23401 ccoggctcga gcggtgctga caaacgcctt gctgttgggc gtcttcctgt gcacggcga
23461 cgccgggta tccctgaata ccatcgccgc gttcaactt aattttcgg cccgggcat
23521 gctcatatgc ctgaccgtgc tgttcgccct tctcgtcgta tcgctgttgt tggtggtcga
23581 ggggtgttg tgtcactacg tgcggtgtt ggtgggcccc cacctggggg ccgtggccgc
23641 cacgggcatc gtcggcctgg cctgcgagca ctattacacc aacggctact acgttgtgga
23701 gacgcagtgg ccggggcc agacggagt ccgcgtcgcc ctcgccctgg tcgccgcctt
23761 tgccctcggc atggccgtgc tccgctgcac ccgcgcctat ctgtatcaca ggcggcacca
23821 caccaaattt tttatgcgca tgcgcgacac gcgacaccgc gcacattccg ccctcaggcg
23881 cgtacgcagt tccatgcgcg gatcgcgaga cggccgccac aggcccgcac ccggcagccc
23941 gcccgggatt cccgaatatg cggaagaccc ctacgcgatc tcatacggcg gccagctcga
24001 ccggtacgga gattccgacg gggagccgat ttacgacgag gtggctgacg accaaaccga
24061 cgtattgtac gccaagatac aacacccgcg gcacctgccc gacgacgagc ccatctatga
24121 caccgttggg gggtacgacc ccgagccgc cgaggaccc gtgtacagca ccgtccgcg
24181 ttggtagctg tttggttccg ttttaataaa ccgtttgtgt taacccgac cgtggtgtat
24241 gtctggtgtg tggagtccga tcccgttact atcaccgttt ccccccccc ccctcaacc
24301 ccggcgattg tgggtttttt aaaacgaca cgcgtgcgac cgtatacaga acattgtttt
24361 ggtttttatt cgctatcgga catgggggt ggaaactggg tggcgggca ggcgctccg
24421 gggtccgc ggtgagtgtg gcgcgagggg gggtccgacg aacgcaggcg ctgtatcccc
24481 gggcccgcg taaccacgcg catatccggg ggcacgtaga aattaccttc ctcttcggac
24541 tcgatatcca cgacatcaaa gtcgtgggcg gtcagcgaga cgacctcccc gtcgtcggtg
24601 atgaggacgt tgtttcggca gcagcaggc cggccctgg agaacgagag gccatagct
24661 cggcgagcgt gtcgtcgaac gccaggcggc tgcttcgctg gatggcctta tagatctccg
24721 gatcgatgcg gacggggta atgatcaggg cgatcggaac ggcctggttc gggagaatgg
24781 acgccttgct gggtcctgcg gcccgagag cccggcgcc gtcctccagg cggaacgtta
24841 cgccctcctc cgcgctggtg cggtgcctgc cgataaacgt caccagatgc gggtgggggg
24901 ggcagtcggg gaagtggctg tcgagcacgt agccctgcac caagatctgc ttaaagttcg
24961 ggtgacgggg gttcgcgaag acgggctcgc ggcggaccag atcccggag ctccaggaca
25021 cggggagat ggtgtggcgt ccgaggtcgg gggcgcaaa cagaagcacc tccgagacaa
```

```
25081 cgccgctatt taactccacc aaggccgat ccgcggga gcaccgcct ttttcgccg
25141 aggcgtggc ctatgaccag gctggtctt gcgtgacgag agcatcctcc ggccggga
25201 cgcgcccggg cgcgaagtat cgcacgatgg gcttcgggat cgaccggata aatgcccgga
25261 acgcctccgg ggaccggtgt gtcatcaagt cctcgtacgc ggaggccgtg gggtcgtgg
25321 ggtccatggg gtcgaaagcg tacttggccc ggcattgac ctcgtaaaag gccagggcg
25381 tcttggggac tgggccagg tagccgtgaa tgtcccgagg acagacgaga atatccaggg
25441 acgcccgac catcccgtg tgaccgtcca tgaggacccc acacgtatgc acgttctctt
25501 cggtgaggtc gctggttcg tggaagataa agcgcgcgt gcggcgccg gcctcgccgc
25561 cgtcgtccgc gcggccacg cagtagcgaa acagcaggct tcgggccgtc ggctcgttca
25621 cccgcccgaa catcaccgcc gaagactgta catccggccg caggctggcg ttgtgcttca
25681 gccactggg cgagaaacac ggacctggg ggccccagcg gagggtggat gcggtcgtga
25741 ggaccccgcg gagcagggcc catagctggc agtcggcctg gttttgcgtg gccgcctcgt
25801 aaaaccccat gaggggccgg ggcgccacgg cgtccgcggc ggccggggc ccgcggcgcg
25861 tcaggcgcca taggtgccgg ccgagtccgc ggtccaccat acccgcctcc tcgaggacca
25921 cggccaggga acatagataa tccaggcggg cccagagggg accgatggcc agagggcgc
25981 ggacgccgcg cagcaacccg cgcaggtggc gctcgaacgt ctcggctagt atatgggagg
26041 gcagccgtt gggatcacc gacgccgacc acatagagtc aaggtccggg gagtcgggat
26101 cggcgtccgg gtcgcggcg tgggtgcccc caggagatag cggaatgtct gggtcggag
26161 gccctgaggc gtcagaaagt gccggcgacg cggcccggggg cttttcgtct gcggtgtcgg
26221 tgcgtgctg atcacgtggg gggttaacgg gcgaatggga gctcgggtcc acagctgacg
26281 tcgtctggg tgggggggc agggacgga aggtggttgt cagcggaaga ctgttagggc
26341 ggggcgctt ggggggctg tcgggccac gagggtgtc ctggccagg gccagggac
26401 gcttagtcac ggtgcgtccc ggcggacatg ctggcctac cgtggactcc atttccgaga
26461 cgacgtgggg gagcggtggt tgagcgcgcc gcagggtgaa cgctgattct cacgacagcg
26521 cgtgccgcgc gcacgggttg gtgtgacaca ggcgggacac cagcaccagg agaggcttaa
26581 gctcgggagg cagcgccacc gacgacagta tcgccttgtg tgtgtgctgg taatttatac
26641 accgatccgt aaacgcgcgc cgaatcttgg gattgcggag gtggccggg atgccctctg
26701 gtacgtcata cgccaggccg tgggtgttgg tctcggccga gttgacaaac agggctggt
```

FIGURE 16
(Continued)

```
26761 gcagcaagca gcgataggcg agcagggcca gggcgaagtc cggcgacagc tggttgttga
26821 aatactggta accgggaaac cgggtcacgg gtacgccag gctcgggcg acgtacagc
26881 taaccaccaa ctccagcagc gtctggccaa gggcgtacag gtcaaccgct aacccgacgt
26941 cgtgcttcag gcggtggttg gtaaattcgg cccgttcgtt gttaaggtat ttcaccaaca
27001 gctccggggg ctggttatac ccgtgaccca ccagggtgtg aaagttggct gtggttaggg
27061 cggtgggcat gccaaacatc cgggggggact tgaggtcgg ctcctggagg caaaactgcc
27121 tccgggcgat cgtggagttg gagttgaggg tgacgaggct aaagtcggcg aggacggcc
27181 gccggagcga gacggcgtcc gaccgcagca tgacgaggat gtggcgcac ttgatatcca
27241 ggtggctgat cccgcaggtg gtgtttaaaa acacaacggc gcgggccagc tccgtgaagc
27301 actggtggag ggccgtcgag accgaggggt ttgttgtgcg cagggacgcc agttggccga
27361 tatacttacc gaggtccatg tcgtacgcgg ggaacactat ctgtcgttgt tgcagcgaga
27421 acccgagggg cgcgatgaag ccgcggatgt tgtgggtgcg gccggcgcgt agagcgcact
27481 ccccgaccaa caggtcgcg atgagctcaa cggcaaacca ctccttttcc tttatggtct
27541 taacggcaag cttatgttcg cgaatcagtt ggacgtcgcc gtatccccca gacccccga
27601 agcttcgggc cccggggatc tcgagggtcg tgtagtgtag ggcggggttg atggcgaaca
27661 cggggctgca tagcttgcgg atgcgcgtga gggtaaggat gtgcgagggg gacgaggggg
27721 gtgcggttaa cgccgcctgg gatctgcgca gggcggcgg gttcagtttg gccgccgtac
27781 cgggcgtctc gggggacgcg cggcgatgag acgagcggct cattcgccat cgggatagtc
27841 ccggcgaag ccgctcgcgg aggccggatc ggtggcggga ccgtggag gagcgggagc
27901 cggcggcgtc ctggagagag gggccgctgg ggcgccgga ggcccgtgt gggttggagt
27961 gtatgtagga tgcgagccaa tccttgaagg accgttggcg tgaccttgg gggctgaggt
28021 tagctgccac atgatcagca ggtcgctgtc tgcgggactc atccatcctt cggccaggtc
28081 gccgtctccc cacagagaag cgttggtcgc tgcttcctcg agttgctcct cctggtccgc
28141 aagacgatcg tccacggcgt ccagggcgtc accaagcgcc ggatcgaggt accgtcggtg
28201 tgcggttaga aagtcacgac gcgccgcttg ctcctccacg cgaattttaa cacaggtcgc
28261 gcgctgtcgc atcatctcta agcgcgcgcg ggactttagc cgcgcctcca attccaagtg
28321 ggccggcttt gcagccataa aggcgccaac aaaccgagga tcttgggtgc tgacgccctc
28381 ccggtgcagc tgcagggtcc ggtccttgta aatcaggct cggaggtgcg tctcggccag
```

FIGURE 16
(Continued)

```
28441 gcgtcggcgc agggccgcgt gggcggcatc tcggtccatt ccgccaccct gcggcgacc
28501 cggggggtgc tctgatagtc tcgcgtgccc aaggccgtg atcgggtac ttcgccgcg
28561 cgaccgcca cccggtgtgc gcgatgtttg gtcagcagct ggcgtccgac gtccagcagt
28621 acctggagcg cctcgagaaa cagaggcaac ttaaggtggg cgcggacgag gcgtcggcgg
28681 gcctcacaat gggcggcgat gccctacgag tgccttttt agatttcgcg acgcgaccc
28741 ccaagcgcca ccagaccgtg gtcccgggcg tcgggacgct ccacgactgc tgcgagcact
28801 cgccgctctt ctcggccgtg gcgcggcggc tgctgtttaa tagcctggtg ccggcgcaac
28861 taaagggcg tgatttcggg ggcgaccaca cggccaagct ggaattcctg gccccgagt
28921 tggtacgggc ggtggcgcga ctgcggttta aggagtgcgc gccggcggac gtggtgcctc
28981 agcgtaacgc ctactatagc gttctgaaca cgtttcaggc cctccaccgc tcgaagcct
29041 ttcgccagct ggtgcacttt gtgcgggact ttgcccagct gcttaaaacc tccttccggg
29101 cctccagcct cacggagacc acgggccccc ccaaaaaacg ggccaaggtg gacgtggcca
29161 cccacggccg gacgtacggc acgctggagc tgttccaaaa aatgatcctt atgcacgcca
29221 cctacttct ggccgccgtg ctcctcgggg accacgagga gcaggtcaac acgttcctgc
29281 gtctcgtgtt tgagatcccc ctgtttagcg acgcggcgt gcgcacttc cgccagcgcg
29341 ccaccgtgtt tctcgtcccc cggcgccacg gcaagacctg gtttctagtg ccctcatcg
29401 cgctgtcact ggcctccttt cgggggatca agatcggcta cacggcgcac atccgcaagg
29461 cgaccgagcc ggtgttgag gagatcgacg cctgcctgcg gggctggttc ggttcggccc
29521 gagtggacca cgttaaaggg gaaaccatct ccttctcgtt tcggacgggg tcgcgcagta
29581 ccatcgtgtt tgcctccagc cacaacacaa acgtaagtcc tctttctttt cgcatggctc
29641 tcccaagggg ccccgggtcg acccgaccca cacccaccca cccacccaca tacacacaca
29701 accagacgcg ggaggaaagt ctgcccgtg ggcactgatt ttattcggg atcgcttgag
29761 gaggccgggg caacggccg ggcaacggtg gggcaactcg tagcaaatag gcgactgatg
29821 tacgaagaga agacacacag gcgccaccg gcgctggtcg ggggatgtt gtccgcgcg
29881 caccgtcccc cgacgacctc ttgcagacgg tccgtgatgc aaggacggcg ggggcctgc
29941 agcagggtga ccgtatccac gggatggcca aagagaagcg gacacaggct agcatcccc
30001 tggaccgcca gggtacactg ggccatcttg gcccacagac acgggcgac gcagggacag
30061 gactccgtta cgacggagga gagccacagt gcgttggcgg aatcgatgtg gggcggcggg
```

```
30121 gcgcaggact cgcagcccce cgggtggttg gtgatcatgg ccaggagcca tcccagatgg
30181 cgggccctgc ttcccggtgg acagagcgac cccaggtcgc tgtccatggc ccagcagtag
30241 atctggccgc tgggaggtg ccaccaggcc cccgggccca aggcgcagca cgcgcccggc
30301 tccgggggg tcttcgcggg gaccagatac gcgccatcca gctcgccgac caatggctcc
30361 tccgcgagct gttcggtggt tgggtgggg gtttcctccg ggggtggc cgcccgtatg
30421 cgggcgaacg tgagggtgca caggagcggg gtcaggggt gcgtcacgct ccggaggtgg
30481 acgatcgcgc agtagcggcg cttgcggtta aagaaaaga gggcaaagaa ggtgttcggg
30541 ggcaaccgca gcgccttggg gcgcgtcaga tacagaaaaa tctcgcagaa gagggcggc
30601 ccggggtctg ggttaggaag ggccacctga cacagaggct cggtgaggac cgttagacac
30661 cgaaagatct tgagccgctc gtccgcccga acgacgcgcc acacaaagac ggagttgaca
30721 atgcgcgcga tagagtcgac gtccgtcccc aggtcgtcga ctctgtcgcg cgtgccgcga
30781 gctccggccc gggaatccgg ccggggcaag gtccccgggg gaccaggcgg cgccagggc
30841 cgccgggtc ccagctgcgc catgccgggg gcggggggag ggcaaacccc agaggcgggg
30901 gccaacgcg cgggaggag tgggtgggcg aggtggccgg gggaaggcgc ccgctagcga
30961 gaacggccgt tcccggacga caccttgcga caaacctaa ggacagcggc ccgcgcgacg
31021 gggtccgaga ggctaaggta ggccgcgatg ttaatggtga acgcaaagcc gccgggaaag
31081 acaactatgc cacagaggcg gcgattaaac cccagcaga ggtaggcgta gctttcccg
31141 ggcaggtatt gctcgcagac cctgcgtggg gctgtggagg ggacggcctc catgaagcga
31201 catttactct gctcgcgttt actgacgtca ccatccatcg ccacggcgat tggacgattg
31261 ttaagcgca gcgtgtctcc gcttgtgctg tagtagtcaa aaacgtaatg gccgtcggag
31321 tcggcaaagc gggccggag gtcgtcgcg agcggacga ccgccgcc ccgaccgcc
31381 cgtccccca ggtgtgccag gacggccagg gcatacgcgg tgtgaaaaaa ggagtcgggg
31441 gcggtccgct cgacggcgca catcaggttc tcgaggagaa tgggaagcg cctggtcacc
31501 tccccaacc acgcgcgttg gtcggggcca aagtcatagc gcaggcgctg tgagattcgc
31561 gggccgccct gaagcgcggc ccggatggcc tggcccaggg ccggaggca cgcagatgt
31621 atgcgcgcgg taaaggcgac ctcggcggcg atgtcaaagg gcgcaggac ggggcgcggg
31681 tggcgcaggg gcacctcgag cgcgggaaag cgtagcagca gtccgcctg cccagcggga
31741 gacagctggt ggggcgcac gacgcgttct gcggcgcagg cctcggtcag ggccgtggcc
```

```
31801 agcgccgagg acagcagcgg aggccgggcg cgtcgccgc cccacgccac ggagttctcg
31861 taggagacga cgacgaagcg ctgcttggtt ccgtagtggt ggcgcaggac cacggagata
31921 gaacgacggc tccacagcca gtccggccgg tgccgccgg ccagggcttc ccatccgcga
31981 tcgaaccact cgaccagcga ccgcggcttt gggtaccag gggtcagggt tagaacgtcg
32041 ttcaggatgt cctcgccccc gggccgtgg ggcacgggg ccacaaagcg gccccgcct
32101 gggggctcca gacccgccaa caccgcatct ggtcagccg cccccatggc gccccgctg
32161 acggcctggt gaaccagggc gccctggcgg agcccgatg caacgccaca ggccgcacgc
32221 ccgtccgag cgcggaccgg gtggcggcgg gtgacgtcct gcactgcccg ctgaaccaac
32281 gcgaggatct cctcgttctc ctgcgcgatg gacacgtcct gggccgcggt cgtgtcgccg
32341 ccggggccg tcagctgctc ctccggggag atggggcggt cggacgcccc gacgatgggc
32401 gggtctgcgg gcgccccgc gtggggccgg gccagggct gcggacgcgg ggacgcgctt
32461 tccccagac ccatggacag gtgggccgca gcctccttcg cggccggcgg ggcggcggcg
32521 ccaagcagag cgacgtagcg gcacaaatgc cgacagacgc gcatgatgcg cgtgctgtcg
32581 gccgcgtagc gcgtgttggg gggacgagc tcgtcgtaac taaacagaat cacgcgggca
32641 cagctcgccc ccgagcccca gcaaggcgc agcgccgcca cggcgtacgg gtcatagacg
32701 ccctgcgcgt tacacaccac gggcagggag acgaacaacc cccggcgct ggacgcacgc
32761 ggaaggaggc caggggtgtgc cggcacgacg ggggccagaa gctcccccac cgcatccgcg
32821 ggcacgtagg cggcaaaagc cgtgcaccac ggggtacagt cgccggtggc atgagccga
32881 gtctggattt cgacctggaa gtttgcggcc gtcccgagtc cggggtggcc gcgcatcagg
32941 gcggcagag ggattcccgc ggccgccagg cactcgctgg atatgatgac gtgaaccaaa
33001 gacgaggcd gacccggcc gtggccgaga tcgtactgga cctgttggc caagtgcgcg
33061 ttcatggttc ggggtggt gtgggtgtgt aggcgatgcg ggtccccga gtccgggga
33121 agggcgtggg tttggagcgc gtatgcgtat tcgccaacgg aggcgtgcgt gcttatgcgc
33181 ggcgcgtttc ttctgtctct agggaatccg aggccaggac tttaactgc tctttgtcga
33241 cgaggccaac tttattcgcc cggatgcggt ccagacgatt atgggctttc tcaaccaggc
33301 caactgcaag attatcttcg tgtcgtccac caacaccggg aaggccagta cgagcttttt
33361 gtacaacctc cgcggggccg cagacgagct tctcaacgtg gtgacctata tgcgatga
33421 tcacatgccg agggtggtga cgcacacaaa cgccacggcc tgttcttgtt atatcctcaa
```

FIGURE 16
(Continued)

```
33481 caagcccgtt ttcatcacga tggacggggc ggttcgcagg accgccgatt tgtttctggc
33541 cgattcctto atgcaggaga tcatcggggg ccaggccagg gagaccggcg acgaccggcc
33601 cgttctgacc aagtctgcgg gggagcggtt tctgttgtac cgccctcga ccaccaccaa
33661 cagcggcctc atggcctcg attgtacgt gtacgtggat cccgcgttca cggccaacac
33721 ccgagcctcc gggaccggcg tcgctgtcgt cgggcggtac cgcgacgatt atatcatctt
33781 cgccctggag cacttttttc tccgcgcgct caggggctcg gccccgccg acatcgcccg
33841 ctgcgtcgtc cacagtctga cgcaggtcct ggccctgcat ccgggggcgt ttcggggcgt
33901 ccgggtggcg gtgagggaa atagcagcca ggactcggcc gtcgccatcg ccacgcacgt
33961 gcacacagag atgcaccgcc tactggcctc ggaggggcc gacgcgggct cgggcccga
34021 ggttctcttc taccactgcg agcctcccgg gagcgcggtg ctgtacccct ttttcctgct
34081 caacaaacag aagacgcccg cctttgaaca ctttattaaa aagtttaact ccggggggcgt
34141 catggcctcc caggagatcg tttcagcgac ggtgcgcctg cagacgacc cggtcgagta
34201 tctgctcgag cagctaaata acctcacga aaccgtctcc cccaacactg acgtccgtac
34261 gtattccgga aaacgaaacg gcgcctcgga tgacttatg gtcgccgtca ttatgccat
34321 ctacctcgcg gcccaggccg gacctccgca cacattcgct cctatcacac ggtcttgtg
34381 agcgcccaat aaacacaccc aggtatgcta cgcacgacca cggtgtcgtc tgttaagggg
34441 gggggaagg ggtgttggc gggaagcgtg ggaacacggg ggattctctc acgacggca
34501 ccagtaccac ccccctgtga acacagaaac cccaaccccaa atcccataaa catacgacac
34561 acaggcatat tttggaattt cttaggtttt tatttattta ggtatgctgg ggtttctccc
34621 tggatgccca ccccaccccc cccgtggtc tagccgggcc ttagggatag cgtataacgg
34681 gggccatgtc tcggaccgc acaacggcg cgccgtaaaa ggtgaacacc cgaaccacgg
34741 gagccagggc caaggtgtct cctagttggc ccgcgtgggt cagccaggcg acgagcgct
34801 cgtaaagcgg cagccttcgc tctccatcct gcatcagggc cggggcttcg gggtgaatga
34861 gctgggcggc ctcccgcgtg acactctgca tctgcaggag agcgttcacg tacccgtcct
34921 gggcacttag cgcaaagagc cggggatta gcgtaaggat gatggtggtt cctccgtga
34981 tcgagtaaac catgttaagg accagcgatc gcagctcggc gtttacggga ccgagttgtt
35041 ggacgtccgc cagcagcgag aggcgactcc cgttgtagta cagcacgttg aggtctggca
35101 gccctccggg gtttctgggg ctgggttca ggtccaggat gcacctggcc acgagccgcg
```

```
35161 ccacgattto gcgcgccagg ggcgatggaa gcggaacggg aaacogcaac gtgaggtcca
35221 gcgaatccag gcgaacgtcc gtcgcttggc cctcgaacac gggcgggacg aggctgatgg
35281 ggtccccgtt acagagatct acggggagg tgttgcgaag gttaacggtg ccggcgtggg
35341 tgaggcccac gtccaggggg caggcgacga ttcgcgtggg aagcaccgg gtgatgaccg
35401 cgggaagcg ccttcggtac gccagcaaca accccaacgt gtcgggactg acgcctccgg
35461 agacgaagga ttcgtgcgcc acgtcggcca gcgtcagttg ccggcggatg gtcggcagga
35521 ataccaccog cccttcgcag cgctgcagcg ccgccgcatc ggggcgcgag atgccogagg
35581 gtatcgcgat gtcagtttca aagccgtccg ccagcatggc gccgatccac gcggcaggga
35641 gtgcagtggt gggtcgggtg gcgggaggag cgcggtgggg gtcagcggcg tagcagagac
35701 gggcgaccaa cctcgcatag gacggggggt gggtcttagg gggttgggag gcgacaggga
35761 ccccagagca tgcgcgggga ggtctgtcgg gcccagacgc accgagagcg aatccgtccg
35821 cggagtcccg gcttggtttt tatgggccc ggcctcgga atcgcggctt gtcggcgggg
35881 acaaaggggg cggggctagg ggcttgcgga aacagaagac gcgtgggata aaagaatcgc
35941 actacccaa ggaagcgcgg ggcggtttat tacagagcca gtccttgag cgggatgcg
36001 tcatagacga gatactgcgc gaagtgggtc tcccgcgcgt gggcttcccc gttgcgggcg
36061 ctgcggagga gggcggggtc gctggcgcag gtgagcgggt aggcctcctg aaacaggcca
36121 cacgggtcct ccacgagttc gcggcacccc gggggcgct taaactgtac gtcgctggcg
36181 gcggtggccg tggacaccgc cgaaccgtc tccacgatca ggcgctccag gcagcgatgt
36241 ttggcggcga tgtcggccga cgtaaagaac ttaaagcagg ggctgagcac cggcgaggcc
36301 ccgttgaggt ggtaggcccc gttatagagc aggtccccgt acgaaaatcg ctgcgacgcc
36361 cacggttgg ccgtggccgc gaaggccgg gacgggtcgc tctggccgtg gtcgtacatg
36421 agggcggtga catctccctc cttgtcccgc gcgtaaacgc cccggcggc gcgtcccgg
36481 gggttgcagg gccggcggaa gtagttgacg tcggtcgaca cggggggtggc gataaactca
36541 cacacggcgt cctggccgtg gtccatccct gcgcgccgcg gcacctgggc gcacccgaac
36601 acgggacgg gctgggacgg cccaggcgg ttccgcca cgaccgcgtt ccgcaggtac
36661 acggctgccg cgttgtccag gagaggggga gccccgcggc ccaggtaaaa gttttgggga
36721 aggttgccca tgtcggtgac gcgggttgcgg acggttgccg tggccacgac ggcggtgtag
36781 cccacgccca ggtccacgtt accgcgcggc tgggtgagcg tgaagtttac ccccgccga
```

FIGURE 16
(Continued)

```
36841 gtttcgtgcc gggccacctg gagctggcc aggaagtacg cctccgacgc gcgctccgag
36901 aacagcacgt tctcagtcac aaagcggtcc tgtcggacga cggtgaaccc aaaccgggga
36961 tggaggcccg tcttgagctg atgatgcaag ccacgggac tgatcttgaa gtacccgcc
37021 atgagcgcgt aggtcagcgc gttctcccg gacgcgctct cgcggacgtg ctgacgacg
37081 ggctgtcgga tcgacgaaaa gtagttgcc cccagagccg gaggggaccag gggacctgc
37141 cgcgacaggt cgcgcagggc cgggggaaa ttgggcgcgt tgccacgtg gtcggcccg
37201 gcgaacagcg cgtggacggg gagggggtaa aaatagtcgc cattttggat ggtatggtcc
37261 agatgctggg gggccatcag caggattccg gcgtgcaacg cccgtcgaa tatgcgcatg
37321 ttggtggtgg acgcggtgtt ggcgccgcg tcgggcgccg ccgagcagag cagcgccgtt
37381 gtgcgttcgg ccatgttgtg ggccagcacc tgcagcgtga gcatggcggg cccgtccact
37441 accacgcgcc cgttgtgaaa catggcgttg acgtgttgg ccaccagatt ggccgggtgc
37501 aggggtgcg cggggtccgt cacggggtcg ctgggcact cctcgcgggg ggcgatctcc
37561 gggaccacca tgttctgcag ggtggcgtat acgcggtcga agcgaacccc cgcggtgcag
37621 cagcggcccc gcgagaaggc gggcaccatc acgtagtagt aaatcttgtg gtgcacggtc
37681 cagtccgccc cccggtgcgg ccggtcatcc gcggcgtccg cggctcgggc ctgggtgttg
37741 tgcagcagct ggccgtcgtt gcggttgaag tccgcggtcg ccacgttaca tgccgccgcg
37801 tacacggggt cgttggcccc cgcgctaacc cggcagtcgc gatggcggtc cagggcgcg
37861 cgccgcatca gggcgtcaca gtccacacg aggggtggca gcagcgcgg gtctgcatt
37921 aggtgattca gctcggcttg cgcctgcccg cccagctccg ggccggtcag ggtaaagtca
37981 tcaacagct gggccagggc ctcgacgtgc gccaccaggt cccggtacac ggccatgcac
38041 tcctcgggaa ggtctcccc gaggtaggtc acgacgtacg agaacagcga gtagtcgttc
38101 acgaacgccg cgcaccgcgt gttgttccag tagctggtga tgcactggac cacgagcgg
38161 gccagggcgc agaagacgtg ctcgctgccg tgtatggcgg cctgcagcag gtaaaacacc
38221 gccgggtagt tgcggtcgtc gaacgcccg cgaacggcgg cgatggtggc gggggccatg
38281 gcgtggcgtc ccaccccag ctccaggccc cgggcgtccc ggaacgccgc cggacatagc
38341 gccaggggca agttgccgtt caccacgcgc caggtggcct ggatctccac cgggcaggcc
38401 ggggaacgt ccccccccgg cagctccacg tcggccaccc ccacaaagaa gtcgaacgcg
38461 gggtgcagct caagagccag gttggcgttg tcgggtgca taaactgtc cgggtcatc
```

FIGURE 16
(Continued)

```
38521 tggccttccg cgacccatcg gacccgcccg tggccaggc gctgccccca ggcgttcaaa
38581 aacagctgct gcatgtctgc ggcggggccg gccggggccg ccacgtacgc cccgtacgga
38641 ttggcggctt cgacggggtc gcggttaagg cccccgaccg ccgcgtcaac gttcatcagc
38701 gaagggtggc acacggtccg gatcgcgtgt tccagagaca ggcgcagcac ctggcggtcc
38761 ttccccaaa aaaacagctg gcggggcggg aaggcgcggg gatccggtg gcggggcg
38821 gggactaggt cccggcgtg cgcggcaaac cgttccatga ccggattgaa caggccagg
38881 ggcaggacga acgtcaggtc catggcgccc accaggggt agggaacgtt ggtggcggcg
38941 tagatgcgct tctccagggc ctccagaaag accagcttct cgccgatgga caccagatcc
39001 gcgcgcacgc gcgtcgtctg gggggcgctc tcgagctcgt ccagcgtctg ccggttcagg
39061 tcgagctgct cctcctgcat ctccagcagg tggcggccca cgtcgtccag acttcgcacg
39121 gccttgccca tcacgagcgc cgtgaccagg ttggcccgt tcaggaccat ctcgccgtac
39181 gtcaccggca cgtcggattc ggtgtcctcc gctttcagga aggactgcag gaggcgctgt
39241 ttgatcgggg cggtggtgac gagcaccccg tcgacggcc gccgcgcgt gtcggcatgc
39301 gtcagacggg gcacggccac ggagggctgc gtggccgtgg tgaggtccac gagccaggcc
39361 tcgacggcct ccggcggtg gcccgccttg cccaggaaaa agctcgtctc gcagaagctt
39421 cgctttagct cggcgaccag ggtcgcccgg gccaccctgg tggccaggcg gccgttgtcc
39481 aggtatcgtt gcatcggcaa caacaaagcc aggggcggcg cctttccag cagcacgtgc
39541 agcatctggt cggccgtgcc gcgctcaaac gcccgagga cggcctggac gttgcagcg
39601 agctgttgga tggcgcgcaa ctggcgatgc gcgccgatac cgtcccgtc cagggcctcc
39661 cccgtgagca gggcgatggc ctcggtggcc aggctgaagg cggcgttcag ggcccggcgg
39721 tcgataatct tggtcatgta attgtgtgtg ggttgctcga tgggtgcgg gcgtcggg
39781 gcaatcagcg gctggtggac ctcgaactgt acgcgccct cgttcatgta ggccagctcc
39841 ggaaacttgg tacacacgca cgccaccgac aacccgagct ccagaaagcg cacgagcgac
39901 agggtgttgc aatacgaacc cagcaggcg tcgaactcga cgtcgtacag gctgtttgca
39961 tcgagcgca cgcggaaaa aaaatcgaac aggqtcgat gcgacgccac ctcgatcgtg
40021 ctaaggaggg acccggtcgg caccatggcc gcggcatacc ggtatcccgg agggtcgcgg
40081 ttgggagctg ccatggggtc gcgtggagat cggctggatc tagcgatatt tgcccgggga
40141 ggctaagatc cacccaaacg cccggccacc cgtgtacgtg ccgacggcc caaggtccac
```

```
40201 cgaaagacac gacggcccg gacccaaaaa ggcggggat gctgtgtgag gggccgggtg
40261 tcggtcgggg gggaaaggca ccgggagaag gctgcggcct cgttccagga gaacccagtg
40321 tccccaacag accoggggac gtgggatccc aggccttata tacccccccc gcccaccccc
40381 cgttagaacg cgacgggtgc attcaagatg gccctggtcc aaaagcgtgc caggaagaaa
40441 ttggcagagg cggcaaagct gtccgccgcc gccacccaca tcgaggcccc ggccgcgcag
40501 gctatcccca gggcccgtgt gcgcagggga tcggtgggcg gcagcatttg gttggtggcg
40561 ataaagtgga aaagcccgtc cggacggaag gtctcgtggg cggcggcgaa caaggcacac
40621 agggccgtgc ctcccaaaaa cacggacatc cccaaaaca ctggcgccga caacggcaga
40681 cgatccctct tgatgttaac gtacaggagg agcgcccgca ccgcccacgt aacgtagtag
40741 ccgacgatgg cggccaggat acaggccggc gccaccaccc ttccggtcag cccgtaatac
40801 atgcccgctg ccaccatctc caacggcttc aggaccaaaa acgaccaaag gaacagaatc
40861 acgcgctttg aaaagaacgg ctgggtatgg ggcggaagac gcgagtatgc cgaactgaca
40921 aaaaatcag aggtgccgta cgaggacaat gaaaactgtt cctccagcgg cagttctccc
40981 tcctccccc cgaaggcggc ctcgtcgacc agatctcgat ccaccagagg aaggtcatcc
41041 cgcatggtca tggggtgtgc ggtggaggtg gggagaccga aacgcaaag ggtcgcttac
41101 gtcagcagga tcccgagatc aaagacaccc gggttcttgc acaaatacca cccgggttgc
41161 atccgcggag gcgagtgttt tgataaggcc gttccgcgcc ttgatataac ctttgatgtt
41221 gaccacaaaa cccggaattt acgcctacgc cccaatgccc acgcaagatg aggtaggtaa
41281 cccccccgtg ggtgtgacgt tgcgttagt tcattggagg ccaaggggaa aaatggggtg
41341 gggaggaaac ggaaaaccca gtaggccgtg tcgggaacac gcccggggtt gtcctcaaaa
41401 ggcagggtcc atactacgga agccgtcgtt gtattcgaga cctgcctgtg cgacgcacgt
41461 cggggttgcc tgtgtccggt tcggcccca ccgcgtgcgg caccacgag gacgagtccg
41521 cgtgctttat tggcgttcca agcgttgccc tccagtttct gttgtcggtg ttccccccata
41581 cccacgccca catccaccgt agggggcctc tgggccgtgt tacgtcgccg cccgcgatgg
41641 agcttagcta cgccaccacc atgcactacc gggacgttgt gttttacgtc acaacggacc
41701 gaaacgggc ctacttcgtg tgcgggggggt gtgtttattc cgtgggcggg ccgtgtgcct
41761 cgcagcccgg ggagattgcc aagtttggtc tggtcgttcg agggacaggc ccagcgacc
41821 gcgtggtcgc caactatgta cgaagcgagc tccgacaacg cggcctgcag gacgtgcgtc
```

FIGURE 16
(Continued)

```
41881 ccattgggga ggacgaggtg tttctggaca gcgtgtgtct tctaaaccog aacgtgagct
41941 ccgagctgga tgtgattaac acgaacgacg tggaagtgct ggacgaatgt ctggccgagt
42001 actgcacctc gctgcgaacc agcccgggtg tgctaatatc cgggctgcgc gtggggcgc
42061 aggacagaat catcgagttg ttgaacacc caacgatagt caacgttcc tgcacttttg
42121 tgtataccc gtcccatac gtgttcgccc tggccaggc gcacctccc cggctcccga
42181 gctcgctgga ggccctggtg agcggcctgt ttgacggcat cccgcccca cgccagtcac
42241 ttgacgccca caacccgcgc acggatgtgg ttatcacggg ccgccgcgcc ccacgaccca
42301 tcgccgggtc ggggcggg tcggggcgcg cgggcgccaa gcgggccacc gtcagcgagt
42361 tcgtgcaagt caaacacatt gacgcgtgg gcccgctgg cgtttcgccg gcgcctccgc
42421 caaacaacac cgactcgagt tccctggtgc ccgggccca ggattccgcc ccgccggcc
42481 ccacgctaag ggagctgtgg tgggtgtttt atgccgcaga ccgggcgctg gaggagcccc
42541 gcgccgactc tggcctcacc cgcgaggagg tacgtgccgt acgtgggttc cgggagcagg
42601 cgtggaaact gtttggctcc gcgggggcc cgcgggcgtt tatcggggcc gcgttgggcc
42661 tgagcccct ccaaagctg gccgtttact actatatcat ccacgagag aggcgcctgt
42721 ccccttccc cgcgctagtc aggctgtag gcggtacac acagcgccac ggcctgtacg
42781 tccctcggcc cgacgaccca gtcttggccg atgccatcaa cgggctggtt cgcgacgcgc
42841 tggcggcgg aaccacagcc gagcagctcc tcatgttcga ccttctcccc ccaaaggacg
42901 tgccggtggg aagcgacgtg caggccgaca gcaccgctct gctgcgcttt atagaatcgc
42961 aacgtctcgc cgtccccggg ggggtgatct ccccgagca cgtcgcgtac cttggtgcgt
43021 tcctgagcgt gctgtacgct ggccgcggc gcatgtccgc agccacgcac accgcgcggc
43081 tgacagggt gacctccctg gtgctagcgg tgggtgacgt ggaccgtctt tccgcgtttg
43141 accgcggagc ggcggcgcg gccagccgca cgcgggccgc cgggtacctg gatgtgcttc
43201 ttaccgttcg tctcgctcgc tccaacacg gacagtctgt gtaaagacc ccaataaacg
43281 tatgtcgcta ctacacctt gtgtgtcaat ggacgcctct ccggggggg gaagggaaag
43321 caaagagggg ctggggagc ggcaccaccg gggcctgaac aascaaacca cagacacggt
43381 tacagtttat tcggtcgggc ggagaaacgg ccgaagccac gccactcta ttcgcgtctc
43441 caaaaaacg ggacacttgt ccggagaacc tttaggatgc cagccagggc ggcggtaatc
43501 ataaccacgc ccagcgcaga ggcggccaga aacccgggcg caattgcggc cacgggctgc
```

FIGURE 16
(Continued))

```
43561 gtgtcaaagg ctagcaaatg aatgacggtt ccgtttggaa atagcaacaa ggccgtggac
43621 ggcacgtcgc tcgaaaacac gcttggggcg ccctccgtcg gccggcggc gatttgctgc
43681 tgtgtgttgt ccgtatccac cagcaacaca gacatgacct ccccggccgg ggtgtagcgc
43741 ataaacacgg cccccacgag ccccaggtcg cgctggtttt gggtgcgcac cagccgcttg
43801 gactcgatat cccgggtgga gccttcgcat gtcgcggtga ggtaggttag gaacagtggg
43861 cgtcggacgt cgacgccggt gagcttgtag ccgatcccc gggcagagg ggagtgggtg
43921 acgacgtagc tggcgctgtg ggtgatgggt accaggatcc gtggtcgac gttggcagac
43981 tgccccccgc acgatgtga ggcctcaggg acgaaggcgc ggatcaggc gttgtagtgt
44041 gcccaacgcg tcagggtcga ggcgaggccg tgggtctgct gggccaggac ttcgaccggg
44101 gtctcggatc gggtggcttg agccagcgcg tccaggataa acacgctctc gtctagatca
44161 aagcgcaggg aggccgcgta tggcgaaaag tggtccggaa gccaaaagag ggttttctgg
44221 tggtcggccc gggccagcgc ggtccggagg tggcgttgg tcgctgcggc gacgtcggac
44281 gtacacaggg ccgaggctat cagaaggctc cggcgggcgc gttccgctg caccgccgag
44341 gggacgccag ccaagaacgg ctgccggagg acagccgagg cgtaaaatag cgccggtgg
44401 acgacgggg tggtcagcac gcggcccct agaaactcgg catacagggc gtcgatgaga
44461 tgggctgcgc tgggcgccac tgctcgtac gccgagggc tatccagcac gaaggcagc
44521 tgatagccca gcgcgtgtaa tgccaagctc tgttcgcgct ccagaatctc ggccaccagg
44581 tgctggagcc gagcctctag ctgcaggcgg gccgtgggat ccaagactga cacattaaaa
44641 aacacagaat ccgcggcaca gccgcggcc ccgcgggcgg ccaacccggc aagcgcgcg
44701 gagtgggcca aaaagcctag cagtcggag aggcagaccg cgccgtttgc gtgggcggcg
44761 ttcacgaaag caaaacccga cgtcgcgaga agcccgtta ggcgccagaa gagaggggg
44821 cgcgggcct gctcggcgcc acgtcccc gagaaaact ccggtatgc ccgcgacagg
44881 aactgggcgt agttcgtgcc ctcctccggg tagccgccca cgcggcggag ggcgtccagc
44941 gcggagccgt tgtcggcccg cgtcaggac cctaggacaa agaccccgata ccggggccg
45001 ccccgggcc cgggaagagc cccccggggg ttttcgtccg cgggtcccc gacccgatct
45061 agcgtctggc ccgcggggac caccatcact tccaccggag ggctgtcgtg catggatatc
45121 acgagcccca tgaattcccg cccgtagcgc gcgcgcacca gcgcggcatc gcacccgagc
45181 accagctccc ccgtcgtcca gatgcccacg ggccacgtcg aggccgacgg ggagaaatac
```

```
45241 acgtacctac ctggggatct caacaggccc cgggtggcca accaggtcgt ggacgcgttg
45301 tgcaggtgcg tgatgtccag atccgtcgtc gggtgccgcc gggcccaac cggcggtcgg
45361 ggggcggtg tatcacgcgg ccgctcggg tggctcgccg tcgccacgtt gtctcccgc
45421 gggaacgtca gggcctcggg gtcaggacg gccgaaaacg ttaccaggc ccgggaacgc
45481 agcaacacgg aggcggctgg attgtgcaag agacccttaa ggggggcgac cgaggggga
45541 ggctgggcgg tcggctcgac cgtggtgggg gcggcaggc tcgcgttcgg gggccggccg
45601 agcaggtagg tcttcggat gtaaagcagc tggcggggt ccgcggaaa ctggccgtg
45661 gtgaccaata caaaacaaaa gcgctcctcg taccagcgaa gaaggggcag agatgccgta
45721 gtcaggttta gttcgtccgg cggcgccaga aatccgcgcg gtggttttg ggggtcgggg
45781 gtgtttggca gccacagacg ccggtgttc gtgtcgcgcc agtacatgcg gtccatgccc
45841 aggccatcca aaaccatgg gtctgtctgc tcagtccagt cgtggacctg accacgca
45901 acgcccaaaa taataaccc cacgaaccat aaaccattcc ccatggggga cccgtccct
45961 aaccacggg gcccgtggct atggcaggc ttgccgcccc gacgttggct gcgagccatg
46021 ggccttcacc cgaacttggg gggtggggtg gggaaaagga agaaacgcgg gcgtattggc
46081 cccaatgggg tctcggtggg gtatcgacag agtgccagcc ctgggaccga acccgcgtt
46141 tatgaacaaa cgacccaaca cccgtgcgtt ttattctgtc ttttattgc cgtcatagcg
46201 cgggttactt ccggtattgt ctccttccgt gtttcagtta gcctcccca tctcccggc
46261 aaacgtgcgc gccaggtcgc agatcgtcgg tatggagccg ggggtggtga cgtgggtctg
46321 gaccatcccg gaggtaagtt gcagcagggc gtcccggcag ccggcgggcg attggtcgta
46381 atccaggata aagacgtgca tgggacggag gcgtttggcc aagacgtcca aggcccaggc
46441 aaacacgtta tacaggtcgc cgttggggga cagcaactcg ggggccgaa acagggtaaa
46501 taacgtgtcc ccgatatggg gttgtgggcc ccgctgctc tgggctcgg cacccgggg
46561 cggcacggcc gtccccgaaa gctgtcccca atcctcccgc cacgcccgc cgccctgcag
46621 atccgccacc gtattggcaa gcagctcgta aacgcggcga atcgcggcca acatagccag
46681 gtcaagccgc tcgccgggcc gctggcgttt ggccaggcgg tcgatgtgtc tgtcctccgg
46741 agggccccc aacacgatgt ttgtgccggg caaggtcggc gggatgaggg ccacgaacgc
46801 cagcacggcc tggggggtca tgctgccat aaggtatcgc gcggccggt aacacaggag
46861 ggcggcgatg ggatggcggt cgaagatgag ggtgagggcc ggggcgggg catgtgagct
```

FIGURE 16
(Continued)

```
46921  cccagcctcc  cctcdgatat  gaggagccag  aacggcgtcg  gtcacggcat  aaggcatgcc
46981  cattgttatc  tgggcgcttg  tcattaccac  cgccgagtcc  ccggccgata  tctcacctg
47041  gtcgaggcgg  tgttgtgtgg  tgtagatgtt  cgcgattgtc  tcggaagccc  ccaacaccg
47101  ccagtaagtc  atcggctcgg  gtacgtagac  gatatcgtcg  cgcgaaccca  gggcaccag
47161  cagttgcgtg  gtggtggttt  tccccatccc  gtggggaccg  tctatataaa  ccgcagtag
47221  cgtggcatt  ttctgctcca  ggcggacttc  cgtggttt  tgctgccggc  gagggcaa
47281  cgccgtacgt  cggttgttat  ggccgcgaga  acgccagcc  tggtcgaacg  cagacgcgtg
47341  ttgatggcag  gggtacgaag  ccatacgcgc  ttctacaagg  cgctggccga  agaggtgcgg
47401  gagtttcacg  ccaccaagat  ctgcggcacg  ctgttgacgc  tgttaagcgg  gtcgctgcag
47461  ggtcgctcgg  tattcgagc  cacacgcgtc  accttaatat  gcgaagtgga  cctgggaccg
47521  cgccgcccg  actgcatctg  cgtgttcgaa  ttcgccaatg  acaagacgct  gggcgggtt
47581  tgtgtcatca  tagaactaaa  gacatgcaaa  tatatttctt  ccggggacac  cgccagcaaa
47641  cgccagcaac  gggccacggg  gatgaagcag  ctgcgccact  ccctgaagct  cctgcagtcc
47701  ctcgcgcctc  cgggtgacaa  gatagtgtac  ctgtgcccg  tcctggtgtt  tgtcgccaa
47761  cggacgctcc  gcgtcagccg  cgtgacccgg  ctcgtcccgc  agaaggtctc  cggtaatatc
47821  accgcagtcg  tgcggatgct  ccagagcctg  tccacgtata  cggtcccat  tgagcctagg
47881  acccagcgag  cccgtcgccg  ccgggcggc  gccgccgggg  ggtctgcgag  cagaccgaaa
47941  aggtcacact  ctggggcgcg  cgaccgccc  gagtcagcgg  ccgcagtt  accaccgcc
48001  gactaaaccc  ccgcctccac  ggagggcggg  gggtgctta  agaggatcgc  ggcgtcttc
48061  tgcgtgccg  tggccaccaa  gaccaaaccc  cgagccgcct  ccgaatgaga  gtgtttcgtt
48121  ccttcccct  ccccddgcgt  cagacaaacc  ctaaccaccg  cttaagcggc  cccgcgagg
48181  tccgaagact  catttggatc  cggcgggagc  caccgacaa  cagccccgg  gttttcccac
48241  gccagacgcc  ggtccgctgt  gccatcgcgc  ccctcatcc  caccccccat  cttgtcccca
48301  aataaaacaa  ggtctggtag  ttaggacaac  gaccgcagtt  ctcgtgtgtt  attttcgctc
48361  tccgcctctc  gcagatggac  ccgtactgcc  catttgacgc  tctggacgtc  tgggaacaca
48421  ggcgcttcat  agtcgccgat  tcccgaaact  tcatcaccc  cgagttccc  cgggactttt
48481  ggatgtcgcc  cgtctttaac  ctccccgggg  agacggcggc  ggagcaggtg  gtcgtcctac
48541  aggccagcg  cacagggct  gccgctgccc  tggagaacgc  cgccatgcag  gcggccgagc
```

FIGURE 16
(Continued)

```
48601 tcccogtcga tatcgagcgc cggttaccgc cgatcgaacg gaacgtgcac gagatcgcag
48661 gcgcctgga ggcgctggag acgacggcgg ccgccgccga agaggcggat gccgcgcgcg
48721 gggatgagcc ggcgggtggg ggcgacgggg gggcgccccc gggtctggcc gtcgcggaga
48781 tggaggtcca gatcgtgcgc aacgacccgc cgtacgata cgacaccaac ctcccgtgg
48841 atctgctaca catggtgtac gcgggcgcg gggcgaccgg ctcgtcgggg gtggtgttcg
48901 ggacctggta cgcactatc caggacggca ccatcacgga tttccctg accacgca
48961 gtgccgactt tgggacggc cggatgtcca agacttcat gacggcgtg gtcctgtccc
49021 tgcagtcgtg cggccggctg tatgtgggcc agcgcaacta ttccgcctc gagtgcgccg
49081 tgttgtgtct ctacctgctg taccgaaaca cgcacggggc cgccgacgat agcgacgcg
49141 ctccggtcac gttcggggat ctgctggacc ggctgcccg ctacctggcg tgcctggccg
49201 cggtgatcgg gaccgagggc ggccggccac agtaccgcta ccgcgacgac aagctcccca
49261 agacgcagtt ccggccggc gggggacgct acgaacacgg agcgctggcg tgcacatcg
49321 tgatcgccac gctgatgcac cacggggtgc tcccggcggc ccggggagac gtccccgggg
49381 acgcgagtac ccacgttaac cccgacggcg tggcgcacca cgacgacata aaccgcgcg
49441 ccgccgcgtt cctcagccgg ggccacaacc tattcctgtg ggaggaccag actctgctgc
49501 gggcaaccgc gaacaccata acggccctgg gcgttatcca gcggctcctc gcgaacggca
49561 acgtgtacgc ggaccgcctc aacaacgcc tgcagctggg catgctgatc ccggagccg
49621 tccttcgga ggccatcgcc cgtggggcct ccgggtccga atcggggcc atcaagagcg
49681 gagacaacaa tctggaggcg ctatgtgcca attacgtgct tccgctgtac cgggccgacc
49741 cggcggtcga gctgaccceag ctgtttccg gcctggccgc cctgtgtctt gacgccagg
49801 ccggcggcc ggtcggtcg acgcggcggg tggtggatat gtcatcgggg gccgccagg
49861 cggcgctggt gcgcctcacc gccctggaac tcatcaacg caccgcaca aacccaccc
49921 ccgtgggga ggttatccac gccacgacg cctggcgat ccaatacgaa cagggcttg
49981 gcctgctggc gcagcaggca cgcattggct tgggctccaa caccaagcgt ttctccgcgt
50041 tcaacgttag cagcgactac gacatgttgt acttttatg tctgggttc attccacagt
50101 acctgtcggc ggtttagtgg gtggtgggcg aggggggagg gggcattagg gagaaagaac
50161 aagagcctcc gttgggtttt ctttgtcct gtactcaaaa ggtcatacc cgtaaacggc
50221 gggctccagt ccggcccgg tggttggcgt gaacgcaacg cgggagctg ggttagcgtt
```

FIGURE 16
(Continued)

```
50281 tagtttagca ttcgctctcg gcttttccgcc cgcccgcga ccgttgcgcc tttttttcg
50241 tccacaaaag tctctgtggg tgcgcgcatg cagccgatg cccggaga ccggatggag
50401 gagccctgc ccgacaggc cgtgccatt tacgtgctg ggttttggc cctgtatgac
50461 agcgggact cgggcgagtt ggcattggat ccggatacgg tgcgggggc cctgcctccg
50521 gataaccac tcccgattaa cgtggaccac cgcgctggct gcgaggtggg cggggtgctg
50581 gccgtggtcg acgaccccg cgggccgttt tttgtggggc tgatcgcctg cgtgcagctg
50641 gagcgcgtcc tcgagacggc cgccagcgct gcgattttcg agcgccgcgg gcgccgctc
50701 tcccgggagg agcgcctgtt gtacctgatc accaactacc tgccctcggt ctcctggcc
50761 acaaacgcc tgggggcgca ggcgcacccc gatcgcacgc tgttcgcgca cgtcgcgctg
50821 tgcgcgatcg ggcggcgcct cggcactatc gtcacctacg acacccggtct cgacgccgcc
50881 atgcgccct ttcgccacct gtcgccggcg tctcgcgagg gggcgcggcg actggccgcc
50941 gaggccgaga tcgcgtcgtc cgggcgcacc tgggcgcccg gcgtggaggc gctgacccac
51001 acgctgcttt ccaccgccgt taacaacatg atgctgcggg acgctggag cctggtggcc
51061 gagcggggc ggcaggccgg gatcgccgga cacacctacc tccaggcgag cgaaaaattc
51121 aaaatgtggg gggcggagcc tgtttccgcg ccggcgcgcg ggtataagaa cgggccccg
51181 gagtccacgg acatacccgc cggctcgatc gctgccgcgc cgcagggtga ccggtgccca
51241 atcgtccgtc agccgcgggt cgccttgtcc ccggtactgt cccccatgaa cccgttccg
51301 acatcgggca cccggcccc cgcgccgccc ggcgacgga gctacctgtg gatcccggcc
51361 tccgattaca accagctcgt cgccggccat gccgcgcccc aaccccagcc gcattccgcg
51421 tttggtttcc cggctgcggc gggggccgtg gcctatgggc ctcacggcgc gggtctttcc
51481 cagcattacc ctccccaccgt cgcccatcag tatcccgggg tgtgttctc gggaccagc
51541 ccactcgagg cgcagatagc cgcgttggtg ggggcatag ccgggaccg ccaggcgggc
51601 ggtcagccgg ccgcgggaga ccctggggtc cgggggtcgg gaaagcgtcg ccggtacgag
51661 gcggggccgt cggagtccta ctgcgaccag gacgaaccgg acgcggacta cccgtactac
51721 cccggggagg ctcgaggcgg gcgcgcggg gtcgactctc ggcgcgcggc cgccagtct
51781 cccgggacca acgagaccat cacggcgctg atggggcgg tgacgtcttt gcagcaggaa
51841 ctggcgcaca tgcgggctag gaccagcgcc ccctatggga tgtacacgcc ggtggcgcac
51901 tatcgccctc aggtgggga gccggaacca acaacgaccc acccggcccc ttgtcccccg
```

FIGURE 16
(Continued)

```
61961 gaggccgtgt atcgccccc accacacagc gcccctacg gtcctccca gggtccggcg
62021 tcccatgccc ccactcccc gtatgccca gctgcctgcc cgccaggccc gccaccgccc
62081 ccatgtcctt ccaccagac gcgcgccct ctaccgacgg agcccgcgtt cccccccgcc
62141 gccaccggat cccaactgga ggcatccaac ggggaggccg gggccttgt caacgccagc
62201 agcgcagcac acgtggacgt tgacacggcc cgcgccgcg atttgttcgt ctctcagatg
62261 atggggccc gctgattgc cccggtcttt ggtaccatgg gatgtcttac tgtatatctt
62321 tttaaataaa ccaggtaata ccaagaaga cccattggtg tatgttcttt tttattggg
62381 aggcgcgggt aggcgggtag ctttacaatg caaagcctt cgacgtggag gaaggcgtgg
62441 ggggaatcg gcactgacca aggggtccg ttttgtcacg ggaaaggaaa gaggaaacag
62501 gcgcggaca ccgggggag tttatgtgtt ccctttctt tcttcccaca cacacaaag
62561 gggtaccaaa caaacaaacc aaagatgca catgcggttt aacacccgtg gtttttattt
62621 acaacaaacc cccgtcaca ggtcgtcctc gtcggcgtca ccgtcttgt tgggaacttg
62681 ggtgtagttg gtgttgcggc gcttgcgcat gaccatgtcg gtgaccttgg cgctgagcag
62741 cgcgctcgtg ccttcttct tggccttgtg ttccgtgcgc tccatggcag acaccagggc
62801 catgtaccgt atcatctccc gggcctggc tagcttggcc tgtcaaagt cgccgcctc
62861 ctcgccctcc ccggacgcgt ccgggttggt ggggttcttg agctcttgg tggttagcgg
62921 gtacagggcc ttcatggggt tgctctgcag ccgcatgacg tagcgaaagg cgaagaaggc
62981 cgccgccagg ccggccagga ccaacagacc caggccagc gcccaaagg ggttggacat
63041 gaaggaggac acgcccgaca cggccgatac cacgccgccc acgatgccca tcaccacctt
63101 gccgaccgcg cgccccaggt cgccatccc ctcgaagaac gcgcccaggc ccgcaaacat
63161 ggcggcgttg gcgtcggcgt ggatgaccgt gtcgatgtcg ggaagcgca ggtcgtgcag
63221 ctggttgcgg cgctggaccct ccgtgtagtc cagcaggccg ctgtccttga tctcgtggcg
63281 ggtgtacacc tccagggga caaactcgtg atcctccagc atggtgatgt tgaggtcgat
63341 gaaggtgctg acggtggtga tgtcggcgcg gctcagctgg tggagtacg cgtactcctc
63401 gaagtacacg tagcccccac cgaaggtgaa gtagccggg tgtccacgg tacacggctc
63461 gatcgcatcg cgcgtcagcc gcagctgtt gttctcccca agctgccct cgaccaacgg
63521 gccctggtct tcgtaccgaa agctgaccag ggggcggctg tagcaggccc cgggccgcga
63581 gctgatgcgc atcgagtttt ggacgatcac gttgtccgcg gcgaccggca cgcacgtgga
```

FIGURE 16
(Continued)

```
53641 gacggccatc acgtagccga gaatccgcga gctcaccggc cggcccacgg tggccgaggc
53701 gatggcgttg gggttcagct tgcgggcctc gttccacagg gtcagctcgt gattctgcag
53761 ctcgcaccac gcgatggcaa cgcggcccaa catatcgttg acatggcgct gtatgtggtt
53821 gtacgtaaac tgcagcctgg cgaactcgat ggaggaggtg gtcttgatgc gctccacgga
53881 cgcgttggcg ctggcccgg gcggcgaggg cgtgggttt ggggcttgc ggctctgctc
53941 tcggaggtgt tcccgcacgt acagctccgc gagcgtgttg ctgagaaggg gctggtacgc
54001 gatcagaaag cccccattgg ccaggtagta ctgcggctgg cccaccttga tgtcgtcgc
54061 gttgtacctg cgggcgaaga tgcggtccat ggcgtcgcgg ggtccttgc cgatgcagtc
54121 cccaggtcc acgcgcgaga gcgggtactc ggtcaggttg gtggtgaagg tggtggatat
54181 ggcgtcggag gagaatcgga aggagccgcc gtactcggag cgcagcatct cgtccacctc
54241 ctgccacttg gtcatggtgc agaacgacgg gcgctttggc acccagtccc aggccacggt
54301 gaacttgggg gtcgtgagca ggttccgggt ggtcggcgcc gtggcccggg ccttggtggt
54361 gaggtgcgc gcgtagaagc cgtcgacctg cttgaagcgg tcggcggcgt agctggtgtg
54421 ttcggtgtgc gaccctccc ggtagccgta aaacggggac atgtacacaa agtcgccagt
54481 cgccagcaca aactcgtcgt acgggtacac cgagcgcgcg tccacctcct cgacgatgca
54541 gtttaccgtc gtcccgtacc ggtggaacgc ctccacccgc gaggggttgt acttgaggtc
54601 ggtggtgtgc cagcccggc tcgtgccggt cgcggcgttg gccggttca gctccatgtc
54661 ggtctcgtgg tcgtcccgt gaaacgcggt ggtctccagg ttgttgcgca cgtacttggc
54721 cgtggaccga cagaccccct tggcgttgat cttgtcgatc acctcctcga aggggacggg
54781 ggcgcggtcc tcaaagatcc ccataaactg ggagtagcgg tggccgaacc acacctgcga
54841 aacggtgacg tctttgtagt acatggtgga cttgaacttg taggggcga tgttctcctt
54901 gaagaccacc gcgatgccct ccgtgtagtt ctgacctcg ggcgggtcg ggcagcggcg
54961 cggctgctcg aactgcacca ccgtggcgcc cgtgggggt gggcacacgt aaagtttgc
55021 atcggtgttc tccgccttga tgtcccgcag gtgctcgcgc agggtggcgt ggccgcggc
55081 gacggtcgcg ttgtcgcagg cggggcgcgg cggctttggg ggtttcggtt ttttgttctt
55141 attcggtttc gggtccccg ttggggggc gccaggggcg ggcggcgccg gagtggcagg
55201 gccccgttc gccgcctggg tcgcggccgc gaccccaggc gtgccggggg aactcggagc
55261 cgccgacacc accaggaccc ccagcgtcaa cccaagagc gccdatacga cgaaccaccg
```

FIGURE 16
(Continued)

```
55321 gcgcccagc gcggggcgc cctggcgcat ggcgggacta cggggcccg tcgtgcccc
55381 cgtcaggtag cctggggcg aggtgctgga ggaccgagta gaggatcgag aaaacgtctc
55441 ggtcgtagac cacgaccgac cggggccga tacagccgtc ggggcgctc tcgacgatgg
55501 ccaccagcgg acagtcggag tcgtacgtga gatatacgcc gggcgggtaa cggtaacgac
55561 cttcggaggt cgggcggctg cagtccggc ggcgcaactc gagctcccg cacggtaga
55621 ccgaggcaaa gagtgtggtg gcgataatca gctcgcgaat atatcgccag gcggcgcgct
55681 gagtgggcgt tattccggaa atgccgtcaa aacagtaaaa cctctgaaat tcgctgacgg
55741 cccaatcagc accgagcc ccgccccca tgatgaaccg ggcgagctcc tccttcaggt
55801 gcggcaggag cccacgttc tcgacgctgt aatacagcgc ggtgttgggg ggctggcga
55861 agctgtggt ggagtgatca aagagggcc cgttgacgag ctcgaagaag cgatgggtga
55921 tgctggggag caggccggg tccacctggt gtcgcaggag agacgctcgc atgaatcggt
55981 gcgcgtcgaa cacgcccggc gcgagcggt tgtcgatgac cgtgccgcg cccgccgtca
56041 gggcgcagaa gcgcgcgcgc gcgcaaagc cgttggcgac cgcggcgaac gtcgcgggca
56101 gcacctgcc gtggacgctg accgcagca tcttctgag ctccccgcg tgctcgcgga
56161 cgcagcgcc caggctggct aacgaccgt tcgtcaggcg gtccgcgtac agccgcgtc
56221 gctccagcac gtccgcggcc gcttgcgtgg cgatgtcccc ccacgtctcg ggccctgcc
56281 cccgggcc gcggcgacgg tcttcgtcct cgcccccgc ccgggagct ccaaccccc
56341 gtgcccttc ctctacggcg acacggtccc cgtcgtcgtc ggggccgcg ccgcccttgg
56401 gcggtccgc cgcgcccccc gccccatgc gcgccagcac gcgacgcagc gcctcctcgt
56461 cgcactgttc ggggctgacg aggcgccgca agagcggcgt cgtcaggtgg tggtcgtagc
56521 acgcgggat gagcgcctcg atctgatcgt cgggtgacgt ggcctgaccg ccgattatta
56581 gggcgtccac catatccagc gccgccaggt ggctcccgaa cgcgcgatcg aaatgctccg
56641 cccgccgcc gaacagcgcc agttccacgg ccaccgcggc ggtctcctgc tgcaactcgc
56701 gccgcgccag cgcggtcagg ttgctggcaa acgcgtccat ggtggtctgg ccggcgcgt
56761 cgccggacgc gagccagaat cgcaattcgc tgatggcgta caggccggc gtggtggcct
56821 gaaacacgtc gtgcgcctcc agcagggcgt cggcctcctt gcggaccgag tcattctcgg
56881 gcgacgggtg gggctgcccg tcgcccccg cggtccgggc cagcgcatgg tccaacacgg
56941 agagcgcccg cgcgcggtcg gcgtccgaca gcccggcggc gtggggcagg taccgccgca
```

FIGURE 16
(Continued)

```
57001 gctcgttggc gtccagccgc acctgcgcct gctggtgacg gtggttacag atacggtccg
57061 ccaggcggcg ggcgatcgtc gcccctggt tcgccgtcac acacagttcc tcgaaacaga
57121 ccgcgcaggg gtgggacggg tcgctaagct ccggggggac gataaggccc gaccccaccg
57181 cccccaccat aaactcccga acgcgtccca gcgggcggt ggcgccgcgc gaggggtga
57241 tgaggtggca gtagttagc tgcttagaa agttctcgac gtcgtgcagg aaacacagct
57301 ccatatggac ggtcccgcca tacgtatcca gctgaccg ttggtgatac ggacagggtc
57361 gggcaggcc catggtctcg gtgaaaacg ccgcacgtc tccgcggtc gcgaacgtct
57421 ccaggctgcc caggagccgc tcgccctga gccacgcgta ctatagcagc aactccaggg
57481 tgaccgacag cgggtgaga aaggccccgg cctgggcctc caggccggc ctcagacgac
57541 gccgcagcgc ccgcacctga agcgcgttca gcttcagttg gggagcttc cccgtccga
57601 tgtgggggtc gcaccgccgg agcagctcta tctgaaacac ataggtctgc acctgccga
57661 gcagggctaa caacttttga cgggcacgg tgggctcgga caccggggcg gccatctcgc
57721 ggcgccgatc tgtaccgcgg ccggagtatg cggtggaccg aggcggtccg tacgctaccc
57781 ggcgtctggc tgagcccgg ggtccccctc ttcggggcgg cctcccgcgg gcccgccgac
57841 cggcaagccg ggagtcggcg gcgcgtgcgt ttctgctcta ttcccagaca ccgcggagag
57901 gaatcacggc ccgcccagag atatagacac ggaacacaaa caagcacgga tgtcgtagca
57961 ataatttatt ttacacacat tcccgccc gcctaggtt cccccaccc caacccctca
58021 cagcatatcc aacgtcaggt ctccttttt gtcgggggc cctcccaa acgggtcatc
58081 cccgtggaac gcccgtttgc ggccggcaaa tgccggtccc ggggccccg ggccgccgaa
58141 ccggcgtcgcg ttgtcgtcct cgcagccaaa atccccaaag ttaaacacct cccccggcgtt
58201 gccgagttgg ctgactaggg cctcggcct gtgcgcacc tcaaggccg cgtcgtcga
58261 ccactcgccg ttgccgcgct ccagggcacg cgcggtcagc tccatcatct cctcgcttag
58321 gtactcgtcc tccaggagcg ccagccagtc ctcgatctgc agctgctggg tgcggggccc
58381 caggcttttc acggtcacca cgaacacgct actggcgacg gccgcccgc cctcggagat
58441 aatgcccgg agctgctcga acagcgagct ttcgtgcgct ccgccgccga ggctcgaggc
58501 cgcgcacaca aaccggccc ggggacaggc caggacgaac ttgcgggtgc ggtcaaaaat
58561 aaggagcggg cacgcgtttt tgccgcccat caggctggcc cagttccgg cctgaaacac
58621 acggtcgttg ccggccatgc cgtagtactt gctgatgctc aacccaaca cgaccatggg
```

FIGURE 16
(Continued)

```
58681 gcgcgccgcc atgacgggcc gcagcaggtt gcagctggcg aacatggacg tccacgcgc
58741 cggatgcgcg tccacggcgt ccatcagcga gcggccacg gctccaggc ccgcccgc
58801 ctgcgcggac cacgcggccg cagcctgcac gctggggga cggcgggacc ccgcgatgat
58861 ggccgtaagg gtgttgatga agtacgtcga gtgatcgcag taccgcagaa tctggtttgc
58921 catgtagtac atcgccagct cgctcacgtt gttgggggcc aggttaataa agtttatcgc
58981 gccgtagtcc aggaaaact ttttaatgaa cgcgatggtc tgatgtcct cgcgcgacag
59041 gagccgggcg ggaagctggt tgcgttggag ggccgtccag aaccactgcg ggttcggctg
59101 gttggacccc ggggcttgc cgttggggaa gatggccgcg tggaactgct tcagcagaaa
59161 gcccagcggt ccgaggagga tgtccacgcg cttgtcgggc ttctggtagg cgctctggag
59221 gctggcgacc cgcgccttgg cggctcgga cgcgttggcg ctcgcgcccg cgaacaacac
59281 ggggtcttg acgcgcagct ccttgggaaa ccccaggtc acgcgggcaa cgtcgccctc
59341 gaagctgctc tcggcggggg ccgtctggcc ggccgttagg ctgggggcgc agatagccgc
59401 cccctccgag agccgcgaccg tcagcgtttt ggccgacaga aaccgttgt taaacatgtc
59461 catcacgcgc cgcagcagca ccggttggaa ttgattgcga aagttgcgcc cctcgacaga
59521 ctgcccggcg aacacccgt ggcactggct cagggccagg tcctgataca cggcgaggtt
59581 ggatcgccgc ccgagaagct gaagcagggg gcatggcccg cacgcgtacg ggtccagcgt
59641 caggacatg gcgtggttgg cctcgccag accgtcgcga aacttgaagt tcctcccctc
59701 caccaggttg cgcatcagct gtccacctc gcggtccacg acctgcatga cgttgttcac
59761 cacgtatgc agggcctcgc ggttggtgat gatggtctcc agccgccca tggccgtggg
59821 gaccgcctgg tccacgtact gcagggctct gagttcggcc atgacgcgct cggtcgccgc
59881 gccgtacgtc tcctgcatga tggtccggga ggtctggat ccgtccgcgc gttcagggc
59941 cgagaaggcg gcgtagttc ccagcacgtc gcagtgctg tacatgctgt tcatggtccc
60001 gaagacgccg atggctccgc gggcgcgct ggcgaacttg ggatggcgcg ccggaggcg
60061 catgagcgtc gtgtgtacgc aggcgtggcg cgtgtcgaag gtgcacaggt tgcagggcac
60121 gtaggtctgg ttggagtccg cgacgtatcg aaacacgtcc atctcctggc gccgacgat
60181 cacgcgccg tgcagcgct ccagtaaaa cagcatcttg gcagcagcg ccgggggaaaa
60241 cccacacagc atggccaggt gctcgccggc aaattcctgg gttccgccga cgagggcgc
60301 ggtgggacga ccctcgaacc cgggcaccac gtgtccctcg cggtccacct gtgggttggc
```

FIGURE 16
(Continued)

```
60361 cgccacgtgg gtcccggca cgaggaagaa gcggtaaaag gagggtttgc tgtggtcctt
60421 tgggtccgcc ggaccggcgt cgtccacctc ggtgagatgg agggccgagt tggtgctaaa
60481 taccatggcc cccacgagtc ccgcggcgcg cgccaggtac gccccgacgg cgttggcgcg
60541 ggccgcggcc gtgtcctggc cctcgcacag cggccatgcg gagatgtgg tgggcggctc
60601 gtcgaagacg gccatcgaca cgatagactc gagggccagg gcggcgtctc cggccatgac
60661 ggaggccagg cgctgttcga accgcccgc cgggcccttg ccgccgccgt cgcgcccacc
60721 ccgcggggtc ttaccctggc tggcttcgaa ggccgtgaac gtaatgtcgg cggggaggggc
60781 ggcgcctcg tggttttcgt caaacgccag gtgggcggcc gcgaggcca cggcgtccac
60841 gtttcggcat cgcagtgcca cggcggcggg tcccacgacc ggctcgaaca ggaggcggtt
60901 gaggaggcgg ttaaaaacg gaagcgggta ggtaaattc tccccgatcg atcggtggtt
60961 ggcgttgaac ggctcggcga tgacccggct aaaatccggc atgaacagct gcaacggata
61021 cacggtatg cggtgcacct ccgcaccgcc tatggttacc ttgtccgagc ctccaggtg
61081 cagaaggtg ttgttgatgc acacggcctc cttgaagccc tggtaacga ccagatacag
61141 gagggcgcgg tccggtcca ggccgaggcg ctcacaagc gctccccg tcgtctcgtg
61201 tttgaggtcg ccggccggg gggtgtagtc cgaaaagcca aaatggcggc gtgccgctc
61261 gcagagtcgc gtcaggttg gggcctgggt gttggggtcc aggtgccggc cgccgtgaaa
61321 gacgtacacg gacgagctgt agtgcgatgg cgtcagttc agggacaccg cggtaccccc
61381 gagcccgtc gtgcgagaac ccacgaccac ggtacgttg gctcaaagc cgctctccac
61441 ggtcaggccc acgaccaggg gcgccacggc gacgtcggca tgccgctgc gcgccgacag
61501 taacgccaga agtcgatgc cttcggatgg acacgcgcga gcgtacacgt atcccagggg
61561 cccggggggg acttgatgg tggttgccgt cttgggcttt gtctccatgt catcctggca
61621 atcggtccgc aaacggaggt aatccggca cgacgagga cgccgacga ggtatgcctc
61681 ccgagcgtca aatccgggg ggggcggcga cggtcaaggg gagggtggga gaccggggtt
61741 ggggaatgaa tccctaccct tcacgacaa ccccgggta accacgggt gccgatgaac
61801 ccggcggct ggcaacgcgg ggtcctgcg agaggcacag atgcttacgg tcaggtgctc
61861 cgggccgggt gcgtctgata tcgcgttggt atatgtacac tttacctggg ggcgtgccgg
61921 accgcaccag ccctccac accccgcgcg tcatcagccg gtgggcgnnn nnnnnnnnn
61981 nnnnnnnnn nnnnnnnnn nnnnnnnnn nnnnnnnnn nnnnnnnnn nnnnnnnnn
```

FIGURE 16
(Continued)

```
62041 nnnnnnnnn nnnnnnnnn nnnnnnnnt tttataata gcggccacgc ccaccggcta
62101 cgtcacgtc ctgtcggccg ccggcggtcc ataagccggg ccggccggc cgacgcgaat
62161 aaaccgggcc gccggccggg gcgccgcgca gcagctcgcc gcccggatcc gccagacaaa
62221 caaggcccct gcacatgccg gccggcgga gctggggggt ccggtaattt tgccatccca
62281 ccaagcggg ttttggggtt tttcctcttc ccacctcccc acctccccc tctttagggg
62341 ttcgggtggg aacaaccgcg atgttttccg gtggcggcgg ccgctgtcc cccggaggaa
62401 agtcggcggc caggcggcg tccgggtttt ttgcgcccgc cggccctcgc ggagccggcc
62461 ggggaccccc gcttgtttg aggcaaaact tttacaaccc ctacctcgcc ccagtcggga
62521 cgcaacagaa gccgaccggg ccaacccagc gccatacgta ctatagcgaa tgcgatgaat
62581 ttcgattcat cgcccgcgg gtgctggacg aggatgcccc ccggagaag cgcgccgggg
62641 tgcacgacgg tcacctcaag cgcgccccca aggtgtactg cgggggggac gagcgcgacg
62701 tcctccgcgt cgggtcggc ggcttatggc cgcggcgtc gcgcctgtgg ggcggcgtgg
62761 accacgccc ggcgggttc gaccccaccg tcaccgtctt tcacgtgtat gacatcctgg
62821 agaacgtgga gcacgcgtac ggcatgcgcg cggccagtt ccacgcgcgg tttatggacg
62881 ccatcacacc gacgggacc gtcatcacgc tcctgggcct gactccggaa ggccaccggg
62941 tggccgttca cgtttacggc acgcggcagt acttttacat gaacaaggag gaggttgaca
63001 ggcacctaca atgccgcgcc ccacgagatc tctgcgagcg catggcgcg gccctgcgcg
63061 agtcccgggg cgcgtcgttc cgggcatct ccgcggacca cttcgaggcg gaggtggtgg
63121 agcgcaccga cgtgtactac tacgagacgc gccccgctct gttttaccgc gtctacgtcc
63181 gaagcgggcg cgtgctgtcg tacctgtgcg acaacttctg cccggccatc aagaagtacg
63241 agggtgggt cgacgccacc acccggttca tcctggacaa cccgggttc gtcaccttcg
63301 gctggtaccg tctcaaaccg ggccggaaca acacgctagc ccagccgcgg gcccgatgg
63361 ccttcgggac atccagcgat gtcgagttta actgtacggc ggacaacctg gccatcgagg
63421 ggggcatgag cgacctaccg gcatacaagc tcatgtgctt cgatatcgaa tgcaaggcgg
63481 gggggagga cgagctggcc tttccggtgg ccgggcaccc ggaggacctg gtcatccaga
63541 tatcctgtct gctctacgac ctgtccacca ccgcctgga gcacgtcctc ctgttttcgc
63601 tcggttcctg cgacctcccc gaatccacc tgaacgagct gggggccagg ggcctgccca
63661 cgccgtggt tctggaattc gacacgcgaat tcgagatgct gttggccttc atgaccttg
```

FIGURE 16
(Continued)

```
63721 tgaaacagta cggaccgag ttcgtgaccg ggtacaacat catcaacttc gactggcct
63781 tcttgctggc caagctgacg gacatttaca aggtccct ggacgggtac ggccgcatga
63841 acggccgggg cgtgtttcgc gtgtgggaca taggccagag ccacttccag aagcgcagca
63901 agataaaggt gaacggcatg tgaacatcg acatgtacgg gattataacc gacaagatca
63961 agctctcgag ctacaagctc aagccgtgg ccgaagccgt cctgaaggac aagaagaagg
64021 acctgagcta tcgcgacatc ccgcctact acgccgcgg gccgcgcaa cgcgggtga
64081 tcgggagta ctgcatacag gattccctgc tgctgggcca gctgtttttt aagttttgc
64141 cccatctgga gctctcggcc gtcgcgcgct tggcgggtat taacatcacc cgcaccatct
64201 acgacggcca gcagatccgc gtctttacgt gcctgctgcg cctggccgac cagaagggct
64261 ttattctgcc ggacaccccag gggcgattta ggggcgccgg gggggaggcg ccaagcgtc
64321 cggccgcagc ccgggaggac gaggagcggc cagaggagga ggggaggac gagaacgaac
64381 gcgaggaggg cgggggcgag cgggagccgg agggcgcgcg ggagaccgcc ggccggcacg
64441 tggggtaccc gggggccagg gtccttgacc ccacttccgg gtttcacgtg aacccgtgg
64501 tggtgttcga cttgccagc ctgtacccca gcatcatcca ggcccacaac ctgtgcttca
64561 gcacgctctc cctgagggct gacgcagtgg cgcacctgga ggcgggcaag gactacctgg
64621 agatcgagat gggggggcga cggctgttct tcgtcaaggc tcacgtgcga gagagcctcc
64681 tcagcatcct cctgcgggac tggctcgcca tgcgaaagca gatccgctcg cggattcccc
64741 agagcagccc cgaggaggcc gtgctactgg acaagcagca ggccgccatc aaggtcgtgt
64801 gtaactcggt gtacgggttc acgggagtgc agcacggact cctgccgtgc ctgcatgttg
64861 ccgacggt gacgaccatc ggccgcgaga tgctgctcgc gacccgcgag tacgtccacg
64921 cgcgctgggc ggccttcgaa cagctcctgg ccgattccc ggaggcggcc gacatgcggg
64981 ccccgggcc ctattccatg cgcatcatct acgggacac ggactccata tttgtgctgt
65041 gcgcgggcct cacggccgcc gggctgacgg ccatgggcga caagatggcg agccacatct
65101 cggcgcgct gtttctgccc cccatcaaac tcgagtgcga aaagacgttc accaagctgc
65161 tgctgatcgc caagaaaag tacatcgcg tcatctaccg gggtaagatg ctcatcaagg
65221 gcgtggatct ggtgcgcaaa aacaactgcg cgtttatcaa ccgcacctcc agggcctgg
65281 tcgacctgct gttttacgac gatacccgtat ccggagcggc cgccgcgtta gccgagccc
65341 ccgcagagga gtggctggcg cgacccctgc ccgagggact gcaggcgttc ggggccgtcc
```

FIGURE 16
(Continued)

```
65401 tcgtagacgc ccatcggcgc atcacogacc cggagaggga catccaggac tttgtcctca
65461 ccgccgaact gagcagacac ccgcgcgcgt acaccaacaa gcgcctggcc cacctgacgg
65521 tgtattacaa gctcatggcc cgccgcgcgc aggtcccgtc catcaaggac cggatcccgt
65581 acgtgatcgt ggcccagacc cgcgaggtag aggagacggt cgcgcggctg gccgcctcc
65641 gcgagctaga cgccgccgcc ccaggggacg agcccgccc ccccgcggcc ctgcctccc
65701 cggccaagcg cccccggag acgccgtcgc atgccgaccc ccgggaggc ggtccaagc
65761 cccgcaagct gctggtgtcc gagctggcg aggatcccgc atacgccatt gccacggcg
65821 tcgcctgaa caggactat tacttctccc acctgtggg ggcggcgtgc gtgacattca
65881 aggccctgtt tggaataac gccaagatca ccgagagtct gttaaaaagg tttattcccg
65941 aagtgtggca ccccccggac gacgtggccg cgcggctccg ggccgcaggg tcggggcgg
66001 tgggtgccgg cgctacggcg gaggaaactc gtcgaatgtt gcatagagcc tttgatactc
66061 tagcatgagc ccccgtcga agctgatgtc cctcatttta caataaatgt ctgcggccga
66121 cacggtcgga atctccgcgt ccgtgggttt ctctgcgttg cgccggacca cgagcacaaa
66181 cgtgctctgc cacacgtggg cgacgaacct gtaccccggg caagcggtga catccggtc
66241 tatgagccgg tagtgcaggt gggcggacgt gccgggaaag atgacgtaca gcatgtggcc
66301 ccgtaagtg gggtccgggt aaaacaacag ccgcgggtcg caogcccgc ctccgcgcag
66361 gatcgtgtgg acgaaaaaaa gctcgggttg gcaagaatc ccggccaaga ggtcctggag
66421 ggggcgttg tgcggtcgg ccaacacgac caaggaggcc aggaaggcgc gatgctcgaa
66481 tatcgtgttg atctgctgca cgaaggccag gattagggcc tcgcggctgg tggcggcaa
66541 ccgccgtct ccgcgttgc acgcgggaca gcaaccccg atgcctaggt agtagcccat
66601 ccggagagg gtcaggcagt tgtcggccaa ggtctggtcc agacagaagg gcagcgacac
66661 gggagtggtc ttcaccaggg gcaccgagag cgagcgcacg atgcgatct cctcggaggg
66721 cgtctgggcg agggcggcga aaggcccg atagcgctgg cgctcgtgta aacacagctc
66781 ctgtttgcgg gcgtgaggcg gcaggtctt ccgggaggcc cgacgcacca cgccagagt
66841 cccgccggcc gcagaggagc gcgaccgccg gcgctccttg ccgtgatagg gcccgggccg
66901 ggagccgcgg cgatggggt cggtatcata cataggtaca caggtgtgc tccagggaca
66961 ggagcgagat cgagtggcgt ctaagcagcg cgcccgcctc acggacaaat gtggcgagcg
67021 cggtgggctt tggtacaaat acctgatacg tcttgaaggt gtagatgagg gcacgcaacg
```

FIGURE 16
(Continued)

```
67081 ctatgcagac acgcccctcg aactcgttcc cgcaggcag ctggccttg tgagcagca
67141 gctcgtcggg atgggtggcg ggggatggc cgaacagaac ccaggggtca acctccatct
67201 ccgtgatggc gcacatgggg tcacagaaca tgtgcttaaa gatggcctcg ggccccgcgg
67261 cccgcagcag gctcacaaac cggcctccgt cccgggctg cgtctggggg tccgcgtcga
67321 gctggtcgac gacgggtacg atacagtcga agaggctcgt gttgttttcc gagtagcgga
67381 ccacggaggc ccggagtctg cgcagggca gccagtaagc ccgcaccagt aacaggttac
67441 acagcaggca ttctccgcg gtgcgccgc gcccccggcc gtgtttcagc acggtggca
67501 tcagagggcc caggtcgagg tcgggctggg catcggggttc ggtaaactgc gcaaagcgcg
67561 gagccacgtc gcgcgtgcgt gcccgcgat gcgcttccca ggactggcgg accgtggcgc
67621 gacgggcctc cgcggcagcg cgcagctggg gccccgactc ccagacggcg ggggtgccgg
67681 cgaggagcag caggaccaga tccgcgtacg cccacgtatc cggcgactcc tccggctcgc
67741 ggtcccggc gaccgtctcg aattccdcgt tgcagagcgc ggcgcgcgta cagcagctgt
67801 ccccgccccc gcgccgaccc tccgtgcagt ccaggagacg ggcgcaatcc ttccagttca
67861 tcagtcaggt ggtaagcgac ggctgcgtgc cggataccgc cgccgacccc gcccctcct
67921 cgccccgga ggccaaggtt acgatgaggg cccgggtggc agactgcgcc aggaacgagt
67981 agttggagta ctgcaccttg gcggctccg gggagggcga gggcttgggt tgcttctggg
68041 catgccgcc gggcaccccg ccgtcggtac ggaagcagca gtggagaaaa aagtgccggt
68101 ggatgtcgtt tatggtgagg gcaaagcgtg cgaaggagcc gaccagggtc gccttcttgg
68161 tgcgcagaaa gtggcggtcc atgacgtaca caaactcgaa cgcggccacg aagatgctag
68221 cggcgcagtg ggcgcccc aggcatttgg cacagagaaa cgcgtaatcg gccacccact
68281 gaggcgagag gcggtaggtt tgcttgtaca gctcgatggt gggcagacc agacagggcc
68341 ggtccagcgc gaaggtgtcg atggccgcg cggaaaaggg cccggtgtcc aaaagcccct
68401 cccacaggg atccggggc gggttgcggg gtcctccgcg cccgcccgaa ccccctccgt
68461 cgccgcccc ccgcgggcc cttgagggg cggtgaccac gtcggcggcg acgtcctcgt
68521 cgagcgtacc gacgggcggc acactatca cgtgactggc agtcaggagc tcggcagga
68581 gagcctcgtt aagagccagg aggctgggat cgaaggccac atacgcgcg tcgaacgccc
68641 ccgccttcca gctgctgccg ggggactctt cgcacaccgc gacgctcgcc aggacccgg
68701 ggggcgaagt tgccatggct gggcgggagg ggcgcagcg ccagcgaact ttacgggaca
```

```
68761 caatcccga ctgagcgctg cggtcccaga ccctggagag tctagacgcg cgctacgtct
68821 cgcgagacgg cgcgcatgac gcggccgtct ggttcgagga tatgacccc gccgagctgg
68881 aggttgtctt cccgactacg gacgccaagc taaactacct gtcgcggacg cagcggctgg
68941 cctccctcct gacgtacgcc cggcctataa aagcgcccga cgacgcgtc gcccgcaga
69001 cccggacac cgcgtgtgtg caggcgagc tgctcgcccg caagcgggaa agattcgcgg
69061 cggtcattaa ccggttcatg gacctgcacc agattctgcg gggctgacgc gcgcgctgtt
69121 gggcgggacg gttcgcgaac ccttggtgg gtttacgcgg ggacgcacgc tcccatcgcg
69181 ggcgccatgg cgggactggg caagccctac accggccacc caggtgacgc cttcgagggt
69241 ctcgttcagc gaattcgct tatcgtccca tctacgttgc gggcggga cggggaggcg
69301 ggcccctact ctccgtccag cctccctcc aggtgcgcct ttcagtttca tggccatgac
69361 gggtccgacg agtcgtttcc catcgagtat gtactgcggc ttatgaacga ctgggccgag
69421 gtccgtgca acccttacct gcgatacag aacaccggcg tgtcggtgct gtttcagggg
69481 tttttcatc gcccacacaa cgcccccggg ggcgcgatta cgccagagcg gaccaatgtg
69541 atcctggggt ctaccgagac gacggggttg tccctcggcg acctggacac catcaagggg
69601 cggctcggcc tggatgcccg gcgatgatg gccagcatgt ggatcagctg ctttgtgcgc
69661 atgcccgcg tgcagctcgc gtttcggttc atgggcccg aagatgccgg acggacgaga
69721 cggatcctgt gccgcgcgc cgagcaggct attacccgtc gccgcgaac ccggcggtcc
69781 cgggaggcgt acggggccga ggccgggctg gggtggccg gaacgggttt ccgggccagg
69841 gggacggtt ttggcccgct cccttgtta acccaagggc cctcccgccc gtggcaccag
69901 gccctgcggg gtcttaagca cctacggatt ggccccccg cgctcgtttt ggcggcggga
69961 ctcgtcctgg gggcgctat ttggtgggtg gttggtgctg gcggcgcct ataaaaaggg
70021 acgcacgcc gcctaatcg ccagtgcgtt ccggacgcct tcgcccaca cagcctccc
70081 gaccgacacc cccatatcgc tcccgacct ccggtcccga tggccgtccc gcaatttcac
70141 cggcccagca ccgttaccac cgatagcgtc cgggcgcttg gcatgcgcgg gctcgtcttg
70201 gccaccaata actctcagtt tatcatggat aacaaccacc cacacccca gggcacccaa
70261 ggggccgtgc gggagtttct ccgcggtcag gcggcggcac tgacggacct tggtctggcc
70321 cacgcaaaca agacgtttac cccgcagcct atgttcgcgg gcgacgcacc ggccgcctgg
70381 ttgcggaccg cgtttggcct gggcgcaac tattcacctt ttgtcgttcg agaaccttcg
```

FIGURE 16
(Continued)

```
70441 acgcccggga cccsgtgagg cccagggagt tccttctggg gtgttttaat caataaaga
70501 ccacaccaac gcacgagcct tgcgtttaat gtcgtgttta ttcaaggag tgggataggg
70561 ttcgacggtt cgaaacttaa cacaccaaat aatcgagcgc gtctagccca gtaacatgcg
70621 cacgtgatgt aggctggtca gcacggcgtc gctgtgatga agcagcgcc ggggggtccg
70681 ctgtaactgc tgttgtaggc ggtaacaggc gggatcagc accgcaggg cgtacgacc
70741 ggtgcgttgc acgtagcgtc gcgacagaac tgcgtttgcc gatacggcg ggggcgaa
70801 ttgtaagcgc gtcacctctt gggagtcatc ggcgtataac gcactgaatg gttcgttgt
70861 tatggggag tgtgttccc cagggagtgg gtcgagcgcc tcggcctgg aatccgagag
70921 gaacaacgag gtggcgtcgg agtcttcgtc gtcagagaca tacagggtct gaagcagcga
70981 cacgggcgtg gggtagcgt cgatgtgtag cgcgaggag gatgcccacg aagacaccc
71041 agacaaggag ctgccgtgc gtggatttgt ggaagacgcg gaagccggga cggatgggcg
71101 gttttgcggt gcccggaacc gaaccgccgg atactcccg ggtgctacat gcccgttttg
71161 gggctgggt tggggctggg gcgcggacag gcggctgacg gtcaaatgcc cccggggcg
71221 cgcagatgtg gcgggcgtgg ccaccggctg ccgtgtagtg gggcggcggg aaaccgggcc
71281 tccgggcgta acaccgcct acagcgtcaa gtatgtgggg ggcgggcctg acgtcggggg
71341 cggggtgacg ggttggaccg cgggaggcgg gggagaggga cctgcgggag aggatgaggt
71401 cggctcggcc ggttgcggc ctaaaacagg ggccgtgggg tcggcggggt cccagggtga
71461 agggagggat tccgcgatt cggacagcga cgcgacagcg gggcgcgtaa ggcgccgctg
71521 cggccgcct agggaaccc tggggggggt tggcgcggga cccgaggtta gcgggggcg
71581 gcggtttcg cccccgggca aaaccgtgcc ggttgcgacc gggggcggaa cgggatcgat
71641 agggagagcg ggagaagcct ggccggcgga ctgggaccg agcgggaggg gcaccaga
71701 caccaaagcg tgggcgctg gctctggggg tttgggaggg gcggggggc gcgcgaaatc
71761 ggtaaccggg gcgacgcgtgt cggggagggc aggcggccgc caaccctggg tggtcgcgga
71821 agcctgggtg gcgcgcgaca gggagcgtgc ccggcggtgt cggcgcgcgc gcgacccgga
71881 cgaagaagcg gcagaagcgc gggaggaggc gggggggcgg gggcggtgg catcgggggg
71941 cgctgggaa ctttgggggg acggcaagcg ccggacgtcg tcgcggggc ccacgggcgc
72001 cggccgcgtg ctttcggccg ggacgcccgg tcgtgcttcg cgagccgtga ctgccggccc
72061 agggggccgc ggtgcacact gggatgtggg gacggactga tcggcggtgg gcgaaagggg
```

```
72121 gtccggggca aggagggcg cggggccgc ggagtcgtca gacgcgaget cctccaggcc
72181 gtgaatccat gcccacatgc gaggagggac gggctcgccg gggtggcgt cggtgaatag
72241 cgtggggcc aggcttccgg gccccaacga gccctccgtc ccaacaaggt ccgccggcc
72301 ggggtcggg ttcggaccg aggggtctg gtgtcgggg gcgcgtggt acacggatg
72361 cccggaat agctccccg acaggagga ggcgtcgaac ggccgccga ggatagctcg
72421 tgcgaggaag gggtcctagt cggtggcgct ggcggcgagg acgtcctcgc cgccgccac
72481 aaacgggagc tcctcgtgg cctcgctgcc aacaaaccgc acgtcggggg ggccggggg
72541 tccgggtttt cccacaacac cgcgacgggg gtcatggaga tgtccacgag cacctgacac
72601 ggcgggcccc gggcgagggg ccgctcggcg atgagcgcgg acaggcgcgg gagctgtgcc
72661 gccagacacg cgttttcgat cgggttcagg tcggcgtgca ggaggcggac ggcccacgtc
72721 tcgatgtcgg acgacacggc atcgcgcaag gggcgtccg gcccgcgagc cgtgagtca
72784 aacagcgtga ggcacagctc cagctccgac tcgcgggaaa aggccgtggt gtcgggagc
72841 gccacgacga cgggcgcgcc caggagcact gccgccagca ccaggtccat ggccgtaacg
72901 cgcgccgcgg gggtgcggtg ggtggcggcg gccggcacgg cgacgtgctg gcccgtgggc
72961 cggtagaggg cgttgggggg agcggggggt gacgcctcgc gcccccccga ggggctcagc
73021 gtctgcccag attccagacg cgcggtcaga agggcgtcga aactgtcata ctctgtgtag
73081 tcgtccggaa acatgcaggt ccaaagagcg gccagcgcgg tgcttgggag acacatgcgc
73141 ccgaggacgc tcaccgccgc cagcgcctgg gcgggactca gctttcccag cgcggcgccg
73201 cgctcggttc ccagctcggg gaccgagcgc cagggcgcca ggggtcggt tcggacaac
73261 ttgccgcggc gccagtctgc cagccgcgtg ccgaacatga ggccccgggt cggagggcct
73321 ccggccgaaa acgctggcag cacgcggatg cgggcgtctg gatgcgggt caggcgctgc
73381 acgaatagca tggaatctgc tgcgttctga aacgcacggg ggagggtgag atgcatgtac
73441 tcgtgttggc ggaccagatc caggcgccaa aaggtgtaaa tgtgttccgg ggagctggcc
73501 accagcgcca ccagcacgtc gttctcgtta aaggaaacgc ggtgcctagt ggagctctgg
73561 ggtccgagcg gcggccaagg ggcgcgcg tcacccccc attccagctg ggccagcga
73621 caccaaact cgcgcgtgag agtggtcgcg acgagggcga cgtagagctc ggccgccgca
73681 tccatcgagg ccccccatct cgcctggcgg tggcgcacaa agcgtccgaa gagctgaaag
73741 ttggcggcct gggcgtcgc gagggccagc tgaagccggt tgatgacggt gaggacgtac
```

FIGURE 16
(Continued)

```
73801 atggccgtga cggtcgaggc cgactccagg gtgtccgtcg gaagcggggg gcgaatgcat
73861 gccgcctcgg gacacatcag cagcgcgccg agcttgtcgg tcacggccgg gaagcagagc
73921 gcgtactgca gtggcgttcc atccgggacc aaaaagctgg gggcgaacgg ccgatccagc
73981 gtactggtgg cctcgcgcag caccaggggc ccgggcctc cgctcactcg caggtacgcc
74041 tcgcccggc ggcgcagcat ctgcgggtcg gctcttggc cgggtggggc ggacgccgg
74101 gcgcgggcgt ctagggcgcg aagatccacg agcagggcg cgggcgcggc ggccgcgccc
74161 gcgccgtct ggcctgtggc cttggcgtac gcgctatata agcccatgcg gcgttggatg
74221 agctcccgcg cgccccggaa ctcctccatc gccatgggg ccaggtcccc ggccaccgcg
74281 tcgaattccg ccaacaggcc ccccagggta tcaaagttca tctcccagga caccttggc
74341 accacctcgt ccgcagccg ggcgctcagg tcggcgtgtt gggccacgcg cccccgagc
74401 tcctccacgg cccccggcccg ctcggcgctc ttggcgccca ggacgccctg gtacttggcg
74481 ggaaggcgct cgtagtcccg ctgggctcgc agccccgaca cagtgttggt ggtgtcctgc
74521 agggcgcgaa gctgctcgca tgccgcgcga aatccctcgg gcgatttcca ggccccccg
74581 cgaacgcggc cgaagcgacc ccatccctcg tcccactccg cctcggcctc ctcgagagac
74641 ctccgcaggg cctcgacgcg gcgacgggtg tcgaagacg cctgcaggcg agcgccctgt
74701 cgcgtcagga ggcccggcc gtcgctgctg gccgcgatta gcgggtgcgt ctcaaaggta
74761 cgctggcat gttccaacca ggcgaccgcc tgcacgtcga gctcgcgcg cttctccgtc
74821 tggtccaaca gaattcgac ctgaccgcg atctcctccg ccgagcgcg ctggtccagc
74881 gtcttggcca cggtcgccgg gacggcgacc accttcagca gggtcttcag attggccaga
74941 cctcggcct cgagctggc ccggcgctcg cgcgcggcca gcacatcccg cagccccgcc
75001 gtgaccgct cggtggcttc ggcgcgctga tgtttggcgc gcaccacggc gtccttggta
75061 tcggcaggt cctgtcgggt cacgaatgcg acgtagtcgg agtacgcgt gtccttcacg
75121 gggtctggt ccacgcgctt cagcgccgcc acgcacgcca ccagcgcgtc ctcgctcggg
75181 cagggcaggg tgacccctgc ccggacaagc tggcggccg ccgccgggtc gttgcgcacc
75241 ggggatatct cctccgggga ggcggcaggt tcagcgcca gcttccgat cgcgcgccg
75301 gcgtcggccc ggagggcgtc caggcgatcg cggatatcca agtactcggc gtagccttt
75361 tcaaaaaacg gcacgtactg gcgcagggcc ggcacgcccc ccaagtcttc cgacaggtgt
75421 agtacggcct cgtggtagtc gataaaccag tcgttcgcct gggccgctc cagcagccc
```

FIGURE 16
(Continued)

```
75481 cccgcgagcc gcagaagccg cgccaggggc tcggtgtcca ccgaaacat gtcggcgtac
75541 gtgtcggccg cggcccaaa ggccgcgctc cagtcgatgc ggtgaatggc tgcgagcggg
75601 gggagcatgg ggtggcgctg gttctcgggg gtgtatggt taaacgcaag ggccgtctcc
75661 agggcaaggg tcacggcttt ggcgttggtt cccagcgcct gtcggccg ctttcggaag
75721 tcccgggggt tgtagccgtg cgtgcccgcc agcgcctgca ggcgacggag ctcgaccacg
75781 tcaaactcgg cactgcttc cacgcggtcc agcacggcct ccacgtcggc ggcccagcgc
75841 tcgtggctac tgcggcgcg ctgggcgcc atcttctctc tgaggtcggc ggtggcggcc
75901 tcaagttcgt cggcgcggcg tcgcgtggag ccgatgacct ttccagctc atgcagggcg
75961 cgccgctgg gggagtggtc ccaggccgtc ccttcggcgt gcaacaggcc cccgaacctg
76021 ccctcgtggc ccgcgaggct ttcccgcgcg ccggtggtcg cgcgcgtgc ggcttggatc
76081 agggaggcat gctctccctt cggttggttg gcggccggc gcacctggac gacaaggtcg
76141 gcggcagccg accctaaggt cgtgagctgg gcgatggccc ccgcgcgtc cagggccaac
76201 cgagtcgcct tgacgtatcc cgcggcgctg tcggccatgg ccgctaggaa ggccaggggg
76261 gaggccggt cgctggcggc cgcgcccagg gccgtcaccg cgtcgaccag gacgcggtgc
76321 gcccgcacgg ccgcatccac cgtcgacgcg gggtctgccg tcgcgacggc ggcgctgccg
76381 gcgttgatgg cgttcgagac ggcgtgggct atgatcgggg cgtgatcggc gaagaactgc
76441 aagagaaacg gagtctcggg ggcgtcgcg aacaggttct tcagcaccac cacgaagctg
76501 ggatgcaagc cggacagagc cgtcgccgtg tcggagtcg ggtgctccag ggcatctcgg
76561 tactgcccca gcagccccca catgtccgcc cgcagcgccg ccgtaacctc aggggcgcc
76621 cccgaacgg cctcgggag gtccgaccag cccgccggca gggaggcccg cagggtcgcc
76681 aggacggccg gacaggcctt tagccccaca aagtcaggga ggggcgcag gaccccctgg
76741 agttgtgca agaacttctc ccgggcgtcg cgggccacct tgcccgctc ccgcgtccc
76801 tcgagcattg cctccaggga gcgcgcgcgc tcccgcaaac ggacacgcgc atcggggcg
76861 agctctgccg tcagcttggc ggcatccatg gccgcgcct gccgcagcgc ttcctcggcc
76921 atgcgcgtgg cctctggaga cagcacgccg tgtcgggt agggcgacg gcgggcgca
76981 ggaacaaagg ccgcgtcgct gtccagctgc tggccaggg ccgcatctag ggcgtcgaag
77041 cgccgcagct cggccagacc cgagctgcgg cgcgcctgct ggtcgttaat gtcgcggatg
77101 ctgcgcgcca gctcgtccag cggcttgcgt tctatcagcc cttggttggc ggcgtccgtc
```

FIGURE 16
(Continued)

```
77161 aggacggaga gcaggccgc caggtcctcg ggggcgtcca gcgtctggcc ccgctgtatc
77221 agatcccgca acaggatggc cgtgggcctg gtcgcgatcg ggggcgggc gggaatggcg
77281 gcgcgctgcg cgatgtcccg cgtgtgctgg tcgaagacag gcagggactc gagcagctgg
77341 accacgggca cgacggcggc cgaagccacg tgaaaccggc ggtcgttgtt gtcgctggcc
77401 tgtagagcct tggcgctgta tacggcccc cggtaaaagt actccttaac cgccccctcg
77461 atcgccgac gggcctgggt ccgcaactcc tccagccgaa cctgaacggc ctcggggcc
77521 agggggggtg ggcgcggagc ccctgcggg gccgcccgg ccgggcggg cattacgcg
77581 aggggccgg cgtgctgtga daccgcgtcg accccgcgag cgagggcgtc gagggcctcg
77641 cgcatctggc gatcctccgc ctcaccccta atctcttcgc cacgggcaaa tttggccaga
77701 gcctggactc tatacagaag cggttctggg tcgtcgggg tggcggggc aaaagggtg
77761 tcgggtggg cctgcgagcg ctccagaagc cactcgccga ggcgtgtata cagattggcc
77821 ggcgggccg cgcgaagctg cagctacagg tccgcagtt ccccgtaaaa ggcgtccgtc
77881 tccgaatga catccctagc cacaaggatc agcttcgcca gcgccaggcg accgatcaga
77941 gagtttcgt ccagcacgtg ctggacgagg ggcagatggg cggccacgtc ggccaggtc
78001 aggcgcgtgg aggcagaaa gtccccccacg gccgttttcc ggggcagcat gctcagggta
78061 aactccaaca gggcggcggc cgggccggcc accccggcct gggtgtgcgt ccgggcccg
78121 ttctcgatga gaaaggcgag gacgcgttca agaaaaaaa taacacagag ctccagcagc
78181 ccgggagaag ccggatacgg cgaccgtaag gcgctgatgg tgagccgcga acacgcggcg
78241 acctgcggg ccaggccgg ggagcacgcg gtgaacttaa ccgccgtggc ggccacgttt
78301 gggtgggcct cgaacagctg ggcaaggtct gcgcccgggg gctcggtga gcggcgagtc
78361 ttcagcgcct cgagggcctg cgaggacgcc ggaacgtgg gcccgtcgtc ctccccgc
78421 tcggcgaccg gcggcccggc cgggtcgggg ggtgccgagg cgaggacagg ctccggaacg
78481 gaggcgggga ccgcggcccc gacggggtt ttgcctttgg gggtggattt cttcttggtt
78541 ttggcagggg gggccgagcg tttcgttttc tccccgaag tcaggtcttc gacgctggaa
78601 ggcggagtcc aggtgggtcg gcggcgcttg ggatggccgg ccgagtagcg tgccggtgc
78661 cgaccaaccg ggacgacgcc catctccagg accgcatgt cgtcgtcatc ttcttcggcc
78721 gcctctgcg cgggggcctt ggggcggag ggaggcggtg gtgggatcgc ggagggtggg
78781 tcggcggagg gggatccgt gggtggggta cccttcaggg ccaccgccca tacatcgtcg
```

```
78841 ggcgccgat tcgggcgctt ggcctctggt tttgccgacg gaccggccgt ccccgggat
78901 gtctcggagg ccatgtcgtc gcgacgggcc cgggtcggtg gcggcgactg ggcggctgtg
78961 ggcggtgtg gccccgtgcc ccctaccccc tcccggggc ccacgccgac gcaggctcc
79021 cccaggccg cgatctgcc ccgcagggg tggtgatgg ccacgcgtcg ttcgctgaac
79081 gcttcgtcct gcaggtaagt ctgcttgcc ccgtaaagat gcagagccgc ggccgtcaag
79141 tccgcaggag ccgcgggttc cgggcccgac ggcacgaaaa adaccatggc tccgccac
79201 cgtacgtccg ggcgatcgcg ggtgtaatac gtcaggtatg gatacatgtc ccccgccgc
79261 acttcggcga tgaacgcggg ggtgccctcc ggaaggccgt gcgggtcaaa aaggtatgcg
79321 gtgtcgccgt ccctgaacag ccccatccct agggggccaa tggttaggag cgtgtacgac
79381 agggggcgca gggcccacgg gccggcgaag aacgtgtgtg cggggcattg tgtctccagc
79441 aggccgcg cgggctcccc gaagaagccc acctcgccgt atacgcgcga gaagacacag
79501 cgcagtccgc cgcgcgcccd tggtactcg aggaagttgg ggagctgac gatcgaacac
79561 atgcgcggcg gcccagggcc cgcggtcgcg cgcgtccact cggcccctc gaccaaacaa
79621 ccctcgatgg cctccgcgga cagaacgtcg cgagggccca catcaaatat gaggctgaga
79681 aaggacagcg acgagcgcat gcacgataca gacccccccg gctccaggtc gggcgcgaac
79741 tggttccgag caccggtgac cacgatgtcg cgatcccccc cgcgttccat cgtggagtgc
79801 ggtggggtgc ccgcgatcat atgtgcccta ctggccagag acccggcctg tttatggacc
79861 ggaccccgg ggttagtgtt gttccgcca cccatgcccc cgtaccatgg cccggttcc
79921 cctgattagg ctacgagtcg cggtgatcgc ttcccaaaaa ccgagctgcg tttgtctgtc
79981 ttgatcttcc ccccccccc cgccgccg cccgccgcc cgcccgcaca ccataacacc
80041 gagaacaaca cacgggggtg ggcgtaacat aataaagctt tattggtaac tagttaacgg
80101 caagtccgtg ggtggcgcga cggtgtccta cgggctcatc tcgtcgtcct cgacggggt
80161 gttggaatga ggcgcccct cgcggtccgc ctggcgtggg ccgtgcccat aggcctcgg
80221 cttctgtgcg tccatgggca taggcgcggg gagactgttt ccggcgtcgc ggacctccag
80281 gtccctggga gactccggtc cggctaacgg acgaaacgcg gaagcgcgaa acacgccgtc
80341 ggtgacccgc aggagctcgt tcatcagtaa ccaatccata ctcagcgtaa cggccagccc
80401 ctggcgagac agatccacgg agtccggaac cgcggtcgtc tggcccaggg ggccgaggct
80461 gtagtccccc caggcccta ggtcgcgacg gctcgtaagc acgacgcggt cggccgcggg
```

FIGURE 16
(Continued)

```
80521 gctttgcggg ggggcgtcct cggcgcatg cgccattacc tctcggatgg ccgcggcgcg
80581 ctggtcggcc gagctgacca agggcgccac gaccacggcg cgctccgtct gcaggccttt
80641 ccacgtgtcg tggagttcct ggacaaactc ggccacgggc tcggtcccg cggccgcgcg
80701 cgcggcttga tagcaggccg agagacgccg ccagcgcgct agaaactgac ccatgaagca
80761 aaaccggggg acctggtctc ccgacagcag cttcgacgcc cgggtgtgaa tgccgacac
80821 aacggacaga aacccgtgaa tttcgcgccg gaccacggcc agcacgttgt cctcgtgcga
80881 cacctgggcc gccagctcgt cgcacacctc caggtgcgcc gtggtttcgg tgatgacgga
80941 acgcaggctc gcgagggacg cgaccagcgc gcgcttggcg tcgtgataca tgctgcagta
81001 ctgactcacc gcgtcccca tggcctcggg gggccagggc cccaggcggt cgggagtgtc
81061 cccgaccacc gcatacaggc ggcgtccgtc gctctcgaac cgacactcga aaaggcgga
81121 gagcgtgcgc atgtgcagcc gcagcagcac gatggcgtcc tccagtggc gaatcagggg
81181 gtctgcgcgc tcggcgaggt cctgcagcac ccccgggcg gccagggcgt acatgctaat
81241 caacaggagg ctggtgccca cctcgggggg cgggggggc tgcagctgga ccaggggccg
81301 cagctgctcg acggcacccc tggagatcac gtacagctcc cggagcagct gtctatgtt
81361 gtggccatc tgcatagtgg ggccgaggcc gcccggcg gcggttcga ggagggtaat
81421 cagcgcgccc agtttggtgc gatggccctc gaccgtgggg agatagccca gcccaaagtc
81481 ccggcccag gccaacacac gcagggcgaa ctgaccggg cgtggaaggt aggcgcgct
81541 acacgtggcc cccaacgcgt ccccgaccac cagggccaga acgtagggga cgaagccgg
81601 gtcggcgagg acgttggggt gaatgccctc gaggcgggg aagcggatct gggtcgccgc
81661 ggccaggtgg acagagggg cgtggctggg ctgcccgacg gggagaagcg cggacagcgg
81721 cgtggccggg gtggtgggg tgatgtccca gtgggtctga ccatacacgt cgatccagat
81781 gagcgccgtc tcgcggagaa ggctgggtcg accggaacta aagcggcgct cggccgtctc
81841 aaactccccc acgagcgccc gccgcaggct cgccagatgt tccgtcggca cggcggacc
81901 catgatacgc gccagtgtct ggctcagaac gccccccgac aggccgaccg cctcgcagag
81961 ccgccgtgc gtgtgctcgc tggcgccctg gaccgcctg aaagttttta cgtagttggc
82021 atagtacccg tattcccgcg ccagaccaaa cacgttcgac ccgcgaggg caatgcaccc
82081 aaagagctgc tggacttcgc cgagtccgtg gccggcgggc gtccgcgcgg gacgccgc
82141 cgccagaaac ccctccaggg ccgaaaggta gtgcgtgcag tgcgagggcg tgaacccagc
```

FIGURE 16
(Continued)

```
82201 gtcgatcagg gtgttgatca ccacggaggg cgaattggta ttctggatca acgtccacgt
82261 ctgctgcagc agagccagca gccgctgctg ggcgccggcg gagggctgct ccccgagctg
82321 cagcaggctg gagacggcag gctggaagac tgccagtgcc gacgaactca ggaacggcac
82381 gtcgggatca aacacggcca cgtccgtccg cagcgcgcc attagcgtcc ccggggcgc
82441 acaggccgag cgcgggctga cgcggctgag ggccgtcgac acgcgcacct cctcgcggct
82501 gcgaaccatc ttgttggcct ccagtgtcgg aatcattatg gcgggtcga tctcccgcac
82561 ggtgtgctga aactgcgcca cagggggcgg cgggaccaca gcccccgct tggggtcgt
82621 caggtactcg tccaccaggg ccaacgtaaa gagggccgt gtgaggggag tgagggtcgc
82681 gtcgtctatg cgctggaggt gcgccgagaa cagcgtcacc cgattactca ccagggccaa
82741 gaaccggagg ccctcttgca cgaacgggc gggaagagc aggctgtacg ccggggtggt
82801 aaggttcgcg ctgggctgcc ccaacgggac cggcgccatc ttgagtgacg tctcccaag
82861 ggctcgatg gaggtccgcg ggtcatggc caagcagctc ttggtgacgg tttgccagcg
82921 gtctatccac tccacggcgc actggcggac gcgaccggc cccaggccg ccgcggtgcg
82981 caggccggcg gaatccagcg catgggacgt gtcggagccg gtgaccgcga ggatggtgtc
83041 cttgatgacc tccatctccc ggaaggcctg gtcggggcc tcggggagag ccaccaccaa
83101 gcggtgtacg agcaaccgg ggaggttctc ggccaagagc gccgtctcc gaagcccgtg
83161 ggcccggtgg agcgcgcaca ggtgttccag cagcggccgt cagcatgcc gcggtctac
83221 cgggcaatg gccgttcccg acaacagaaa cgccgccatg gcggcgcgca gcttggccgt
83281 ggccagaaac gccgggtcgt ccgcccgtt tgccgtctcg gccgtggggg ttggcggttg
83341 gcgaaggccg gctaggctcg tcaataggcg ctgcataggt ccgtccgagg gcggaccggc
83401 gggtgaggtc gtgacgacgg gggcctcgga cgggagaccg cggtctgcca tgacgccggg
83461 ctcgcgtggg tggggacag cgtagaccaa cgacgagatc gggcgggaat gactgtcgtg
83521 cgctgtaggg agcggcgaat tatcgatccc ccggcgcct ccaggaacc cgcaggcgtt
83581 gcgagtaccc cgcgtcttcg cggggtgtta taggccact taagtcccgg catcccgttc
83641 gcggaccag gcccggggga ttgtccggat gtcgggcag ccggacggc gtggttgcg
83701 gactttctgc gggcgcgcc aaatggcct ttaaacgtgt gtatacggac gcgccgggcc
83761 agtcggccaa cacaacccac cggaggcggt agccgcgttt ggctgtgggg tgggtggttc
83821 cgccttgcgt gagtgtcctt tcgacccccc tccccgggt tttgttaggt cgcgatctgc
```

```
83881 agtcgcaatg aagaccaatc cgctaccgga aacccttcc gtgtggggcg ggagtacgt
83941 ggaactccc cccaccacac gcgataccga gggacagggc ctgcttcgc gcgtcctgcg
84001 ccccccgatc tctcgccgcg acggcccagt gctcccagg gggtcgggac ccggagggc
84061 ggccagcacg ctgtggttgc ttggctgga cggcacagac gcgccctg gggcgtgac
84121 cccaacgac gataccgaac aggccctgga caagatcctg cggggcatca tgcgcggggg
84181 ggggccctg atctgctacc cgcgccatca tctaacccgc caagtgatcc tgacggatct
84241 gtgccaaccc aacgcggatc gtgccgggac gctgctbctg gcgctgcggc acccgccga
84301 cctgcctcac ctggcccacc agcgcgccc gccaggcgg cagaccgagc ggctgggcga
84361 ggcctggggc cagctgatgg aggcgaccgc cctgggtcg gggcgagccg agagcgggtg
84421 cacgcgcgcg ggcctcgtgt cgtttaactt cctggtgycg gcgtgtgccg cctcgtacga
84481 cgcgcgcgac gccgccgatg cggtacgggc ccacgtcacg gccaactacc gcggacgcg
84541 ggtggggcg cgcctggatc gttttccga gtgtctgcgc gccatggttc acacgcacgt
84601 cttcccccac gaggtcatgc ggttttttgg gggctggtg tgtgggtca cccaggacga
84661 gctagcgagc gtcacgcccg tgtgcgccgg gccacaggag gcggcgcaca ccggccaccc
84721 gggccggccc cgctcggccg tgatcctccc ggcgtgtgcg ttcgtggacc tggacgccga
84781 gctgggggctg ggggccggg gtgcggcgtt tctgtacctg gtattcactt accgccagcg
84841 ccgggaccag gagctgtgtt gtgtgtacgt gatcaagagc cagctcccc cgcgcgggtt
84901 ggagccggcc ctggagcggc tgttgggcg cctccggatc accaacacga ttcacggcac
84961 cgaggacatg acgcccccgg cccaaactg aaacccgac ttcccctcg cgggctggc
85021 cgccaatccc caaaccccgc gttgctggc tggccaggtc acgaacccc agttcgccga
85081 caggctgtac cgctggcagc cggacctgcg gggcgccc accgacgca cctgtacgta
85141 cgccgccttt gcagagctcg gcatgatgcc cgaggatagt cccgctgcc tgcacgcac
85201 cgagcgcttt gggcggtca gcgtccccgt tgtcatcctg gaaggcgtgg tgtggcgccc
85261 cggcgagtgg cgggcatgcg cgtgagcgta gcaaacgccc cgcccacaca acgctccgcc
85321 cccaaccct tcccgcatgt cactcgtggt tcgttgaccc ggacgtccgc caaataaagc
85381 cactgaaacc cgaaacgcga gtgttgtaac gtcctttggg cgggaggaag ccacaaaatg
85441 caaatggat acatggaagg aacacaccc cgtgactcag gacatcggcg tgtcctttg
85501 ggtttcactg aaactggccc gcgcccaacc cctgcgcgat gtggataaaa agccagcgcg
```

FIGURE 16
(Continued)

```
85561 ggtggtttag ggtaccacag gtgggtgctt tggaaacttg tcggtcgccg tgctcctgtg
85621 agctggtc cctccccgt ttccttgcg ctcccgcctt cggacctgc tcttgcctat
85681 cttctttggc tctcggtgcg attcgtcagg cagcggctt gtcgaatctc gacccacca
85741 ctcgccggac ccgccgacgt ccctctcga gcccaccgaa accgccgcg tctgttgaaa
85801 tggccagccg cccagcagca tcctctcccg tgaagcgcg ggccccggtt gggggacagg
85861 aggccggcgg ccccagcgca gccacccagg gggaggccgc cgggcccct ctcgccacg
85921 gccaccacgt gtactgccag cgagtcaatg gcgtgatggt gctttccgac aagacgccg
85981 ggtccggtc ctaccgcatc agcgatagca acttgtcca atgtggttcc aactgcacca
86041 tgatcatcga cggagacgtg gtgcgcgggc gcccccagga cccggggcc gggcatccc
86101 ccgctccctt cgttgcggtg acaaacatcg gagccggcag cgacggcggg accgccgtcg
86161 tggcattcgg gggaaccca cgtcgtcgg cggggacgtc tacggtacc cagacggccg
86221 acgtccccac cgaggccctt ggggccccc ctcctcctcc ccgcttcacc ctgggtggcg
86281 gctgttgttc ctgtcgcgac acacggcgcc gctctgcggt attcgggggg gagggggatc
86341 cagtcggccc cgcggagttc gtctcggacg accggtcgtc cgattccgac tcggatgact
86401 cggaggacac ggactcggag acgctgtcac acgcctcctc ggacgtgtcc ggcggggcca
86461 cgtacgacga cgcccttgac tcgattcgt catcggatga ctccctgcag atagatggcc
86521 ccgtgtcg cccgtggagc aatgacaccg cgccctgga tgtttgcccc gggacccccg
86581 gccgggcgc cgacgccggt ggtccctcag cggtagaccc acacgcgccg acgccagagg
86641 ccggcgctgg tcttgcggcc gatcccgccg tggcccggga cgacgcggag gggctttcgg
86701 acccctggcc acgtctggga acgggcacgg cctaccccgt ccccctggaa ctcacgcccg
86761 agaacgcgga ggccgtggcg cgctttctgg gagatgccgt gaaccgcgaa ccgcgctca
86821 tgctggagta cttttgccgg tcgcccgcg aggaaaccaa ggtgtcccc cccaggacat
86881 tggcagccc ccctcgcctc acggaggacg actttgggct tctcaactac gcgctcgtgg
86941 agatgcagcg cctgtgtctg gacgttcctc cggtcccgcc gaacgcatac atgccctatt
87001 atatcaggga gtatgtgacg cggctggtca acggttcaa gccgctggtg agacggtccg
87061 ctcggcttta acgcatcctg ggggttctgg tgcactgcg gatccggacc cggaggcct
87121 cctttgagga gtggctgcga tccaaggaag tggccctgga ttttggcctg acggaaaggc
87181 ttcgcgagca cgaagcccag ctggtgatcc tggcccaggc tctggaccat tacgactgtc
```

```
87241 tgatccacag cacaccacac acgctggtcg agcggggct gcaatcggcc ctgaagtatg
87301 aggagtttta cctaaagcgt tttggcggga actacatgga gtccgtcttc cagatgtaca
87361 cccgcatcgc cggcttttig gcctgccggg ccacgcgcgg catcgccac atcgcctgg
87421 ggcgagaggg gtcgtggtgg gaaatgttca gttcttttt ccaccgctc tacgaccacc
87481 agatcgtacc gtcgaccgcc gccatgctga acctgggac ccgcaactac tacacctcca
87541 gctgctacct ggtaaaccc caggccacca caacaaggc gaccctgcgg gccatcacca
87601 gcaacgtcag tgccatccte gcccgcaacg ggggcatcgg gctatgcgtg caggcgttta
87661 acgactccgg ccccgggacc gccagcgtca tgcccgccct caaggtcctt gactcgctgg
87721 tgcggcgca caacaaagag agcgcgcgtc cgaccggcgc gtgcgtgtac ctggagccgt
87781 ggcacaccga cgtgcgggcc gtgatccga tgaaggggt cctcgccggc gaagaggccc
87841 agcgctgcga caatatcttc agcgccctct ggatgccaga cctgtttttc aagcgcctga
87901 ttcgccacct ggacggcgag aagaacgtca catggaccct gttcgaccgg gacaccagca
87961 tgtcgctcgc cgactttcac ggggaggagt tcgagaagct ctaccagcac ctcgaggtca
88021 tggggttcgg cgagcagata cccatccagg agctggccta tggcattgtg cgcagcgagg
88081 ccacgaccgg gagcccttc gtcatgttca aagacgcggt gaaccgccac tacatctacg
88141 acaccccaggg ggcggccatc gccggctcca acctctgcac cgagatcgtc catccggct
88201 ccaagcgatc cagtggggtc tgcaacctgg gaagcgtgaa tctgcccga tggtctcca
88261 ggcagacgtt tgacttggg cggctacgcg acgccgtgca ggcgtgcgtg ctgatggtga
88321 acatcatgat cgacagcacg ctacaaccca cgccccagtg caccgcggc aacgacaacc
88381 tgcggtccat gggaatcggc atgcagggcc tgcacacggc ctgcctgaag ctggggctgg
88441 atctggagtc tgccgaattt caggacctga acaaacacat cgctgaggtg atgctgctgt
88501 cggcgatgaa gaccagcaac gcgctgtgcg ttcgcgggc ccgtccctcc aaccacttta
88561 agcgcagcat gtatcgcgcc ggccgctttc actgggagcg ctttcggac gccggccgc
88621 ggtacgaggg cgagtgggag atgctacgcc agagcatgat gaaacacggc ctgcgcaaca
88681 gccagtttgt cgcgctgatg cccaacgccg cctggcgca gatctcggac gtcagcgagg
88741 gctttgcccc cctgttcacc aaccgttca gcaaggtgac ccggacggc gagacgctgc
88801 gccccaacac gtcctgcta aaggaactgg aacgcacgtt tagcgggaag cgcctcctgg
88861 aggtgatgga cagtctcgac gccaagcagt ggtccgtggc gcaggcgctc ccgtgcctgg
```

FIGURE 16
(Continued)

```
88921 agcccaccca cccctccgg cgattcaaga ccgcgtttga ctacgaccag aagttgttga
88981 tcgactgtg tgcggaccgc gccccctacg tcgaccatag ccaatccatg accctgtatg
89041 tcacggagaa ggcggacggg accctccag cctccaccct ggtccgcctt ctggtccacg
89101 catataagcg cggactaaaa acaggatgt actactgcaa ggttcgcaag gcgaccaaca
89161 gcgggtctt tggcggcgac gacaacattg tctgcacgag ctgcgcgctg tgacgacaa
89221 accccctccg cgccaggcc gcgccactg tcgtcgcgt cccacgctct ccctgctgc
89281 catggattcc gcggcccag ccctctcccc cgctctgacg gccttacgg gccagacgc
89341 gacggcggac ctggcgatcc agattccaaa gtgcccgac ccgagaggt acttctacac
89401 ctccagtgt cccgacatta accacctgcg ctccctcagc atccttaacc gctggctgga
89461 aactgagctt gttttcgtgg gggacgagga ggacgtctcc aagctttccg agggcgagct
89521 cagcttttac cgcttcctct tcgctttcct gtcggccgcc gacgactgg ttacggaaaa
89581 cctgggcggc ctctccggcc tgtttgagca gaaggacatt ctccactact acgtggagca
89641 ggaatgcatc gaagtcgtac actcgcgcgt gtacaacatc atccagctgg tgcttttcca
89701 caacaacgac caggcgcgcc gcgagtacgt ggccggcacc atcaaccacc cggccatccg
89761 cgccaaggtg gactggttgg aagcgcgggt gcgggaatgc gcctccgttc cggaaaagtt
89821 cattctcatg atcctcatcg agggcatctt ttttgccgcc tcgtttgccg ccatcgccta
89881 ccttcgcacc aacaaccttc tgcgggtcac ctgccagtca aacgacctca tcagccggga
89941 cgaggccgtg cacacgacgg cctcgtgtta catctacaac aactacctcg gcgggcacgc
90001 caagccccg ccgaccgcg tgtacgggct gttccgccag gcggtcgaga tcgagatcgg
90061 attttatccga tccaggcgc cgacggacag ccatatcctg agcccggcgg cgctggcggc
90121 catcgaaaac tacgtgcgat tcagcgcgga tcgctgttg ggccttatcc acatgaagcc
90181 actgttttcc gcccacccc cgacgccag cttccgctg agctcatgt ccaccgacaa
90241 acacaccaat ttttcgagt gtcgcagcac ctcctacgcc gggcggtcg tcaacgatct
90301 gtgagtgtcg cggcgcgtt ctacccgtgt ttgcccataa taaacctctg aacgaaactt
90361 tgggtctcat tgtgattctt gtcaggacg cggggtggg agaggataaa agcggcgca
90421 aaagcagta accaggtccg tccagattct gcgggcatag aataccataa ttttattggt
90481 gggtcgtttg ttcggggaca agcgcgctcg tctgacgttt gggctactcg tcccagaatt
90541 tggccaggac gtccttgtag aacgcgggtg gggggcctg ggtccgcaac tgctccagaa
```

FIGURE 16
(Continued)

```
90601 acctgtcggc gatatcaggg gccgtgatat gccgggtcac gatagatcgc gccaggtttt
90661 cgtcgcggat gtcctggtag ataggcaggc gtttcagaag agtccacggc cccgctact
90721 tggggccgat aagcgatatg acgtacttaa tgtagcggtg ttccaccagc tcggtgatgg
90781 tcatgggatc ggggagccag tccagggact ctggggcgtc gtggatgacg tgggtcgcc
90841 ggttggccac ataactgcgg tgctcttcca gcagctgcgc gttcgggacc tggacgagct
90901 cgggcgggt gagtatctcc gaggaggacg acctggggcc ggggtggccc ccgtaacgt
90961 cccggggatc caggggagg tcctcgtcgt cttcgtatcc gccggcgatc tgttgggtta
91021 gaatttcggt ccacgagacg agcgtctcgg tgccgccggc ggccggcggc agaggggcc
91081 tggtttccgt ggagcgcgag ctggtgtgtt cccggcggat ggcccgccgg gtctgagagc
91141 gactcggggg ggtccagtga cattcgcgca gcacatcctc cacggaggcg taggtgttat
91201 tgggatggag gtcggtgtgg cagcggacaa agagggccag gaactggggg tagctcatct
91261 taaagtactt cagtatatcg cgacagttga tcgtgggaat gtagcaggcg ctaatatcca
91321 acacaatatc acagcccatc aacaggaggt cagtgtccgt ggtgtacacg tacgcgaccg
91381 tgttggtgtg atagaggttg gcgcaggcat cgtccgcctc caactgaccc gagttaatgt
91441 aggcgtaccc caggggccgg agaacgcgaa tacagaacag atgcgccaga cgcagggcg
91501 gcttcgaggg cgcggcggac ggcagcgcgg ctcggaccc ggccgtcccc cgggtccccg
91561 aggccagaga ggtgccgcgt cggcgcatgt tggaaaaggt agagctgggt ctggagtcgg
91621 tgatggggga aggcggtgga gaggcgtcca cgtcactggc ctcctcgtcc gtccggcact
91681 gggccgtcgt gcgggccagg atggccttgg ctccaaacac aaccggctcc atacaattga
91741 cccgcgatc ggtaacgaag atgggaaaa gggacttttg ggtaaacacc tttaataagc
91801 gacagaggca gtgtagcgta atggcctcgc ggtcgtaact ggggtatcgg cgctgatatt
91861 tgaccaccaa cgtgtacatg acgttccaca ggtccacggc aatggggtg aagtaccgg
91921 ccgggcccc aaggcccgg cgcttgacca gatggtgtgt gtggcaaac ttcatcatcc
91981 cgaacaaacc catgtcaggt cgattgtaac tgcggatcgg cctaactaag gcgtggttgg
92041 tgcgacggtc cgggacaccc gagcctgtct ctatgtgtat ggtgacccag acaacaacac
92101 cgacacaaga ggacaataat ccgttagggg acgtctttta taatttcgat ggcccaactc
92161 cacgcggatt ggtgcagcac cctgcatgcg ccggtgcggg ccaaccttcc cccgctcat
92221 tgcctcttcc aaaagggtgt ggcctaacga gctgggggcg tattaatca ggctagcgcg
```

FIGURE 16
(Continued)

```
92281 gcgggcctgc cgtagtttct ggctcggtga gcgacggtcc ggttgcttgg gtccctggc
92341 tgccatcaaa acccaccct cgcagcggca tacgcccct ccgcgtcccg cacccgagac
92401 cccggccgg ctgcctcac cacgaagcc caactcgtca ctgtggggtg ttcccagcc
92461 gcgttgggat gacggattcc cctggaggtg tggcccgc ctccaagtg gaggacgcgt
92521 cggacgcgtc cctcgggcag ccggaggagg gggcgcctg ccaggtggtc ctgcagggcg
92581 ccgaacttaa tggaatccta caggcgtttg cccgctgcg cacgagcctt ctggactcgc
92641 ttctggttat gggcgaccgg ggcatccta tccataacac gatctttggg gagcaggtgt
92701 tcctgcct ggaacactcg caattcagtc ggtatcgtg gcgggaccc acggcggcgt
92761 tcctgtctct cgtggaccag aagcgctccc tcctgagcgt gtttcgcgcc aaccagtacc
92821 cggacctacg tcgggtggag ttggcgatca cgggccaggc cccgtttcgc agctggttc
92881 agcgcatatg gacgacgacg tccgacggcg aggccgttga gctagccagc gagacgctga
92941 tgaagcgcga actgacgagc tttgtggtgc tggttcccca gggaacccc gacgttcagt
93001 tgcgcctgac gaggccgcag ctcaccaagg tccttaacgc gacggggcc gatagtgcca
93061 cgcccaccac gttcgagctc ggggttaacg gcaaaattt cgtgttcacc acgagtacct
93121 gcgtcacatt tgctgcccgc gaggagggcg tgtcgtccag caccagcacc caggtccaga
93181 tcctgtccaa cgcgctcacc aaggcgggcc aggcggccgc caacgccaag acggtgtacg
93241 gggaaaatac ccatgcacc ttctctgtgg tcgtcgacga ttgcagcatg cgggcggtgc
93301 tcggcgact gcaggtcggc gggggcaccc tcaagttctt cctcaagacc cccgtcccca
93361 gtctgtgcgt caccgccacc ggtccaacg ctgtatcggc ggtatttctc ctgaaaccc
93421 agaagatttg cctggactgg ctggtcata gccagggtc tccttcagcc gggagctcgg
93481 cctccggc ctctgggagc gagccaacag acagcaagga ctccgtcg gacgcggtca
93541 gccacggcga tccggaagac ctcgatggcg ctgccggc gggagggcg gggcctagc
93601 acgctgtcc gatgccgtcg tcgaccacgc gggtcactcc cacgaccaag cggggcgct
93661 cggggcga ggatgcgagc gcggacacgg cctaaagaa acctaagacg gggtcgccca
93721 ccgcacccc gccgcagat ccagtccccc tggacacgga ggacgactcc gatgcggcgg
93781 acggacggc ggcccgtccc gccgctccag acgcccggag cggaagccgt tacgcgtgtt
93841 actttcgcga cctcccgacc ggagaagcaa gccccggcgc cttctccgcc ttcgggggg
93901 ggcccaaac ccgtatggt tttggattcc cctgacgggg cggggccttg gcggccgccc
```

FIGURE 16
(Continued)

```
93961 aactctagca ccatccgggg ttaatgtaaa taaacttggt attgcccaac actctccgc
94021 gtgtcgcgtg tggttcatgt gtgtgcctgg cgtccccac cctcgggttc gtgtatttcc
94081 tttccctgtc cttataaaag ccgtatgtgg gggctgacg gaaccacccc gcgtgccatc
94141 acggccaagg cgcgggatgc tccgcaacga cagccaccgg gccgcgtccc cggaggacgg
94201 ccagggacgg gtcgacgacg gacggccaca cctcgcgtgc gtggggccc tggcgcgggg
94261 gttcatgcat atctggcttc aggccgccac gctgggtttt gcgggatcgg tcgttatgtc
94321 gcgcgggccg tacgcgaatg ccgcgtctgg ggcgttcgcc gtcgggtgcg ccgtgctggg
94381 ctttatgcgc gcacccctc aactcgcgcg gcccacgcg cggatatacg cctggctcaa
94441 actgcggcc ggtggagcgg ccattgttct gtggagtctc gggagcccg gcacgcagcc
94501 ggggccccg gccccgggcc cggccaccca gtgctggcg ctgggcgccg cctatgcggc
94561 gctcctggtg ctgccgatg acgtctatcc gtctttctc ctcgcccgg ggcccctgtt
94621 cgtcggcacc ctggggatgg tcgtcggcgg gctgacgatc ggaggcagcg cgcgctactg
94681 gtggatcggt gggccgacg cggccgcctt ggccgcggcg gtgttggcgg gccgggggc
94741 gaccaccgcc aggggctgct tctccagggc gtgccccgac caccgccgcg tctgcgtcat
94801 cgtcgcaggc gagtctgttt accgccgccc ccggaggac ccagagcgac ccggggaccc
94861 cgggccaccg tcccccccga cacccaacg atcccagggg ccgccggccg atgaggcgc
94921 accggccggg gtagcgcggc ccgaaaacgt ctgggtgccc gtggtcacct ttctgggggc
94981 ggggcgctc gccgtcaaga cggtgcgaga acatgcccgg ggaacgcagg gccgggcct
95041 gccgctgtgg cccccaggtgt ttctcggagg ccatgtggcg gtgccctga cggagctgtg
95101 tcaggcgctt ggcccctggg aacttacgga cccgctgctg tttgttcacg ccggactgca
95161 ggtcatcaac ctcgggttgg tgtttcggtt ttccgaggtt gtgtgtatg cggcgctagg
95221 gggtgccgtg tggatttcgt tggcgcaggt gctggggctc cggcgtcgcc tgcgcaggaa
95281 ggaccccggg gacggggccc ggttggcggc gacgcttcgg ggcctcttct tctccgtgta
95341 cgcgctgggg tttggggtgg gggcgctgct gtgccctccg gggtcaacgg gcgggcggtc
95401 gggcgattga tatattttc aataaaaggc attagtcccg aagaccgccg gtgtgtgatg
95461 atttcgccat aacacccaaa ccccggatgg ggccagggta taaattccgg aaggggacac
95521 gggctaccct cactaccgag ggcgcttggt cgggaggccg catcgaacgc acacccccat
95581 ccggtggtcc gtgtggaggt cgttttcagt gcccggtctc gctttgcggg gaacgctagc
```

FIGURE 16
(Continued)

```
95641 cgatccctcg cgaggggag gcgtagggca tggcccggg gcgggtggc cttgccgtgg
95701 tcctgtggag cctgttgtgg ctcggggcgg gggtgtccgg gggctcggaa actgcctcca
95761 ccgggcccac gatcaccgcg ggagcggtga cgaacgcgag cgaggccccc acatcggggt
95821 ccccggtc agccgccagc ccggaagtca cccccacatc gaccccaaac cccaacaatg
95881 tcacacaaaa caaaactacc cccaccgagc cggccagccc ccaacaacc cccaagccca
95941 cctccacgcc caaagcccc cccacgtcca cccccgaccc caaacccaag aacaacacca
96001 cccccgccaa gtcgggccgc cccactaaac cccacgggcc cgtgtggtgc gaccgccgcg
96061 acccattggc ccggtacggc tcgcgggtgc agatccgatg ccggtttcgg aattccaccc
96121 gcatggagtt ccgcctccag atatggcgtt actccatggg tccgtccccc ccaatcgctc
96181 cggctccga cctagaggag gtcctgacga acatcaccgc cccaccggg ggactcctgg
96241 tgtacgacag cgccccaac ctgacggacc cccacgtgct ctgggcggag ggggccggcc
96301 cgggtgccga ccctccgttg tattctgtca ccgggccgct gccgacccag cggctgatta
96361 tcggcgaggt gacgcccgcg acccagggaa tgtattactt ggcctggggc cggatggaca
96421 gcccgcacga gtacgggacg tgggtgcgcg tccgcatgtt ccgccccccg tctctgaccc
96481 tccagcccca cgggtgatg gagggtcagc cgttcaaggc gacgtgcacg gccgacgcct
96541 actaccgcg taaccccgtg gagttggtct ggttcgagga cgaccgccag gtgtttaacc
96601 cgggccagat cgacacgcag acgcacgagc accccgacgg gttcaccacc gtctctaccg
96661 tgacctccga ggctgtcggc ggccaggtcc cccgcggac attcacctgc cagatgacgt
96721 ggcaccgcga ctccgtgaca ttctcgcgac gcaatgccac cgggctggcc ctggtgctgc
96781 cgcggcaac catcaccatg gaatttgggg tccggcatgt ggtctgcacg gccggctgcg
96841 tccccgaggg cgtgacgttt gctggttcc tgggggacga cccctcaccg gcggctaagt
96901 cggccgttac ggcccaggag tcatgcgacc accccgggct ggctacggtc cggtccaccc
96961 tgcccatttc gtacgactac agcgagtaca tctgtcggtt gaccggatat ccggccggga
97021 ttcccgttct agaacaccac ggcagtcacc agcccccacc cagggacccc accgagcggc
97081 aggtgatcga ggcgatcgag tgggtgggga ttggaatcgg ggttctcgcg gcggggtcc
97141 tggtcgtaac ggcgatcgtg tacgtcgtcc gcacatcaca gtcgcggcag cgtcatcggc
97201 ggtaacgcga gaccccccg ttaccttttt aatatctata tagtttggtc ccccctctat
97261 ccggccacc gctgggcgct ataaagccgc caccctctct tccctcaggt catccttggt
```

```
97321  cgatcccgaa cgacacacgg cgtggagcaa aacgcctccc cctgagccgc tttcctacca
97381  acacacggc atgcctctgc gggcatcgga acacgcctac cggcccctgg gccccgggac
97441  acccccatg cgggctcggc tcccccgccgc ggctggggtt ggcgtcggga ccatcatcgg
97501  gggagttgtg atcattgccg cgtggtcct cgtgccctcg cgggcctcgt gggcacttto
97561  cccatgcgac agcggatggc acgagttcaa cctcgggtgc atatcctggg atccgacccc
97621  catggagcac gagcaggcgg tcggcggctg tagcgcccg gcgacctga tccccgcgc
97681  ggctgccaaa cagctggccg ccgtcgcacg cgtccagtcg gcaagatcct cgggctactg
97741  gtgggtgagc ggagacggca ttcgggccag cctgcggcatc gtcgacggcg tcggcggtat
97801  tgaccagttt tgcgaggagc ccgcccttcg catatgctac tatcccccgca gtcccggggg
97861  ctttgttcag tttgtaactt cgacccgcaa cgcgctgggg ctgccgtgag gcgcgtgtac
97921  tgcggtctgt ctcgtctcct cttctcccct tccctcccccc tccgcatccc aggatcacac
97981  cggccaacga gggttggggg gtccggcacg gacccaaaat aataaacaca caatcacgtg
98041  cgataaaaag aacacgcggt ccctgtggt gttttggtt attttatta aatctcgtcg
98101  acaaacaggg gggaagggggc gtggtctaga gacggcagca cgggcggagg cgttcacggg
98161  ctccggcgtc cttcgcgttt aagcttggtc aggagggcgc tcagggcggc gacgttggtc
98221  gggccgtcgt tggtcagggc gttggctcga tggcgggcga ggacgggcga gggctcaac
98281  ggcggggcg gggccccggt gggccccggg gggaaaata gggcggatcc ccccagtcg
98341  tacagggat tttccgactc aatgtacggg gaggccggcg atgcattcgc cgtgttcacg
98401  cagacgtttt cgtagacccg catccatggt atttcctcgt agacacgccc cccgtcctcg
98461  cgcacggtct cgtatattga ctcgtcgtcc tcgtaggggg cgtgccgttc gcgggccgag
98521  gcggcgtggg tggtttgcg gcgggcgtcg tcgtcgtcgt cgtcggccgt cagataccgtg
98581  gcttccatct ggtcggggttc tccctccggg gcgggtcccc acacccgtgg ccgatcgagg
98641  ctccccagag acgcgctcg gacgaggagg gggcacgtcg ccgccggcgg tgcctgtcg
98701  ggtcccgcga cgttacgggc cgggagccgc ggggcaccct cccccatgtg cgtgtaatac
98761  gtggccggct gtgcggccgc agcgggggc tccgcgaccg ggtcgttcgt atccggaagc
98821  gggggccccg cgccgtccga gcggcgcctc cggaacctcc gggtggacgc ggggtcgag
98881  tgtaggcgag gtcgggggag gggcggggc tcgttgtcgc gccgcgccg ctgaatcttt
98941  tcccgacagg tccgaccccct agcgcgatgc ccccccgggc cgctggccat gtcgtccggg
```

FIGURE 16
(Continued)

```
99001 ggaggcccg cggaccacgt cgtccggcga gacgcacga gccgcaggat ggactcgtag
99061 tggagcgacg gcgcccgct gcggagcaga tccgcggcca gggcggcccc gaaccaagcc
99121 ttgatgctca actccatccg ggcccagctg ggggcggtca tcgtggggaa cagggggcg
99181 gtggtccgac agaaacgctc ctggctgtcc accgcggccc gcagatactc gttgttcagg
99241 ctgtcggtgg cccagacgcc gtaccggtg agggtcgcgt tgatgatata ctgggcgtgg
99301 tgatggacga tcgacagaac ctccaccgtg gatacgacgg tatccacggt cccgtacgta
99361 ccgccgctcc gcttgccggt ctgccacagg ttggctaggc gcgtcaggtg gcccaggacg
99421 tcgctgaccg ccgccctgag agccatgcac tgcatggagc cggttgtgcc gctgggaccc
99481 cggtccagat ggcgcgcgaa cgtttccgcg ggcgcctccg ggctgccgcc gagcgggagg
99541 aaccggcgat tggagggact cagccggtga catacgtgct tgtctgtcgt ccacagcatc
99601 caggacgccc accggtacag cacggagacg taggccagga gctcgttgag ccgcagtgcg
99661 gtgtcggtgc tggggcggct tgggtccgcc gggcgcataa agaacatgta ctgctgaatc
99721 cgatggaggg cgtcgcgcag gccggccacg gtgggggcgt acttggccgc cacggcccg
99781 ctcttgaacg gggtgcgcgc cagcagcttt ggcgccaggg tgggccgcag cagcacgtga
99841 aggctggggt cgcagtcgcc cacggggtcc tcggggacgt ccaggccgct gggcaccacc
99901 gtctgcaggt acttccagta ctgcgtgagg atggcgcggc tcaactggcc gccgggcagc
99961 tccacctgcc ccagcgcctg ggtggcggcc gaagcgtagt gccggatgta ctgtagtgc
100021 gggtcgctgg cgagcccgtc cacgatcaaa ctctcgggaa ccgtgttgtg ttgccgcgcg
100081 gccaaccgga cgctgcgatc ggtgcaggtc agaaacgccg gctgcgcgtc gtcggagcgc
100141 tgccgcaagg ccgccacggc cgcgctaagg agccctccg gggtggggag cagacaccg
100201 ccgaagatgc gccgctcggg aacgcccgcg ttgtcgtcgc ggatcaggtt ggcaggcgtc
100261 aggcaccgcg ccagtcgcag ggagctcgcg ccgcgtcc gggctgcat ggtgacgcc
100321 gttcggtcgg gaccgccgg tcggagttat gccgcgtcca gggccatcgg ggcgcttttt
100381 atcgggagga gcttatgggc gtggcgggcc tccagcccg gtcgcgcgcc tccccgacac
100441 gtgcgcccgc agggcggcgg ccccctcgtc tccatcagc agtttcctaa actgggacat
100501 gatgtccacc acgcggaccc gcgggcccaa cacggacccg ccgcttacgg gggcggggg
100561 gaagggctcc aggtccttga gaagaaaggc ggggtctgcc gtcccggaca cggggcccg
100621 gggcgctgag gaggcggggc gtagatccac gtgctccgcg gccgcgcgga cgtccgccca
```

FIGURE 16
(Continued)

```
100681 gaacttggcg ggggtggtgc gcgcgtacag gggctgggtc gctcggagga cgcacgcgta
100741 gcgcagggga gtgtacgtgc ccacctcggg ggccgtgaat ccccgtcaa acgcggccag
100801 tgtcacgcac gccaccacgg tgtcggcaaa gccagcagc cgctgcagga cgagcccggc
100861 ggccagaatg gcgcgcgtgg ccgccgcgtc gtccggcgc cggtgcgcgt cccgcacgc
100921 ccgggcgtac tttaaggtca cggtcgccag ggccgtgtgc agcgcgtaca cgccagcgcc
100981 cagcacggcg ttgagcccgc tgttggcgag cagccggcgc gctgcggtgt cgcccagcgc
101041 ctcgtgctcg gccccacga ccgcggggct tccaggggc agggcgcgaa acagctcctc
101101 ccgcgcacg tcgcaaagg cggggtggtg cacgtgcggg tgcaggcgcg ccccacgac
101161 cacggagagc cactggaccg tctgctccgc catcaccgcc agcacatcca gacgcgccc
101221 caggaaggcg gcctccgcg tcaaaacgca cggacggcg tcgggattga agcgggcgag
101281 caggcccccg gtggccaggt acgtcatgcg gccggcatag cggcgggcca cgcgacagtc
101341 ggggtccagc agcgcgcgca cccggggcca gtacagcagg gaccccagcg agctgcggaa
101401 cacccggcg tcggggccgg attggggga cactaacccc ccgcgctca gtaacggcac
101461 ggccgcggcc ccgacgggac gcaacgccgt gaggctcgcg aaatgccgcc tcagctggc
101521 cgccctgtcg tccaggtcag acccgcgcgc ctccgcgta aggagcgtcc cgcacacca
101581 cccgttgatg gccagccgca cgacggcatc cgccaaaaag ctcatcgcct gggcggggct
101641 ggttttttgtt cgacgatccg tcaggtcaag aatcccatcg cccgtgatat accaggccaa
101701 cgcctcgcc tgctgcaggg tttggcggaa aaacaccgcg gggttgtcgg gggaggcgaa
101761 gtgcatgacc cccacgcgcg ataaccgaa cgcgctatcc ggacacgggt aaaacccggc
101821 cggatgcccc agggctaggg cggagcgcac ggactcgtcc cacacggcaa cctgagggc
101881 cagtcgatcc aacgggaatg ccgcccggag ctccgggccc ggcaacgctc actccagaac
101941 ctccaccttg ggcggggaac gggcccccgcc gccgtcctcc ggccgacgg cttccgggta
102001 gtcgtcctcc tcgtactgca gctcctctag gaacagcggc gacggcgcca ccgcgaacc
102061 gccgaccgc cccaaaatag ccgcgcgtc gaaggaccc aggtatcccc cctgcaggcg
102121 ctgcggagga ccgcgggaa cctcatcatc atcgtccagg cgaccgcgca ccgactggct
102181 acgggccgca tcgggcccgg ggcgctgccg ggacgctcgg cgatgggatg tgggcgggc
102241 ttccgacgcg cgccgtcgtc gggctcgggg gccttcccgt cgacggcgca cgggcggctc
102301 gtcgccagcc atatcctcca gagcctctag ctgcatgtcg tcatcccgc ggaacacgc
```

```
102361 acgcaggtac ccoatgaacc ccacccatc gcccgctggc tcgtccgcca cgggcgaggc
102421 gcggggcgg gtggatgcgc gactcctgcg ccccgcgggt tcgcgagccg acatggtggc
102481 gatagacgcg ggttatcgga tgtccgctac cccccaaaaa agaaaaagac cccacagcgc
102541 ggatggaggc cagggtaggt gccgccggac ccactcgcga tgggaatgga cgggagcgac
102601 gggccggcg caaaaaacg cagtatctcc cgcgaaggct accgccgcc ccagccccg
102661 gccaaatgcg gaaacggtcc cgcgctctcg cctttatacg cgggccgccc tgcgacaca
102721 tcaccgtcc gtggtttcga atctacacga caggcccgca gacgcggcta acacaacgc
102781 cggcaaccca gaccccagtg ggttggtcga gcggtcccgt ctcctggcta gttcttccc
102841 ccaccaccaa ataatcagac gacaacccgca ggttttgtaa tgtatgtgct cgtgtttatt
102901 gtggatacga accggtgacg ggaggggaaa acccagacgg gggatgcggg tccggtcgcg
102961 cccctaccc accgtactcg tcaattccaa gggcatcggt aaacatctgc tcaaactcga
103021 agtcggccat atccagagcg ccgtaggggg cggagtcgtg ggggtaaat ccggccccg
103081 gggaatcccc gtccccaac atgtccagat cgaaatcgtc tagcgcgtcg gcatgcgcca
103141 tcgccaagtc ctcgccgtct aagtggagct cgtcccccag gctgacatcg gtcgggggg
103201 ccgtcgacag tctgcgcgtg tgtccgcgg ggagaaagga caggcgcgga gccgccagcc
103261 ccgcctcttc gggggcgtcg tcgtccggga gatcgagcag gccctcgatg gtagacccgt
103321 aattgttttt cgtacgcgcg cggctgtacg cgtgttcccg catgaccgcc tggagggcg
103381 aggtcgtgaa gctggaatac gagtccaact tgcccgaat aacaccata aagtaccag
103441 aggcgcggc ctggtgcca tgcaggtgg gagggtcgt caacggcgcc cctggctcct
103501 ccgtagccgc gctgcgcacc agcgggaggt taaggtgctc gcgaatgtgg tttagctccc
103561 gcagcggcg ggcctcgatt ggcactcccc ggacggtgag cgctccgttg acgaacatga
103621 agggctggaa cagacccgcc aactgacgcc agctctccag gtcgtaacag aggcagtcaa
103681 acaggtcggg ccgcatcatt tgctcggcgt acgcggccca taggatctcg cgggtcaaaa
103741 atagatacaa atgcaaaaac agaacacgcg ccagacgagc ggtctctcgg tagtacctgt
103801 ccgcgatcgt ggcgcgaagc atttctccca ggtgcgatc gcgtccggc atgtgcct
103861 ggcggtgcag atgccggacg ctgcgcgca ggtaccggta caggccgag cagaagttgg
103921 ccaacacggt tcgatagctc tcctcccgcg cccgtagctc ggcgtggaag aaacgagaga
103981 gcgcttcgta gtagagcccg aggccgtcgc gggtggcgg aagcgtcggg aagccacgt
```

FIGURE 16
(Continued)

```
104041 cgccgtgggc gcgaatgtcg atttgggcgc gttcggggac gtacgcgtcc cccattcca
104101 ccacatcgct gggcagcgtc gataggaatt tacactcccg gtacaggtcg gcgttggtcg
104161 gtagcgccga aaacagatcc tcgttccagg tatcgagcat ggtacatagc gcggggcccg
104221 cgctaaagcc caagtcgtcg aggagacggt taaagagggc ggcgggggg acgggcatgg
104281 gtggggaggg catgagctgg gcctggctca ggcgccccgt tgcgtacagc gggggggccg
104341 ccggggtgtt tttgggaccc ccggctgggc ggggggcgg tggcgaagcg ccgtccgcgt
104401 tcatgtcggc aaacagctcg tcgaccaaga ggtccattgg gtggggttga tacgggaaag
104461 acgacatcgg gctttgatg cgatcgtccc cgccgccca gagagtgtgg gacgccgac
104521 ggcgcgggaa gagaaaaacc cccaaacgcg ttagaggacc ggacggacct tatgggggga
104581 agtggcagc gggaacccg tccgttcccg aggaatgaca gcccgtggtc gccaccacgc
104641 atttaagcaa cccgcacggg ccgccccgta catcgtgact tcccccaca ttggctcctg
104701 tcacgtgaag gcgaaccgag ggcggctgtc caacccagcc ccgccaccc agtcccggtc
104761 ccgtcggat tgggaaacaa aggcacgcaa cgccaacacc gaatgaaccc ctgttggtgc
104821 tttattgtct gggtacggaa gttttcactc gacgggccgt ctgggcgag aagcggagcg
104881 ggctggggct cgaggtcgct cggtggggcg cgacgccgca gaacgccctc gagtcgccgt
104941 ggccgcgtcg acgtcctgca ccacgtctgg attcaccaac tcgttggcgc gctgaagcag
105001 gttttgccc tgcagaccg tcacgcggat ggtggtgatg ccaaggagtt cgttgaggtc
105061 ttcgtctgtg cgcggacgcg acatgtccca gagctggacc gccgccatcc gggcatgcat
105121 ggccgccagg cgcccgaccg cggcgcagaa gacgcgcttg ttaaagccgg ccaccggggg
105181 ggtccatggc gcgtcgggt ttggggggc ggtgctaaag tgcagctttc tggccagccc
105241 ctgcgcggt gtcttggatc gggttggcgc cgtcgacgcg gggcgtctg ggagtgcggc
105301 ggattctggc tgggccgatt tcctgccgcg ggtggtatcc gcagccggg ccgcgggc
105361 cttagtcgcc acccgctggg ttcgggggc ccgggggcg gtggtgggtg tgcgtccggc
105421 ccctccggac ccagcgggtg gcggaggtgc ccgcgcaggc cccgggccgg acaaaaccgc
105481 ccggaaacg gacgccgcg tcggggac ctcgggtgt tcgtcgtctt cggatgacga
105541 gccccgtag agggcataat ccgactcgtc gtactggacg aaacggacct cgcccctctg
105601 gcgcgagcgt gtctgtaggg cgccacggcg ggaggtgtca ggggactat cgggactcgc
105661 cataactgaa gacgggtgt agtacagatc ctcgtactca tcgcggaa ctcccgcgg
```

```
105721 acccgacttc acggagcggc gagaggtcat ggttccacga acacgctagg gtcggatgcg
105781 cggacaatta ggcctgggtc cggacggcgg gggtggtgca ggtgtggaga ggtcgagcga
105841 tagggcggc ccgggagaga agagagggtc cgcaaaaccc actggggatg cgtgagtggc
105901 cctctgtggg cggtggggga gagtcttata ggaagtgcat ataaccacaa cccatgggtc
105961 taaccaatcc ccagggccca agaaacagac acgcccaaa cggtctcggt ttccgcgagg
106021 aagggaagt cctgggacac cctccacccc caccoctcac cccacacagg gcgggttcag
106081 gcgtgcccgg cagccagtag cctctggcag atctgacaga cgtgtgcgat aatacacacg
106141 cccatcgagg ccatgcctac ataaagggc accagggccc ccggggcaga catttggca
106201 gtgttttggg tctcgcaccg cgcgccccg atcccatgc gcccgcctc ctcgccggc
106261 ggctccccgt gcgggcccgc gtctcccgtc gctaaggcga cgagcaagac aaacaacagg
106321 cccgcccgac agacccttct gggggggtcc atcgtcccta acaggaagat gagtcagtgg
106381 ggatccgggg cgatccttgt ccagccggac agcttgggtc ggggtacga tggcgactgg
106441 cacacggccg tcgctactcg cggggcgga gtcgtgcaac tgaacctggt caacaggcgc
106501 gcggtggctt ttatgccgaa ggttagcggg gactccggat gggccgtcgg gcgcgtctct
106561 ctggacctgc gaatggctat gccggctgac ttttgcgcga ttattcacgc cccgcgcta
106621 gccagcccg ggcaccacgt aatactgggt cttatcgact cggggtaccg cggaaccgtt
106681 atggccgtgg tcgtagcgcc taaaaggacg cgggaatttg cccccgggac cctgtgggtc
106741 gacgtgacgt tcctggacat cctggcgacc cccccggccc tcaccgagcc gatttccctg
106801 cggcagttcc cgcaactggc gccccccct ccaaccgggg ccgggatacg cgaagatcct
106861 tggttggagg gggcgctcgg ggccccaagc gtgactacgg ccctaccggc gcgacgccga
106921 gggcggtccc tcgtctatgc cggcgagctg acgccggttc agatggaaca cggggacgg
106981 gtacgagaag ccatcgcctt ccttccaaaa cgcgaggagg atgccggttt cgacattgtc
107041 gtccgtcgcc cggtcaccgt ccggcaaac ggcaccacgg tcgtgcagcc atccctccgc
107101 atgctccacg cggacgccgg gccgcgggcc tgtatgtgt tggggcggtc gtcgtcaac
107161 gacccgcggcc tcctggtcgt tcctacgcgc tggctccccg ggcacgtatg tgcgtttgtt
107221 gtttacaacc ttacggggt tcctgtgacc ctcgaggccg gcgtcaaggt cgcccagctc
107281 ctggttgcgg gggcggacgc tcttccttgg atcccccgg acaactttca cgggaccaaa
107341 gcgcttcgaa actaccccag gggtgttccg gactcaaccg ccgaacccag gaacccgccg
```

```
107401 ctcctggtgt ttacgaacga gtttgacgcg gaggccdccc cgagcgagcg cggaccggg
107461 ggttttggct ctaccggtar ttagcccaca gctttgggtt cgttccggc aataaaaac
107521 gtttgtatcg catcttcct gtgtgtagtt gtttatgttg gatgcctgtg ggtctatcac
107581 acccgccct ccatccaca aacacaaaac acacgggttg gatgaaaaca cgcatttatt
107641 gacccaaaac acacggagct gctcgagatg ggccagggcg aggtgcggtt gggaggctg
107701 taggtctggg aacggacacg cggggacacg attccggttt ggggtccggg agggcgtcgc
107761 cgtttcggc ggcaggcgcc agcgtaacct ccggggggcgg cgtgtggggg tgcccaagg
107821 agggcgcctc ggtcacccca atccccccg accgggttcc cccggcaacc ccgaaggcgg
107881 agaggccaag ggcccgttcg gcgatggcca catcctccat gaccacgtca ctctcggcca
107941 tgctccgaat agcctgggag acgagcacat ccgcggactt gtcagcgcc cccacggaca
108001 tgtacatctg caggatggtg gccatacacg tgtccgccag gcgccgcatc ttgtcctgat
108061 gggccgccac ggcccccgtcg atcgtggggg cctcgagccc ggggtggtgg cgcgccagtc
108121 gttctaggtt caccatgcag gcgtggtacg tgcgggccaa ggcgcggcc ttcacgaggc
108181 gtcgggtgtc gtccaggac ccaggcgt catcgagcgt gatggggcg ggaagtagcg
108241 cgttaacgac cgccagggcc tcctgcagcc gcggctccgc ctccgagggc ggaacggccg
108301 cgcggatcat ctcatattgt tcctcggggc gcgctcccca gccacatata gcccgagaa
108361 gagaagccat cgcgggcggg tactggccct tgggcgcgcg gacgcaatgg ggcaggaaga
108421 cgggaaccgc gggagaggc gggcggccgg gactcccgtg gaggtgaccg cgctttatgc
108481 gaccgacggg tgcgttatta cctcttcgat cgccctcctc acaaactctc tactggggc
108541 cgagctggtt tatatattca gctacgacgc atacacgcac gatggccgtg ctgacgggcc
108601 cacggagcaa gacaggttcg aagagagtcg ggcgctctac caagcgtcgg gcgggctaaa
108661 tggcgactcc ttccgagtaa cctttttgttt attggggacg gaagtgggtg ggacccacca
108721 ggcccgcggg cgaacccgac ccatgttcgt ctgtcgcttc gagcgagcgg acgacgtcgc
108781 cgcgctacag gacgccctgg cgcacggggac ccgctacaa ccgaccaca tgcagccac
108841 cctggacgcg gaggccacgt tcgcgatgca tgcgaacatg atcctggctc tcaccgtggc
108901 catcaacaac gccagccccc gcacggacg cgaccgcc gggcgcagt atgatcaggg
108961 cgcgtcccta cgctcgctcg tgggcgcac gtccctggga caacgcggcc ttaccacgct
109021 atacgtccac cacgaggcgc gcgtgcttgc cgcgtaccgc agggcgtatt atggaagcgc
```

FIGURE 16
(Continued)

```
109081  gcagagtccc tctggtttc ttagcaaatt cgggcggac gaaaaagcc tggtgctcac
109141  cactcggtac tacctgctc aggcccagcg tctgggggc gcggggcca cgtacgacct
109201  gcaggcatc aaggacatct gcgccaccta cgcgattccc cacgccccc gcccgacac
109261  cgtcagcgc gcgtcctga cctgtttgc cgccatcacg cggttctgtt gcacgagcca
109321  gtacgccgc ggggcgcgg cggccggtt tccgtttac gtggagcgcc gtattgcggc
109381  cgacgtccgc gagaccagtg cgctggagaa gttcataacc cacgatcgca gttgcctgcg
109441  cgtgtccgac cgtgaattca ttacgtacat ctacctggcc cattttgagt gtttcagccc
109501  cccgcgccta gccacgcatc ttgggccgt gacgacccac gacccaacc ccgggcag
109561  cacggagcag ccctcgcccc tgggcaggga ggccgtggaa caatttttt gtcacgtgcg
109621  cgcccaactg aatatcgggg agtacgtcaa acacaacgtg accccccggg agaccgtcct
109681  ggatggcgat acggccaagg cctacctgcg cgatcgcacg tacgcgcccg gggccctgac
109741  gcccgcccc gcgtattgcg gggccgtgga ctccgccacc aaaatgatgg ggcgtttggc
109801  ggacgccgaa aagctcctgg tccccgcggg gtggccgcg tttgccccg ccagtccggg
109861  ggaggacacg gcgggcggca cgccgcccs acagacstgc ggaattgtca agcgcctcct
109921  gagactggcc gccacggaac agcagggcac cacacccccg gcgatcgcgg cgcttatcg
109981  taatgcggcg gtgcagactc ccctgcccgt ctaccggata tccatggtcc ccacgggaca
110041  ggcatttgcc gcgctggcct gggacgactg ggtccgcata acgcgggacg ctgcctggc
110101  cgaagcggtc gtgtccgccg aagcggcggc gcacccgac cacggcgcgc tgggcaggcg
110161  gctcacggat cgcatccgcg cccagggccc cgtgatgccc cctgcggcc tggatgccgg
110221  gggcagatg tacgtgaatc gcaacgagat attcaacggc gcgctggcaa tcacaaacat
110281  catcctggat ctcgacatcg ccctgaagga gccgtcccc tttgccggc tccacgaggc
110341  cctgggctac tttaggcgcg gggctctggc tgcggttcag ctcctgtttc ccgcggccg
110401  cgtggacccc gacgcatatc cctgttattt tttcaaaagc gcatgtcggc ccggcccggc
110461  gtccgtgggt tccggcagcg gactggcaa cgacgacgac ggggactggt tccctgcta
110521  cgacgacgcc ggtgatgagg agtgggcgga ggaccgggc gccatggaca catcccacga
110581  tccgcggac gacgaggttg cctactttga cctgtgccac gaagtcggcc ccacggcgga
110641  acctgcgaa acggattcgc ccgtgtgttc ctgcaccgac aagatcggac tgcgggtgtg
110701  catgccgtc cccgccccgt acgtcgtcca cggttctcta acgatgcggg gggtggacg
```

FIGURE 16
(Continued)

```
110761 ggtcatccag caggcggtgc tgttggaccg agattttgtg gaggccatcg ggagctacgt
110821 aaaaaacttc ctgttgatcg atacgggagt gtacgccac ggccacagcc tgcgcttgcc
110881 gtattttgcc aaaatcgccc ccgacgggcc tgcgtgcgga aggctgctgc cagtgtttgt
110941 gatccccccc gcctgcaaag acgttccggc gtttgtcgcc gcgcacgccg accgcggcg
111001 cttccatttt cacgcccgc ccacctatct cgttccccc cgggagatcc gtgtcctgca
111061 cagcctgggt ggggactatg tgagcttctt tgaaggaag gcgtcccgca acgcgctgga
111121 acctttggg cgacgcgaga cctgacgga ggtcctgggt cggtacaacg tacagcgga
111181 tgcgggaggg acgtcgagg ggttcgcatc ggaactgctg gggcggatag tcgcgtgcat
111241 cgaaacccac tttcccgaac acgccggcga atatcaggcc gtatccgtcc ggcgggccgt
111301 cagtaaggac gactgggtcc tcctacagct agtccccgtt cgcggtaccc tgcagcaaag
111361 cctgtcgtgt ctgcgcttta agcacggccg ggcgagtcgc gccacggcgc ggacattcgt
111421 cgcgctgagc gtcggggca acaaccgcct gtgcgtgtcc ttgtgtcagc agtgctttgc
111481 cgccaaatgc gacagcaacc gcctgcacac gctgtttacc attgacgccg gtacgccatg
111541 ctcgcagtcc gttccctgca gaacctctca accgtcgtct tgataacggc gtacggcctc
111601 gtgctcgtgt ggtacaccgt cttcggtgcc agtccgctgc accgatgtat ttacgcggta
111661 cgccccaccg gcaccaacaa cgacaccgcc ctcgtgtgga tgaaatgaa ccagaccta
111721 ttgtttctgg gggcccgac gcacccccc aaggggcgt ggcgcaacca cgcccatatc
111781 tgctacgcca atcttatcgc gggtagggtc gtgcccttcc aggtccacc cgacgccatg
111841 aatcgtcgga tcatgaacgt ccacgaggca gttaactgtc tggagaccct atggtacaca
111901 cgggtgcgtc tggtggtcgt agggtggttc ctgtatctgg cgttcgtcgc cctccaccaa
111961 cgccgatgta tgtttggtgt cgtgagtccc gcccacaaga tggtggcccc ggccacctac
112021 ctcttgaact acgcaggccg catcgtatcg agcgtgttcc tgcagtaccc ctacacgaaa
112081 attacccgcc tgctctgcga gctgtcggtc cagcggcaaa acctggttca gttgtttgag
112141 acggaccgg tcacctctt gtaccaccgc ccgccatcg gggtcatcgt aggctgcgag
112201 ttgatgctac gctttgtggc cgtgggtctc atagtcggca ccgcttcat atcccggggg
112261 gcatgtgcga tcacataccc cctgtttctg accatcacca actggtgttt tgtctccacc
112321 atcggcctga cagagctgta ttgtattctg cggcggggcc cggcccccaa gaacgcagac
112381 aaggcgccg cccgggggcg atccaagggg ctgtctggcg tctgcgggcg ctgttgttcc
```

FIGURE 16
(Continued)

```
112441 atcatcctct cgggcatcgc agtgcgattg tgttatatcg ccgtggtggc cgggtggtg
112501 ctcgggcgc ttcactacga gcaggagatc cagaggcgcc tgtttgatgt atgacgtcac
112561 atccaggccg gcggaaaccg gaacggcata tgcaaattgg aaactgtcct gtcttgggc
112621 ccaccaccc gacgcgtcat atgcaaatga aaatcggtcc cccgaggcca cgtgtagcct
112681 ggatcccaac gaccccgccc atgggtccca attggccgtc ccgttaccaa gaccaaccca
112741 gccagcgtat ccacccccgc ccgggtcccc gcggaagcgg aacggtgtat gtgatatgct
112801 aattaaatac atgccacgta ttatggtgt ctgattggtc cttgtctgtg ccggaggtgg
112861 ggcggggccc ccgcccgggg ggcggaacga ggagggttt gggagagccg gcccggcac
112921 cacgggtata aggacatcca ccaccccgcc ggtggtggtg tgcagccgtg ttccaaccac
112981 ggtcacgctt ctgtgcctct cccgattcg ggcccggtcg ctcgctaccg gtgcaccacc
113041 accagaggcc atatccgaca cccagcccc gacggcagcc gacagcccgg tcatggcgac
113101 tgacattgat atgctaattg acctggcct ggacctctcc gacagcgatc tggacgagga
113161 ccccccgag ccggcggaga gccgccgcga cgacctggca tggacagca gcgggagtg
113221 ttcctcgtcg gacgaggaca tggaagaccc ccacggagag gacggaccgg agccgatact
113281 cgacgccgct cgcccggcgg tccgcccgtc tcgtccagaa gaccccggcg taccccagcac
113341 ccagacgcct cgtccgacgg agcggcaggg cccaacgat cctcaaccag cgcccacag
113401 tgtgtggtcg cgcctcgggg ccggcgacc gtcttgctcc cccgagcagc acggggcaa
113461 ggtggcccgc atccaaccc cacgacaa agcccagcct gcccgcgggcg gacgccgtgg
113521 gcgtcgcagg ggtcggggtc gcggtggtcc cgggccgcc gatggtttgt cggacccccg
113581 ccggcgtgcc ccagaacca atcgcaaccc ggggggaccc cgccccgggg cggggtggac
113641 ggacggcccc ggcgccccc atggcgaggc gtggcgcgga agtgagcagc ccgaccaccc
113701 ccgaggcccg cggacacggg gcgtgcgcca agcacccccc ccgctaatga cgctggcgat
113761 tgccccccg cccgcggacc ccgcgcccc ggccccggag cgaaaggcgc ccgccgccga
113821 caccatcgac gccaccacgc ggttggtcct gcgtccatc tccgagcgcg cgggggtcga
113881 ccgaatcagc gagagctttg gcggcagcgc acaggtcatg cacgacccct ttggggggca
113941 gccgtttccc gcgcgaata gccctgggc ccggtgttg gcgggccaag gagggccctt
114001 tgacgccgag accagacggg tctcctggga aaccttggtc gccacggcc cgagcctcta
114061 tcgcactttt gcgggcaatc ctcgggccga atcgacccgcc aaggccatgc gcgactggt
```

FIGURE 16
(Continued)

```
114121 gctgcgccaa gaaaatttca tcgaggcgct ggcctccgcc gacgagacgc tggcgtggtg
114181 caagatgtgc atccaccaca acctgccgct gcgccccag gacccatta tcgggacggc
114241 cgcggctgtg ctggataacc tcgccacgcg cctgcggccc tttctccagt gctacctgaa
114301 ggcgcgaggc ctgtgcggcc tggacgaact gtgttcgcgg cggcgtctgg cggacattaa
114361 ggacattgca tccttcgtgt ttgtcattct ggccaggctc gccaacgcg tcgagcgtgg
114421 cgtcgcggag atcgactacg cgacccttgg tgtcgggtc ggagagaaga tgcatttcta
114481 cctcccgcgg ggctgcatgg cgggcctgat cgaaatccta gacacgcacc gccaggagtg
114541 ttcgagtcgt gtctgcgagt tgacggccag tcacatcgtc gcccccgt acgtgcacgg
114601 caaatatttt tattgcaact ccctgtttta ggtacaataa aaacaaaaca tttcaaacaa
114661 atcgcccac gtgttgtcct tctttgctca tggccggcgg ggcgtgggtc acggcagatg
114721 gcggggtgg gcccggcgta cggcctgggt gggcggaggg aactaaccca acgtataaat
114781 ccgtcccgc tccaaggccg gtgtcatagt gccttagga gcttccgcc cgggcgcatc
114841 cccctttg cactatgaca gcgaccccc tcaccaacct gttcttacgg gccccggaca
114901 taaccacgt tgccccct tactgcctca acgccacctg gcaggccgaa acggccatgc
114961 acaccagcaa aactgactcc gcttgcgtgg ccgtgtggag ttacctggtc cgcgcctcct
115021 gtgagaccag cggcacaatc cactgcttt tctttgtggt atacaaggac acccaccata
115081 ccctccgct gattaccgag ctccgcaact ttgcggacct ggttaaccac ccgccggtcc
115141 tacgcaact ggaggataag cgcggggtgc ggctgcggtg tgcgcggccg tttagcgtcg
115201 ggacgattaa ggacgtctct gggtccggcg cgtcctcggc gggagagtac acgataaacg
115261 ggatcgtgta ccactgccac tgtcggtatc cgttctcaaa acatgctgg atgggggcct
115321 ccgcggccct acagcacctg cgctccatca gctccagcgg catggccgcc cgcgcggaag
115381 agcatcgacg cgtcaagatt aaaattaagg cgtgatttcc aacccccat gaatgtgt
115441 aaccccccc aaaaaataa agagccgtaa cccaaccaaa ccaggcgtgg tgtgagtttg
115501 tggacccaaa gccctcagag acaacgcgac aggccagtat ggaccgtgag actttattt
115561 attaactcac agggcgctt accgccacag gaataccaga ataatgacca cgacaatcgc
115621 gaccacccca aatacagcat ggcgcccac cacgccacaa cagccctgtc gccggtatgg
115681 ggcatgatca gacgagccgc gagccgcgcg ttgggccctg tacagctcgc gcgaattgac
115741 cctaggaggc cgccacgcgc acgagttttg cgttcgtcgc tggtcgtcgg gcaccaaagc
```

FIGURE 16
(Continued)

```
115801 ccggacggc tgttcggtcg aacgaacgga cacgacagtg gcataggttg ggggtggtc
115861 cgacatagcc tcggcgtacg tcgggaggcc cgacaagagg tcccttgtga tgtcgggtgg
115921 ggccacaagc ctggtttccg gaagaaacag ggggttgcc aataacccgc cagggccaaa
115981 actccggcc tggcgcacgt cgttcggcgc ggcgccggc gcgccgagcg gcccgctggg
116041 cggcttggcg tgagcggtcc cgctccgacg cctcgccctc tccggaggag gttggtggaa
116101 ttggcacgga cgacaggggc ccagcagagt acggtggagg tgggtccgtg ggggtgtcca
116161 gatcaataac gacaaacggc ccctcgttcc taccagacaa gctatcgtag ggggcgggg
116221 gatcaacaaa cgcgttcccc gcgctccata gacccgagtc gggttgcgcc gcctccgaag
116281 ccatggatgc gccccaaagc cacgactccc gcgcgctagg tccttgggt aagggaaaag
116341 gcctactcc ccatccaagc cagctaagtt aacgggctac gccttcgggg atgggactgg
116401 cacccggcg gatttgttg ggctggcatg cgtcgcccaa ccgagggccg cgtccacggg
116461 acgcctt tataacccg ggggtcattc ccaacgatca catgcaatct aactggctcc
116521 cctctcctcc cctctcccct ctccctctc ccctctcccc tctcccctct ccctcttag
116581 gttggggggt ggtccgacat agcctcggcg tacgtcggga ggccgacaa gaggtccctt
116641 gtgatgtcgg gtgggccac aagcctggtt tccggaagaa acagggggt tgccaagcgg
116701 ccggccgc gctcccccc ccccggggcc gtgtccttgc tttccccccg tctcccccc
116761 cctcctcctc cttctcctcc tcctcgttttt tccaaaccc gccaaccgg ccggccgg
116821 ccggccacc gccgccacc cacccaccgc gggagaccca gcccggtcc cccgttcccc
116881 ggggccgtt atctccagcg cccgtccgg cgcgccgcc ccgccgcta aacccatcc
116941 cgcccccggg aacccacata taagcccca gccacacgca agaacagaca cgcagaacgg
117001 ctgtgtttat ttaaataaac cgatgtcgga ataacaaac acaacaccc gcgacggggg
117061 gacggaggga ggggggtgac ggggggacggg aacagacaca aaaacaacc acaaaaaac
117121 agccaccccc gacaccccc accccagtct cctcgccttt tcccacccac cccacgcccc
117181 cactgagccc ggtcgatcga cgagcacccc cgccccgcc cctgccccgg cgaccccgg
117241 cccgcacgat cccgacaaca ataacaaccc caacggaaag cggcggggtg ttggggagg
117301 cgaggaacaa ccgaggggaa cggggatgg aaggacggga agtggaagtc ctgatacccc
117361 tcctacaccc ccctgccttc catcctccgg cccccccgcga gtccacccgc cggccggcta
117421 ccgagaccga acacggcggc cgccgcagcc gccgcagccg ccgccgacac cgcagagccg
```

FIGURE 16
(Continued)

```
117481 gcgcgagcac acacaagcgg cagaggcaga aaggccccga gtcattgttt atgtggccgc
117541 gggccagcag acggcccgcg acaccccca gcccgtgtgg gtatccggcc cccgccacg
117601 cgccggtcca ttaagggcgc gcgtgcccgc gagatatcaa tccgttaagt gctctgcaga
117661 cagggcacc gcgcccggaa atccattagg ccgcagacga ggaaaataaa attacatcac
117721 ctacccacgt ggtgctgtgg cctgttttg ctgcgtcatc tgagccttta taaagcggg
117781 ggcgggccg tgccgatcgc gggtggtgcg aaagactttc cgggcgcgtc cgggtgccgc
117841 ggctctccgg gccccctgc agccgggcg gccaaggggc gtcggcgaca tcctcccct
117901 aagcgcggc cggccgctgg tctgttattt gttttcccg tttcggggt ggggggggtt
117961 acggtttctg ttttttaaac ccgtctgggg tgtttttcgt tccgtcgccg ggatgtttcg
118021 ttcgttcggc ccctcacggg gcgaaggccg cgtacggccc gggacgaggg gccccgacc
118081 gcggcggtcc gggcccgtc cgggcccgct cgccggcacg cgacgcgaaa aaggccccc
118141 ggaggctttt ccgggttccc ggccggggc ctgagataaa caatcggggt tacgccaac
118201 ggccggcccc cgtggcggcc cggcccggg ccccggcgga ccaaggggc ccggccgg
118261 ggccccacaa cggccggcg catgcgctgt gttttttttt tcctcggtgt tctgccgggc
118321 tccgtagcct ttcctgttct agcttcttcc ccccccctt cttcacccc agtaccctcc
118381 tccctccctt cctccccgt tatccactc gtcgagggcg cccggtgtc gttcaacaaa
118441 gacgccgcgt ttccaggtag gttagacacc tgcttctccc caatagaggg gggggaccc
118501 aaacgacagg ggcgcccca gaggctaagg tcggccacgc cactcgcggg tgggctcgtg
118561 ttacagcaca ccagcccgtt cttttccccc cctcccaccc ttagtcagac tctgttactt
118621 accgtccga ccaccaactg cccccttatc taagggccgg ctggaagacc gccaggggt
118681 cggccggtgt cgctgtaacc cccacgcca atgaccacg tactccaaga aggcatgtgt
118741 cccaccctgc ctgtgttttt gtgcctggct ctctatgctt gggtcttact gcctggggg
118801 gggatgcgg gggaggggg gtgtggaagg aaatgcacgg cgcgtgtgta ccccccccc
118861 aaagttgttc ctaaagcgag gatatggagg agtggcgggt gccggggac gggggtgatc
118921 tctggcacgc gggggggaa gggtcggggg agggggggat ggggtaccgg cccacctggc
118981 cgacgcgggt gcgcgtgcct ttgcacacca accccacgtc cccggcggt ctctaagaag
119041 caccgcccc cctccttcat accaccgagc atgcctgggt gtgggttggt aaccaacacg
119101 cccatccct cgtatcctgt gattctctgg ctgcaccgca ttcttgttct ataactatgt
```

FIGURE 16
(Continued)

```
119161 tcctgtttct gtctcccccc caccoctccg ccccacdacc caacaccoac gtctgtggtg
119221 tggccgaccc ccttttgggc gcccgtcca gccaccactc ccgtcctttg ttgcccata
119281 gtgtagttaa cccccccccc gcccttgtg ggggccagag gccaggtcag tccggcgcgg
119341 caggcgctcg cggaaactta acacccacac ccagccact gtggttctgg ctccatgcca
119401 gtggcaggat gcttcgggg atggtggtc aggcagcccg ggccgcggct ctgtggttaa
119461 caccagagcc tgcccaacat ggcaccccca ctcccacgca ccccactcc cacgcaccc
119521 cactcccacg caccccact cccacgcacc cccactccca cgcaccccca ctcccacgca
119581 ccccactcc cacgcacccc cactcccacg caccccact cccacgcacc cccactccca
119641 cgcaccccca ctcccacgca ccccactcc cacgcacccc cactcccacg caccccaag
119701 atccatccaa cacagacagg gaaagatac aaagtaaac ctttatttcc caatagacag
119761 caaaatccc ctgagttttt tattagggcc aacactaaag accogctggt gtgtggtgcc
119821 cgtgtcttc acttcccct cccgacacg gattggctgg tgtagtggc gcggccagag
119881 accacccagc acccgacccc cctcccacaa aacacggggg ggtccctta ttgttttccc
119941 tcgtcccggg tcgacgcccc ctgctcccg gaccaaggt gcggagaccg caggctggg
120001 aagtccaggg cgccactag ggtgcccgg tcgaacagca tgttcccac gggggtcatc
120061 cagaggctgt tccactccga cgcgggggcc gtcgggtact cggggggcat cacgtggtta
120121 cccgcggtct cggggagcag ggtgcggcgg ctccagccgg ggaccgcggc ccgcagccgg
120181 gtcgccatgt ttccgtctg gtccaccagg accacgtacg ccccgatgtt cccgtctcc
120241 atgtccagga tgggcaggca gtccccgtg atagtcttgt tcacgtaagg cgacagggcg
120301 accacgctag agaccccga gatgggcagg tagcgcgtga ggccgcccgc ggggacggcc
120361 ccggaagtct ccgcgtggcg cgtcttccgg gcacacttcc tggccccg cggcccagaa
120421 gcagcgcggg ggccgaggga ggtttcctct tgtctccctc ccagggcacc gacggcccg
120481 cccgaggagg cggaagcgga ggaggacgcg gccccggcgg cggaagaggc ggccccgcg
120541 ggggtcgggg ccgaggagga agaggcagag gaggaagagg cggaggcgc cgaggacgtc
120601 aggggggtcc cagggccacc ctggacgcgc ccccccggcc ctgagtcgga ggggggtgc
120661 gtcggcgccc tcttggcccc tgccggcgcg agggggggac gcgtggactg gggggagggg
120721 ttttcctggc ccgaccgcg cctcttcctc ggacgcaccg ccgcctcctg ctcgacagag
120781 acggggagg ggagcgggc ggcgccggag ggggtgcggc cgcgggaggg cccgtgccca
```

```
120841 ccctccacgc ccggcccccc cgagccgcgg gccaccgtcg cacgcgccg gcacagactc
120901 tgttcttggt tcgggcctg agccagggac gagtgcgact ggggcacacg gcgcgcgtcc
120961 gcgggcggg cggccggctc cgcccgggg gccggggcgc ggggccggg cccggaggc
121021 gggctcgca cgcacggggc caggccgcg cggggcgcg cgggtcccga cgcggccgag
121081 gacgcggggg gccggggcg gggggcgag ccggcatgg gcgccgcggg gggctgtgg
121141 ggagaggccg gggggagtc gctgatcact atggggtctc tgttgtttgc aaggggggcg
121201 ggtctgttga caagggggcc cgtccggcc ctcggccgcc ccgcctccgc ttcaacaacc
121261 ccaacccaa cccaacccc cccggagggg ccagacgccc cccgcggcgc cgcggctcgc
121321 gactggcggg agccgccgcc gccgctgctg ttggtggtgg tgttggtgtt actgctgccg
121381 tgtggccga tgggcgcga gggggcgct gtccgagccg cggccggctg ggggctgcg
121441 ttagacgccc cgcccgtcac gggggcgcg gcggtgcctc tgcgtggggg ggcgcgggc
121501 gtccggcggg gggcgggcgg gacgtagtct gctgcaagag acaacggggg gcgcgatcag
121561 gttacgcccc ctccccggcc cgcccttcc tcgcccgccc gccattcct cctcctcct
121621 cctcccacag ggtcttgcc gccccccgcc tcacgtcgt ccaggtcgtc gtcatcctcg
121681 tccgtggtgg gctccgggtg ggtgggcgac agggccctca ccgtgtgccc cccagggtc
121741 aggtaccgcg gggcgaaccg ctgattgccc gtccagataa agtccacggc cgtgcccgcc
121801 ctgacggcct cctcggcctc catgcgggtc tgggggtcgt tcacgatcgg gatggtgctg
121861 aacgaccgc tgggcgtcac gcccactatc aggtacacca gcttggcgtt gcacagcggg
121921 caggtgttgc gcaattgcat ccaggttttc atgcacggga tgcagaagcg gtgcatgcac
121981 gggaaggtgt cgcagcgcag gtgggcgcg atctcatccg tgcacacggc gcacacgtcg
122041 ccctcgtcgc tccccccgtc ctctcgaggg ggggcgcccc cgcaactgcc gcggtcttcc
122101 tcgcggggg ggctccccc cagacccgcc cctccatcca cgcctgcgg cccagcaagc
122161 cccgtctcga acagttccgt gtccgtgctg tccgctcgg aggcggagtc gtcgtcatgg
122221 tggtcggcgt cccccgccc ccccacttcg gtatccgcct cagagtcgct gctgtccggc
122281 aggtctcggt cgcagggaaa caccaagaca tccggggcgg gctaagggga aaaaagggggg
122341 gcgggtaaga atgggggggg atttccagcg tcaatcagcg cccacgagtt ccccctctcc
122401 cccccgcct cacaaagtcc tgcccccctg ctggcctcgg aagagggggg agaaagggggt
122461 ctgcaaccaa aggtggtctg ggtccgtcct ttggatcccg accctcttc ttccctcttc
```

FIGURE 16
(Continued)

```
122521 tccgccctc cagacgcacc ggagtcgggg gtcccacggc gtccccaaa tatggcgggc
122581 ggctcctccc cacccccta gatgcgtgtg agtaagggg gcctgcgtat gagtcagtgg
122641 ggaccacgcc cccaacacgg cgacccggt ccctgtgtgt tgttgtggg ggcgtgtctc
122701 tgtgtatgag tcaggggtc ccacggcgac cccgggccct gcgtctgagt caaaggggcc
122761 atgtgtatgt gttggggtc tgtatatata aagtcagggg gtcacatggc gaccccaac
122821 agggcgaccc cggtccctgt atataggg tcagggggtt ccgcgcccc taacatggcg
122881 ccccggtcc ctgtatatat agtgtcacgg ggttccacgc ccctaacat ggcgcccaa
122941 catggcgccc ggctcccgtg tatgagtggg ggtccccaa catggggcc ggttccaggg
123001 taagggtcgg gggtcccca acatggcgcc cccaatatg gcgcccaga catggcgccc
123061 ggccctcac ctcgcgctgg gggcggccct caggccggcg ggtactcgct ccggggcggg
123121 gctccatggg ggtcgtatgc ggctggaggg tgcggacgg agggtccctg ggggtcgcaa
123181 cgtaggcggg gcttctgtgg tgatgcggag aggggggcggc ccgagtctgc ctggctgctg
123241 cgtctcgctc cgagtgccga ggtcaaatg cgaccagacc gtcgggccag ggctaactta
123301 taccccacgc cttccctc cccaaaggg cggcagtgac gattcccca atggccgcgc
123361 gtcccagggg aggcaggccc accgcgggc ggccccgtcc ccggggacca acccggcgcc
123421 cccaaagaat atcattagca tgcacggccc ggcccccgat ttggggacc aaccggtgt
123481 ccccaaaga acccattag catgccctc ccgccgacg aacaggggct tggcctgcgt
123541 cggtgccctg gggcttcccg cctccccgaa gaaactcatt accataccg gaacccagg
123601 ggaccaatgc gggttcattg agcgaccgc gggccaatgc gcgaggggcc gtgtgttccg
123661 ccaaaaagc aattagcata accccggaacc ccaggggagt ggttacgcgc ggcgcgggag
123721 gcggggaata ccggggttgc ccattaaggg ccgcgggaat tgccggaagc gggaagggcg
123781 gccggggccg cccattaatg agtttctaat taccatacgg ggaagcggaa caaggcctct
123841 tgcaagtttt taattaccat accgggaagt gggcggcccg gcccattggg cggtaactcc
123901 cgccaatgg gccgggcccc gaagactcgg cggacgctgg ttggccgggc cccgccgcgc
123961 tgcgggccgc cgattggaca gtcccgcccc cgaggcgggc ccgccttggg ggcggaccgg
124021 ctccagcgt atatatgcgc ggctcctgcc atcgtctctc cggagagcgg cttggtgcgg
124081 agctccgggg agctccgcgg aagaccagg cgcctcgggt gtaacgttag accgagttcg
124141 ccgggcggc tcgcgggcc agggccgggg cacggccctc gggccccagg cacggcccga
```

FIGURE 16
(Continued)

```
124201 tgaccgcctc ggcctccgcc accggcgcc ggaaccgagc ccggtcggcc cgctcgcggg
124261 cccacgagcc gcggcgcgcc aggcgggcgg ccgaggccca gaccaccagg tggcgcaccc
124321 ggacgtgggg cgagaagcgc accgcgcgg gggtcgcggg ggtcgcgggg gtcgcggggg
124381 tgtcggggt cgcggggtc gcggggtcg cggggtcgc ggggggctcc ggcgcccct
124441 ccccgccgc ggtcgcagg cgcaggcgcg ccaggtgctc cgcggtgacg cgcaggcgga
124501 gggcgaggcg cggcggaagg cggaagggggc gcgaggggg gtgggagggg tcagcccgc
124561 ccccggggcc cacgccgggc ggtggggacc ggggccgggg ggcggcggcg gtgggcgggg
124621 cctctggcgc cggctcgggc gggggctgt ccggccagtc gtcgtcatcg tcgtcgtcgg
124681 acgcggactc gggaacgtgg agccactggc gcagcagcag cgaacaagaa ggcgggggcc
124741 caccggcggg gggcggcgg gggcggccg cgggcgcgct cctgaccgcg ggttccgagt
124801 tgggcgtgga ggttacctgg gactgtcgg ttgggacggc gcccgtgggc ccgggcggcc
124861 ggggcggcg ggggccgcga tggcggcggc ggcgggccat ggagacagag agcgtgccgg
124921 ggtggtagag tttgacaggc aagcatgtgc gtgcagaggc gagtagtgct tgcctgtcta
124981 actcgctagt ctcggccgcg gggggccgg gctgcccgcc gccgcgcttt aaagggccgc
125041 gcgcgaccc cgggggtgt gtttcggggg ggcccgtttt tggggtctgg ccgctcctcc
125101 ccgctcctc ccgtctgtg ggtgggcta ctccccgct cctccccgc tactccacg
125161 ctcctcccg tctgtgggtg gggctcctcc ccgctcccg cggccccgcc ccccatgcc
125221 gccgcgcg cgcacgccgc ccggaccgcc gcccgccttt tttgcgcgcc gccccgcgcg
125281 cggggggccc gggctgccac aggtgtaaca acaccaacag aacaccaaca gcacggcgca
125341 ccggcgactc cggttcctca tccacacgtc acgtcatcca acacacctgc ccaacaacac
125401 aactcacagc gacaactcac cgcgcaacaa ctcctgttcc tcatccacac gtcacggagc
125461 accccccgct cctccagacg tcccccagcg caacagccg ctcctgtcac acaccacagc
125521 ccagccctc ccagccccca gccctccca gcccagccc tcccagccc cagccctccc
125581 cagcccagc cctcccagc ccagccctc ccagcccca gcctcccca gcccagccc
125641 tcccagccc cagcctccc cagcccagc cctcccagc ccagccctc ccagcccca
125701 gccctcccca gccgcgtccc gcgctccctc gggggggttc gggcatctct acctcagtgc
125761 cgccaatctc aggtcagaga tccaaaccct ccggggggcg ccgcgcacca ccaccgcccc
125821 tgcccctc ccgcccctcg cccctcccg cccctcgccc cctcccgccc ctcgcccct
```

FIGURE 16
(Continued)

```
125881 cccgccctc gccacctccc gccctcgc ccctccgcc cctcgcccc tcccgccct
125941 cgccactcc cgccctcga ataaacaacg ctactgcaaa acttaatcag gtcgttgccg
126001 tttattgcgt cttcgggttt cacaagcgcc ccgcccgtc ccggccgtt acagcaccc
126061 gtcccctcg aacgcgccgc cgtcgtcttc gtcccaggcg ccttcccagt ccacaacgtc
126121 ccgtcgcggg ggcgtggcca agcccgcctc cgccccagc acctccacgg cccccgccgc
126181 cgccagcacg gtgccgctgc ggcccgtggc cgaggccag cgaatcccgg gcggcgccgg
126241 cggcagggcc cccgggccgt cgtcgtcgcc gcgcagcacc agcggggggg cgtcgtcgtc
126301 gggctccagc agggcgcggg cgcaaaagtc cctccgcggc ccgcgccacc gggccgggcc
126361 ggcgcgcacc gcctcgcgcc ccagcgccac gtacacgggc cgcagcggcg cgcccaggcc
126421 ccagcgcgcg caggcgcggt gcgagtgggc ctcctcctcg cagaagtccg gcgcgccggg
126481 cgtcatggcg tcggtggtcc ccgaggccgc cgccccggcg tccagcgccg gcagcacggc
126541 ccggcggtac tcgcgcgggg acatgggcac cggcgtgtcc ggcgcgaagc gcgtgcgcac
126601 gcggtagcgc acgttgccgc cgcgcgcacag gcgcagcggc ggcgcgtcgg ggtacaggcg
126661 cgcgtgcgcg gcctccacgc gcgcgaagac ccccgggccg aacacgcggc ccgaggccag
126721 cacccgtgcgg cgcaggtcgc gcgccgccgg ccagcgcacg gcgcactgca cggcgggcag
126781 caggtcgcac gccaggtagg cgtgctgccg cgacaccgcg ggccgtcgg cgggccagtc
126841 gcaggcgcgc acggtgttga ccacgatgag ccgccggtcg ccggcgtgg cgagcagccc
126901 cagaaactcc acggcccgg cgaaggcag gtcccgcgtg gacagcagca gcacgccctg
126961 cgccgccagc gccgacacgt cggggcgcc ggtccagttg cccgcccagg cggccgtgtc
127021 cggccagcac agccggttgg ccagggccgc cagcaggcag gacagcccgc cgcgctcggc
127081 ggaccactcd ggcggccccc ccgaggcccc gccgccggcc aggtcctcgc ccggcagcgg
127141 cgagtacagc accaccacgc gcacgtcctc ggggtcggg atctggcgca tccaggccgc
127201 catgcggcgc agcgggcccg aggcgcgcag ggggccaaag aggcggcccc cggcggcccc
127261 gtggggtgg gggttctagt cgtcgtcgcc gcagccgcac gcggcctggg cggcggggc
127321 gggcccggcg caccgcgcgg cgatcgaggc cagggccgc gggtcaaaca tgagggccgg
127381 tcgccagggg acgggaacac gcgggtggtc cgtgagctcg gcacggcgc gcggggagca
127441 gtaggcctcc aggggcggcgg ccgcgggcgc cgccgtgtgg ctgggccccg ggggctgccg
127501 ccgccagccg ccagggggt cggggccctc ggcgggccgg cgcgacagcg ccacggggcg
```

```
127561 cgggcggcc tgcgccgcgg cggcccgggg cgccgcggc tgggcggggg cgggctcggg
127621 ccccggggc gtggagggg gcgcggcgc ggggagggg gcgcggcgt ccgagccggg
127681 gggtccgcg ccgctcttct tcgtcttcgg gggtcgcggg ccgccgcctc cgggcggccg
127741 ggccgggccg ggactcttgc gcttgagccc ctcccgcggc gcggcggagg cggcggccgc
127801 gacccccgaa gacgaagaag agcggcgcgg acccgccgcc agcaggggc gcaggctctg
127861 gttctcaaac agcaggtccg cggcggcggc ggccgcggag ctcggcaggc gcgggtcccg
127921 cggcagcgcg ggacccaggg cccggcgac caggctcacg gcgcgcacgg cggccacggc
127981 ggcctcgctg ccgccggcca agcgcaggtc cctgcgcagg cgcatgagca ccagcgcgtc
128041 gcgcacgaac cgcagctcgc gcagccacgc gcgcaggcgg ggcgcgtcgg cgtgcggcgg
128101 cggcagggaa gcggggcccg cgggtccctc cggccgcggg gggctggcgg gccgggcccc
128161 ggccagcccc gggacggccg ccaggtcgcc gtcgaagccc tcggccagcg cctccaggat
128221 cccgcggcag gcggccaggc actccacggc cacgcggccg gcctgggcgc ggcgcccggc
128281 gtcgtcgtcg gcgtcggcgt ggcgggcggc gtcggggtcg tcgccccccg cggggggaggc
128341 gggcgcggcg gacagccgcc ccaggggggc gaggatcccc gcggcgccgt acccggcggg
128401 caccgcgcgc tcgccggtg cggcggcggc ggcgacgacg gcggcggcga cccctcgtc
128461 atctgcgccg gcgccgggc tcccgcggc cccgtcagc gcagcgttct cgcgcgccaa
128521 caggggcgcg taggcgcggc gcaggctggt cagcaggaag cccttctgcg cgcggtcgta
128581 tcggcggctc atggccacgg cggccgccgc gtgagccagg cccagccga agcggccggc
128641 cgccatggcg tagcccaggt ggggcacggc ccgcgccacg ctgccggtga tgaaggagct
128701 gctgttgcgc gcgggcgccg agatccggaa gcaggcctgg tccagcgcca cgtccccggg
128761 gaccacgcgc gggttctgga gccacccat ggcctccgcg tcggggtgt acagcagccg
128821 cgtgatcagg gcgtactgct gcgcggcgtc gcccagctcg ggcgcccaca cggccgcgg
128881 ggcgcccgag gcctcgaacc ggcgtcgcgc ctcctccgcc tcgggcgccc cccagaggcc
128941 cgggcggctg tcgcccaggc cgccgtacag caccccgccc ggggcggg gcccggcgcc
129001 gggccacggc tccccgatga cgtacccgtc gcgatagcgc gcgtagaagg cgcggaggc
129061 cgcgtcggcg tccagctcga cccgccgggg ctgcccggcc gtgaagcggc ccgtggcgtc
129121 gcggccggcc accgccgcgc gggccggcg gcgctcgatg cggcccgcgg aggccgcggg
129181 ggtcctcgcc gctgccgggg gcttgggcgc ggcctcggag agggggggtg gcccgggcgg
```

```
129241 gggcggcgtc cgcccggggg attccggcga cgcgctcgac ggacccgcc cgacggccg
129301 cgcctcgcgt gcgtggtcgg acgcgtcgtt gccgtcgtcg tcctcgtcct cgtcggacga
129361 cgaggacgaa gaggatgcgg acgacgagga cgaggacccg gagtccgacg aggtcgatga
129421 cgccgatggc cgccgccggc cgtgacgacg tctctgcgg ggctgggccg gcgggcgcgg
129481 cgacaggcgg tccgtggggt ccggatacgc gccgcgtagc gggcctccc gtgcgcggcc
129541 ccggccggg gccggtagc cggcggcgtc ggctgcgtcg tcgtactcgt cccgtcatc
129601 gtcgtcggct cgaaggcgg gggtccgggg cggcgaggcc gcgggtcgg ggtcgggat
129661 cgtcggacg gcctcctcta ccatggagg cagcagggcc agctgtcgcg gcgagacggc
129721 gtcccggcg tcctcgccgg cgtcggtgcc cgccgcgggg gccctccgt cccgcgggc
129781 gtcgtcgagg tcgtgggggt ggtcggagtc gtggtcgggg tcgtcccgc cctcctccgt
129841 ctccgcgccc caccgaggg cccccgctc gtcgcggtct gggctcgggg tgggcggcgg
129901 cccgtcggtg gggcccgggg agcggggcg ctgttgttc tccgacgcca tcgccgatgc
129961 gggcgatcc tccggggata cgactgcgac ggcggacgta gcacggtagg tcacctacgg
130021 actctcgatg gggaggggc gagacccacg gaccccgacg accccgccg tcgacgcgga
130081 actagcgcgg aacggtcgat gcttgggtgg gaaaaaggac agggacggcc gatcccctc
130141 ccgcgttcg tccgcgtatc ggcgtcccgg cgcggcgagc gtctgacggt ctgtctctgg
130201 cggtcccgcg tcgggtcgtg gatccgtgtc ggcagccgcg ctccgtgtgg acgatcgggg
130261 cgtcctcggg ctcatatagt cccagggcc ggcgggaagg agagcagcg gaggccgccg
130321 gccccccgcc cccacggcgg gcccgcccg aacggaattc cattatgcac gacccccgcc
130381 cgacgccggc acgccggggg cccgtggccg cggccgttg gtcgaacccc cggccccgcc
130441 catccgcgcc atctgccatg ggcgggcga tagggcgggt gggcccgcgc ccgcccagc
130501 atggcatctc attaccgccc gatccggcgg tttccgcttc cgttccgcat gctaacgagg
130561 aacggcagg gggcggggcc cgggtcccga cttcccggtt cggcggtaat gagatacgag
130621 cccccgcgcg ccgttggacg tccccgggcc ccaggtcccg ccccgcggac gccgggacca
130681 acggacggc gggcggacca agggccgccc gccttgccgc cccccattg gccggcgggc
130741 gggaccgccc caaggggcg gggccgccgg gtaaagaag tgagaacgcg aagcgttcgc
130801 acttcgtccc aatatatata tattattagg gcgaagtgcg agcactggcg ccgtgcccga
130861 ctccgcgccg gcccgggggg cgggccgggg cggcggggg cgggtctctc cggcgcacat
```

FIGURE 16
(Continued)

```
130921 aaaggcccgg cgcgaccgac gcccgcagac ggcgccggcc acgaacgacg ggagctgctg
130981 cggagcacgc ggaccgggag cgggactcgc agagggccgt cggagcggac ggcgtcggca
131041 tcgcgacgcc ccggctcggg atcgggatcg catcggaaag ggacacgcgg aaagacccac
131101 ccaccccacc cacgaaacac aggggacgca ccccggggc ctccgacgac agaaacccac
131161 cggtccgcct ttttgcacgg gtaagcacct tgggtgggcg gaggagggcg gaggaggggg
131221 gacgcggggg cggaggaggg gggacgcggg ggcggaggag gggggacgcg ggggcggagg
131281 aggggggacg cggggcgga ggaggggggct caccccgcgtt cgtgccttcc cgcaggagga
131341 acgtcctcgt cgaggcgacc ggcggcgacc gttgcgtgga ccgcttcctg ctcgtcgggg
131401 cgacgggcgg cgaccgttgc gtggaccgct tcctgctcgt cgggcgacc ggcggcgacc
131461 gttgcgtgga ccgcttcctg ctcgtcgggg ggggggggg gaagccactg tggtcctccg
131521 ggacgttttc tggatggccg acattcccc aggcgctttt gcgccttgtg taaagcgcg
131581 gcgtcccgct ctccgatccc cgcccctggg cacgcgcaag cgcaagcgcc ctgcccgccc
131641 cctctcatcg gagtctgagg tcgaaacgga tacagccttg gagtctgagg tcgaatccga
131701 gacagaatcg gattcgaccg agtctgggga ccaggaggaa gccccccgca tcggtggccg
131761 tagggccccc cggaggcttg gggggcggtt ttttctggac atgtcggcgg aatccaccac
131821 ggggacggaa acggatacgg cggtgtcgga cgaccccgac gacacgtccg actggtctta
131881 tgacgacatt ccccccacgac ccaagcgggc ccgggtaaac ctgcggtca cgagctctcc
131941 cgatcggcgg gatggggtta ttttcctaa gatggggcgg gtccggtcta ccgggaaaac
132001 gcagccccgg gcccaaccc cgtcggcccc aagcccaaat gcaatgctac ggcgctcggt
132061 gcgccaggcc cagaggcgga gcagcgcacg atggaccccc gacctgggct acatgcgcca
132121 gtgtatcaat cagctgtttc gggtcctgcg ggtcgcacgg gacccccacg gcagtgccaa
132181 ccgcctgcgc cacctgatac gcgactgtta cctgatggga tactgccgag cccgtctggc
132241 cccgcgcacg tggtgccgct tgctgcaggt gtccggcgga acctggggca tgcacctgcg
132301 caacaccata cgggaggtgg aggctcgatt cgacgccacc gcggaacccg tgtgcaaact
132361 tccttgtttg gaggccagac ggtacggccc ggagtgtgat cttagtaatc tcgagattca
132421 tcttcagcgcg agaagcgatg atgaaatctc cgatgccacc gatctggagg ccgccggttc
132481 ggaccacacg ctgcgtcccc agtccgacac ggaggatgcc ccctccccg ttacgctgga
132541 aaccccagaa cccgcgggt cctcgctgt gcgtctggag gatgagtttg gggagtttga
```

FIGURE 16
(Continued)

```
132601 ctggacccc caggagggct ccagccctg gctgtctgcg gtcgtggccg ataccagctc
132661 cgtggaacgc ccgggcccat ccgattctgg ggcgggtcgc gccgcagaag accgcaagtg
132721 tctggacggc tgccggaaaa tgcgcttctc cacegcctgc ccctatccgt gtagcgacac
132781 gtttctcgg ccgtgagtcc ggtcgcccg acccctttgt atgtcaccaa aataaagac
132841 caaaatcaaa gcgtttgtcc cagcgtctta atggcgggaa ggcggagag aacagacca
132901 cgcggacatg ggggtgttt ggggtttat tgcaccggg gctaaaggg tggtaacggg
132961 atagcagatg tgaggaagtc ggggccgttc gccgcgaacg gcgatcagag ggtcagtttc
133021 ttgcggacca cggaccggcg atgtgggttg ctcgtctggg acctcgggca tgcccatada
133081 cgcacaacac ggacgccgca ccggatggga cgtcgtaagg gggcctgggg tagctggtg
133141 gggtttgtgc agagcaatca ggaccgcag ccagcgcata caatcgcgct cccgtccgtt
133201 tgtcccgggt agtaccagc cgtactggta ttcgtaccgg ctgagcaggg tctccagggg
133261 gtggttgggg gccgcggga acgggtcca cgccacggtc cactcgggca aaaccgagt
133321 cggcacggcc cacggttctc ccaccacgc gtctggggtc ttgatggcga taaatcttac
133381 cccgagccgg atttttggg cgtattcgag aaacggcaca cacagatccg ccgcgcctac
133441 caccacaag tggtagatgc gaggggggct ggtggtct cggtgcagca gtcggaagca
133501 cgccacggcg tccacgacct cggtgctctc caaggggctg tcctccgcaa acaggcccgt
133561 ggtggtgttt ggggggcagc gacaggacct agtgcgcacg atcgggcggg tgggtttggg
133621 taagtccatc agcggctcgg ccaaccgtcg aaggttggcc ggacgaacga cgaccgggt
133681 accagggggt tctgatgcca aaatgcggca ctgcctaagc aggaagctcc acagggcggg
133741 gcttgcgtcg acggaagtcc ggggcagggc gttgttctgg tcaaggaggg tcattacgtt
133801 gacgacaaca acgccatgt tggtatatta caggccgtg tccgatttgg ggcacttgca
133861 gatttgtaag gccatgcacg gcggggagac aggccgacgc ggggggctgct ctaaaaattt
133921 aagggccta cggtccacag accogccttc ccgggggggg ggcccttgga gcgaccggca
133981 gcgtaggcgt ccgggggagg ggaggtgat ttacgggggg gtaggtcagg gggtgggtcg
134041 tcaaactgcc gctccttaaa acccagggc ccgtcgttcg gggtgctcgt tggttggcac
134101 tcacggtgcg gcgaatggcc tgtcgtaagt tttgtcgcgt ttacggggga cagggcagga
134161 ggaaggagga ggccgtcccg ccggagacaa agccgtcccg ggtgtttcct catggccct
134221 tttataccc agccgaggac gtgtgcctgg actcccgcc ccggagacc cccaaacctt
```

FIGURE 16
(Continued)

```
134281 cccacaccac accacccagc gaggccgagc gcctgtttca tctgcaggag atccttgccc
134341 agatgtacgg aaaccaggac tacccatag aggacgaccc cagcgcggat gccgcggacg
134401 atgtcgacga ggacgcccg gacgacgtgg cctatccgga ggaatacgca gaggagcttt
134461 ttctgcccgg ggacgcgacc ggtccctta tggggccaa cgaccacatc cctccccgt
134521 gtggcgcatc tccccggt atacgacgac gcagccggga tgagattggg gccacgggat
134581 ttaccgcgga agagctggac gccatggaca gggaggcggc tcgagccatc agccgcggcg
134641 gcagccccc ctcgaccatg gccaagctgg tgactggcat gggctttacg atccaggag
134701 cgctcacccc aggatcggag gggtgtgtct ttgatagcag ccacccagat tacccccaac
134761 gggtaatcgt gaaggcgggg tggtacacga gcacgagcca cgaggcgcga ctgctgaggc
134821 gactggacca cccgcgatc ctgccctcc tggacctgca tgtcgtctcc ggggtcacgt
134881 gtctggtcct ccccaagtac caggccgacc tgtataccta tctgagtagg cgcctgaacc
134941 cgctgggacg cccgcagatc gcagcggtct ccggcagct ctaagcgcc gtgactaca
135001 ttcaccgcca gggcattatc caccgcgaca ttaagaccga aatatttt attaacaccc
135061 ccgaggacat ttgctggggg gactttggtg ccgcgtgctt cgtgcaggt tcccgatcaa
135121 gcccttccc ctacggaatc gccgaaccca tcgacaccaa cgccccgag gtcctggccg
135181 gggatccgta taccacgacc gtcgacattt ggagcgccgg tctggtgatc ttcgagactg
135241 ccgtccacaa cgcgtccttg ttctcggccc ccgcggccc caaaggggc ccgtgtgaca
135301 gtcagatcac ccgcatcatc cgacaggccc aggtccacgt tgacgagttt tcccgcatc
135361 cagaatcgcg cctcacctcg cgctaccgct cccgcgcggc cgggaacaat cgccgcctt
135421 acaccgacc ggcctggacc cgctactaca agatggacat agacgtcgaa tatctggttt
135481 gcaaagccct caccttcgac ggcgcgctta gcccagcgc cgcagagctg cttttgtttgc
135541 cgctgtttca acagaaatga ccgcccccgg gggcggtgc tgtttgcggg ttggcacaaa
135601 aagacccga ccccgtctg tggtgttttt ggcatcatgt cgccgggcgc catgcgtgcc
135661 gttgttccca ttatcccatt cctttggtt cttgtcggtg tatcggggt tccaccaac
135721 gtatcctcca acacccaacc ccaactccag accaccggtc gtccctcgca tgaagcccc
135781 aacatgaccc agaccggcac caccgactct cccaccgcca tcagccttac cacgcccgac
135841 cacacacccc ccatgccaag tatcggactg gaggaggagg aggaagagga ggaggggcc
135901 ggggatggcg aacatcttaa ggggggagat gggacccgtg acaccctacc ccagtccccg
```

```
135961 ggtccagccg tcccgttggc cggggatgac gagaaggaca aaccaaccg tccgtagtc
136021 ccaccccg gtcccaacaa ctccccgcg cgcccgaga ccagtcgacc gaagacacc
136081 cccaccagta tcgggccgct ggcaactcga ccacgacc aactccctc aaaggggcga
136141 ccttggttc cgacgcctca acataccccg ctgttctcgt tcctcactgc ctccccgcc
136201 ctggacaccc tcttcgtcgt cagcaccgtc atccacacct tatcgttttt gtgtattggt
136261 gcgatggcga aacacctgtg tggcggttgg tccagacgcg ggcgacgcac acacctagc
136321 gtgcgttacg tgtgcctgcc gtccgaacgc gggtagggta tggggcgggg gatggggaga
136381 gcccacatgc ggaaagcaag aacaataaag gcggtggtat ctagttgata tgcatctctg
136441 ggtgttttg gggtgtggcg gacgcgggc ggtcattgga cggggtgcag ttaaatacat
136501 gccgggacc catgaagcat gcgcgacttc cgggcctcgg aacccaccg aaacggccaa
136561 cggacgtctg agccaggcct ggctatccgg agaaacagca cacgacttgg cgttctgtgt
136621 gtcgcgatgt ctctgcgcgc agtctggcat ctggggcttt tgggaagcct cgtggggct
136681 gttcttgccg ccacccatcg gggacctgcg gccaacacaa cggaccctt aacgcaagcc
136741 ccagtgtccc ctcacccag ccctgggg ggctttgccg tcccctcgt agtcggtggg
136801 ctgtcgccg tagtcctggg gcgggcgtgt ctgcttgagc tcctgcgtcg tacgtgccgc
136861 gggtgggggc gttaccatcc ctacatggac ccagtcgtcg tataattccc cccccctt
136921 ctccgcatgg gtgatgtcgg gtccaaactc cgacaccac cagctggcat ggtataaatc
136981 acgggtgcgc cccccaaacc atgtccggca gggggatggg ggggcgaatg cggagggcac
137041 ccaacaacac cgggctaacc aggaaatccg tggccccggc ccccaataaa gatcgcggta
137101 gccggccgt gtgacactat cgtccatacc gaccacaccg acgaatcccc taaggggggag
137161 gggccatttt acgaggagga gggtataaa aaagtctgtc tttaaaagc agggggttagg
137221 gagttgttcg gtcataagct tcagcgcgaa cgaccaacta ccccgatcat cagttatcct
137281 taaggtctct tttgtgtggt gcgttccggt atggggggg ctgccgccag gttgggggcc
137341 gtgattttgt ttgtcgtcat agtgggcctc catgggtcc gcggcaaata tgccttggcg
137401 gatgcctctc tcaagatggc cgacaccaat cgtttcgcg gcaaagacct tccggtcctg
137461 gaccagctga ccgaccctcc ggggtccgg cgcgtgtacc acatccaggc gggcctaccg
137521 gaccgttcc agcccccag cctcccgatc acggtttact acgccgtgtt ggagcgcgcc
137581 tgccgcagcg tgctcctaaa cgcaccgtcg gaggcctccc agattgtccg cggggcctcc
```

FIGURE 16
(Continued)

```
137641 gaagacgtcc ggaaacaacc ctacaacctg accatcgctt ggtttggat gggaggcaac
137701 tgtgctatcc ccatcacggt catggagtac accgaatgct cctacaacaa gtctctgggg
137761 gcctgtccca tccgaacgca gccccgctgg aactactatg acagcttcag cgccgtcagc
137821 gaggataacc tggggttcct gatgcacgcc ccgggtttg agaccgccgg cacgtacctg
137881 cggctcgtga agataaacga ctggacggag attacacagt ttatcctgga gcaccgagcc
137941 aagggctcct gtaagtacgc cctcccgctg cgcatccccc cgtcagcctg cctgtccccc
138001 caggcctacc agcaggggt gacggtggac agcatcggga tgtgcccccg cttcatcccc
138061 gagaaccagc gcaccgtcgc cgtatacagc ttgaagatcg ccgggtggca cgggccaag
138121 gcccatacac cgagcaccct gtgccccg gagctgtccg agacccccaa cgccacgcag
138181 ccagaactcg cccggaaga cccgaggat tggccctct tggaggaccc cgtggggacg
138241 gtgggccgc aatcccacc aaactggcac ataccgtcga tccaggacgc cgcgacgcct
138301 taccatcccc cggccacccc gaacaacatg gcctgatcg ccggcgcggt gggcggcagt
138361 ctcctggcag ccctggtcat ttgcggaatt gtgactgga tcgccgccg cactcaaaaa
138421 gccccaaagc gcatacgcct ccccacatc cggaagacg accagccgtc ctcgcaccag
138481 cccttgtttt actagatacc cccccttaat gggtgcgggg gggtcaggtc tgcggggttg
138541 ggatgggacc ttaactccat ataaagcgag tctggaaggg gggaaaggcg gacagtcgat
138601 aagtcggtag cggggacgc gcacctgttc cgctgtcgt accacagct ttttttgcga
138661 accgtccgt tccggatgc cgtgccgccc gttgcaggc ctggtgctcg tggcctctg
138721 ggtctgtgcc accagcctgg ttgtccgtgg cccacggtc agtctggtat caaactcatt
138781 tgtggacgcc ggggccttgg ggcccgacgg cgtagtggag gaagacctgc ttattctcgg
138841 ggagcttcgc tttgtggggg accaggtccc ccacaccacc tactacgatg gggtcgtaga
138901 gctgtggcac tacccatgg gacacaaatg cccacgggtc gtgcatgtcg tcacggtgac
138961 cgcgtgccca cgtcgcccg ccgtggcttt cgccctgtgt cgcgcgaccg acaacactca
139021 cagcccgca tatcccacc tggagctgaa tctggcccaa cagccgcttt tcgggtccg
139081 gagggcgacg cgtgactatg ccgggtgta cgtgttacgc gtatgggtcg tggacgcacc
139141 aaacgccagc ctgtttgtcc tggggatggc catagccgcc gaagggactc tggcgtacaa
139201 cggctcggcc catggctcct gcgacccgaa actgttccg tattcggccc cgcgtctggc
139261 ccggcgagc gtataccaac ccgccccaa ccggactcc acacctcga acaccactc
```

FIGURE 16
(Continued)

```
139321 cacccctcg accaccacc ccaccccc gaccaccacc tccatccc cgaccaccac
139381 ctccaccccc tcgaccacca actccacccc ctcgaccacc acctccaccc cctcgaccac
139441 catcccgct ccccaagcat cgaccacacc cttccccacg ggagacccaa accccaaccc
139501 tcacggggtc aaccacgaac ccccatcgaa tgccacgcga gcgaccgcg actcgcgata
139561 cgcgctaacg gtgaccagaa taatccagat agccatcccc gcgtccatta tagcctggt
139621 gtttctgggg agctgtattt gcttatacaa cagatgtcaa cgccgctacc gacgctccg
139681 ccgccgatt tacaacccc agatacccac gggcatctca tgcgcggtga acgaagcggc
139741 catggcccgc ctggagccg agctcaaata gcatcagagc accccccca aatcccggag
139801 ccggtcgtca cgcacgccaa tgccctccct gacggccatc gccgaagagt cggagcccgc
139861 ggggcggct ggcttccga cgccccccgt ggacccacg acatccaccc caacgcctcc
139921 cctgttggta taggtccacg gccactggcc ggggcacca cataaccgac cgcagtcact
139981 gagttggaa taaaccggta ttatttacct atatccgtgt atgtccattt ctttccccc
140041 ccccccccc cggaaaccca aagaaggaag caaagaatgg atgggaggag ttcaggaagc
140101 cgggagagg gccgcggcg catttaaggc gttgttgtgt tgactttggc tcttctggcg
140161 ggttggtgcg gtgctgtttg ttgggctccc attttacccg aagatcggct gctatccccg
140221 ggacatggat cgcggggcgg tggtggggtt tcttctaggt gtttgtgttg tatcgtgctt
140281 ggcggaatg cccaaaacgt cctggagacg ggtgagtgtc ggcgaggacg tttcgttgct
140341 tccagctccg gggcctacgg ggcgcggccc gacccagaaa ctactatggg ccgtggaacc
140401 cctggatggg tcggcccct tacaccgtc gtgggtctcg ctgatgcccc ccaagcaggt
140461 gccgagacg gtcgtggatg cggcgtgcat gcgcgctccg gtcccgctgg cgatggcgta
140521 cgccccccg gcccatctg cgaccggggg tctacgaacg gacttcgtgt ggcaggagcg
140581 cgcggccgtg gttaaccgga gtctggttat tcacggggtc cgagagacgg acagcggct
140641 gtatccctg tccgtgggcg acataaagga cccggctcgc caagtggcct cggtggtcct
140701 ggtggtgcaa ccggcccag ttccgacccc accccgacc ccagccgatt acgacgagga
140761 tgacaatgac gagggcgagg gcgaggacga aagtctagcc ggcactccg ccagcgggac
140821 cccggctc ccgcctccc ccgccccc gaggtcttgg cccagcgccc cgaagtctc
140881 acacgtgcgt ggggtgaccg tgcgtatgga gactccggaa gctatcctgt tttccccgg
140941 ggaggcgttt agcacgaacg tctccatcca tgccatcgcc cacgacgacc agacctacac
```

FIGURE 16
(Continued)

```
141001 catggacgtc gtctggttga ggttcgacgt gccgacctcg tgtgccgaga tgcaatata
141061 cgaatcgtgt ctgtatcacc cgcagctccc agagtgtctg tcccggccg acgctccgtg
141121 cgccgcgagt acgtggacgt ctcgcctggc cgtccgcagc tacgcggggt gttccagaac
141181 aaaccccccg ccgcgctgtt cggccgaggc tcacatggag cccttccggg ggctggcgtg
141241 gcaggcggcc tccgtcaatc tggagttccg ggacgcgtcc ccacaacact ccggcctgta
141301 tctgtgcgtg gtgtacgtca acgaccatat tcacgcatgg ggccacatta ccatcagcac
141361 cgcggcgcag taccggaacg cggtggtgga acagcccctc ccacagcgcg gcgcggattt
141421 ggccgagccc accaccccgc acgtcggggc ccctccccac gcgcccccaa cccacggcgc
141481 cctgcggtta ggggcggtga tggggccgc cctgctgctg tctgcgctgg ggttgtcggt
141541 gtgggcgtgt atgacctgtt ggcgtaggcg tgcctggcgg gcggttaaaa gcagggcctc
141601 gggtaagggg cccacgtaca ttcgcgtggc cgacagcgag ctgtacgcgg actggagctc
141661 ggacagcgag ggagaacgcg accaggtccc gtggctggcc ccccggaga gacccgactc
141721 tccctccacc aatggatccg gctttgagat cttatcacca acggctccgt ctgtataccc
141791 ccgtagcgat gggcatcaat ctcgccgcca gctacaacc tttggatccg gaaggccga
141841 tgccgttac tccaggcct ccgattcgtc cgtcttctgg taaggcgccc catcccgagg
141901 ccccacgtcg gtcgccgaac tgggcgaccg ccggcgaggt ggacgtcgga gacgagctaa
141961 tgccgatttc cgacgaacgc ggacccccc gacatgaccg cccgccctc gccacgtcga
142021 ccgcgccctc gccacaccg cgaccccgg gctacacggc cgttgtctcc ccgatggccc
142081 tccaggctgt cgacgccccc tccctgtttg tcgcctggct ggccgctcgg tggctccggg
142141 gggcttccgg cctgggggcc gtcttgtgtg ggattgcgtg gtatgtgacg tcaattgccc
142201 gaggcgcata aaggggccggt ggtccgccta gccgcagcaa attaaaaatc gtgagtcact
142261 gcgacgcaa cttcccaccc ggagctttct tccggcctcg atgacgtccc ggctctccga
142321 tcccaactcc tcagcgcgat ccgacatgtc cgtgccgctt tatccacgg cctcgccagt
142381 ttggtcgaa gcctactact cggaaagcga agacgaggcg gccaacgact tcctcgtacg
142441 catgggccgc caacagtcgg tattaaggcg tcgacgcaga cgcacccgct ggtcggcat
142501 ggtgatcgcc tgtctcctcg tggccgttct gtcgggcgga tttggggcgc tcctgatgtg
142561 gctgctccgc taaaagaccg catcgacacg cgcgtccttc ttgtcgtctc tcttcccccc
142621 atcacccgc aatttgcacc cagcctttaa ctacattaaa ttgggttcga ttggcaatgt
```

```
142681  tgtctcccgg ttgattttg gtgggtggg gagtgggtgg gtggggagtg ggtgggtggg
142741  gagtgggtgg gtggggagtg ggtgggtggg gagtgggtgg gtggggagtg ggtgggtggg
142801  gagtgggtgg gtggggagtg ggtgggtggg gagtgggtgg gtggggagtg ggtgggtggg
142861  gagtgggtgg gtggggagtg ggtgggtggg gagtgggtgg gtggggagtg ggtgggtggg
142921  gagtgggtgg gtggggagtg gcaggaaga aacaagcccg accaccagac agaaaatgta
142981  accatacccc aaccgactct ggggctgtt tgtggggtcg gaaccatagg atgaacaaac
143041  caccccgtac ctcccgcacc cttgggtgcg ggtggctcat cggcatctgt ccggtatggg
143101  ttgttcccca cccactcgcg ttcggacgtc ttagaatcat ggcggtttct atgccgacat
143161  cggtttctcc ccgcaataa gacacgatgc gataaaatct gtttgtgaaa tttattaagg
143221  gtacaaattg ccctagcaca ggggtggggt tagggccggg tccccacacc caaacgcacc
143281  aaacagatgc aggcagtggg tcgagtacag cccgcgtac gaacacgtcg atgcgtgt
143341  cagacagcac cagaagcac aggccatcaa caggtcgtgc atgtgtcggt gggtttggac
143401  gcggggggcc atggtggtg ataaagttaa tggccgccgt ccgccagggc cacaggggcg
143461  acgtctcttg gttggcccgg agccactggg tgtggaccag ccgcgcgtgg cggcccaaca
143521  tggcccctgt agccggggc gggggatcgc gcacgtttgc agcgcacatg cgagacacct
143581  cgaccacggt tcggaagaag gccccggtggt ccgcgggcaa catcaccagg tgcgcaagcg
143641  cccgggcgtc cagagggtag agccctgagt catccgaggt tggctcatcg ccgggtcat
143701  gccgcaagtg cgtgtgggtt gggcttccgg tgggcggac gcgaaccgcg gtgtggagcc
143761  cgacgcgggc ccgagcgtac gctccatctt gtggggagaa ggggtctggg ctcgcaggg
143821  gggcatactt gccgggcta tacagacccg cgagccgtac gtggttcgcg ggggtgcgt
143881  gggtccggg gctcccgggg aggccggggg tccggggtt gtggtggatc catgggtca
143941  cgcggtaccc tgggtctct gggagctcgc ggtactctgg gttccctagg ttctcggggt
144001  ggtcgcggaa cccgggcctc ccggggaaca gcggtgtcc tggggattgt tggcggtcgg
144061  acggcttcag atggcttcga gatcgtagtg tccgcaccga ctcgtagtag accgaatct
144121  ccacattgcc ctgccgcttg atcattatca cccgttgcg ggggtccgga gatcatgcgc
144181  gggtgtcctc gaggtgcgtg aacacctctg gggtgcatgc cggcggacgg cacgccttt
144241  aagtaaacat ctgggtcgcc cggcccaact ggggccgggg gttgggtctg gctcatctcg
144301  agagccacgg ggggaaccac cctccgccca gaaacttggg cgatggtcgt acccgggact
```

FIGURE 16
(Continued)

```
144361 caacgggtta ccggattacg gggactgtcg gtcacggtcc cgccggttct tcgatgtgcc
144421 acaccaagg atgcgttggg ggcgatttg ggcagcagcc cggagagcg cagcagga
144481 cgctccgggt cgtgcacggc ggttctggcc gcctcccggt cctcacgccc ccttttattg
144541 atctcatcgc gtacgtcggc gtacgtcctg ggccaaccc gcatgttgtc caggaaggtg
144601 tccgccattt ccagggcca cgacatgtc cccccccc cccgacgag caggaagcgg
144661 tccacgcaac ggtcgccgcc ggtcgcccg acgagcagga agggtccac gcaacggtcg
144721 ccgccggtcg cccgacgag caggaagcgg tccacgcaac ggtcgccgcc ggtcgcctcg
144781 acgaggacgt tcttcctgcg ggaaggcacg aacgcgggtg agccccctcc tccgccccg
144841 cgtcccccct cctcagccc cgcgtccccc ctcctccgcc cccggtccc cctcctcg
144901 cccccgcgtc ccccctcctc cgccctccta cgcccaccca aggtgcttac ccgtgcaaaa
144961 aggcggaccg gtgggtttct gtcgtcggag gccccgggg tgcgtccct gtgtttcgtg
145021 ggtgggtgg gtgggtcttt ccgcgtgtcc ctttccgatg cgatcccgat cccgagccgg
145081 ggcgtcgcga tgccgacgcc gtccgctccg acggcctct gcgagtccg ctccggtcc
145141 gcgtgatccg cagaagctcc cgtcgttcgt ggccggcgcc gtctgcgggc gtcggtcgcg
145201 ccggccttt atgtgcgccg gagagacccg ccccccgccg cccgggcccg ccccggggc
145261 cggcgcggag tcgggcacgg cgccagtgct cgcacttcgc cctaataata tatatacatt
145321 gggacgaagt gcgaacgctt cgcgttctca cttctttac ccggcggccc cgccccttg
145381 gggcggtcc gcccgccggc caatggggg gcggcaaggc gggcggccct tgggccgccc
145441 gccgtcccgt tggtcccggc gtcggcggg cgggaccggg ggcccggga cggccaacgg
145501 gcgcgcgggg ctcgtatctc attaccgccg aaccgggaag tcggggccg ggccccgccc
145561 cctgccgctt cctcgttagc atgcggaacg gaagcggaaa ccgccggatc gggcggtaat
145621 gagatgccat gcggggcggg gcgcggcc accgccta gcgccccgcc catggcagat
145681 ggcgcggatg ggcgggcg ggggttcgac caacggccg cggcacggg ccccggcgt
145741 gccggcgtcg gggcggggtc gtgcataatg gaattccgtt cggggcggc ccgccgtggg
145801 gggggggc cggcggactc cgctgctcct ccttcccgcc ggccctggg actatatgag
145861 cccgaggacg ccccgatcgt ccacacggag cgcggctgcc gacacggatc cacgacccga
145921 cgcgggaccg ccagagacag accgtcagac gctcgccgcg ccgggacgcc gatacgcgga
145981 cgaagcgcgg gagggggatc ggccgtccct gtccttttc ccacccaagc atcgaccggt
```

```
146041 ccgcgtagt tcagcgtcga cggcggggt cgtcggggtc cgtgggtctc gccccctacc
146101 catcgagagt ccgtaggtga actaccgtgc tacgtccgcc gtcgcagtcg tatcccgga
146161 ggatcgcccc gcatcggcga tggcgtcgga aacaagcag cgcccaggct cccagggccc
146221 caccgacggg ccgccgttca cccgagccc agaccgcgac gagcggggg cctcgggtg
146281 gggcgcggag acggaggagg gcggggacga cccgaccac gaccccgacc accccacga
146341 cctcgacgac gcccggcggg acggagggc cccgcggcg ggcaccgacg ccggcgagga
146403 cgccggggac gccgtctcgc cgcgacagct ggccctgctg gcctccatgg tagaggaggc
146461 cgtccggacg atccgaccgc ccgaccccga ggcctgccg cccggaccc ccgccttcg
146521 agccgacgac gatgacgggg acgagtacga cgacgcagcc gacgccgccg gcgaccggc
146581 cccggccgg ggccgcgcac gggaggcccc gctacgcggc gcgtatccgg accccacgga
146641 ccgcctgtcg ccgcgccgc cggccagcc gccgcagaga cgtcgtcacg gccggcggcg
146701 gccatcggcg tcatcgacct cgtcggactc cgggtcctcg tcctcgtcgt ccgcatcctc
146761 ttcgtcctcg tcgtccgacg aggacgagga cgacgacggc aacgacgcgg ccgaccacgc
146821 acgcgaggcg cgggccgtcg ggcggggtcc gtcgagcgcg gcgccggaag ccccggggcg
146881 gacgccgccc ccgcccgggc caccccccct ctccgaggcc gcgcccaagc cccgggcggc
146941 ggcgaggacc ccgcggcct ccgcgggccg catcgagcgc cgccgggccc gcgcggcggt
147001 ggccggccgc gacgccacgg gccgcttcac ggccggcag cccggcggg tgagctgga
147061 cgccgacgcg gcctccggcg cctctacgc gcgctatcgc gacgggtacg tcagcgggga
147121 gccgtggccc ggcgccgggc cccgcccc gggcgggtg ctgtacggcg gcctggcga
147181 cagccgccg ggctctggg gggcgccga ggcggaggag gcgcgacgcc ggttcgaggc
147241 ctcgggcgcc ccggcggccg tgtgggcgcc cgagctggc gacgccgcg agcagtacgc
147301 cctgatcacg cggctgctgt acacccgga cgcggaggcc atgggtggc tccagaaccc
147361 gcgtggtc cccggggacg tggcgctgga ccaggcctgc ttccggatct cgggcgccgc
147421 gcgcaacagc agctccttca tcacccggcag cgtggcgcgg gccgtgccc acctggcta
147481 cgccatggcg gccggccgct tcggctgggg cctggcgcac gcggcggccg ccgtggccat
147541 gagccgccga tacgaccgcg cgcagaaggg cttcctgctg accagcctgc gccgcgccta
147601 cgcgcccctg ttggcgcgcg agaacgcggc gctgacgggg gccgcgggga gcccggcgc
147661 cggcgcagat gacgaggggg tcgccgccgc cgtcgtcgcc gccgccgccg caccgggcga
```

FIGURE 16
(Continued)

```
147721 gcgcgcggtg ccggccgggt acggcgccga ggggatcctc gccgccctgg ggcggctgtc
147781 cgccgcgccc ggctccccg cggggggcga cgaccccgac gccgcccgcc acgccgacgc
147841 cgacgacgac gccgggcgcc gcgcccaggc cggccgcgtg gccgtggagt gcctggccgc
147901 ctgccgcggg atcctggagg cgctggtcga gggcttcgac ggcgacctgg cggccgtccc
147961 gggctggcc ggggccggc ccgccagccc ccgcggccg gagggacccg cgggccccgc
148021 tcccgccg ccgccgcacg ccgacgcgcc ccgcctgcgc ggtggctgc gcgagctgcg
148081 gttcgtcgc gacgcgctgg tgctcatgcg cctgcgcggg gacctgcgcg tggcggcgg
148141 cagcgaggcc gccgtggccg ccgtgcgcgc cgtgagcctg gtcgccgggg ccctgggtcc
148201 cgcgctgccg cgggaccgc gcctgccgag ctccgcggcc gccgccgcg cggacctgct
148261 gtttgagaac cagagcctgc gccccctgct ggcggcgggt ccgcgccgct cttcttcgtc
148321 ttcggggtc gggccgccg cctccgccgc gccgcgggag gggcgcaagc gcaagagtcc
148381 cggcccggcc cggccgcccg gaggcggcgg cccgcgaccc ccgaagacga agaagagcgg
148441 cgcggacgcc cccggctcgg acgcccgcgc ccccctcccc gcgcccgcgc ccccctccac
148501 gcccccgggg cccgagcccg ccccccgccca gcccgcggcg cccggggccg ccgcggcgca
148561 ggccgcccg cgccccgtgg agctgtcgcg ccggcccgcc gagggccccg accccctggg
148621 cggctggcgg cggcagcccc cggggcccag ccacacggcg gcgccgcgg ccgccgccct
148681 ggaggcctac tgctcccgc gcgccgtggc cgagctcacg gaccacccgc tgttcccgt
148741 ccctggcga ccggccctca tgtttgaccc gcgggccctg gcctcgatcg ccgcgcggtg
148801 cgcgggccc gccccgcg cccaggccgc gtgcggcgg ggcgacgacg acgagaaccc
148861 ccaccccac ggggccgccg ggggccgcct ctttggcccc ctgcgcgcct cgggcccgct
148921 gcgccgcatg gcggcctgga tgcgccagat cccgagccc gaggacgtgc gcgtggtggt
148981 gctgtactcg ccgctgccgg gcgaggacct ggccggcgc ggggctcgg ggggccgcc
149041 ggagtggtcc gccgagcgcg gcggctgtc ctgcctgctg ggggccctgg ccaacgggct
149101 gtgcgggccg gacacggacg cctgggcggg caactggacc ggcgcccccg acgtgtcggc
149161 gctgggcgcg cagggcgtgc tgctgatgtc cacgcgggac atggccttcg ccgggccgt
149221 ggagtttctg gggctgctcg ccagcgccgg cgacgggcgg ctcatcgtgg tcaacaccgt
149281 gcgcgcctgc gactggcccg ccgacgggcc cgcggtgtcg cggcagcacg cctacctggc
149341 gtgcgacctg ctgccgccg tgcagtgcgc cgtgcgctgg ccggcggcgc gcgacctgcg
```

FIGURE 16
(Continued)

```
149401 ccgcacggtg ctggcctcgg gccgcgtgtt cggcccgggg gtcttcgcgc gcgtggaggc
149461 cgcgcacgcg cgcctgtacc ccgacgcgcc gccgctgcgc ctgtgccgcg gcgcaacgt
149521 gcgctaccgc gtgcgcacgc gcttcggccc ggacacgccg gtgcccatgt cccgcgcga
149581 gtaccgccgg gccgtgctgc cggcgctgga cggccgggcg gcggcctggg ggaccaccga
149641 cggcatggcg cccggcgcgc cggacttctg cgaggaggag gcccactgc accgcgcctg
149701 cgcgcgctgg ggcctgggcg cgccgctgcg gcccgtgtac gtgggcgctgg ggcgcgaggc
149761 ggtgccgcc ggccggcc ggtggcgcgg gccgcggagg gactttgcg cccgcgccct
149821 gctggagccc gacgacgacg ccccccgct ggtgctgcgc ggcgacgacg acggcccggg
149881 ggccctgccg ccggcgccgc ccgggattcg ctgggcctcg gccacgggcc gcagcggcac
149941 cgtgctggcg gcggcggggg ccgtggaggt gctgggcgcg gaggcgggct tggccacgcc
150001 ccgcgacgg gacgttgtgg actggaaggg cgcctgggac gaagacgacg ggggcgcgtt
150061 cgagggggac gggtgctgt aacgggccgg gacggggcgg ggcgcttgtg aaaccgaag
150121 acgcaataaa cggcaacgac ctgattaagt tttgcagtag cgttgtttat tcgaggggcg
150181 ggaggggcg aggggcggga ggggcgagg ggcgggaggg ggcgaggggc gggagggggc
150241 gaggggcggg agggggcgag gggcgggagg gggcgagggg cgggaggggg cgaggggcgg
150301 gaggggcga gggcggtgg tggtgcgcgg gcgccccgg agggtttgga tctctgacct
150361 gagattggcg gcactgaggt agagatgccc gaacccccct gagggagcgc gggacgcggc
150421 tggggagggc tgggctggg gagggctggg gctggggagg gctggggctg gggagggctg
150481 gggctgggga gggctggggc tgggagggc tggggctggg gagggctggg gctggggagg
150541 gctggggctg gggagggctg gggctgggga gggctggggc tgggagggc tgggctggg
150601 gagggctggg gctgtggtgt gtgacaggag cggcgtgttg cgctggggga cgtctggagg
150661 agcggggggt gcgcggtgac gtgtggatga ggaacaggag ttgttgcgcg gtgagttgtc
150721 gctgtgagtt gtgttgttgg gcaggtgtgt tggatgacgt gacgtgtgga tgaggaaccg
150781 gagtcgccgg tgcgccgtgc tgttggtgtt ctgttggtgt tgttacacct gtggcagccc
150841 gggcccccg cgcgggggc ggcgcgcaaa aaaggcgggc ggcggtccgg gcggcgtgcg
150901 cgcgcgcggc gggcgtgggg ggcggggccg cgggagcggg ggaggagccc cacccacaga
150961 cgggaggag cggggagga gcggggagg agcggggag gagcccacc cacagacggg
151021 gaggagcggg ggaggagcgg ccagaccca aaacgggcc ccccgaaac acaccccccg
```

161081 ggggtcgcgc gcggccctt aaagcgcggc ggcgggcagc ccgggccccc cgcgg

FIGURE 16
(Continued)

McKrae ICP4 amino acid sequence (SEQ ID NO: 2)

```
   1 masenkqrpg spqptdgppp tpspdrdarg algwgaetee ggddpdhdpd hphdlddarr
  61 dgrapaagtd agedagdavs prqlaliasr veeavrtipt pdpaaspprt pafradddg
 121 deyddaadaa gdrapargra reaplrgayp dptdrlsprp paqppqrrrh grrrpsasst
 181 ssdsgsssss sasssssssd ededddgnda adharearav grgpssaape apgrtppppg
 241 ppplseaapk praaartpaa sagrlerrra raavagrdat grftagqprr valdadaasq
 301 afyaryrdgy vsqepwpqay ppppqrvlyg gigdsrpglv gapeaeearr rfeasgapaa
 361 vwapelgdaa qqyalitrll ytpdasamgw lqnprvvpqd valdqacfri sqaarnsssf
 421 itgsvaravp hlqysmaaqr fqwglahaaa avamarrydr aqkqflltsl rrayapllar
 481 enaaltgaag spqagaddeq vaaavvaaaa apgeravpag ygaagilaal qrlsaapasp
 541 agqddpdaar hadadddaqr raqagrvave claacrylle alaegfdgdl aavpqlagar
 601 paspprpegp agpaspppph adaprlrawl relrfvrdal ylmrlrqdlr vaqgseaava
 661 avravslvaq algpalprdp rlpssaaaaa adllfenqsl rpllaaqprr sssssqvaaa
 721 asaapreqrk rkspgpacpp gggprppkt kksqadapgs darapipapa ppstppgpep
 781 apaqpaapra aaaqarprpv alsrrpaegp dplggwsrqp pgpshtaapa aaaleaycsp
 841 ravaeltdhp lfpvpwrpal sfdpralasl aarcagpapa aqaacgggdd denphphgaa
 901 ggrlfgplra sgplrrmaaw mrqipdpedv rvvvlysplp gedlagggas ggppewsaer
 961 gqlscllaal anrlcgpdta awagnwtgap dvsalgaqgv lllstrdlaf agaveflgll
1021 asagdrrlly vntvracdwp adgpavsrgh aylacdllpa vqcavrwpaa rdlrrtvlas
1081 grvfgpgvfa rveaaharly pdapplrlcr ggnvryrvrt rfgpdtpvpm spreyrravl
1141 paldgraaas qttdamapga pdfceeeahs hracarwqlg aplrpvyval greavragpa
1201 rwrgprrdfc arallepddd applvlrqdd dgpgalppap pgirwasatg rsgtvlaaaq
1261 avevlgaeag latpprrdvv dwegawdedd ggafagdqvl
```

FIGURE 17

HSV McKrae strain amino acid sequence of ICP22 (SEQ ID NO: 3)

```
  1 madispgafa pcvkarrpal rspplgtrkr krparplsse sevetdtale sevesetasd
 61 stesgdqeea prlggrrapr rlggrffldm saesttgtet dtavsddpdd tsdwsyddip
121 prpkrarvnl rltsspdrrd gvifpkmgrv rstretqpra ptpsapspna mlrrsvrqaq
181 rrssarwtpd lgymrqcinq lfrvlrvard phgsanrlrh lirdcylmgy crarlaprtw
241 crllqvsggt wgmhlrntir evearfdata epvcklpcle arrygpecdl snleihlsat
301 sddeisdatd leaagsdhtl asqsdtedap spvtletpep rgslavrled efgefdwtpq
361 egsqpwlsav vadtssverp gpsdsgagra aedrkcldgc rkmrfstacp ypcsdtflrp
```

FIGURE 18

HSV McKrae strain amino acid sequence of ICP47 (SEQ ID NO: 4)

1 mawalemadt fldnmrvgpr tyadvrdain krgredreaa rtavhdpexp llrspgllpk
51 iapnaslgva hrrtggtvtd sprspvtr

F

HSV McKrae strain nucleotide sequence of ICP4 (SEQ ID NO: 5)

```
126001 tttattgcgt cttcgggttt cacaagcgcc ccgcccgtc ccggcccgtt acagcaccc
126061 gtccccctcg aacgcgccgc cgtcgtcttc gtcccaggcg ccttccagt ccacaacgtc
126121 ccgtcgcggg gggcgtggca agcccgcctc cgccccagc acctccacgg ccccgccgc
126181 cgccagcacg gtgccgctgc ggccccgtggc cgaggcccag cgaatcccgg gcggcgccgg
126241 cggcagggcc ccgggccgt cgtcgtcgcc gcgcagcacc agcggggggg cgtcgtcgtc
126301 gggctccagc agggcgcggg cgcaaaagtc cctccgcggc ccgcgccacc gggccgggcc
126361 ggcgcgcacc gcctcgcgcc ccagcgccac gtacacgggc cgcagcggcg cgcccaggcc
126421 ccagcgcgcg caggcgcggt gcgagtgggc ctcctcctcg cagaagtccg gcgcgccggg
126481 cgccatggcg tcggtggtcc ccgaggccgc cgcccggccg tcagcgccg cagcacggc
126541 ccggggtac tcgcgcgggg acatgggcac cggcgtgtcc gggccgaagc gcgtgcgcac
126601 gcggtagcgc acgttgccgc cgcggcacag gcgcagcggc ggcgcgtcgg ggtacaggcg
126661 cgcgtgcgcg ggctccacgc gagcgaagac cccgggccg aacacgcggc ccgaggccag
126721 caccgtgcgg cgcaggtcgc gcgccgcgg ccagcgcacg gcgcactgca cggcgggcag
126781 caggtcgcac gccaggtagg cgtgctgccg cgacaccgcg ggcccgtcgg cgggccagtc
126841 gcaggcgcgc acgtgttga ccacgatgag ccgccggtcg ccggcgctgg cgagcagccc
126901 cagaaactcc acggccccgg cgaaggccag gtcccgcgtg gacagcagca gcacgccctg
126961 cgcgcccagc gccgacacgt cggggggcgc ggtccagttg cccgcccagg cggccgtgtc
127021 cggccggcac agccggttgg ccagggccgc cagcaggcag gacagcccgc ccgcctcggc
127081 ggaccactcc ggccggcccc ccgaggcccc gccgccggcc aggtcctcgc ccggcagcgg
127141 cgagtacagc accaccacgc gcacgtcctc gggtcgggg atctggcgca tccaggccgc
127201 catgcggcgc agcgggcccg aggcgcgcag ggggccaaag aggcggcccc cggcggccc
127261 gtggggtgg gggttctcgt cgtcgtcgcc gccgccgcac gcggcctggg ccggcggggc
127321 gggccggcg cacccgcgcgg cgatcgaggc cagggccgc gggtcaaaca tgagggcgg
127381 tcgccagggg acggggaaca gcggtggtc cgtgagctcg gccacggcgc gcgggagca
127441 gtaggcctcc agggcggcgg ccgcgggcgc cgccgtgtgg ctggccccg ggggctgccg
127501 ccgccagccg cccaggggt cggggccctc ggcgggccgg cgcgacagcg ccacggggcg
127561 cgggcgggcc tgcgcgcggg cggcccgggg cgccgcgggc tgggcggggg cgggctcggg
```

FIGURE 20

```
127621  cccegggge  gtggagggg  gegeggege  gggagggg  gegeggegt  ccgagegg
127681  ggcgtcagcg  ccgtcttct  tcgtcttcgg  gggtcgcgg  ccgccgcctc  cgggcggccg
127741  ggccgggccg  ggactcttgc  gcttgcgccc  ctcccgcggc  gcggcggagg  cggcggccgc
127801  gaccccgaa  gacgaagaag  agcggcgcgg  acccgccgcc  agcaggggc  gcaggctctg
127861  gttctcaaac  agcaggtccg  cggcggcgg  ggccgcggag  ctcggcaggc  gcgggtcccg
127921  cggcagcgcg  ggacccaggg  ccccggcgac  caggtcacg  gcgcgcacgg  cggccacggc
127981  ggcctcgctg  ccgccggcca  cgcgcaggtc  cccggcagg  cgcatgagca  ccagcgcgtc
128041  gcgcacgaac  cgcagctcgc  gcagccacga  gcgcaggcgg  gggcgtcgg  cgtgcggcgg
128101  cggcggggaa  gcggggcccg  cgggtccctc  cggccgcggg  gggctggcgg  gccgggcccc
128161  ggccagcccc  gggacggccg  ccaggtcgcc  gtcgaagccc  tcggccagcg  cctccaggat
128221  cccgcggcag  gcggccaggc  actccacggc  cacgcggccg  gcctgggcgc  ggcgtccggc
128281  gtcgtcgtcg  gcgtcggcgt  ggcgggcggc  gtcggggtcg  tcgccccag  cggggaggc
128341  gggcgcggcg  gacagccgcc  ccaggcggc  gaggatcccc  ggggcgccgt  acccggcggg
128401  caccgcgcgc  tcgcccggtg  cggcggcggc  ggcgacgacg  gcggcggcga  ccccctcgtc
128461  atctgcgccg  gcgccggggc  tccccgcggc  cccgtcagc  gccgcgttct  cgcgcgccaa
128521  caggggcgcg  taggcgcggc  gcaggctggt  cagcaggaag  cccttctgcg  cgcggtcgta
128581  tcggcggctc  atggccacgg  ccgccgccgc  gtgcgccagg  cccagccga  acgggccggc
128641  cgccatggcg  tagcccaggt  ggggcacggc  ccgagccacg  ctgccggtga  tgaaggagct
128701  gctgttgcgc  gcggcgcccg  agatccggaa  gcaggcctgg  tccagcgcca  cgtccccggg
128761  gaccacgcgc  gggttctgga  gccacccat  ggcctccgcg  tccggggtgt  acagcagccg
128821  cgtgatcagg  gcgtactgct  gcgcggcgta  gcccagctcg  ggcgccaca  cggccgcgg
128881  ggcgccgag  gcctcgaacc  ggcgtcgcg  ctcctccgcc  tcgggcgccc  cccagaggcc
128941  cggcggctg  tcgcccaggc  cgccgtacag  caccgccc  gggcgcggg  gccgggcgcc
129001  gggccacggc  tcccgatga  cgtaccgtc  gcgatacgc  gcgtagaagg  cgccggagc
129061  cgtcggcg  tccagctcga  cccgacggg  ctgcccggcc  gtgaagcggc  ccgtggcgtc
129121  gcggcggcc  acgccgcgc  gggccaggcg  gcgctcgatg  cggcccgcgg  aggccgcggg
129181  ggtcctcgcc  gccgccgggg  gcttgggcgc  ggcctcggag  aggggggtg  gcccgggcgg
129241  gggcggcgtc  cgcccggggg  cttccggcgc  cgcgctcgac  ggaccccgcc  cgacggcccg
```

FIGURE 20
(Continued)

```
129301 cgcctcgcgt gcgtggtcgg ccgcgtcgtt gccgtcgtcg tcctcgtcct cgtcggacga
129361 cgaggacgaa gaggatgcgg acgacgagga cgaggacccg gagtccgacg aggtcgatga
129421 cgccgatggc cgccgccggc cgtgacgacg tctctgcggc ggctgggccg gcgggcgcgg
129481 cgacaggcgg tccgtggggt ccggatacgc gccgcgtagc gggcctccc gtgcgcggcc
129541 ccggccggg gccggtcgc cggcggcgtc ggctgcgtcg tcgtactcgt cccgtcatc
129601 gtcgtcggct cgaaaggcgg gggtccgggg cggcgaggcc gcggggtcgg gcgtcgggat
129661 cgtcggacg gcctcctcta ccatggaggc cagcagggcc agctgtcgcg gcgagacggc
129721 gtcccggcg tcctcgccgg agtcggtgcc cgccgcgggg gccctccgt ccgccgggc
129781 gtcgtcgagg tcgtggggt ggtcggggtc gtggtcgggg tcgtcccgc cctcctccgt
129841 ctccgcgccc cacccgaggg cccccgctc gtcgcggtct gggctcgggg tgggcggcgg
129901 cccgtcggtg gggcccgggg agccgggcg ctgcttgttc tccgacgcca tcgccgatgc
129961 ggggcgatcc tccgggata cgactgcgac ggcggacgta gcacggtagg tcacgtacgg
```

FIGURE 20
(Continued)

HSV McKrae strain nucleotide sequence of ICP22 (SEQ ID NO: 6)

```
132481 ggtcctccgg gacgttttct ggatggccga catttcccca ggcgcttttg tgccttgtgt
132541 aaaagcgcgg cgtcccgctc tccgatcccc gccctgggc acgcgaagc gaagcgccc
132601 tgcccgcccc ctctcatcgg agtctgaggt cgaatccgag acagccttgg agtctgaggt
132661 cgaatccgag acagcatcgg attcgaccga gtctggggac caggaggaag ccccccgcat
132721 cggtggccgt agggcccccc ggaggcttgg ggggcggttt ttctggaca tgtcggcgga
132781 atccaccacg gggacggaaa cggatgcgtc ggtgtcggac gaccccgacg acacgtccga
132841 ctggtcttgt gacgacattc ccccacgacc caagcgggcc cgggtaaacc tgcggctcac
132901 tagctctccc gatcggcggg atggggttat ttttcctaag atggggcggg tccggtctac
132961 ccgggaaacg cagccccgyg ccccacccc gtcggcccca agcccaaatg caatgctccg
133021 gcgctcggtg cgccaggccc agaggcggag cagcgcacga tggaccccg acctgggcta
133081 catgcgccag tgtatcaatc agctgtttcg ggtcctgcgg gtcgcccggg accccacgg
133141 cagtgccaac cgcctgcgcc acctgatacg cgactgttac ctgatgggat actgccgagc
133201 ccgtctggcc ccgcgcacgt ggtgccgctt actgcaggtg tccggcggga actggggcat
133261 gcacctgcgg aacaccatac gggaggtgga ggctcgattc gacgccaccg cagaacccgt
133321 gtgcaagctt ccttgtttgg aggccagacg gtacggcccg gagtgtgatc ttagtaatct
133381 cgagattcat ctcagcgcga caagcgatga tgaaatctcc gatgccaccg atctggaggc
133441 cgccggttcg gaccacacgc tcgcgtccca gtccgacacg gaggatgccc cctcccccgt
133501 tacgctggaa accccagaac ccgcgggtc cctcgctgtg cgtctggagg atgagtttgg
133561 ggagtttgac tggaccccc aggagggctc ccagccctgg ctgtctgcgg tcgtggccga
133621 taccagctcc gtggaacgcc cgggcccatc cgattctggg gcgggtcgcg cagcagaaga
133681 ccgcaagtgt ctggacggct gcggaaaat gcgcttctcc accgctgcc cctatccgtg
133741 cagcgacacg tttctccggc cgtgagtccg gtcgcccga cccccttgta tgtcccaaa
```

FIGURE 21

HSV McKrae strain nucleotide sequence of ICP47 (SEQ ID NO: 7)

```
145081 tccgcccaga gactcgggtg atggtcgtac ccgggactca acgggttacc ggattacggg
145141 gactgtcggt cacggtcccg ccggttcttc gatgtgccac acccaaggat gcgttggggg
145201 cgatttcggg cagcagcccg ggagagcgca gcaggggacg ctccgggtcg tgcacggcgg
145261 ttctggccgc ctcccggtcc tcacgcccc ttttattgat ctcatcgcgt acgtcggcgt
145321 acgtcctggg cccaaccccgc atgttgtcca ggaaggtgtc cgccatttcc agggcccacg
145381 acatgctttt cccgccgacg agcaggaagc ggtccacgca acggtcgccg ccggtcgcct
```

FIGURE 22

Human cytomegalovirus enhancer nucleotide sequence (SEQ ID NO: 8)

gaagatctctttggttatatagcataaatcaatattggctattggccattgcatacgttgtatccatatcataatatgt
acattatattggctcatgtccaacattaccgccatgttgacattgattattgactagttattaatagtaatcaatt
acggggtcattagttcatagcccatatatggagttccgcgttacataacttacggtaaatggcccgcctggctgacc
gcccaacgacccccgcccattgacgtcaataatgacgtatgttcccatagtaacgccaatagggactttccattgac
gtcaatgggtggagtatttacggtaaactgcccacttggcagtacatcaagtgtatcatatgccaagtacgccccct
attgacgtcaatgacggtaaatggcccgcctggcattatgcccagtacatgaccttatgggactttcctacttggca
gtacatctacgtattagtcatcgctattaccatggtgatgcggttttggcagtacatcaat

FIGURE 23

Calcitonin gene-related peptide promoter (SEQ ID NO: 9)

```
aatgggtttg ggtgtgtgta aatgagtgtg
acggaagcg agtgtgagct tgatctaggc agggaccaca cagcactgtc acacctgcct
gctctttagt agaggactga agtgcggggg tggggtacg gggccggaat agaatgtctc
tgggacatct tggcaaacag cagccggaag caaaggctt gttgtgcaaa cggctcaggc
aggtgatgga tggcagggta ggaaggggga ggtccagagg tctggatgga ggcttccgca
tctgtacctt gcaactcacc cctcaggccc agcaggtcat cggccccctc ctcacacatg
taatgacgta gaagagtacc ccgggacagt ccgggagat ggagattcgg aaagtatcca
tggagctctt acagaatccc ctgtgcggac caggaaactc ttgtagatcc ctgcctatct
gaggcccagg cgctgggctg tttctcacaa tattccttca agatgagatt gtggtcccca
tttcaaagat gagtacactg agcctctgtg aagttacttg cccatgatca cacaaccagg
aattgggcca actgtaattg aactcctgtc taacaaagtt cttgctccca gctccgtctc
ttgtttccca cgagccctgg ccctctgtgg gtaataccag ctactggagt cagatttctt
gggccagaa ccacccttta ggggcattaa cctttaaaat ctcacttggg caggggtctg
ggatcagagt tggaagagtc cctacaatcc tggaccctt ccgccaaatc gtgaaaccag
gggtggagtg gggcgaggt tcaaaaccag gccggactga gaggtgaaat tcaccatgac
gtcaaactgc cctcaaattc cagctcactt taagggcgtt acttgttggt gccccaacca
tgggccacca tttccatcaa tgacctcaat gcaaatacaa gtgggacggt cctgctgacg
cctccaggtt ctggaagcat gaggc acccaggg gcaaaggacc cctccgccca
ttggttgctg tgcactggcg gaactttccc gacccacagc ggcgggaata agagcagtcg
ctggcgctgg gaggcatcag agacactgcc cagccaagt gtcgccgcg cttccacagg
gctctggctg gacgccgccg ccgccgctgc
```

FIGURE 24

Bovine growth hormone polyadenylation signal nucleotide sequence (SEQ ID NO: 10)

ggatcccgactgtgccttctagttgccagccatctgttgtttgcccctcccccgtgccttccttgaccctggaaggt
gccactcccactgtcctttcctaataaaatgaggaaattgcatcgcattgtctgagtaggtgtcattctattctggg
gggtggggtggggcaggacagcaaggggaggattgggaagacaatagcaggcatgctggggaagatcctc

HSV VECTORS FOR DELIVERY OF NT3 AND TREATMENT OF CIPN

CROSS REFERENCE TO RELATED APPLICATIONS

The present application is the National Stage of International Application No. PCT/US17/24083, filed Mar. 24, 2017, which claims priority to U.S. Provisional Application No. 62/313,399, filed Mar. 25, 2016, the entire contents of which are herein incorporated by reference.

SEQUENCE LISTING

In accordance with 37 CFR 1.52(e)(5), the present specification makes reference to a Sequence Listing (submitted electronically as a .txt file named "2017-05-17 SL 2012073-0011_ST25". The .txt file was generated on May 17, 2017, and is 230,836 bytes in size. The entire contents of the Sequence Listing are herein incorporated by reference.

BACKGROUND

Chemotherapy-induced peripheral neuropathy (CIPN) can result from chemotherapy damaging peripheral nerves and can be a disabling side effect of cancer treatment.

SUMMARY OF THE INVENTION

The present disclosure encompasses the finding that a NT3 gene product can be remarkably effective in providing prophylactic and/or therapeutic treatment of chemotherapy-induced peripheral neuropathy (CIPN). CIPN often follows the first dose of chemotherapy and increases in severity as treatment continues. CIPN can disrupt the quality of life of patients undergoing chemotherapy treatment. Among other things, the present disclosure provides high-transducing herpes simplex virus (HSV) vectors capable of entering the dorsal root ganglia (DRG) of patients in order to prevent, inhibit, or treat CIPN. The present disclosure particularly demonstrates that delivery of a NT3 gene product with a viral vector can effectively treat CIPN. In certain embodiments, the viral vector is based on HSV. In certain embodiments, the viral vector is based on a McKrae strain of HSV. In certain embodiments, the viral vector based on HSV is variant relative to HSV at least in that one or more immediate early genes is not functional.

In some embodiments, the disclosure provides compositions and methods to prevent, inhibit, slow progression, and/or delay onset of neuropathy. In some embodiments, the neuropathy is caused by chemotherapeutics. In some embodiments, the disclosure provides compositions and methods that allow for increased doses of chemotherapeutics and/or increased frequency and/or longer duration of treatment. In some embodiments, the disclosure provides compositions and methods to reverse existing neuropathy, including but not limited to, neuropathy caused by one or more chemotherapeutics.

In some embodiments, the disclosure provides a variant of herpes simplex virus (HSV) McKrae strain whose genome contains an alteration such that the variant fails to express one or more immediate early genes, wherein the genome comprises a nucleic acid molecule encoding a neurotrophin 3 polypeptide.

In some embodiments, the disclosure provides a variant of herpes simplex virus (HSV) McKrae strain whose genome contains an alteration such that the variant fails to express a functional protein characterized by SEQ ID NO: 2, wherein the genome comprises a nucleic acid molecule encoding a neurotrophin 3 polypeptide.

In some embodiments, the disclosure provides a variant of herpes simplex virus (HSV) McKrae strain whose genome contains an alteration such that the variant fails to express a functional protein characterized by SEQ ID NO: 16, wherein the genome comprises a nucleic acid molecule encoding a neurotrophin 3 polypeptide.

In some embodiments, the disclosure provides a composition comprising: a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide; and a pharmaceutically acceptable carrier.

In some embodiments, the disclosure provides a composition comprising: a vector comprising a variant of herpes simplex virus (HSV) McKrae strain whose genome contains an alteration such that the variant fails to express a functional protein characterized by SEQ ID NO. 2, wherein the genome comprises a nucleic acid molecule encoding a neurotrophin 3 polypeptide; and a pharmaceutically acceptable carrier.

In some embodiments, the disclosure provides a composition comprising: a vector comprising a variant of herpes simplex virus (HSV) McKrae strain whose genome contains an alteration such that the variant fails to express a functional protein characterized by SEQ ID NO. 16, wherein the genome comprises a nucleic acid molecule encoding a neurotrophin 3 polypeptide; and a pharmaceutically acceptable carrier.

In some embodiments, the disclosure provides a composition for use as a medicament comprising: a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide; and a pharmaceutically acceptable carrier.

In some embodiments, the disclosure provides a composition for use as a medicament comprising: a vector comprising a variant of herpes simplex virus (HSV) McKrae strain whose genome contains an alteration such that the variant fails to express a functional protein characterized by SEQ ID NO: 2, wherein the genome comprises a nucleic acid molecule encoding a neurotrophin 3 polypeptide; and a pharmaceutically acceptable carrier.

In some embodiments, the disclosure provides a composition for use as a medicament comprising: a vector comprising a variant of herpes simplex virus (HSV) McKrae strain whose genome contains an alteration such that the variant fails to express a functional protein characterized by SEQ ID NO: 16, wherein the genome comprises a nucleic acid molecule encoding a neurotrophin 3 polypeptide; and a pharmaceutically acceptable carrier.

In some embodiments, the disclosure provides uses of a composition in the manufacture of a medicament for treatment of neuropathy, wherein the composition comprises a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide.

In some embodiments, the disclosure provides uses of a composition in the manufacture of a medicament for treatment of neuropathy, wherein the composition comprises a vector comprising a variant of herpes simplex virus (HSV) McKrae strain whose genome contains an alteration such that the variant fails to express a functional protein characterized by SEQ ID NO: 2, wherein the genome comprises a nucleic acid molecule encoding a neurotrophin 3 polypeptide; and a pharmaceutically acceptable carrier.

In some embodiments, the disclosure provides uses of a composition in the manufacture of a medicament for treatment of neuropathy, wherein the composition comprises a vector comprising a variant of herpes simplex virus (HSV) McKrae strain whose genome contains an alteration such that the variant fails to express a functional protein characterized by SEQ ID NO: 16, wherein the genome comprises a nucleic acid molecule encoding a neurotrophin 3 polypeptide; and a pharmaceutically acceptable carrier In some embodiments, the disclosure provides compositions for use in the treatment of neuropathy, comprising: a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide; and a pharmaceutically acceptable carrier.

In some embodiments, the disclosure provides compositions for use in the treatment of neuropathy, comprising: a vector comprising a variant of herpes simplex virus (HSV) McKrae strain whose genome contains an alteration such that the variant fails to express a functional protein characterized by SEQ ID NO: 2, wherein the genome comprises a nucleic acid molecule encoding a neurotrophin 3 polypeptide; and a pharmaceutically acceptable carrier.

In some embodiments, the disclosure provides compositions for use in the treatment of neuropathy, comprising: a vector comprising a variant of herpes simplex virus (HSV) McKrae strain whose genome contains an alteration such that the variant fails to express a functional protein characterized by SEQ ID NO: 16, wherein the genome comprises a nucleic acid molecule encoding a neurotrophin 3 polypeptide; and a pharmaceutically acceptable carrier.

In some embodiments, the vector further comprises a promoter operatively linked to a sequence encoding neurotrophin 3 In some embodiments, the vector further comprises an enhancer upstream of the promoter.

In some embodiments, the promoter is tissue specific. In some embodiments, the promoter is neuron specific. In some embodiments, the promoter is a human cytomegalovirus (HCMV) promoter. In some embodiments, the promoter is a calcitonin gene-related peptide (CGRP) promoter.

In some embodiments, the vector comprises an HCMV enhancer and a CGRP promoter. In some embodiments, the vector comprises a bovine growth hormone (BGH) polyadenylation signal.

In some embodiments, the carrier is a polyol. In some embodiments, the carrier is glycerol. In some embodiments, the glycerol is at a concentration ranging from about 1% to about 30%. In some embodiments, the concentration of glycerol is about 5% to about 25%. In some embodiments, the concentration of glycerol is about 5% to about 15%. In some embodiments, the concentration of glycerol is about 10%.

In some embodiments, a nucleic acid molecule encoding a neurotrophin 3 polypeptide is codon optimized. In some embodiments, a nucleic acid molecule encoding a neurotrophin 3 polypeptide has a nucleic acid sequence that is identical to SEQ ID NO: 23. In some embodiments, a nucleic acid molecule encoding a neurotrophin 3 polypeptide has a nucleic acid sequence that is at least 70%, 80%, 85%, 90%, 95%, or 99% identical to SEQ ID NO: 23.

In some embodiments, a nucleic acid molecule encoding a neurotrophin 3 polypeptide has a nucleic acid sequence that is identical to SEQ ID NO: 25. In some embodiments, a nucleic acid molecule encoding a neurotrophin 3 polypeptide has a nucleic acid sequence that is at least 70%, 80%, 85%, 90%, 95%, or 99% identical to SEQ ID NO: 25.

In some embodiments, a neurotrophin 3 polypeptide has an amino acid sequence that is identical to SEQ ID NO: 20. In some embodiments, a neurotrophin 3 polypeptide has an amino acid sequence that is at least 70%, 80%, 85%, 90%, 95%, or 99% identical to SEQ ID NO: 20.

In some embodiments, the disclosure provides methods of inhibiting the development or progression of neuropathy in a subject, the method comprising administering to the subject a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide.

In some embodiments, the disclosure provides methods of inhibiting the development or progression of neuropathy in a subject, the method comprising administering to the subject a vector comprising a variant of herpes simplex virus (HSV) McKrae strain whose genome contains an alteration such that the variant fails to express a functional protein characterized by SEQ ID NO: 2, wherein the genome comprises a nucleic acid molecule encoding a neurotrophin 3 polypeptide.

In some embodiments, the disclosure provides methods of inhibiting the development or progression of neuropathy in a subject, the method comprising administering to the subject a vector comprising a variant of herpes simplex virus (HSV) McKrae strain whose genome contains an alteration such that the variant fails to express a functional protein characterized by SEQ ID NO: 16, wherein the genome comprises a nucleic acid molecule encoding a neurotrophin 3 polypeptide.

In some embodiments, the disclosure provides methods of treating neuropathy in a subject, the method comprising administering to the subject a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide.

In some embodiments, the disclosure provides methods of treating neuropathy in a subject, the method comprising administering to the subject a vector comprising a variant of herpes simplex virus (HSV) McKrae strain whose genome contains an alteration such that the variant fails to express a functional protein characterized by SEQ ID NO: 2, wherein the genome comprises a nucleic acid molecule encoding a neurotrophin 3 polypeptide.

In some embodiments, the disclosure provides methods of treating neuropathy in a subject, the method comprising administering to the subject a vector comprising a variant of herpes simplex virus (HSV) McKrae strain whose genome contains an alteration such that the variant fails to express a functional protein characterized by SEQ ID NO: 16, wherein the genome comprises a nucleic acid molecule encoding a neurotrophin 3 polypeptide.

In some embodiments, the neuropathy is a peripheral neuropathy. In some embodiments, the neuropathy is iatrogenic. In some embodiments, the neuropathy is a result of a cancer treatment. In some embodiments, the neuropathy is a result of chemotherapy.

In some embodiments, the chemotherapy comprises a platinum based chemotherapeutic. In some embodiments, the chemotherapeutic is selected from the group consisting of cisplatin, oxaliplatin carboplatin, satraplatin, picoplatin, nedaplatin, triplatin, lipoplatin, and combinations thereof.

In some embodiments, the chemotherapy comprises a taxane or taxane derivative chemotherapeutic. In some embodiments, the chemotherapeutic is selected from the group consisting of paclitaxel, docetaxel, cabazitaxel, and combinations thereof. In some embodiments, the chemotherapeutic is nab-paclitaxel.

In some embodiments, the chemotherapy comprises a plant alkaloid chemotherapeutic. In some embodiments, the chemotherapeutic is selected from the group consisting of vincristine, vinblastine, vinorelbine, and combinations thereof.

In some embodiments, the chemotherapy comprises a proteasome inhibitor chemotherapeutic. In some embodiments, the chemotherapeutic is bortezomib.

In some embodiments, the chemotherapy comprises an antimitotic chemotherapeutic. In some embodiments, the chemotherapeutic is selected from the group consisting of monomethyl auristatin E (MMAE), brentuximab vedotin, glembatumumab, AGS67E, and combinations thereof.

In some embodiments, the chemotherapy comprises eribulin.

In some embodiments, the chemotherapy comprises thalidomide.

In some embodiments, the vector is administered by contact with the skin of a subject. In some embodiments, the vector is administered intradermally. In some embodiments, the vector is administered to one or more hands of the subject. In some embodiments, the vector is administered to one or more feet of the subject.

In some embodiments, the subject has previously been diagnosed to have an existing neuropathy. In some embodiments, wherein the existing neuropathy comprises one or more symptoms selected from pain, numbness, tingling, burning, hyperalgesia, allodynia, and impaired proprioception.

In some embodiments, in a method of treating a subject having cancer with a chemotherapeutic agent, an improvement comprises administering to the subject a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide, wherein the vector is administered to promote tolerance against chemotherapy induced neuropathy.

In some embodiments, in a method of treating a subject having cancer with a chemotherapeutic agent, an improvement comprises administering to the subject a vector comprising a variant of herpes simplex virus (HSV) McKrae strain whose genome contains an alteration such that the variant fails to express a functional protein characterized by SEQ ID NO. 2 [ICP4 polypeptide sequence], wherein the genome comprises a nucleic acid molecule encoding a neurotrophin 3 polypeptide, wherein the vector is administered to promote tolerance against chemotherapy induced neuropathy.

In some embodiments, in a method of treating a subject having cancer with a chemotherapeutic agent, an improvement comprises administering to the subject a vector comprising a variant of herpes simplex virus (HSV) McKrae strain whose genome contains an alteration such that the variant fails to express a functional protein characterized by SEQ ID NO 16 [GPRRSSSSSGVAA], wherein the genome comprises a nucleic acid molecule encoding a neurotrophin 3 polypeptide, wherein the vector is administered to promote tolerance against chemotherapy induced neuropathy.

BRIEF DESCRIPTION OF THE DRAWINGS

The drawings are for illustration purposes only, not for limitation.

FIG. 2 also shows that a McKrae strain ICP4 mutant that expresses NT3 shows greater efficacy than a KOS strain ICP4 mutant that expresses NT3. Both viruses were made with the same vector.

FIG. 16 depicts an exemplary HSV McKrae strain nucleotide sequence (SEQ ID NO: 1) which is identified as accession number JQ730035.1

FIG. 17 depicts an exemplary HSV McKrae strain ICP4 amino acid sequence (SEQ ID NO: 2).

FIG. 18 depicts an exemplary HSV McKrae strain ICP22 amino acid sequence (SEQ ID NO: 3).

FIG. 19 depicts an exemplary HSV McKrae strain ICP47 amino acid sequence (SEQ ID NO: 4).

FIG. 20 depicts an exemplary HSV McKrae strain nucleotide sequence of ICP4 (SEQ ID NO: 5).

FIG. 21 depicts an exemplary HSV McKrae strain nucleotide sequence of ICP22 (SEQ ID NO: 6).

FIG. 22 depicts an exemplary HSV McKrae strain nucleotide sequence ICP47 (SEQ ID NO: 7).

FIG. 23 depicts an exemplary human cytomegalovirus enhancer nucleotide sequence (SEQ ID NO: 8).

FIG. 24 depicts an exemplary calcitonin gene-related peptide nucleotide sequence (SEQ ID NO: 9).

FIG. 25 depicts an exemplary bovine growth hormone polyadenylation signal (SEQ ID NO: 10).

DEFINITIONS

Figure 1:
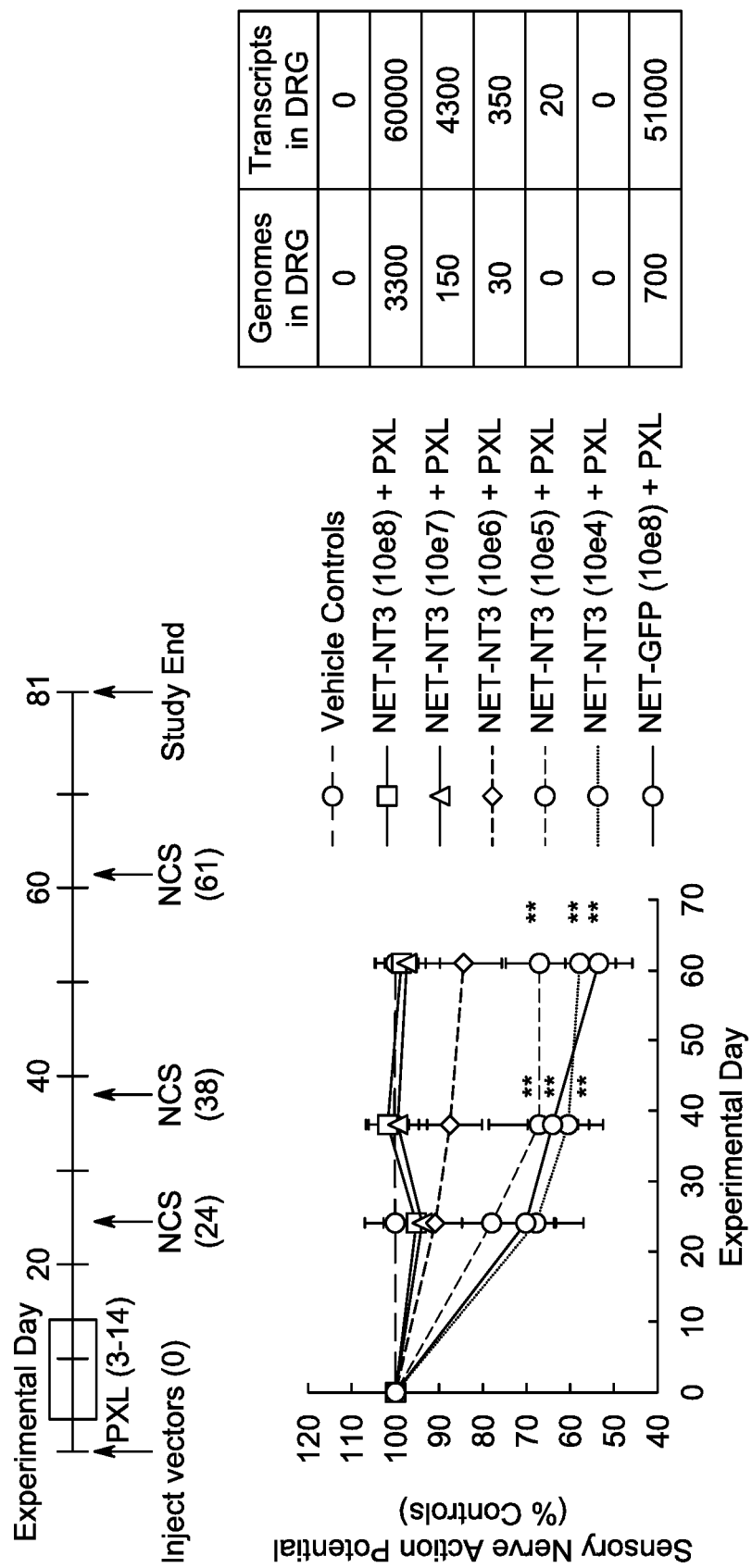
FIG. 1 depicts an exemplary graph showing sensory nerve action potentials (SNAPs) in groups of mice that were administered paclitaxel or vehicle control and different doses of an HSV vector expressing NT3 or GFP. The number of genomes and transcripts of NT3 in dorsal root ganglion (DRG) increased with dose.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time.

Agent: As used herein, the term "agent" refers to a compound or entity of any chemical class including, for example, polypeptides, nucleic acids, saccharides, lipids, small molecules, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc.

Amelioration: As used herein, the term "amelioration" refers to the prevention, reduction or palliation of a state, or improvement of the state of a subject. Amelioration includes, but does not require complete recovery or complete prevention of a disease, disorder or condition.

Animal: As used herein, the term "animal" refers to any member of the animal kingdom. In some embodiments, "animal" refers to humans, of either sex and at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 40%, 3%, 2%, 1%, or less in either direction (greater than or less than) of the stated reference value unless otherwise stated or otherwise evident from the context (except where such number would exceed 100% of a possible value).

Characteristic sequence: As used herein, the term "characteristic sequence" refers to a sequence that is found in all members of a family of polypeptides or nucleic acids, and therefore can be used by those of ordinary skill in the art to define members of the family.

Combination therapy: As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

Composition: As used herein, the term "composition" or a "pharmaceutical composition" refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

Engineered: As used herein, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present disclosure, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Inhibit: As used herein, the term "inhibit" or "inhibiting" refers to slowing, stopping, reducing, or delaying onset. In some embodiments, inhibiting neuropathy comprises slowing progression of pathology or symptoms. In some embodiments, inhibiting neuropathy comprises reducing severity of tissue damage and/or associated neurological symptoms. In some embodiments, inhibiting neuropathy comprises delaying the onset of tissue damage and/or associated neurological symptoms.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Marker element: As used herein, the term "marker element" refers to a detectable or selectable agent. In some embodiments, a "marker element" is a detectable or selectable nucleic acid sequence. In some embodiments a "marker element" is an expression product (e.g., RNA or protein) whose presence or absence is detectable and/or selectable in cells. In some embodiments, an expression product is or comprises an enzyme. In some embodiments, an expression product is a fluorophore.

Nucleic acid: As used herein, the term "nucleic acid" refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present disclosure. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded, in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil, glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid, pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevent or prevention: As used herein, the terms "prevent" or "prevention", when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Subject: As used herein, the term "subject" refers to a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Treatment: As used herein, the term "treatment" (also "treat" or "treating") refers to any administration of a substance that partially or completely alleviates, ameliorates, relieves, inhibits, delays onset of, reduces severity of, and/or reduces incidence of one or more symptoms, features, and/or causes of a particular disease, disorder, and/or condition (e.g., neuropathy). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated to a viral genome or portion thereof. Certain vectors are capable of autonomous replication in a host cell into which they are introduced (e.g., bacterial vectors having a bacterial origin of replication, episomal mammalian vectors, herpes simplex virus (HSV) vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION

Various aspects of the invention are described in detail in the following sections. The use of sections is not meant to limit the invention. Each section can apply to any aspect of the invention. In this application, the use of "or" means "and/or" unless stated otherwise or clear from context to be disjunctive.

The present disclosure provides, among other things, compositions comprising HSV vectors and methods for use and production of the same. In particular, the present disclosure relates to HSV McKrae strain vectors for delivery of NT3 to a subject suffering from or susceptible to neuropathy.

Chemotherapy-Induced Peripheral Neuropathy (CIPN)

Peripheral neuropathy results from damage to peripheral nerves, which often causes weakness, numbness and pain, usually in the hands and feet, though it can also affect other areas of the body. Peripheral neurons send information from the central nervous system to the rest of the body (and vice versa). Peripheral neuropathy can result from traumatic injuries, diabetes mellitus, medications, infections, metabolic problems, inherited causes, and exposure to toxins. Peripheral neuropathy caused by chemotherapy medications is one of the most common side effects of chemotherapy and can be disabling. The most common symptoms of CIPN are pain (which may be present at all times or may come and go, like shooting or stabbing pain), a burning sensation, tingling ("pins and needles" feeling or electric/shock-like pain), loss of feeling (which can be numbness or a lessened ability of sense pressure, touch, heat or cold), trouble using fingers to pick up or hold things/dropping things, balance problems, trouble with tripping or stumbling while walking, increased sensitivity to cold or heat, increased sensitivity to touch or pressure, shrinking muscles, muscle weakness, trouble swallowing, constipation, difficulty passing urine, changes in blood pressure and decreased or no reflexes.

When chemotherapy drugs are administered systemically, they typically spread throughout the body and certain types can damage different nerves CIPN symptoms tend to start farthest away from the head and move closer over time. In most cases, CIPN symptoms start in the feet, and then are later noticeable in the hands. Symptoms may start in the toes and then move to the feet, ankles and legs, or can start in the fingers and move to the hands, wrists and arms. CIPN can begin any time after chemotherapy treatment starts and symptoms often increase in severity as treatments continue.

Particular chemotherapeutic agents are linked to CIPN. These agents include: taxanes (e.g. paclitaxel), platinum compounds (e.g. oxaliplatin), proteasome inhibitors (e.g. bortezomib), vinka alkaloids (e.g. vincristine), thalidomide, lenalidomide, epothilones, antimitotic agents (e.g., eribulin, monomethyl auristatin E), antibody drug conjugates (e.g., vedotin), and others. CIPN can occur for a short duration or it can occur over a long period of time. Factors that influence the duration of CIPN symptoms include: age, the presence of other medical conditions that cause neuropathy (e.g. diabetes or HIV infection), prescription drugs, family history of neuropathy, the chemotherapeutic agent or combination of chemotherapeutic agents used (including those used in the past), the dose of chemotherapeutic agent, frequency of dosing of chemotherapeutic agent(s), and the total amount of chemotherapeutic agent(s) given over time.

Different chemotherapeutics affect different components of the nervous system, from the level of the sensory cell bodies in the dorsal root ganglion (DRG) to the distal axon. The DRG is a prominent target as it is less protected by the blood-nerve barrier and more vulnerable to neurotoxic damage. Disruption of microtubule dynamics is another common mechanism of neurotoxicity. Microtubules are central to axonal transport processes, and critical for energy and material delivery. In additional to energy deficiency, chemotherapeutics may damage the peripheral vasculature. Another target of neurotoxicity can include direct axonal toxicity at the distal terminals.

Treatments that have been used for CIPN include vitamin E, calcium and magnesium, anti-seizure drugs (such as carbamazepine (Tegretol)), antidepressants (such as venlafaxine (Effexor)) and glutathione. The success of these treatments has been inconsistent.

Diagnosis of CIPN can also be determined by sensory nerve action potentials (SNAP) (See Velasco & Bruna et al. (2013) *Neurol Neurosurg Psychiatry* doi:10.1136/jnnp-2013-305334, incorporated herein by reference in its entirety). An increased number of acute neuropathic symptoms and the amplitude decrease of a sensory nerve action potential (e.g., of radial and dorsal sural nerves) at mid-treatment are associated with a risk of developing a more severe chemotherapy induced neuropathy.

Chemotherapeutic Agents

As mentioned above, certain chemotherapeutic agents are more frequently associated with CIPN than others. These agents include: taxanes (e.g. paclitaxel), platinum compounds (e.g. oxaliplatin), bortezomib, vinka alkaloids (e.g. vincristine), thalidomide, lenalidomide, epothilones, antibody drug conjugates (e.g. MMAE-MAB), and others.

Cisplatin

Cisplatin is a chemotherapeutic agent that is classified as an alkylating agent. Cisplatin produces interstrand, intrastrand and monofunctional adduct cross-linking in DNA, the most prevalent form being a 1,2-intrastrand d(GpG) and d(ApG) crosslinks. Sensory polyneuropathy occurs at high frequency after exposure to amounts of cisplatin as low as 200 mg/m2. Cumulative doses of Cisplatin greater than 300 mg/m$^2$ uniformly result in a severe sensory neuropathy, thereby limiting the maximum therapeutic dose possible. Rodent models of cisplatin treatment faithfully recapitulate aspects of the human disease.

Cisplatin can be used to treat testicular, ovarian, bladder, head and neck, esophageal, small and non-small cell lung, breast, cervical, stomach and prostate cancers. Cisplatin can also be used to treat Hodgkin's and non-Hodgkin's lymphomas, neuroblastoma, sarcomas, multiple myeloma, melanoma and mesothelioma. Cisplatin can be administered intravenously. The usual cisplatin injection dose for the treatment of testicular cancer in combination with other approved chemotherapeutic agents is 20 mg/m$^2$ intravenously (i.v.) daily for 5 days per cycle. As a single agent, the usual cisplatin injection for the treatment of metastatic ovarian tumors is a dose of 100 mg/m$^2$ IV per cycle once every four weeks. The usual cisplatin injection dose for the treatment of metastatic ovarian cancer in combination with cyclophosphamide is 75 to 100 mg/m$^2$ (i.v.) per cycle once every four weeks. As a single agent, the usual cisplatin injection for the treatment of advanced bladder cancer is a dose of 50 to 70 mg/m$^2$ (i.v.) per cycle once every three to four weeks depending on the extent of prior exposure to radiation therapy and/or prior chemotherapy. For heavily pretreated patients an initial dose of 50 mg/m$^2$ per cycle repeated every four weeks is recommended. The inorganic compound cis-diamminedichloroplatinum(II), commonly referred to as Cisplatin or cis-DDP, is commonly used in the treatment of cancer.

Oxaliplatin

Oxaliplatin is a chemotherapeutic agent that is classified as an alkylating agent. Oxaliplatin can be used to treat colon or rectal cancer that has metastasized and it is often administered with other chemotherapeutic agents. Oxaliplatin can be administered intravenously.

The recommended administration of oxaliplatin is in combination with 5-fluorouracil/leucovorin every 2 weeks. For advanced disease, treatment is recommended until disease progression or unacceptable toxicity. For adjuvant use, treatment is recommended for a total of 6 months (12 cycles). In the recommended regimen, Day 1 of treatment involves administration of oxaliplatin 85 mg/m$^2$ intravenous infusion in 250 to 500 mL 5% dextrose injection and leucovorin 200 mg/m$^2$ intravenous infusion in 5% Dextrose Injection both given over 120 minutes at the same time in separate bags using a Y-line, followed by 5-fluorouracil 400 mg/m$^2$ intravenous bolus given over 2 to 4 minutes, followed by 5-fluorouracil 600 mg/m$^2$ intravenous infusion in 500 mL 5% dextrose injection (recommended) as a 22 hour continuous infusion. Day 2 of treatment involves administration of leucovorin 200 mg/m$^2$ intravenous infusion over 120 minutes, followed by 5-fluorouracil 400 mg/m$^2$ intravenous bolus given over 2 to 4 minutes, followed by 5-fluorouracil 600 mg/m$^2$ intravenous infusion in 500 mL 5% dextrose injection (recommended) as a 22 hour continuous infusion.

When used as adjuvant therapy in patients with Stage III colon cancer, a dose reduction of oxaliplatin to 75 mg/m$^2$ is recommended for consideration in patients experiencing Grade 2 neurosensory events. When used in patients with advanced colon cancer, a dose reduction of oxaliplatin to 65 mg/m$^2$ is recommended for consideration in patients experiencing Grade 2 neurosensory events. For patients with persistent Grade 3 neurosensory events, it is typically recommended that discontinuation of therapy should be considered.

Paclitaxel

Paclitaxel is a chemotherapeutic agent that is classified as a plant alkaloid, a taxane and an antimicrotubule agent. Paclitaxel can be used to treat breast, ovarian, lung, bladder, prostate, melanoma, esophageal, as well as other types of solid tumor cancers. It has also been used in Kaposi's sarcoma. Paclitaxel can be administered intravenously.

Paclitaxel is an antimicrotubule agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions. In addition, paclitaxel induces abnormal arrays or "bundles" of microtubules throughout the cell cycle and multiple asters of microtubules during mitosis.

For patients with carcinoma of the ovary, the following regimens have been recommended. For previously untreated patients with carcinoma of the ovary, one of the following recommended regimens may be given every 3 weeks. In selecting the appropriate regimen, differences in toxicities should be considered. One recommended regimen is paclitaxel administered intravenously over 3 hours at a dose of 175 mg/m$^2$ followed by cisplatin at a dose of 75 mg/m$^2$. Another recommended regimen is paclitaxel administered intravenously over 24 hours at a dose of 135 mg/m$^2$ followed by cisplatin at a dose of 75 mg/m$^2$. In patients previously treated with chemotherapy for carcinoma of the ovary, paclitaxel has been used at several doses and schedules; however, an optimal regimen is not yet clear. Another recommended regimen is paclitaxel 135 mg/m$^2$ or 175 mg/m$^2$ administered intravenously over 3 hours every 3 weeks.

For patients with carcinoma of the breast, the following regimens have been recommended. For the adjuvant treatment of node-positive breast cancer, the recommended regimen is paclitaxel, at a dose of 175 mg/m$^2$ intravenously over 3 hours every 3 weeks for 4 courses administered sequentially to doxorubicin-containing combination chemotherapy. After failure of initial chemotherapy for metastatic disease or relapse within 6 months of adjuvant chemotherapy, paclitaxel at a dose of 175 mg/m$^2$ administered intravenously over 3 hours every 3 weeks has been reported to be effective. Another recommended regimen is 75 mg/mg$^2$ every week for 12 weeks as part of adriamycin, cyclophosphamide, and a taxane.

For patients with non-small cell lung carcinoma, the recommended regimen, given every 3 weeks, is paclitaxel administered intravenously over 24 hours at a dose of 135 mg/m$^2$ followed by cisplatin, 75 mg/m$^2$.

For patients with AIDS-related Kaposi's sarcoma, the recommended regimen is paclitaxel administered at a dose of 135 mg/m$^2$ given intravenously over 3 hours every 3 weeks or at a dose of 100 mg/m$^2$ given intravenously over 3 hours every 2 weeks (dose intensity 45 to 50 mg/m$^2$/week).

Bortezomib

Bortezomib is a chemotherapeutic agent that is classified as a proteasome inhibitor. Bortezomib can be used to treat multiple myeloma and mantle cell lymphoma in patients who have received at least one prior therapy. Paclitaxel can be administered intravenously or as a subcutaneous injection into the thigh or abdomen.

The recommended starting dosage of bortezomib is 1.3 mg/m$^2$ and it may be administered intravenously at a concentration of 1 mg/mL or subcutaneously at a concentration of 2.5 mg/mL. Retreatment with bortezomib may be considered for patients with multiple myeloma who had previously responded to treatment with bortezomib and who have relapsed at least 6 months after completing prior bortezomib treatment. Treatment may be started at the last tolerated dose. When administered intravenously, bortezomib is administered as a 3 to 5 second bolus intravenous injection.

In patients with previously untreated multiple myeloma, bortezomib is administered in combination with oral melphalan and oral prednisone for nine 6-week treatment cycles. In cycles 1-4, bortezomib is administered twice weekly (days 1, 4, 8, 11, 22, 25, 29 and 32). In cycles 5-9, bortezomib is administered once weekly (days 1, 8, 22 and 29). It is typically recommended that at least 72 hours elapse between consecutive doses of bortezomib.

In patients with previously untreated mantle cell lymphoma, bortezomib (1.3 mg/m$^2$) may be administered intravenously in combination with intravenous rituximab, cyclophosphamide, doxorubicin and oral prednisone (VcR-CAP) for six 3-week treatment cycles. Bortezomib is administered first followed by rituximab. Bortezomib is administered twice weekly for two weeks (Days 1, 4, 8, and 11) followed by a 10-day rest period on Days 12-21. For patients with a response first documented at cycle 6, two additional VcR-CAP cycles are recommended.

In patients who have relapsed multiple myeloma or relapsed mantle cell lymphoma, bortezomib (1.3 mg/m$^2$/dose) is administered twice weekly for 2 weeks (Days 1, 4, 8, and 11) followed by a 10-day rest period (Days 12-21). For extended therapy of more than 8 cycles, bortezomib may be administered on the standard schedule or, for relapsed multiple myeloma, on a maintenance schedule of once weekly for 4 weeks (Days 1, 8, 15, and 22) followed by a 13-day rest period (Days 23 to 35). Patients with multiple myeloma who have previously responded to treatment with bortezomib (either alone or in combination) and who have relapsed at least 6 months after their prior bortezomib therapy may be started on bortezomib at the last tolerated dose. Retreated patients are administered bortezomib twice weekly (Days 1, 4, 8, and 11) every three weeks for a maximum of 8 cycles. At least 72 hours should elapse between consecutive doses of bortezomib. Bortezomib may be administered either as a single agent or in combination with dexamethasone.

Starting bortezomib subcutaneously may be considered for patients with pre-existing or at high risk of peripheral neuropathy. Patients with pre-existing severe neuropathy should be treated with bortezomib only after careful risk-benefit assessment. Patients experiencing new or worsening peripheral neuropathy during bortezomib therapy may require a decrease in the dose and/or a less dose-intense schedule. The current dose or schedule modification guidelines for patients who experience bortezomib-related neuropathic pain and/or peripheral neuropathy are as follows. For patients with Grade 1 signs and symptoms of CIPN (with pain) or for patients with Grade 2 symptoms (moderate symptoms; limiting instrumental Activities of Daily Living (such as preparing meals, shopping for groceries or clothes, using telephone, managing money, etc.)), guidelines recommend that bortezomib is reduced to 1 mg/m$^2$. For patients with Grade 2 symptoms (with pain) or Grade 3 (severe symptoms; limiting self-care Activities of Daily Living (such as bathing, dressing and undressing, feeding self, using the toilet, taking medications, and not bedridden)), guidelines recommend withholding bortezomib therapy until toxicity resolves and when re-starting therapy, treating with a reduced dose of bortezomib at 0.7 mg/m$^2$ once per week. For patients with Grade 4 symptoms (life-threatening consequences; urgent intervention indicated), guidelines recommend discontinuing treatment with bortezomib.

Vincristine

Vincristine is a chemotherapeutic agent that is classified as a plant alkaloid. Vincristine can be used to treat acute leukemia, Hodgkin's and non-Hodgkin's lymphoma, neuroblastoma, rhabdomyosarcoma, Ewing's sarcoma, Wilms' tumor, multiple myeloma, chronic leukemia, thyroid cancer and brain tumors. Paclitaxel can be administered intravenously. The mechanism of action of vincristine has been related to the inhibition of microtubule formation in mitotic spindles, resulting in an arrest of dividing cells at the metaphase stage.

The usual dose of vincristine for pediatric patients is 1.5 to 2 mg/m$^2$. For pediatric patients weighing 10 kg or less, the starting dose is typically 0.05 mg/kg, administered once a week. The usual dose of vincristine for adults is 1.4 mg/m$^2$. A 50% reduction in the dose of vincristine is recommended for patients having a direct serum bilirubin value above 3 mg/100 mL. The drug is typically administered intravenously at weekly intervals.

Thalidomide

Thalidomide is a chemotherapeutic agent that is classified as an immunomodulatory agent and an antiangiogenic agent. Thalidomide can be used to treat newly diagnosed multiple myeloma and is under investigation for use in treating renal cell carcinoma, glioblastoma multiforme and Waldenströms macroglobulinemia. Thalidomide can be administered orally.

The usual dosage of thalidomide for the treatment of multiple myeloma is administered in combination with dexamethasone in 28-day treatment cycles. The dose of thalidomide is 200 mg administered orally once daily with water, preferably at bedtime and at least 1 hour after the evening meal. The dose of dexamethasone is 40 mg daily administered orally on days 1-4, 9-12, and 17-20 every 28 days. Patients who develop adverse reactions such as constipation, somnolence, or peripheral neuropathy may benefit by either temporarily discontinuing the drug or continuing at a lower dose. With the abatement of these adverse reactions, the drug may be started at a lower dose or at the previous dose based on clinical judgment.

Lenalidomide

Lenalidomide is a chemotherapeutic agent that is classified as immunomodulatory agent and an antiangiogenic agent. Lenalidomide can be used to treat multiple myeloma (in combination with dexamethasone) and mantle cell lymphoma wherein the disease has relapsed or progressed after two prior therapies, one of which included bortezomib. Lenalidomide can be administered orally.

The recommended starting dose of lenalidomide for the treatment of multiple myeloma is 25 mg orally once daily on Days 1-21 of repeated 28-day cycles in combination with dexamethasone. For patients >75 years old, the starting dose of dexamethasone may be reduced. The recommended starting dose of lenalidomide for the treatment of mantle cell lymphoma is 25 mg/day orally on Days 1-21 of repeated 28-day cycles for relapsed or refractory mantle cell lymphoma.

Epothilones

Epothilones, like taxanes, prevent cancer cells from dividing by interfering with tubulin, but in early trials epithilones have been reported to have better efficacy and milder adverse effects than taxanes. Several synthetic epothilone analogs are undergoing clinical development for treatment of various cancers. One analog that has been approved for the treatment of breast cancer is ixabepilone. Ixabepilone, in combination with capecitabine is indicated for the treatment of metastatic or locally advanced breast cancer in patients after failure of an anthracycline and a taxane. Ixabepilone as monotherapy is indicated for the treatment of metastatic or locally advanced breast cancer in patients after failure of an anthracycline, a taxane, and capecitabine. The recommended dosage of ixabepilone is 40 mg/m$^2$ administered intravenously over 3 hours every 3 weeks. Doses for patients with body surface area (BSA) greater than 2.2 m$^2$ should be calculated based on 2.2 m$^2$.

Monomethyl Autistatin E (MMAE) Antibody Drug Conjugates

Monomethyl auristatin E (MMAE) is a synthetic antineoplastic agent. Due to high toxicity, it has not been approved for use as a drug itself. However, it has been approved for use linked to a monoclonal antibody (MAB) which directs it to the cancer cells. MMAE has been tested with various monoclonal antibodies. Brentuximab vedotin targets the protein CD30, which is found on malignant cells in anaplastic large cell lymphoma and Hodgkin's lymphoma. Glembatumumab targets the glycoprotein GPNMB, which is found in aggressive melanoma, glioma, breast cancer and other tumors.

Brentuximab vedotin is indicated for treatment of patients with classical Hodgkin lymphoma (HL) after failure of autologous hematopoietic stem cell transplantation (auto-HSCT) or after failure of at least two prior multi-agent chemotherapy regimens in patients who are not auto-HSCT candidates, classical HL at high risk of relapse or progression as post-auto-HSCT consolidation, and systemic anaplastic large cell lymphoma (sALCL) after failure of at least one prior multi-agent chemotherapy regimen.

The usual administration of brentuximab vedotin is as an intravenous infusion over 30 minutes every 3 weeks until the disease progresses or there is unacceptable toxicity. For classical HL post-auto-HSCT consolidation treatment, brentuximab vedotin treatment is typically initiated within 4-6 weeks post-auto-HSCT or upon recovery from auto-HSCT. These patients typically continue treatment until a maximum of 16 cycles, until the disease progresses or there is unacceptable toxicity. The recommended starting dosage for patients with normal renal and hepatic function is 1.8 mg/kg up to 180 mg. The recommended starting dosage for patients with mild (creatinine clearance >50-80 mL/min) or moderate (creatinine clearance 30-50 mL/min) renal impairment is 1.8 mg/kg up to 180. It is typically recommended that if a patient has severe (creatinine clearance less than 30 mL/min), the patient should avoid use of brentuximab vedotin. The recommended starting dosage for patients with mild (Child-Pugh A) hepatic impairment is 1.2 mg/kg up to 120 mg, while it is typically recommended that if a patient has moderate (Child-Pugh B) or severe (Child-Pugh C) hepatic impairment, the patient should avoid use of brentuximab vedotin.

Viral Vectors and HSV

Viral vectors can be used to facilitate the transfer of nucleic acids into cells. Known viral vectors include those derived from retroviruses, adenoviruses, adeno-associated virus (AAV), vaccinia virus, and baculovirus. Vectors derived from herpes simplex viruses (HSV), such as herpes simplex virus 1 (HSV-1) and herpes simplex virus-2 (HSV-2) are particularly useful for delivery of agents (e.g., NT3) to specifically targeted tissues. Considerations for choosing a particular vector and delivery system include, for example, characteristics of target cells, desired longevity of expression, virulence and invasiveness of the vector; and, size of the genetic material to be transferred.

HSV-1 vectors can typically accommodate up to 25 kb of foreign DNA sequences. HSV-1 has an approximate 152-kb double-stranded linear DNA genome that can be maintained episomally in the nucleus of cells. The HSV-1 virion is enveloped and approximately 110 nm in diameter. Viral infection is initiated in epithelial cells of the skin or mucosal membranes by binding of the viral envelope glycoproteins to heparin sulfate moieties on the plasma membrane. HSV is particularly well suited for the delivery of genes to the nervous system and possesses a natural tropism for sensory neurons. The virus can establish a latent state in which viral genomes persist for the life of the host as an intranuclear episomal element. The life-long persistence of latent genomes in human trigeminal ganglia without the development of sensory loss or histologic damage to the ganglia exemplifies the effectiveness of the latency mechanisms. Wild-type HSV virus may be reactivated from latency under the influence of a variety of stresses. However, recombinant viral vectors that are rendered replication defective retain the ability to establish a persistent quiescent state in neurons yet are unable to replicate (or reactivate) in the nervous system.

Vectors based upon HSV-1 may have one or more HSV genes necessary for replication rendered nonfunctional (e.g., by deletion or disruption). HSV genes necessary for replication include, for example, immediate early genes such as ICP4 and ICP27. In some embodiments, the disclosure provides replication defective HSV vectors with one or more of ICP0, ICP4, ICP22, ICP27, and ICP47 deleted or disrupted. In some embodiments, the disclosure provides HSV vectors with a nonfunctional ICP4 gene. In some embodiments, the disclosure provides HSV vectors with nonfunctional ICP4, ICP22, and ICP47 genes. In some embodiments, the disclosure provides an HSV vector with ICP4 deleted and ICP22 and ICP47 disrupted. In some embodiments, the disclosure provides an HSV vector with ICP4 deleted and expression of ICP22 and ICP47 disrupted or delayed. In some embodiments, the disclosure provides an HSV vector with ICP4 deleted ICP0, ICP22, ICP27, and/or ICP47 not expressed as immediate early genes.

HSV-1 vectors that have deleted HSV genes can be produced in cell lines that express the deficient protein in trans. In some embodiments, HSV-1 vectors are produced in a mammalian cell line. In some embodiments, HSV-1 vectors are produced in a mammalian cell line of Vero lineage. In some embodiments, the cell line expresses ICP4. In some embodiments, the cell line expresses one or more of ICP0, ICP4, ICP22, ICP27, and ICP47. In some embodiments, the cell line expresses ICP4 and at least one additional immediate early gene. In some embodiments, the cell line expresses ICP4, ICP22, and ICP 47. In some embodiments, the cell line expresses ICP4, ICP22, and UL55. In some embodiments, the cell line expresses ICP4, ICP27 and UL55. In some embodiments, the cell line comprises a nucleic acid molecule having a simian virus 40 polyadenylation signal (SV40 pA). In some embodiments, viral vectors are produced in Vero 6-5C cells. In some embodiments, viral vectors are produced in Vero D cells.

McKrae Strain

At least 17 strains of HSV-1 have been isolated, including but not limited to, McKrae, strain 17, strain F, H129, HF10, MacIntyre, Strain HF, ATCC 2011 and KOS (for review, see Watson et al., Virology (2012)). A McKrae strain was isolated from a patient with herpes simplex keratitis and subsequently passaged in tissue culture. A partial genome sequence of McKrae is shown in FIG. 16 (SEQ ID NO: 1) (accession number JQ730035).

Inter-strain differences in HSV-1 peripheral replication and virulence are observed after injection into animals. McKrae undergoes spontaneous or induced reactivation at a higher frequency than other known strains and is among the most virulent HSV-1 strains. McKrae is also more neuroinvasive than other known strains, such as strain 17, KOS, F, and H129. In one study, KOS or McKrae was injected into the cornea and genital tract of mice to compare pathogenesis (Wang et al. (2013) Virus Res. 173(2):436-440. Each was found to replicate to a similar extent in the corneal epithelium and trigeminal ganglia; however. McKrae titers were over 100 fold higher in brainstem. Upon intravaginal injection, McKrae and KOS replicated to a similar extent except for a transient spike in McKrae titer at four days. McKrae, but not KOS, elicited significant inflammation of external genitalia along with weight loss in the animals. KOS was not detected in neural tissue and McKrae was rarely detected.

In some embodiments, the disclosure provides HSV viral vectors with deletion of genes that render HSV replication defective, but do not reduce HSV neuroinvasiveness. Thus, the HSV vectors are able to traverse the peripheral nervous system to reach neurons in the dorsal root ganglion upon administration to the skin.

HSV genes influence viral characteristics and phenotype. There are at least 9 genes and several non-coding sequences unique to McKrae strain. In addition to those associated with pathogenesis and latency reactivations, such as RL1, RS1, and RL2, three UL genes (UL36, UL49A, UL56) and three US genes (US7, US10, and US1) are unique for McKrae strain. In addition to gene variations, non-coding sequences such as LAT, 'a' sequence, and miRNAs contain variations unique to McKrae.

One or more of following gene and non-coding sequences can be considered characteristic of McKrae strain. In McKrae, RL1 (ICP34.5) has an extended P-A-T repeat between residues 159 and 160 that results in 8 iterations, while other strains contain only 3-5 iterations. The P-A-T repeat is thought to influence cellular localization of the ICP34.5 protein. (Mao & Rosenthal, J. Biol. Chem. 277(13):11423-31 (2012). ICP34.5 is thought to be a neurovirulence factor involved in viral replication and anti-host response.

McKrae strain also contains an extended repeat element of six iterations of the internal tandem repeat STPSTTT (SEQ ID NO: 11) located within the coding sequence of US07 (gI). Additionally in McKrae, UL 36 contains a premature stop codon introduced due to a G nucleotide deletion in a mononucleotide string encoding amino acid residue 2453 (nt 72,535) and UL 56 (180 aa) contains a single base pair insertion at nucleotide 115,992 (amino acid 97). McKrae strain also contains an extended ORF in US10 resulting from a single bp insertion at nucleotide 143,416 and the frameshift causes a stop codon loss in McKrae and a unique C-terminal protein sequence. McKrae has amino acid differences at UL49A at residues 28 and 51 compared to other strains. McKrae has histidine and threonine at residues 28 and 51, respectively, whereas strain 17 has arginine and threonine and other strains (e.g., KOS) have histidine and alanine. Also, McKrae strain contains reduced tandem repeats found at the UL-RI, junction (49 bp in McKrae as opposed to 181 bp in strain 17 and KOS) and approximately 330 nucleotides missing immediately following the UL-RL junction repeat. McKrae also contains unique variation within the 'a' sequence direct repeat 2 (DR2) array. Instead of a series of unbroken tandem repeats, the McKrae DR2 repeats are interrupted twice by identical guanine-rich sequences.

Major variation within the LAT intron between strains is due to differences in a repeat element (GCACCCCCACTC-CCAC) (SEQ ID NO: 12) that varies in iteration number beginning at nucleotide 119,482 in McKrae strain, with McKrae containing 13 repeats while strains F, H129 and 17 contain 9 repeats and KOS contains 15 repeats. Also, tandem repeat variation between strains is found beginning in McKrae at base 125,520. McKrae repeat elements include twelve iterations of CCCCAGCCCTCCCCAG (SEQ ID NO: 13)

and eight iterations of CCCCTCGCCCCCTCCCG (SEQ ID NO 14). The first repeat unit is unique from other strains in that it contains a G-A transition, and strain McKrae contains three iterations more than any other strain. The McKrae strain second repeat element is collapsed, missing 188 nucleotides relative to all other strains, and separated from the upstream repeat by a 100% conserved sequence of 105 bp containing miR-H5.

McKrae further contains a unique coding sequence for ICP4 that is not found in other known strains. (Watson et al., Virology (2012)). ICP4 is an immediate early transcriptional regulator and has been implicated in reactivation. Whereas other strains contain an alanine rich region (AASAP-DAADALAAA) (SEQ ID NO: 15) between residues 707 and 720, in McKrae the alanine rich region is replaced by a serine rich sequence [GPRRSSSSSGVAA] (SEQ ID NO: 16). The serine rich block of substitutions present in McKrae is adjacent to the nuclear localization signal (NLS) (amino acid 728-734). A change in conformation of this region may alter the NLS and in turn affect localization of not only ICP4, but also other viral proteins (e.g. ICP0, ICP8) that are affected by ICP4 localization (Knipe and Smith, 1986). Thus, this region may influence viral phenotype in part by altering the localization of proteins to the nucleus.

Replication Defective McKrae Vector

McKrae Backbone

Viral genes are expressed in a tightly regulated, ordered cascade, which begins with the production of the immediate-early (IE) genes. The resulting IE proteins, which include infected cell proteins ICP0, ICP4, ICP22, ICP27, and ICP47, are responsible for regulating viral gene expression during subsequent phases of the replication cycle. Replication-defective variant viruses are defective for one or more functions that are essential for viral genome replication or synthesis and assembly of viral particles. Such viruses can be propagated in complementing cell lines expressing the missing gene product(s), however, in normal (i.e., non-complementing) cells, the viruses express viral gene products but do not replicate to form progeny virions.

Replication-defective viruses can be created through various methods known in the art for modifying genes. In some embodiments, one or more nucleotides are rendered different relative to the wild-type sequence. In some embodiments, one or more nucleotides are deleted. In some embodiments, the deletion of one or more nucleotides creates a premature stop codon. In some embodiments, the deletion of one or more nucleotides creates a gene encoding a truncated polypeptide. In some embodiments, the deletion of one or more nucleotides creates a gene encoding a nonfunctional polypeptide. In some embodiments, the deletion of one or more nucleotides renders a gene nonfunctional by disruption. In some embodiments, a gene is disrupted by deletion of its promoter.

In some embodiments, one or more genes are deleted to render a virus replication defective. In some embodiments, the gene encoding ICP0 is fully or partially deleted. In some embodiments, the gene encoding ICP4 is fully or partially deleted. In some embodiments, the gene encoding ICP22 is fully or partially deleted. In some embodiments, the gene encoding ICP27 is fully or partially deleted. In some embodiments, the gene encoding ICP47 is fully or partially deleted. In some embodiments, the gene encoding ICP 4 is fully or partially deleted, without disrupting expression of any additional immediate early genes. In some embodiments, the gene encoding ICP4 is fully or partially deleted, and one or more other immediate early (IE) genes are disrupted. In some embodiments, the gene encoding ICP4 is deleted and ICP22 and ICP47 are disrupted.

HSV-1 IE promoters contain one or more copies of an IE-specific regulatory sequence of consensus TAATGARAT (SEQ ID NO: 19) (where R is a purine). These motifs are normally located within a few hundred base pairs of the proximal IE promoter sequences, but in conjunction with their flanking sequences they are discrete functional entities which can confer IE-specific regulation to other proximal promoter elements of different temporal class. In some embodiments, replication-defective viruses are created by deleting nucleotides in an IE-specific regulatory sequence. In some embodiments, an TE-specific regulatory sequence contains an internal deletion. In some embodiments, an IE-specific regulatory sequence contains a terminal deletion. In some embodiments, an IE-specific regulatory sequence is completely deleted.

Figure 33:
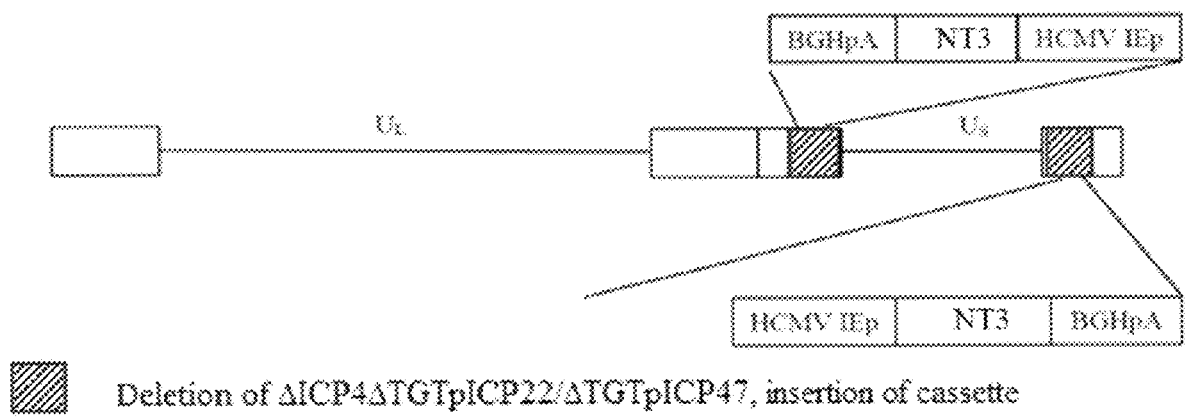
FIG. 33 depicts a schematic of an exemplary replication defective McKrae strain viral vector.

A schematic of an exemplary replication defective McKrae strain viral vector is depicted FIG. 33. FIG. 33 shows complete deletions of both copies of the viral ICP4 gene, and a human cytomegalovirus (HCMV) immediate early promoter driven expression cassette inserted within both copies of the deleted ICP4 loci. The expression cassette contains NT3 for expression in target cells. The extent of the ICP4 deletion results in the removal of the upstream promoter sequences of two additional immediate early viral genes: ICP22 and ICP47.

Payload

Viral vectors in accordance with the present disclosure contain a nucleic acid molecule comprising the payload of the vector. In some embodiments, a payload comprises a nucleic acid molecule that encodes a protein. In some embodiments, a payload comprises a nucleic acid molecule that comprises a sequence complementary to a nucleic acid sequence that encodes a protein. In some embodiments, a payload encodes a nucleic acid molecule that is regulatory. In some embodiments, a payload encodes a small interfering RNA (siRNA) polynucleotide. In some embodiments, a payload encodes a micro RNA (miRNA) polynucleotide.

In some embodiments, the payload is a nucleic acid molecule that encodes a protein that is exogenous to the target tissue or subject to which the vector is administered. In some embodiments, the payload is a nucleic acid molecule that encodes a protein that is endogenous to the target tissue or subject to which the vector is administered. In some embodiments, a nucleic acid molecule is codon optimized. In some embodiments, the payload comprises a neuroptrophin. In some embodiments, the payload comprises a plurality of neurotrophins. In some embodiments, the payload comprises an NT3 polypeptide.

Neuroptrophins

Neurotrophins (NTFs) are a class of small target-derived trophic factor proteins that were initially identified by their ability to prevent programmed cell death of neurons during development. Nerve growth factor (NGF) is an NTF that has been reported to be required for survival of sympathetic peripheral nervous system (PNS) and sensory central nervous system (CNS) neurons during development. In addition to NGF, there exist other NTFs that share approximately 50% amino acid homology with NGF including brain derived neurotrophic factor (BDNF), neurotrophin-3 (NT3), and neurotrophin-4/5 (NT-4). The NTFs bind to two types of post-synaptic receptors; a high affinity ($KD=10^{-11}$ M) tropomyosin-related tyrosine kinase (Irk) receptor and the low affinity ($KD=10^{-9}$ M) $p75^{NTR}$ receptor (a member of the tumor necrosis factor receptor family). In the adult, NTFs can promote both neuron cell survival and cell death, aid in the preservation and regrowth of axonal networks, and modulate synapses. These different functions appear to result from the interactions between the pro-form and the processed mature form of the peptides, which are both released from target tissues, with the Irk and/or p75 receptors.

Although studies have reported that systemic treatment with neurotrophins can protect against the progression of peripheral neuropathy from causes such as diabetes, clinical trials using recombinant human NGF failed to effectively treat neuropathy in human subjects. It is believed herein that such studies failed at least in part due to the inability to provide an adequate local target concentration of these short-lived bioactive peptides through systemic delivery. HSV-based gene transfer can provide adequate local concentrations of NTFs directly to peripheral nerves, while sparing potential off site effects by targeted gene delivery and expression.

Neurotrophin 3

Neurotrophin 3 (NT3) is produced by the NTF3 gene. NT3 has been localized to peripheral and central nerves in humans. NT3 is believed to support the survival and differentiation of new and existing neurons. A representative amino acid sequence of human NT3 is:

```
                                        (SEQ ID NO: 20)
M S I L F Y V I F L A Y L R G I Q G N N M D Q R S L
P E D S L N S L I I K L I Q A D I L K N K L S K Q M
V D V K E N Y Q S T L P K A E A P R E P E R G G P A
K S A F Q P V I A M D T E L L R Q Q R R Y N S P R V
L L S D S T P L E P P P L Y L M E D Y V G S P V V A
N R T S R R K R Y A E H K S H R G E Y S V C D S E S
L W V T D K S S A I D I R G H Q V T V L G E I K T G
N S P V K Q Y F Y E T R C K E A R P V K N G C R G I
D D K H W N S Q C K T S Q T Y V R A L T S E N N K L
V G W R W I R I D T S C V C A L S R K I G R T.
```

In humans, an endogenous nucleic acid sequence that encodes NT3 is:

```
                                        (SEQ ID NO: 21)
    taacacagac tcagctgcca gagcctgctc ttaacacctg
    tgtttccttt tcagatctta caggtgaaca aggtgatgtc
    catcttgttt tatgtgatat ttctcgctta tctccgtggc
    atccaaggta acaacatgga tcaaaggagt ttgccagaag
    actcgctcaa ttccctcatt attaagctga tccaggcaga
    tattttgaaa aacaagctct ccaagcagat ggtggacgtt
    aaggaaaatt accagagcac cctgcccaaa gctgaggctc
    cccgagagcc ggagcgggga gggcccgcca agtcagcatt
    ccagccggtg attgcaatgg acaccgaact gctgcgacaa
    cagagacgct acaactcacc gcgggtcctg ctgagcgaca
    gcacccccctt ggagcccccg cccttgtatc tcatggagga
    ttacgtgggc agccccgtgg tggcgaacag aacatcacgg
    cggaaacggt acgcggagca taagagtcac cgaggggagt
    actcggtatg tgacagtgag agtctgtggg tgaccgacaa
    gtcatcggcc atcgacattc ggggacacca ggtcacggtg
    ctgggggaga tcaaaacggg caactctccc gtcaaacaat
    attttatga aacgcgatgt aaggaagcca ggccggtcaa
    aaacggttgc aggggtattg atgataaaca ctggaactct
    cagtgcaaaa catcccaaac ctacgtccga gcactgactt
    cagagaacaa taaactcgtg ggctggcggt ggatacggat
    agacacgtcc tgtgtgtgtg ccttgtcgag aaaaatcgga
    agaacatgaa ttggcatctc tccccatata taaattatta
    ctttaaatta tatgatatgc atgtagcata taaatgttta
    tattgttttt atatattata agttgaccttt tatttattaa
    acttcagcaa ccctacagta tataagcttt tttctcaata
    aaatcagtgt gcttgccttc
```

In some embodiments, the disclosure provides nucleic acid molecules having a codon optimized sequence for encoding an NT3 polypeptide. In some embodiments, a codon optimized sequence is according to the following nucleic acid sequence (including flanking BamHI restriction sites (ggatcc, (SEQ ID NO: 22)):

```
                                        (SEQ ID NO: 23)
GGATCCATGGTCACTTTCGCAACTATTCTGCAGGTCAACAAGGTCATGTCT
ATTCTGTTCTATGTCATCTTTCTGGCTTATCTGAGAGGCATTCAGGGGAAC
AATATGGACCAGAGAAGCCTGCCAGAAGATTCCCTGAACTCTCTGATCATT
AAGCTGATCCAGGCAGACATTCTGAAGAACAAACTGTCAAAGCAGATGGTG
GATGTCAAAGAAAATTACCAGAGCACACTGCCAAAGGCAGAGGCTCCACGA
GAGCCTGAACGAGGAGGACCAGCAAAATCCGCCTTCCAGCCCGTGATCGCT
ATGGACACAGAGCTGCTGCGGCAGCAGCGGAGATATAACTCTCCTAGAGTG
CTGCTGTCTGACAGTACTCCACTGGAACCCCCTCCACTGTACCTGATGGAG
GATTATGTGGGCTCTCCTGTGGTCGCTAATCGCACCAGTAGGCGCAAGCGA
TACGCAGAGCACAAAAGCCATCGAGGGGAATATTCCGTGTGCGATTCAGAG
AGCCTGTGGGTCACAGACAAGAGCTCCGCCATCGATATTCGGGACACCAA
GTGACTGTCCTGGGGGAAATCAAGACCGGAAATAGTCCCGTGAAACAGTAC
TTTTATGAGACTAGATGCAAGGAAGCCAGGCCTGTCAAAAACGGATGTCGG
GGCATTGACGATAAGCATTGGAATAGTCAGTGTAAAACCTCACAGACATAC
GTGAGGGCTCTGACCAGCGAGAACAACAAGCTGGTCGGCTGGCGCTGGATT
AGAATTGACACTAGCTGCGTCTGCGCCCTGAGTAGGAAGATTGGAAGAACT
TAAATTGGCATCTCTGGATCC
```

In some embodiments, a codon optimized sequence is according to the following nucleic acid sequence (including a 43 bp leader sequence (SEQ ID NO: 24):
GCGGAGGACTCTGGACAGTAGAGGCCCCGGGACGACCGAGCTG, (SEQ ID NO: 25)
CGCGGATCCGCGGAGGACTCTGGACAGTAGAGGCCCCGGGACGACCGAGCT

GATGGTCACCTTTGCCACCATCCTGCAAGTGAACAAAGTGATGAGCATCCT

GTTCTACGTGATCTTCCTGGCCTACCTGCGGGGCATCCAGGGCAACAACAT

GGACCAGAGAAGCCTGCCCGAGGACAGCCTGAACTCCCTGATCATCAAGCT

GATCCAGGCCGACATCCTGAAGAACAAGCTGAGCAAGCAGATGGTGGACGT

GAAAGAGAACTACCAGAGCACCCTGCCCAAGGCCGAGGCCCCTAGAGAACC

TGAAAGAGGCGGCCCTGCCAAGAGCGCCTTCCAGCCTGTGATCGCCATGGA

TACCGAGCTGCTGAGACAGCAGCGGCGGTACAACAGCCCCAGAGTGCTGCT

GAGCGACAGCACCCCTCTGGAACCTCCCCCCCTGTACCTGATGGAAGATTA

CGTGGGCAGCCCCGTGGTGGCCAACCGGACCAGCAGAAGAAAGAGATACGC

CGAGCACAAGAGCCACCGGGGCGAGTACAGCGTGTGCGATAGCGAGAGCCT

GTGGGTCACCGACAAGAGCAGCGCCATCGACATCAGAGGCCACCAAGTGAC

CGTGCTGGGCGAGATCAAGACCGGCAACTCCCCCGTGAAGCAGTACTTCTA

CGAGACACGGTGCAAAGAGGCCAGACCCGTGAAGAACGGCTGCCGGGGCAT

CGACGACAAGCACTGGAACAGCCAGTGCAAGACCAGCCAGACCTACGTGCG

GGCCCTGACCAGCGAGAACAACAAGCTCGTGGGCTGGCGGTGGATCAGAAT

CGACACCAGCTGCGTGTGCGCCCTGAGCCGGAAGATCGGCAGAACATAAGT

TTAAACCGCGGGATCCGCGC

Regulatory Elements

The inclusion of non-native regulatory sequences, gene control sequences, promoters, non-coding sequences, introns, or coding sequences in a nucleic acid of the present disclosure is contemplated herein. The inclusion of nucleic acid tags or signaling sequences, or nucleic acids encoding protein tags or protein signaling sequences, is further contemplated herein. Typically, the coding region is operably linked with one or more regulatory nucleic acid components.

A promoter included in a nucleic acid of the present disclosure can be a tissue- or cell type-specific promoter, a promoter specific to multiple tissues or cell types, an organ-specific promoter, a promoter specific to multiple organs, a systemic or ubiquitous promoter, or a nearly systemic or ubiquitous promoter. Promoters having stochastic expression, inducible expression, conditional expression, or otherwise discontinuous, inconstant, or unpredictable expression are also included within the scope of the present disclosure. A promoter of the present disclosure may include any of the above characteristics or other promoter characteristics known in the art.

Examples of known promoters include, but are not limited to, the cytomegalovirus (CMV) promoter CMV/human beta 3 globin promoter GFAP promoter, chicken beta actin (CBA) promoter the 3-glucuronidase (GUSB) promoter and ubiquitin promoters such as those isolated from human ubiquitin A, human ubiquitin B, and human ubiquitin C.

In some embodiments, a promoter is a neuron specific promoter in that it is a promoter having specific expression in neurons, preferential expression in neurons, or that typically drives expression of an associated coding sequence in neurons or a subset of neurons but not in one or more other tissues or cell types. Examples of such promoters include calcitonin gene-related peptide (CGRP), synapsin I (SYN), calcium/calmodulin-dependent protein kinase II, tubulin alpha I, neuron-specific enolase, microtubule-associated protein 1B (MAP1B), and platelet-derived growth factor beta chain promoters, as well as derivatives thereof. In some embodiments, the promoter is a calcitonin gene-related peptide (CGRP) promoter or derivative thereof.

Other regulatory elements may additionally be operatively linked to the payload, such as an enhancer and a polyadenylation site. In some embodiments, an enhancer comprises a human cytomegalovirus (HCMV) sequence. In some embodiments, a polyadenylation site comprises a bovine growth hormone (BGH) polyadenylation signal.

In some embodiments, a promoter is a chimeric of one or more promoters or regulatory elements found in nature. In some embodiments, the viral vectors comprise a payload whose expression is driven by a CGRP promoter with an HCMV enhancer sequence.

Preparation of Vectors

The present disclosure relates particularly to McKrae strain viral vectors that are replication defective. In some embodiments, viral vectors are generated by deletion or disruption of one or more immediate early genes. Viral genes may be deleted or disrupted using methods of recombinant technology known in the art. In some embodiments a viral vector of the present disclosure may be rendered replication defective as a result of a homologous recombination event. In some embodiments, replication defective viral vectors are generated by deletion of an ICP4 gene. In some embodiments, replication defective viral vectors are generated by deletion of an ICP4 gene and deletion of a promoter for one or more other immediate early genes (e.g., ICP22 and/or ICP47).

In some embodiments, viral vectors of the present disclosure are generated by deletion of loci encoding one or more ICPs (e.g., ICP4) through homologous recombination. In some embodiments, generation of a viral vector of the present disclosure includes a step of homologous recombination of a first plasmid with a second plasmid. In some embodiments, the first plasmid contains nucleic acid sequences homologous to regions of an HSV genome that are adjacent to a nucleic acid region of an HSV genome that is intended to be replaced. In some embodiments, the second plasmid contains an HSV genome, or fragment thereof. In some embodiments, the first plasmid contains nucleic acid sequence encoding a polypeptide of interest (e.g., NT3) between the homologous nucleic acid sequences. In some embodiments, the polypeptide of interest may be or include a marker protein that is detectable by fluorescence, chemiluminescence, or other property, which can be used to select for vectors resulting from successful homologous recombination.

In some embodiments, a viral vector of the present disclosure is generated by homologous recombination of a first plasmid containing a nucleic acid sequence homologous to regions upstream of the ICP4 promoter including the viral origin contained within the short inverted repeat regions of HSV, with a second plasmid containing an HSV McKrae strain genome.

In some embodiments, a vector is made by first replacing both copies of the ICP 4 loci by homologous recombination using plasmid SASB3 and screening for green fluorescent protein (GFP)-expressing plaques. In some embodiments, a plasmid is constructed by cloning the Sph I to Afl HIII (Sal I linkere) fragment (1928 bp) of the HSV-1 KOS strain genome (nucleotides 124485-126413) into Sph 1/Sal I digested pSP72 followed by insertion of the 695 bp Bgl II to BamH I fragment (nucleotides 131931 to 132626) containing regions upstream of the ICP4 promoter including the viral origin contained within the short inverted repeat regions into the Bgl H to BamH I sites of the vector plasmid. In some embodiments, a plasmid is constructed by cloning a HCMV-eGFP fragment in the BamHI site of a plasmid as described above. In some embodiments, a plasmid as described above is then recombined into a specific locus of a wild-type McKrae virus. In some embodiments, the resulting vector is isolated using a stable cell line that expresses one or more genes deleted or disrupted in the HSV genome that are required for replication.

Characterization of Vectors

Viral vectors in accordance with the present disclosure can be characterized by genomic sequencing in order to determine if the expected vector was successfully created. Any method of sequencing known in the art is acceptable for this purpose. Methods of sequencing include, for example, nanopore sequencing, single molecule real time sequencing (SMRT), DNA nanoball (DNB) sequencing, pyrosequencing and using DNA arrays.

The expression of a payload from a viral vector can be detected by any method known in the art for detecting proteins or nucleic acids. Methods of detecting protein expression include immunohistochemistry, flow cytometry, Western blotting, enzyme-linked immunosorbent assay (ELISA), immune-electron microscopy, individual protein immunoprecipitation (IP), protein complex immunoprecipitation (Co-IP), chromatin immunoprecipitation (ChIP), RNA immunoprecipitation (RIP), immunoelectrophoresis, spectrophotometry, and bicinchoninic acid assay (BCA). Methods of detecting nucleic acid expression include Southern blotting, Northern blotting, polymerase chain reaction (PCR), quantitative PCR, and RT-PCR.

In some embodiments, the present disclosure provides methods for testing the ability of viral vectors to transduce neurons. In some embodiments, the neurons are peripheral neurons. In some embodiments, the neurons are sensory neurons. In some embodiments, the neurons comprise dorsal root ganglia (DRG).

In some embodiments, a viral vector preparation may be injected into the one or more dermatomes corresponding to a section of DRG for example, the left and right L4, L5, and L6 DRG. DRG are removed are removed and DNA is isolated from the DRG and analyzed for vector genome copies using a qPCR assay that targets a sequence within HSV-1. In some embodiments, a qPCR assay targets a sequence within the HSV-1 glycoprotein (UL-22) gene.

Applications/Uses

Viral vectors in accordance with the present disclosure are useful for a wide variety of therapeutic applications. In some embodiments, vectors as described herein are useful to deliver one or more payloads to one or more target cells. In some embodiments, target cells reside in tissues that are poorly vascularized and difficult to reach by systemic circulation. In some embodiments, target cells are cells susceptible to infection by HSV. In some embodiments, target cells are particularly susceptible to infection by a McKrae strain of HSV. In some embodiments, target cells are or include one or more of neuronal cells. In some embodiments, target cells are dorsal root ganglion (DRG) cells.

Gene Therapy

Viral vectors in accordance with the present disclosure are useful in any context in which gene therapy is contemplated. For example, viral vectors comprising a heterologous nucleic acid segment operably linked to a promoter are useful for any disease or clinical condition associated with reduction or absence of the protein encoded by the heterologous nucleic acid segment, or any disease or clinical condition that can be effectively treated by expression of the encoded protein within the subject. Viral vectors that contain an expression cassette for synthesis of an RNAi agent (e.g., one or more siRNAs or shRNAs) are useful in treating any disease or clinical condition associated with overexpression of a transcript or its encoded protein in a subject, or any disease or clinical condition that may be treated by causing reduction of a transcript or its encoded protein in a subject. Viral vectors that comprise an expression cassette for synthesis of one or more RNAs that self-hybridize or hybridize with each other to form an RNAi agent targeted to a transcript encoding a cytokine may be used to regulate immune system responses (e.g., responses responsible for organ transplant rejection, allergy, autoimmune diseases, inflammation, etc.). Viral vectors that provide a template for synthesis of one or more RNAs that self-hybridize or hybridize with each other to form an RNAi agent targeted to a transcript of an infectious agent or targeted to a cellular transcript whose encoded product is necessary for or contributes to any aspect of the infectious process may be used in the treatment of infectious diseases.

Administration

Compositions comprising viral vectors as described herein may be formulated for delivery by any available route including, but not limited to parenteral (e.g., intravenous), intradermal, subcutaneous, oral (e.g., inhalation), transdermal (topical), transmucosal, rectal, and vaginal. Preferred routes of delivery include intradermal. In some embodiments, pharmaceutical compositions include a viral vector in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. In some embodiments, viral vectors are formulated in glycerol. In some embodiments, viral vectors are formulated in approximately 10% glycerol in phosphate buffered saline.

It is advantageous to formulate compositions in dosage unit form for ease of administration and uniformity of dosage. Dosage unit form as used herein refers to physically discrete units suited as unitary dosages for the subject to be treated; each unit containing a predetermined quantity of a viral vector calculated to produce the desired therapeutic effect in association with a pharmaceutical carrier.

The pharmaceutical composition can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a viral vector can include a single treatment or, in many cases, can include a series of treatments.

Compositions

In some embodiments, the active agents, i.e., a viral vector of the disclosure and/or other agents to be administered together with a viral vector of the disclosure, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. In some embodiments the composition is targeted to particular cell types or to cells that are infected by a virus.

Combination Therapy

According to the present disclosure, provided compositions may be administered in combination with one or more other active agents and/or therapeutic modalities, such as known therapeutic agents and/or independently active biologically active agents. In some embodiments, provided compositions include one or more such other active agents; in some embodiments, such other active agents are provided as part of distinct compositions. In some embodiments, combination therapy involves simultaneous administration of one or more doses or units of two or more different active agents and/or therapeutic modalities; in some embodiments, combination therapy involves simultaneous exposure to two or more different active agents and/or therapeutic modalities, for example through overlapping dosing regimens.

In some embodiments, provided compositions include or are administered in combination with one or more other active agents useful for the treatment of the relevant disease, disorder and/or condition. In some embodiments, provided compositions are administered in combination with (e.g., prior to, simultaneously with, and/or subsequently to) chemotherapeutics.

EXAMPLES

Example 1: Preparation of Vectors

This example describes methods of preparing and formulating exemplary vectors for gene therapy.

Genetic Structure of Vector

A vector is made by first replacing both copies of the ICP4 loci by homologous recombination using a plasmid and screening for marker element expressing plaques. A plasmid is constructed by cloning a fragment of a HSV-1 genome comprising regions upstream of the ICP4 promoter including the viral origin contained within the short inverted repeat regions. The plasmid is further modified by cloning a marker element, for example HCMV-eGFP, fragment into the plasmid. This plasmid is then recombined into the ICP4 locus of a wild-type HSV virus. The resulting vector is isolated using a stable ICP4 expressing Vero cell line, such as '6-5C'. Vero 6-5C cells are complementing cells that express ICP4.

In order to replace the marker element (e.g., GFP) with a gene of interest (GOI) in the vector described above, a plasmid is constructed by cloning HCMV-GOI-pA into the plasmid. Plaques which do not express the marker element are isolated and tested by ELISA for GOI expression.

Production of Crude Vector

ICP4 complementing Vero cells are cultured in tissue culture flasks using complete media (DMEM supplemented with FBS, HEPES, and Pen Strep) and expanded into 6-12×T175 flasks at a seeding density of 3-4×10$^4$ cells/cm$^2$. The culture flasks are incubated at 37° C./7.5% $CO_2$ for 3-4 days.

When cells are 1-2 days over confluent, they are infected at a multiplicity of infection (MOI) of ~0.1 with a virus stock of known concentration. The infection is initiated by removing the culture supernatant from each flask and infecting with complete media containing the appropriate amount of a virus stock. The virus is adsorbed on the cell monolayers by incubating the cultures for 1.5-2 hours, shaking and rotating the flasks every 15-20 minutes. After the adsorption step, an additional complete medium is added to each flask and the cultures are incubated again at 37° C./7.5% $CO_2$.

Approximately 48 hours after initiating the infection, the flasks are viewed by microscope to confirm cells show signs of cytopathogenic effect and detachment from the flask surface. At that point the cells and supernatant are harvested, pooled together, and centrifuged at ~1500×g for ~10 min. The supernatant is removed from the cell pellet and held separately for later processing.

The cell pellet is resuspended in 4-5 mL of complete media, homogenized, and then frozen at −80° C. After the cell suspension has been frozen for >20 minutes, it is thawed and centrifuged at ~1500×g for ~10 min. This second cell pellet supernatant is removed and combined with the first collected supernatant.

The pooled supernatant is aliquoted into centrifuge tubes. The virus is then centrifuged at ~40,000×g for ~30 minutes at 2-8° C. in order to pellet the virus. After the centrifugation step is completed, the supernatant from the tubes is removed and discarded. The following day the virus pellets are homogenized by pipetting and pooled together. The resuspended virus stock is then aliquoted into cryovials typically at volumes of ~120 µL per vial. Complete medium (200-300 µL) is added to the virus pellets in order to cover them with liquid and are stored at 2-8° C. overnight to loosen the virus particles. The vials are labeled and frozen at −80° C. Later, a frozen vial is thawed in order to perform a virus plaque titration assay to determine the concentration of the prepared virus stock prior to using in any in vivo or in vitro studies.

Manufacture of Clarified Vector

Cell Thaw and Expansion

Vero cells (e.g., Vero 6-5, VeroD cells) from a working cell bank are thawed at 37° C. and transferred to a conical tube and pooled. VeroD cells are complementing cells that express or ICP4, ICP27, and UL55. The cells are vialed at approximately 1.0×10$^7$ viable cells/mL/tube. The cells are gradually diluted with complete medium and a sample is removed to obtain viable cell counts. The cells are plated in tissue culture flasks at a density of 3.0-5.0×10$^4$ cells/cm$^2$.

The cells are incubated at 37° C., 7.5% $CO_2$ and examined periodically by phase microscopy. The cells are passaged while subconfluent. The complete medium is removed, rinsed with PBS, and the cells are dissociated. The flasks are incubated until the cells detach, then they are re-suspended in complete medium, pooled, counted and seeded into new flasks at a density between 1.0-4.0×10$^4$ cells/cm$^2$. The cells are expanded and allowed to extend to 1-2 days post-confluence prior to infection.

Infection with Vector

When the cells reach the desired confluence, a model flask is subcultured and the cells are counted to estimate the number of cells per cell factory. A master virus bank vector inoculum is prepared by thawing the appropriate volume required to obtain a multiplicity of infection (MOI) of 0.1 and diluting the stock with complete medium up to the target volume desired for the infection. The cell factories are infected by an initial adsorption period followed by incubation for the first day of infection in complete medium After approximately 24 hours, the culture medium is removed and replaced with an equal volume of serum-free medium. The cell factories are placed in the incubator and the temperature is reduced to 33° C./with 7.5% $CO_2$. The cultures are monitored daily and the percent cytopathic effect estimated by visual inspection.

Crude Viral Harvest and Clarification

The infection is stopped by placing the cell factories in a biosafety cabinet and pooling the supernatant and cell debris into a sterile bag. This bulk unclarified harvest is sampled for adventitious agents. After sampling, the sodium chloride level of the harvest is increased and then it is mixed. The harvest is then aliquoted into centrifuge tubes and the cell debris removed by centrifugation. The supernatant is pooled into a sterile bag. After pre-treatment of a clarification filter capsule with sterile water, the virus-containing supernatant is then pumped through the filter capsule into another sterile bag, followed by sterile water to recover remaining virus in the capsule. The bag is mixed and the filtrate is stored overnight at 4° C.

Afterwards, the filtrate is warmed and adjusted to ~2 mM $MgCl_2$ by addition of 2 volumes of 3 mM $MgCl_2$ in sterile water. The diluted filtrate is mixed and treated with an endonuclease.

Cation Exchange Column Chromatography

A BPG 400 column is packed with SP high performance resin, sanitized with 0.5N NaOH and equilibrated with wash buffer (PBS pH 7.0) and strip buffer (1M NaCl-PBS pH 7.0) before loading endonuclease treated virus.

The process bag containing the endonuclease-treated filtrate is connected to the inlet using a tubing welder and the virus is loaded onto the column. The flow through is collected in a sterile bag. The virus capture step is followed by washing with PBS until the UV absorbance returns to baseline. The pump is stopped and a process bag containing 0.45 M NaCl-PBS (pH 7.0) is connected to the inlet. The outlet tubing is transferred to a sterile container in a biosafety cabinet. The buffer is pumped into the column and when the UV absorbance begins to increase sharply, the column outlet is transferred to a new sterile container to collect the eluted virus. The collection is stopped after the UV absorbance returns to near baseline. This is the purified viral elute fraction. A process bag containing strip buffer is connected to the inlet and the end of the outlet tubing is transferred into a sterile bottle to collect the strip fraction. The buffer is pumped through the column until UV absorbance reaches a peak and returns to near baseline. The collected elute is stored at 4° C. overnight.

Tangential Flow Filtration

The tangential-flow filtration system, using a 0.1 micrometer pore size hollow fiber filter cartridge is prepared by assembling the tubing and cartridge and sterilizing the system by autoclaving. The system is flushed with sterile PBS (pH 7.0) and the virus eluate fraction is added to the system reservoir and equilibrated by recirculation. After equilibration, the permeate collection pump is turned on and filtrate is collected. The system is run until the loaded volume is reduced to approximately 500 ml. The retentate in the reservoir is diluted with DPBS (pH 7.0) with continuous constant volume diafiltration, and the product in the retentate is recovered when the permeate conductivity is within 10% of the diafiltering buffer (DPBS pH 7.0).

Formulation, Final Filtration and Packaging

The recovered retentate is adjusted to 10% final volume with sterile glycerol and mixed well prior to filtering through a 0.45 μm disc filter unit. The product is dispensed into labeled cryovials for storage at ≤−65° C.

Example 2: Prevention of CIPN (Paclitaxel) with Vector Comprising NT3

This example shows exemplary data for the prevention of CIPN caused by paclitaxel with a McKrae strain HSV vector comprising NT3. A replication-defective HSV-1 vector as described above was injected into the footpad of rats. As shown in FIG. 1, paclitaxel resulted in a significant decrease in sensory nerve action potentials (SNAPs). Additionally, animals pretreated with an HSV-1 vector comprising NT3 were protected in a dose-dependent manner.

Example 3: Prevention of CIPN (Paclitaxel) with Vector Comprising NT3

This example shows exemplary data for the prevention of CIPN caused by paclitaxel with a McKrae strain HSV vector comprising NT3.

Taxanes (paclitaxel, docetaxel, cabazitaxel) are a group of antineoplastic drugs derived from yew trees (*Taxus* sp.) that are commonly used for the treatment of a wide variety of cancers. The mechanisms by which taxanes work are distinct from the platin drugs. Taxanes are plant alkaloids that stabilize microtubules by inhibiting the depolymerization of tubulin resulting in large and dysfunctional microtubules. Microtubules are essential for cell division, thus taxanes are potent mitotic inhibitors. Vincristine, another plant alkaloid derived neoplastic drug, inhibits mitosis by impeding the assembly of microtubules. Apart from their role in mitosis, microtubules are also necessary for axonal transport in neurons, thus chemotherapeutic agents, such as the taxanes, which interfere with the proper functioning of microtubules, cause neuropathy by interfering with normal axonal transport.

Figure 2:
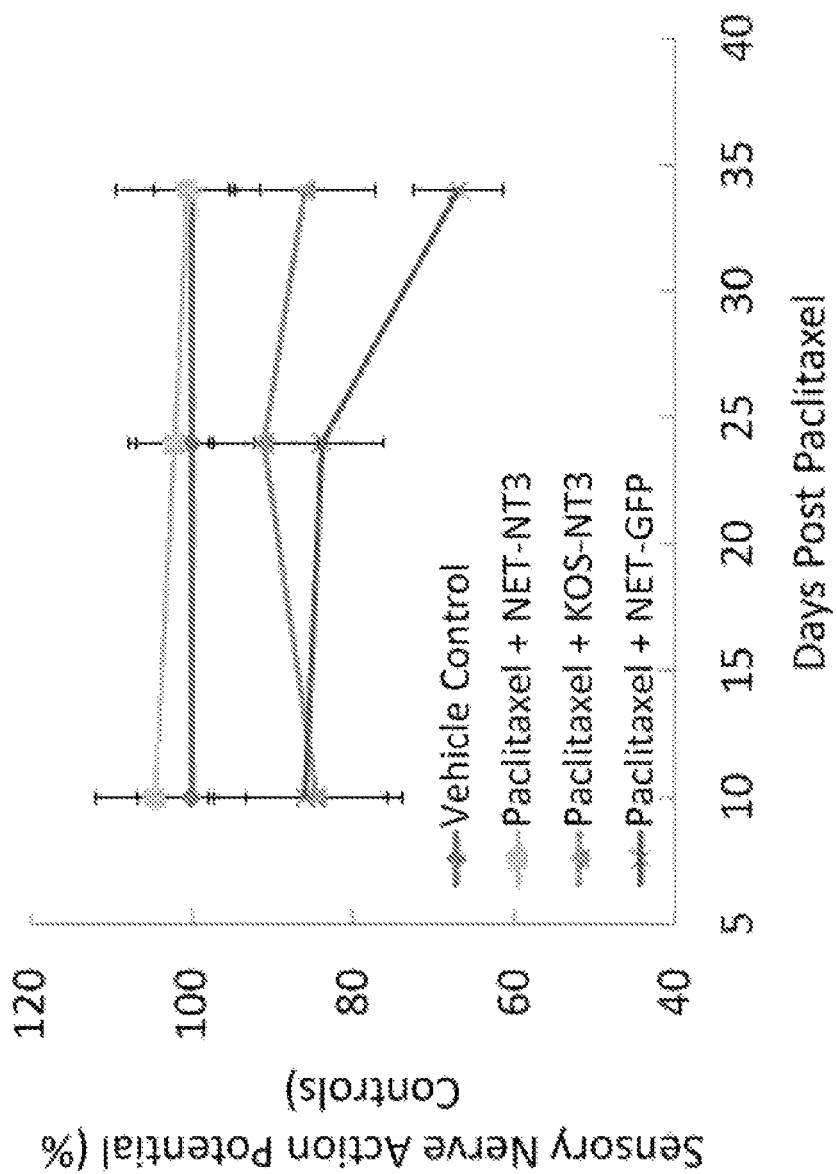
FIG. 2 depicts an exemplary graph that shows SNAPs as a percentage of control levels post-administration of paclitaxel in animals treated with either vehicle control or a HSV vector.

Four groups of animals were treated with a replication-defective HSV-1 vector or vehicle control prior to receiving paclitaxel. Administration of the vector or vehicle control was injected into the footpad of rats. Animals treated with a replication-defective HSV-1 vector were administered a KOS strain vector comprising NT3, a McKrae strain vector comprising NT3 or a McKrae strain vector comprising green fluorescent protein (GFP). As shown in FIG. 2, based on analysis of SNAPs, the McKrae strain vector comprising NT3 (NET-NT3) protected against CIPN more effectively than the KOS strain vector comprising NT3.

Figure 3:
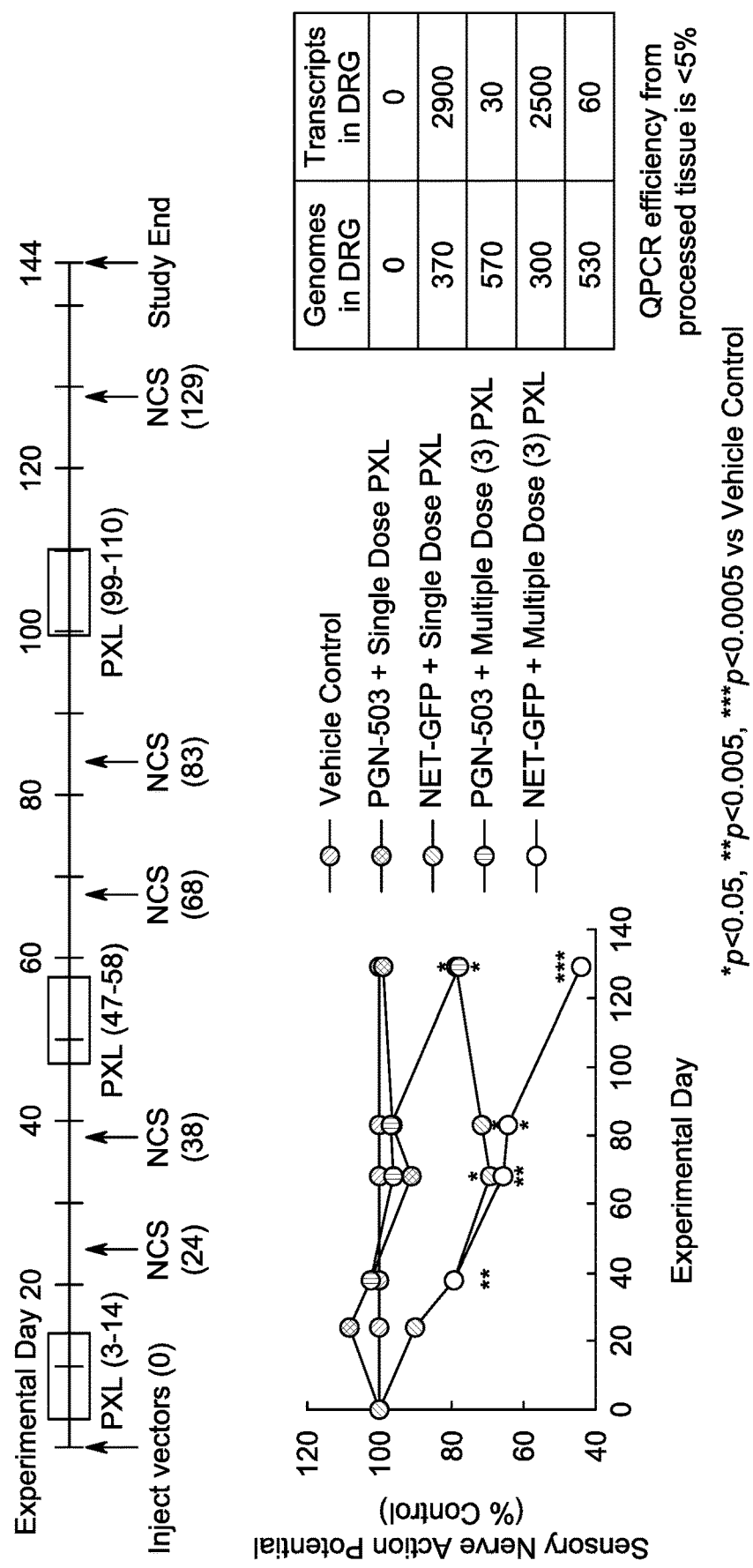
FIG. 3 depicts an exemplary graph that shows SNAPs as a percentage of control levels post-administration of paclitaxel in animals treated with an HSV vector expressing NT3 or GFP.

In another study, animals were administered a replication-defective HSV-1 vector comprising either NT3 or GFP, and then were administered multiple dosings of paclitaxel or vehicle. As shown in FIG. 3, the vector comprising NT3 was capable of protecting against multiple dosings of paclitaxel, as evidenced by the percent of SNAPs relative to control.

In another study, female BALB/c mice were injected subcutaneously into the plantar surface of both hind paws with 25 μl containing $1 \times 10^{10}$ PFU/mL of either a NT3 vector or a GFP vector. Three days following vector inoculation the mice began paclitaxel treatment consisting of 30 mg/kg paclitaxel intraperitoneally (i.p.) three times per week for two weeks (M-W-F, M-W-F). On days 3, 10, 24, 41, 61, and 116 following the final paclitaxel dose, neuropathy was assessed by NCS.

Figure 4:
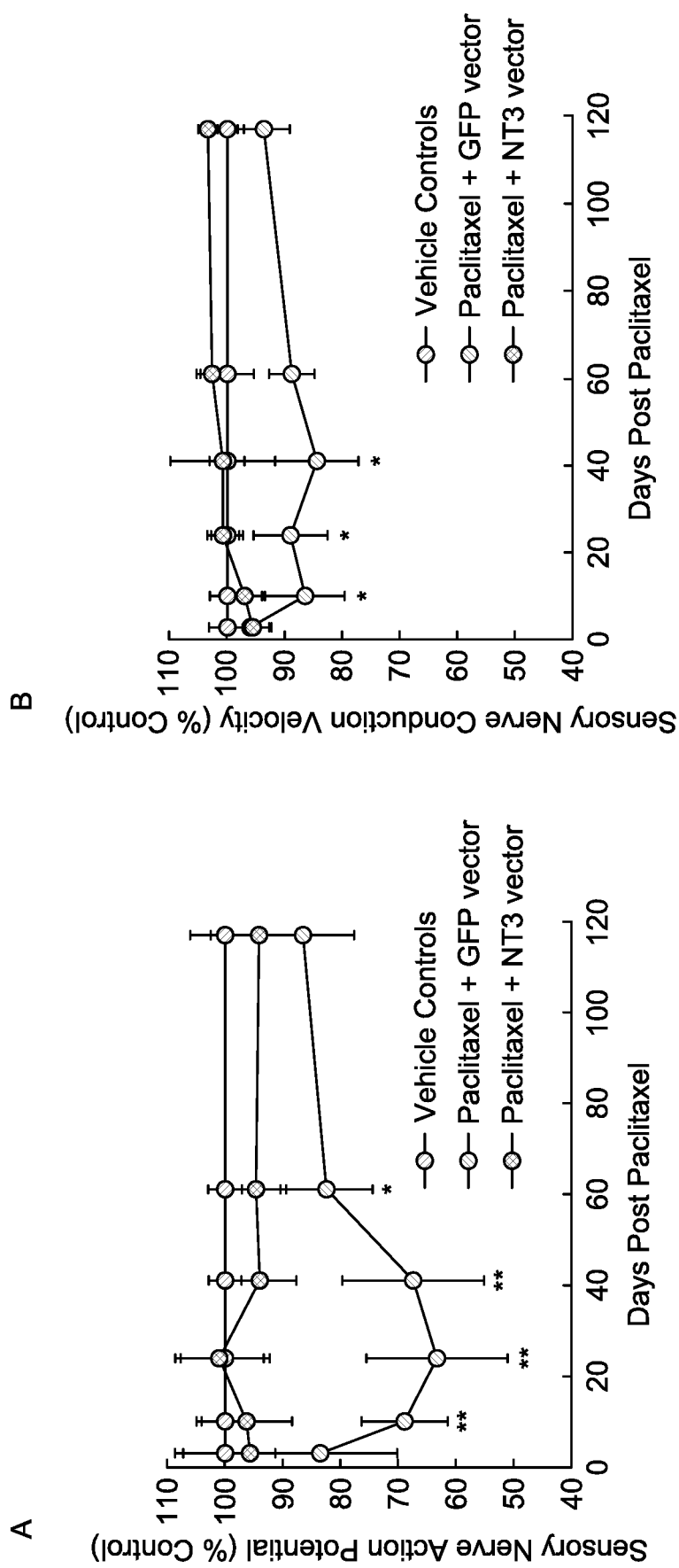
FIG. 4 (comprising panels A and B) depicts exemplary graphs that show SNAPs (panel A) and sensory nerve conduction velocity (SNCV) (panel B) as a percentage of control levels post-administration of paclitaxel in animals treated with either vehicle control, an HSV vector expressing GFP, or an HSV vector expressing NT3.

As shown in FIG. 4, mice treated with paclitaxel developed a peripheral neuropathy characterized by a 20-35% reduction in the evoked sensory nerve amplitude potential (SNAPs) and 15% reduction in conduction velocity (SNCV) from days 3-61 compared to untreated control mice. This reduction in SNAPs is similar to that found in rats treated with cisplatin. Mice injected with the NT3 vector, but not those given the GFP vector, were protected from developing peripheral neuropathy and had SNAPs and SNCV that was indistinguishable from untreated control mice. This protection lasted for the entire time course of the study.

Example 4: Dose-Down Study for Protection Against Paclitaxel-Induced Peripheral Neuropathy This example shows exemplary data for determining the lowest effective dose of a replication-defective McKrae strain HSV-1 vector to protect against paclitaxel-induced peripheral neuropathy.

Five groups of mice (N=6) were injected with a replication-defective McKrae strain HSV-1 vector in doses ranging from $5\times10^4$ to $5\times10^8$ total PFU. Three days later the mice began paclitaxel treatments. At 24 days post paclitaxel, nerve conduction analysis was performed on these mice and the results compared to a group of mice that received a GFP vector ($5\times10^8$ total PFU) and intact control mice that received vehicle injections.

Figure 5:
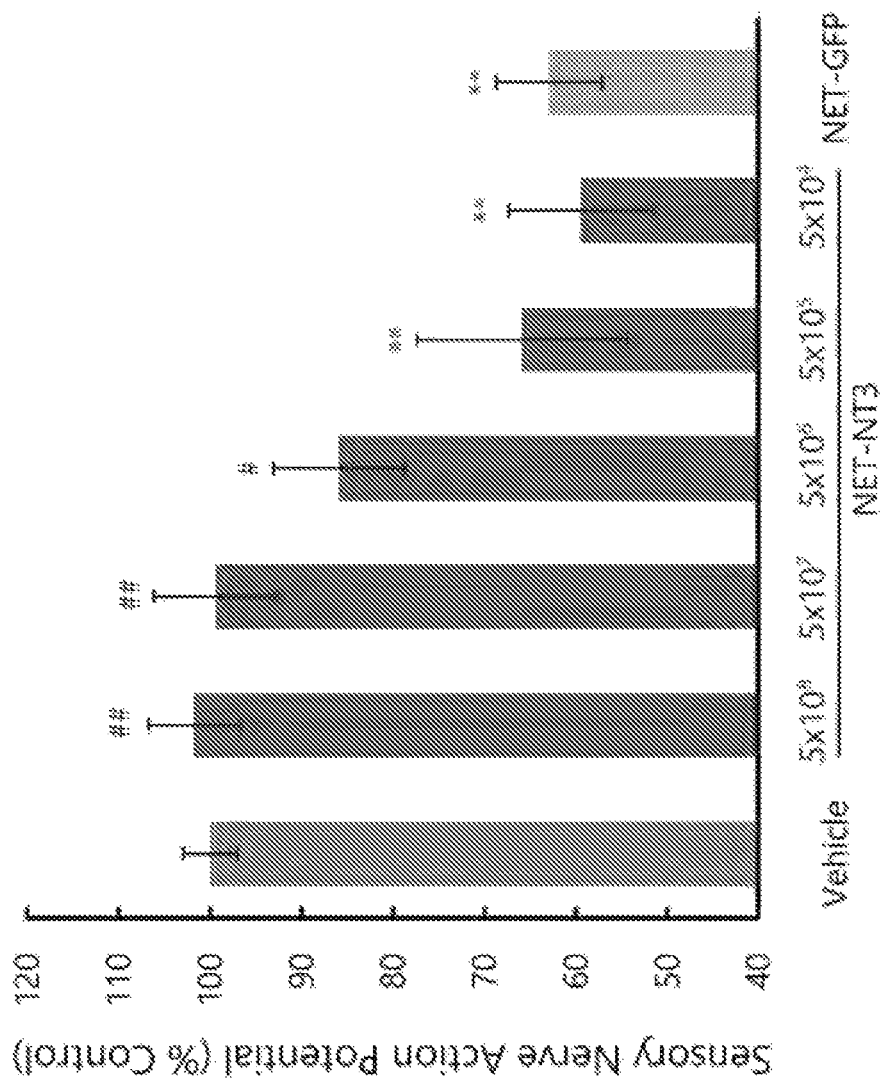
FIG. 5 depicts exemplary graphs that show SNAPs as a percentage of control levels in animals treated with either vehicle control, an HSV vector expressing GFP, or different dosages of a HSV vector expressing NT3.

As shown in FIG. 5, mice pretreated with the two highest doses of the NT3 vector, $5\times10^8$ and $5\times10^7$ total PFU, were fully protected against the development of paclitaxel-induced peripheral neuropathy as measured by sensory nerve action potentials (SNAPs). Mice pretreated with $5\times10^6$ total PFU of the NT3 vector had a lower average SNAP value than the two highest doses, though it wasn't statistically significantly different than the vehicle group, suggesting that this dose was partially protective. The two lowest doses of the NT3 vector provided no protection. These data suggest that $5\times10^6$ total PFU was the lowest effective dose of the NT3 vector for the prevention of paclitaxel-induced peripheral neuropathy in this paradigm.

Figure 6:
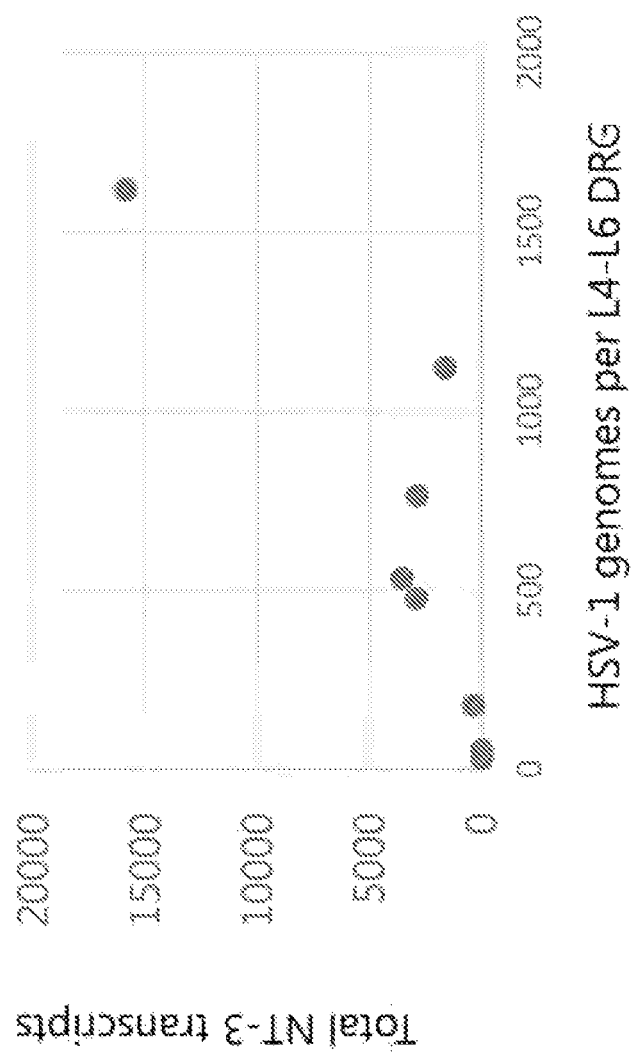
FIG. 6 depicts an exemplary graph that shows the total number of NT3 transcripts and the number of HSV-1 genomes per L4-L6 DRG 131 days post-administration of an HSV vector expressing NT3 in animals that received paclitaxel.
Figure 7:
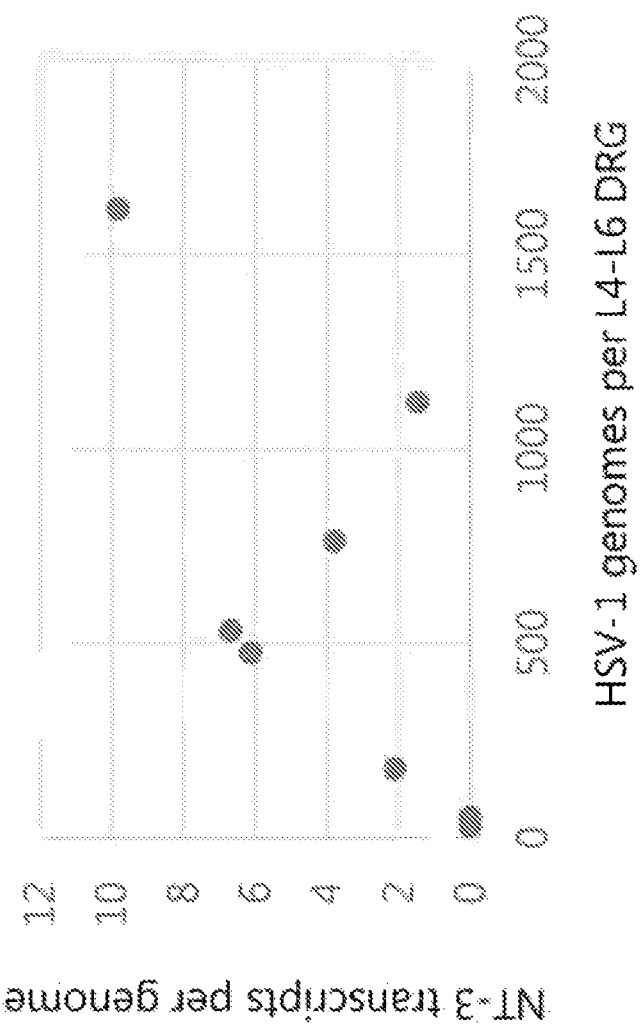
FIG. 7 depicts an exemplary graph that shows the total number of NT3 transcripts per genome and the number of HSV-1 genomes per L4-L6 DRG 131 days post-administration of an HSV vector expressing NT3 in animals that received paclitaxel.

Example 5: Analysis of Expression of Payload after Treatment with Paclitaxel This example shows exemplary data for the expression of transcripts relative to the number of HSV-1 genomes after administration of a replication-defective HSV-1 vector and paclitaxel. As shown in FIG. 6, NT-3 transcripts in the DRG were detectable in six of the eight animals tested 131 days post-administration of an HSV vector expressing NT3. Those animals with levels of NT3 transcripts below the level of detection correlated with a low total number of HSV-1 genomes per L4-L6 DRG. Additionally, as shown in FIG. 7, when the data were analyzed as NT3 transcripts per genome rather than total number of NT3 transcripts, six of the eight animals were in the range of 0 to 9.8 transcripts per genome.

Figure 8:
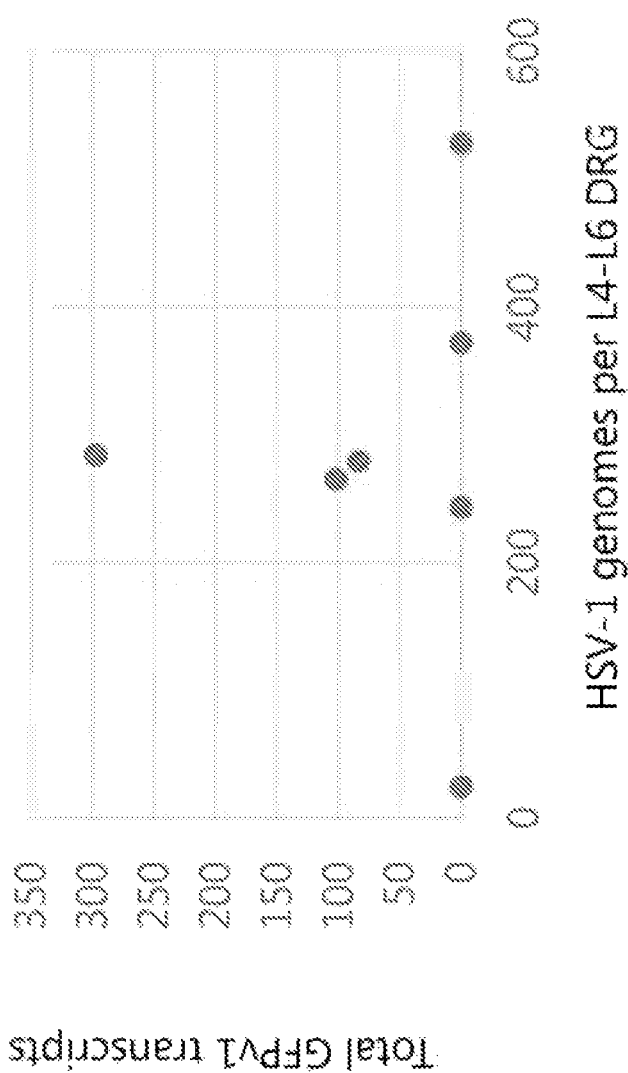
FIG. 8 depicts an exemplary graph that shows the total number of GFP transcripts and the number of HSV-1 genomes per L4-L6 DRG 131 days post-administration of an HSV vector expressing NT3 in animals that received paclitaxel.
Figure 9:
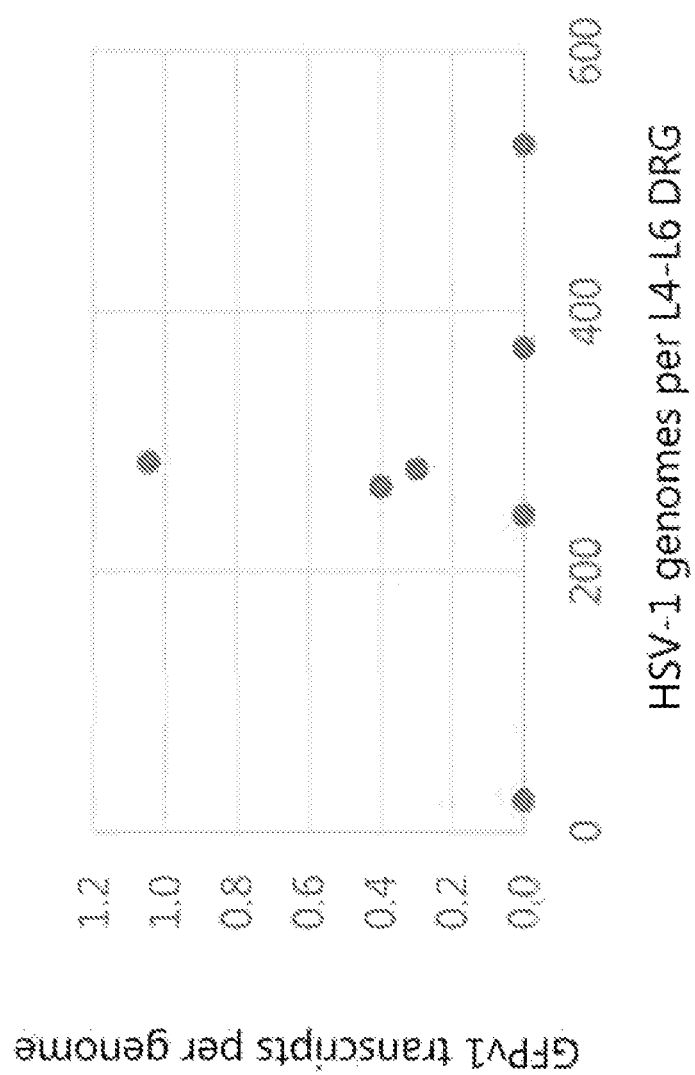
FIG. 9 depicts an exemplary graph that shows the total number of GFP transcripts per genome and the number of HSV-1 genomes per L4-L6 DRG 131 days post-administration of an HSV vector expressing NT3 in animals that received paclitaxel.

The same experiment was also performed with animals that were administered paclitaxel and a replication-defective HSV-1 vector comprising GFP. As shown in FIG. 8, GFP transcripts were detectable in three of seven animals tested 131 days post-administration of the GFP expressing vector. The GFP transcript levels were approximately 10-fold lower than those seen in the animals administered the NT3 vector. Additionally, as shown in FIG. 9, when the data were analyzed as GFP transcripts per genome rather than total number of GFP transcripts, three of the seven animals were in the range of 0 to 1.0 transcripts per genome (as opposed to 0 to 9.8 for animals administered the NT3 vector.

Figure 10:
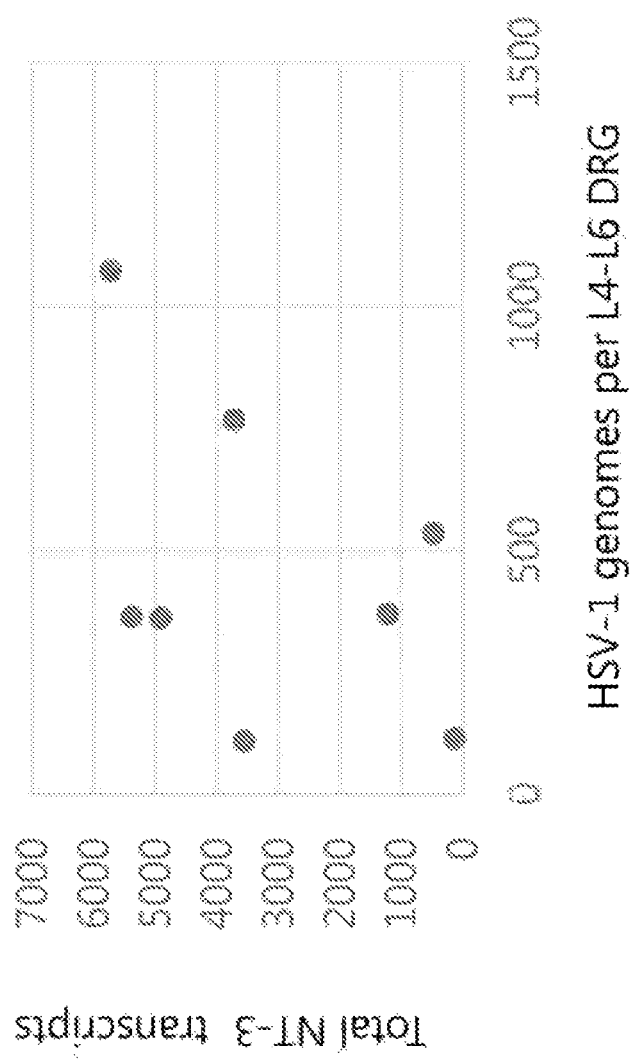
FIG. 10 depicts an exemplary graph that shows the total number of NT3 transcripts and the number of HSV-1 genomes per L4-L6 DRG 77 days post-administration of an HSV vector expressing NT3 in animals that received vincristine.
Figure 11:
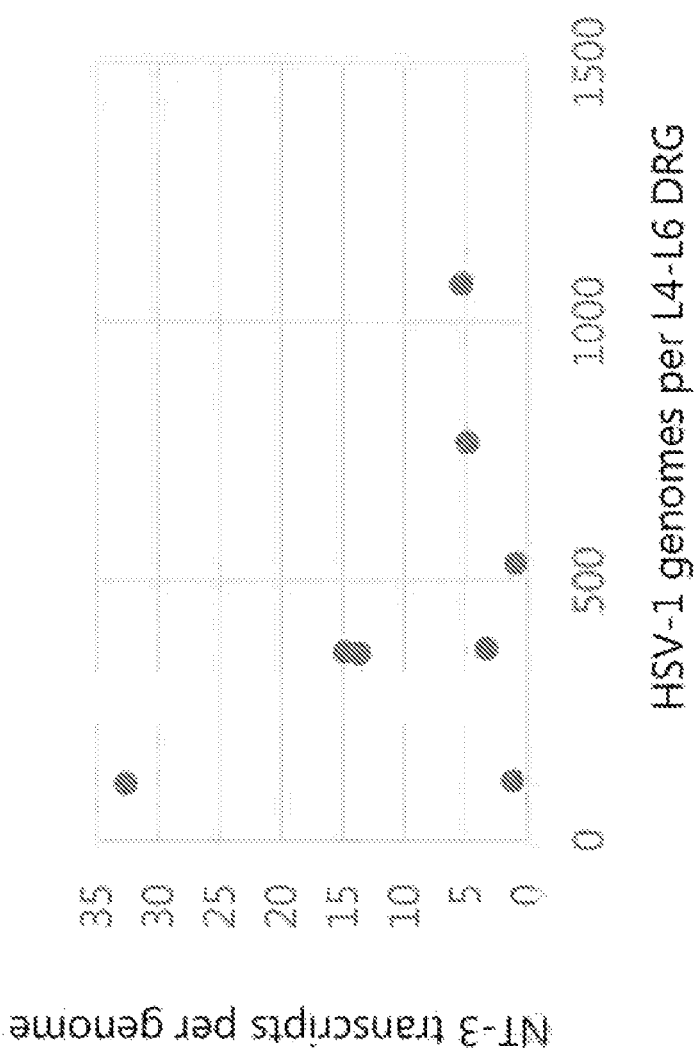
FIG. 11 depicts an exemplary graph that shows the total number of NT3 transcripts per genome and the number of HSV-1 genomes per L4-L6 DRG 77 days post-administration of an HSV vector expressing NT3 in animals that received vincristine.

Example 6: Analysis of Expression of Payload after Treatment with Vincristine This example shows exemplary data for the expression of transcripts relative to the number of HSV-1 genomes after administration of a replication-defective HSV-1 vector and vincristine. As shown in FIG. 10, NT-3 transcripts in the DRG were detectable in all eight animals tested 77 days post-administration of the HSV vector expressing NT3. Additionally, as shown in FIG. 11, when the data were analyzed as NT3 transcripts per genome rather than total number of NT3 transcripts, all eight animals were in the range of 2 to 32 transcripts per genome.

Figure 12:
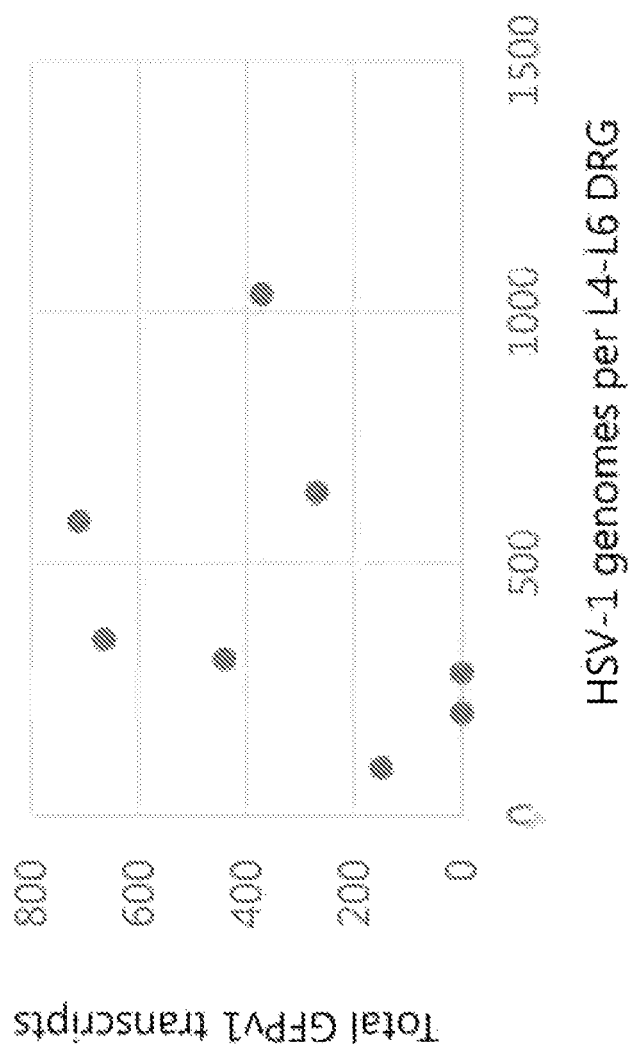
FIG. 12 depicts an exemplary graph that shows the total number of GFP transcripts and the number of HSV-1 genomes per L4-L6 DRG 77 days post-administration of an HSV vector expressing NT3 in animals that received vincristine.
Figure 13:
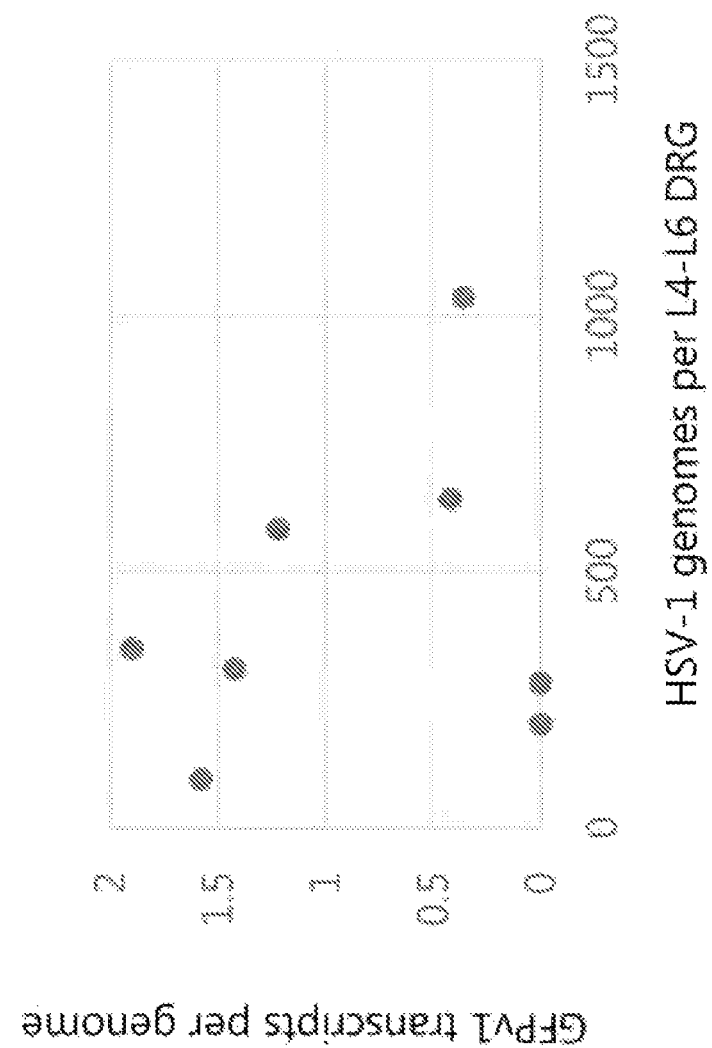
FIG. 13 depicts an exemplary graph that shows the total number of GFP transcripts per genome and the number of HSV-1 genomes per L4-L6 DRG 77 days post-administration of an HSV vector expressing NT3 in animals that received vincristine.

The same experiment was also performed with animals that were administered vincristine and a replication-defective HSV-1 vector comprising GFP. As shown in FIG. 12, GFP transcripts were detectable in six of eight animals tested 77 days post-administration of the GFP expressing vector. The GFP transcript levels were significantly lower than those seen in the animals administered the NT3 vector. Additionally, as shown in FIG. 13, when the data were analyzed as GFP transcripts per genome rather than total number of GFP transcripts, three of the seven animals were in the range of 0 to 1.8 transcripts per genome (as opposed to 2 to 32 for animals administered the NT3 vector.

Example 7: Prevention of CIPN (Oxaliplatin) with Vector Comprising NT3

This example shows exemplary data for the prevention of CIPN caused by oxaliplatin with a HSV vector comprising NT3.

The cytotoxicity of oxaliplatin, like other platinum compounds (cisplatin, carboplatin), is thought to result from inhibition of DNA synthesis in cells. In particular, oxaliplatin forms both inter- and intra-strand cross links in DNA, which prevent DNA replication and transcription, causing cell death. Oxaliplatin is used for treatment of colorectal cancer, typically along with folinic acid and 5-fluorouracil in a combination known as FOLFOX. Both an acute and a persistent neuropathy can occur with oxaliplatin use. The acute, reversible neuropathy (e.g., acute transient paresthesia, dysesthesia, and hypoesthesia in hands, feet, perioral area, or throat, jaw spasm, abnormal tongue sensation, dysarthria, ocular pain, a feeling of chest pressure) may occur within hours or 1-2 days following oxaliplatin administration and generally resolves within 14 days; it frequently recurs with further administration of the drug. A persistent sensory neuropathy (e.g., paresthesias, dysesthesias, hypoesthesias, impaired proprioception) can occur without any prior acute neuropathic event and typically persists for weeks to months following oxaliplatin administration.

Female BALB/c mice were injected subcutaneously into the plantar surface of both hind paws with 25 µl containing $1\times10^{10}$ PFU/mL of either a NT3 vector or a GFP vector. Three days following vector inoculation the mice began oxaliplatin treatment consisting of 3.5 mg/kg oxaliplatin (i.v.) biweekly for six weeks. On days 3, 17, 35, 41, 56, and 111 days following the final oxaliplatin dose, neuropathy was assessed by NCS.

Figure 14:
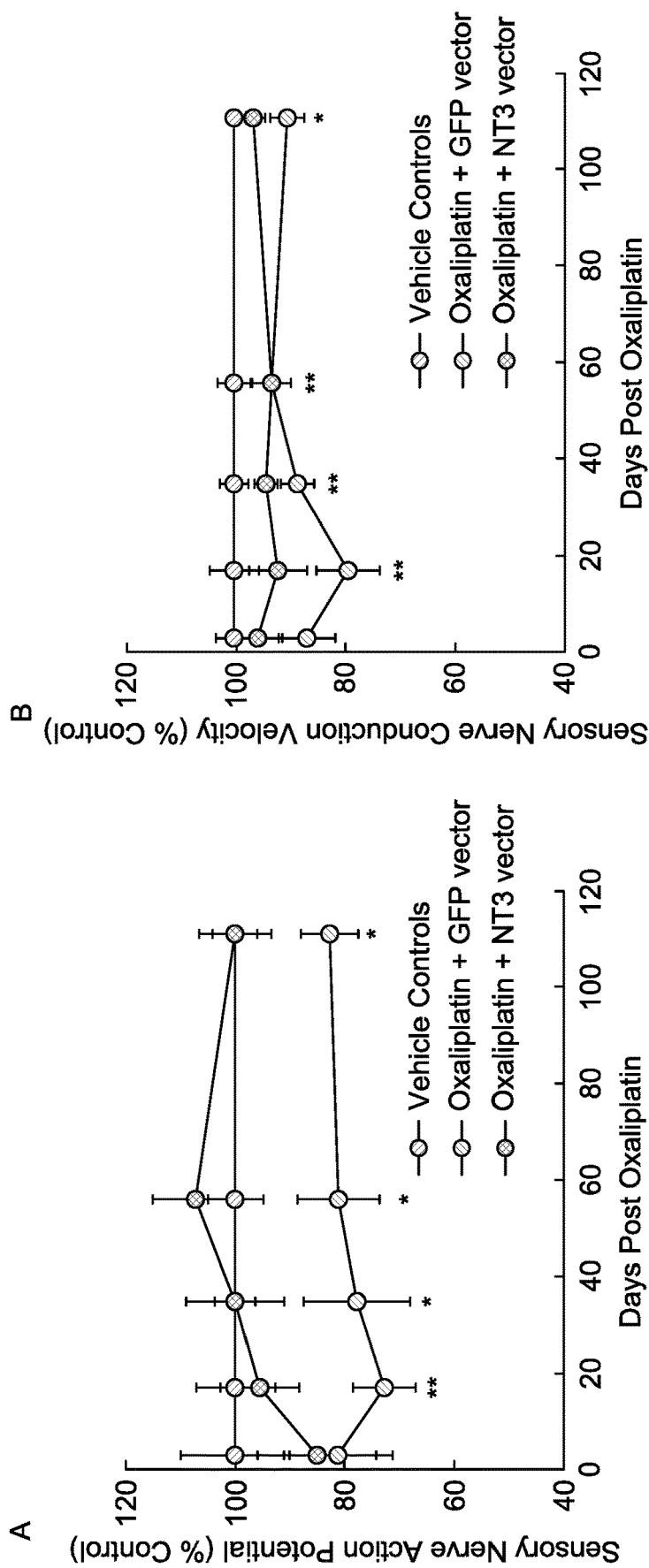
FIG. 14 (comprising panels A and B) depicts exemplary graphs that show SNAPs (panel A) and SNCV (panel B) as a percentage of control levels post-administration of oxaliplatin in animals treated with either vehicle control, an HSV vector expressing GFP, or an HSV vector expressing NT3.

As shown in FIG. 14 mice treated with oxaliplatin developed a peripheral neuropathy characterized by a 20-30% reduction in the evoked sensory nerve amplitude potential (SNAPs) and 10-20% reduction in conduction velocity (SNCV) from days 3-111 compared to untreated control mice. This reduction in SNAPs is similar to that found in mice treated with paclitaxel. Mice injected with the NT3 vector, but not those given the GFP vector, were protected from developing peripheral neuropathy and had SNAPs and SNCV indistinguishable from untreated control mice. This protection lasted for the entire time course of the study.

Example 8: Prevention of CIPN (Bortezomib) with Vector Comprising NT3

This example shows exemplary data for the prevention of CIPN caused by bortezomib with a HSV vector comprising NT3.

Bortezomib is FDA approved drug in a class of anticancer agents known as proteasome inhibitors. The cytotoxicity of these compounds is likely due to the disruption of critical cell signaling pathways, such as cell cycle regulation and gene transcription leading to cell cycle arrest and apoptosis. Bortezomib is usually used in the treatment of multiple myeloma and recurrent mantle cell lymphoma, though is also used for solid tumors. Like the taxanes and platins, the major clinically significant dose-limiting side effect is peripheral neuropathy, which is characterized by numbness and tingling that occurs in a distal stocking-and-glove pattern. Severe neuropathic pain frequently develops after the first treatment cycle.

Female BALB/c mice were injected subcutaneously into the plantar surface of both hind paws with 25 µl containing $1 \times 10^{10}$ PFU/mL of either a NT3 vector or a GFP vector. Three days following vector inoculation the mice began bortezomib treatment consisting of 0.8 mg/kg bortezomib (in 5%/5%/90% ethanol/tween80/saline) (i.v.) biweekly for four weeks. On days 12 and 26 days following the final bortezomib dose neuropathy was assessed by NCS.

Figure 15:
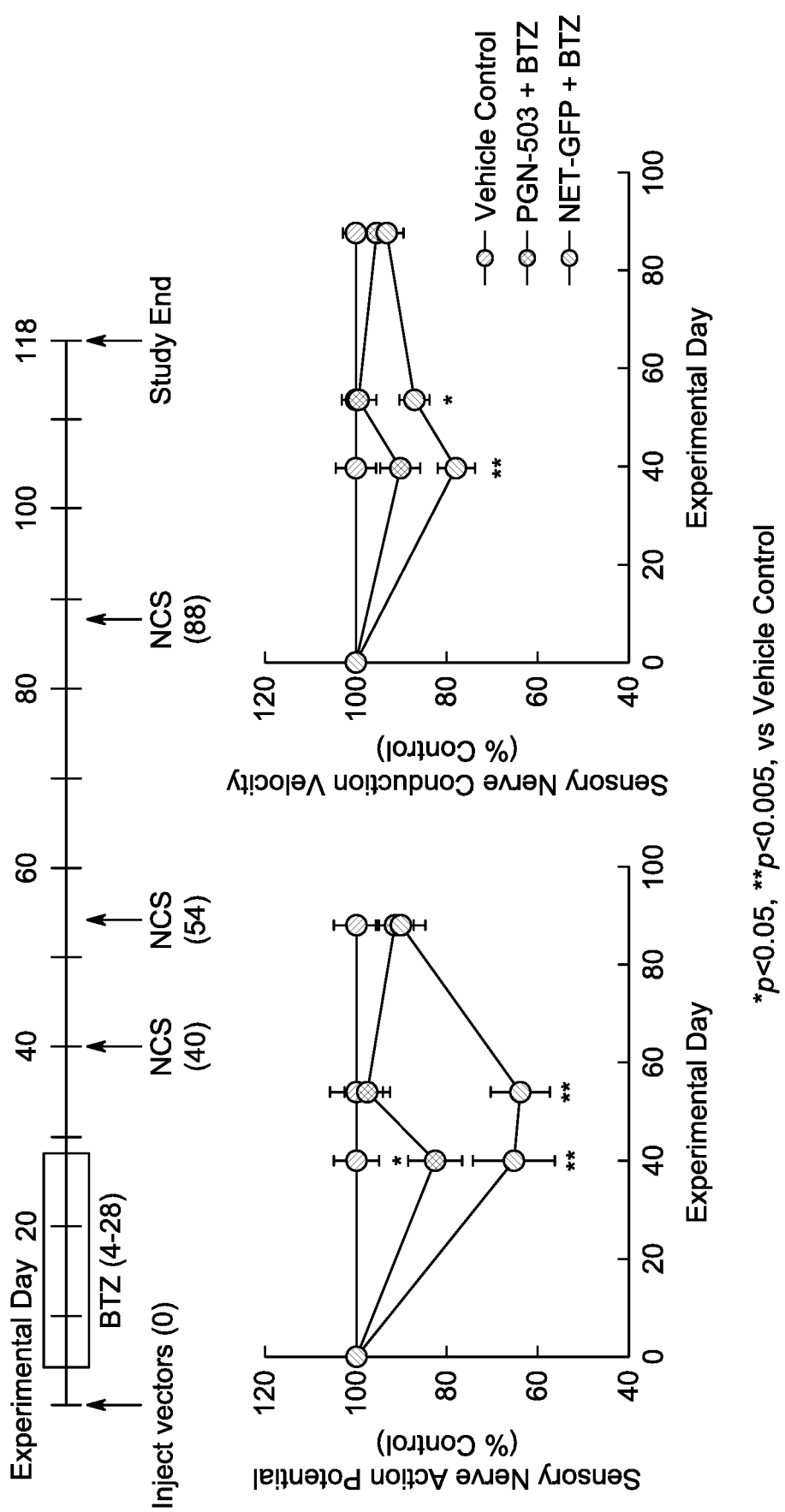
FIG. 15 depicts exemplary graphs that show SNAPs (left panel) and SNCV (right panel) as a percentage of control levels post-administration of bortezomib in animals treated with either vehicle control, an HSV vector expressing GFP, or a HSV vector expressing NT3.
Figure 26:
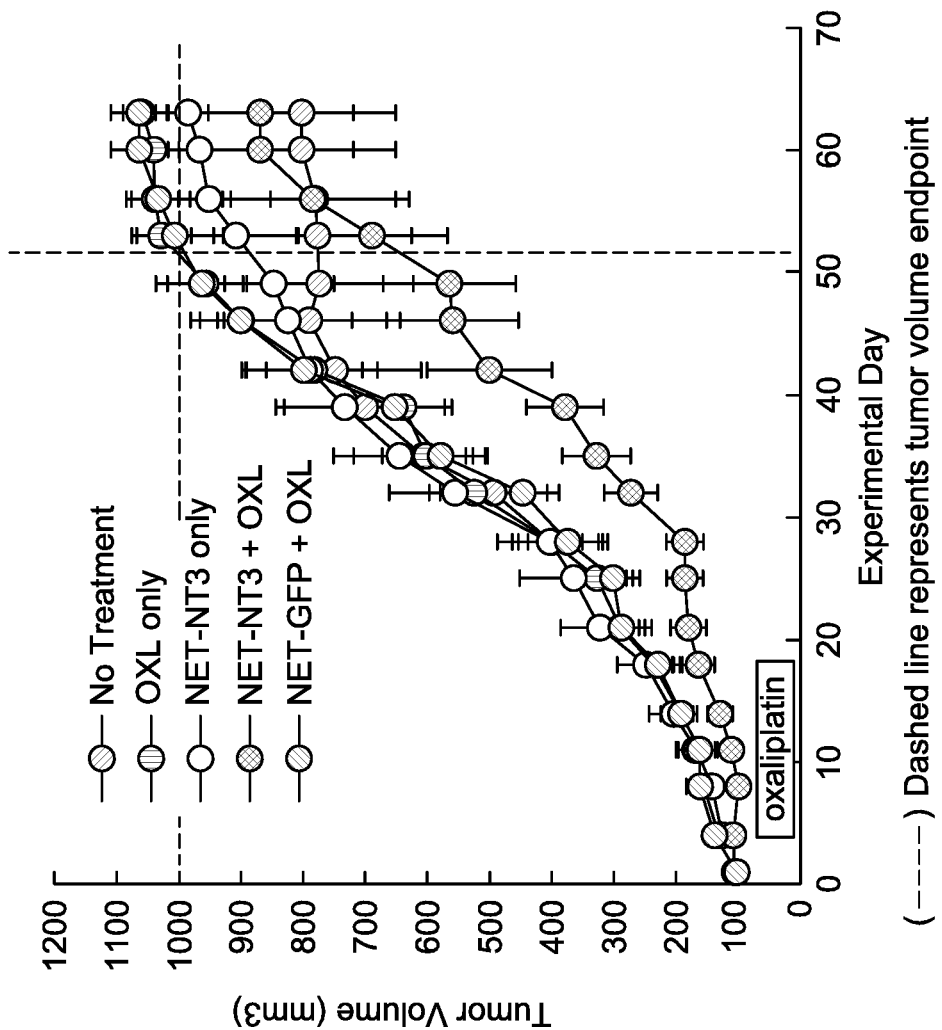
FIG. 26 depicts an exemplary graph that shows injection with an HSV vector expressing NT3 did not interfere with oxaliplatin treatment in a nude mouse model.
Figure 27:
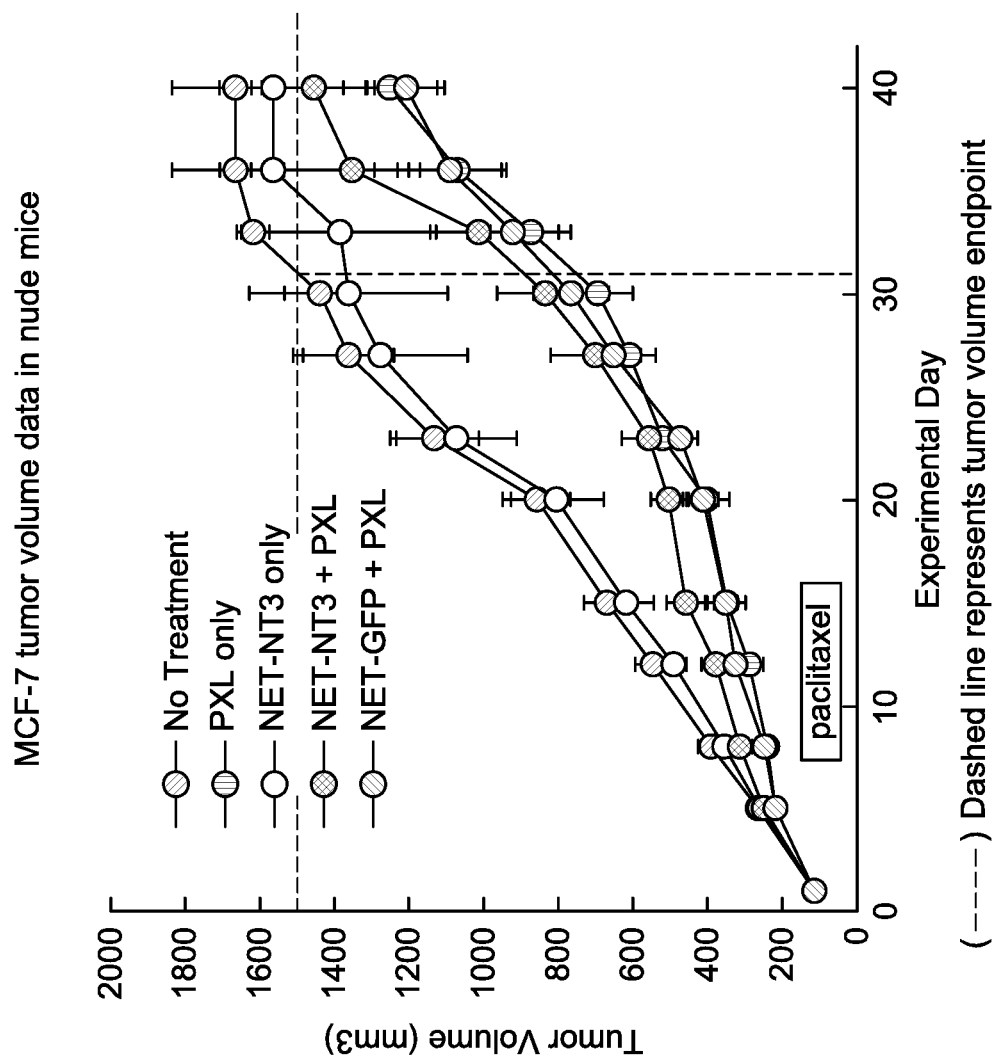
FIG. 27 depicts an exemplary graph that shows injection with an HSV vector expressing NT3 did not interfere with paclitaxel treatment in a nude mouse model.
Figure 28:
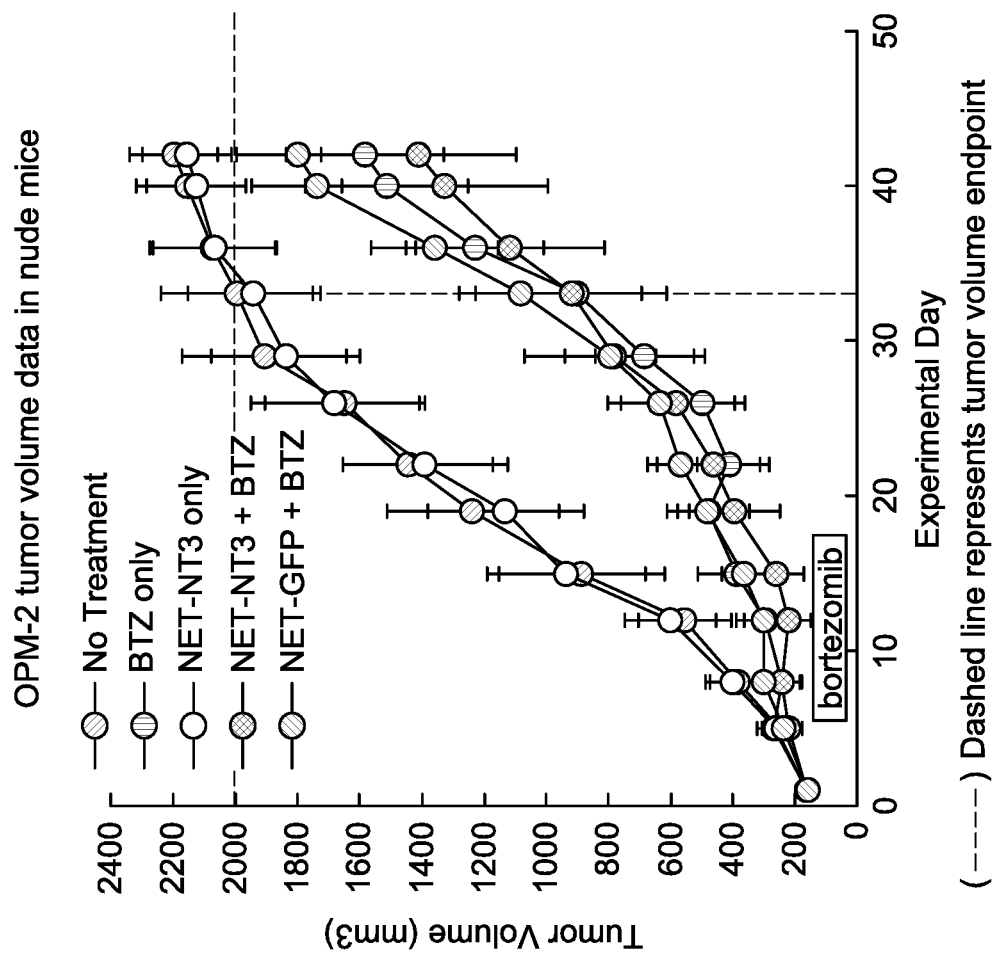
FIG. 28 depicts an exemplary graph that shows injection with an HSV vector expressing NT3 did not interfere with bortezomib treatment in a nude mouse model.
Figure 29:
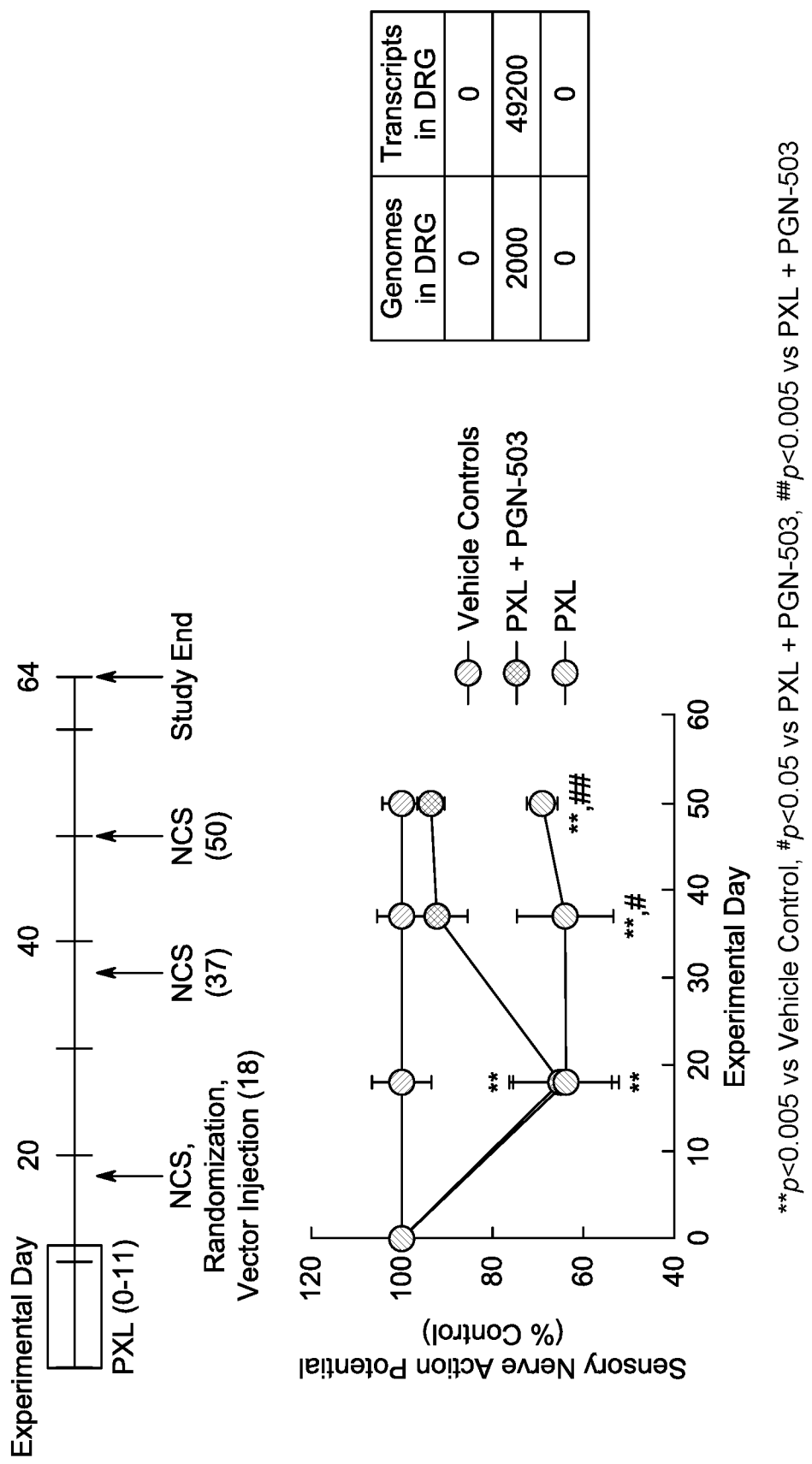
FIG. 29 depicts the ability of a HSV NT3 vector to reverse the neuronal damage associated with neuropathy. This indicates that a HSV NT3 vector can reverse existing CIPN.
Figure 30:
FIG. 30 depicts an exemplary graph that shows NT3 expression from a HCMV promoter lasted longer than GFP expression. Vector specific NT-3 and GFP transcript data expressed in dorsal root ganglion (DRG) are plotted from four different animal CIPN studies at 47, 77, 131, and 165 days
Figure 31:
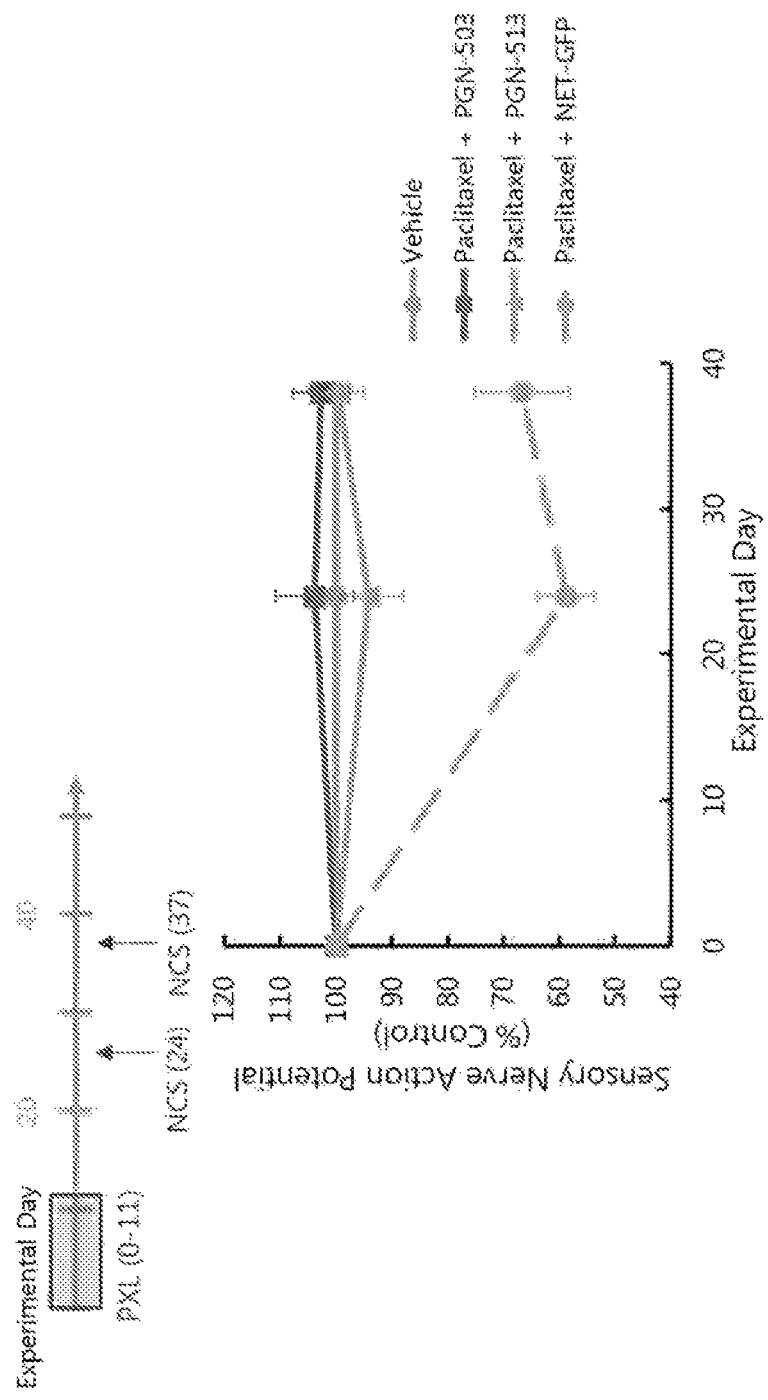
FIG. 31 depicts an exemplary graph that shows NT3 expression with a HCMV promoter (PGN-503) compared to NT3 expression with a chimeric HCMV-CGRP promoter (PGN-513). Each provides protection against paclitaxel-induced peripheral neuropathy.
Figure 32:
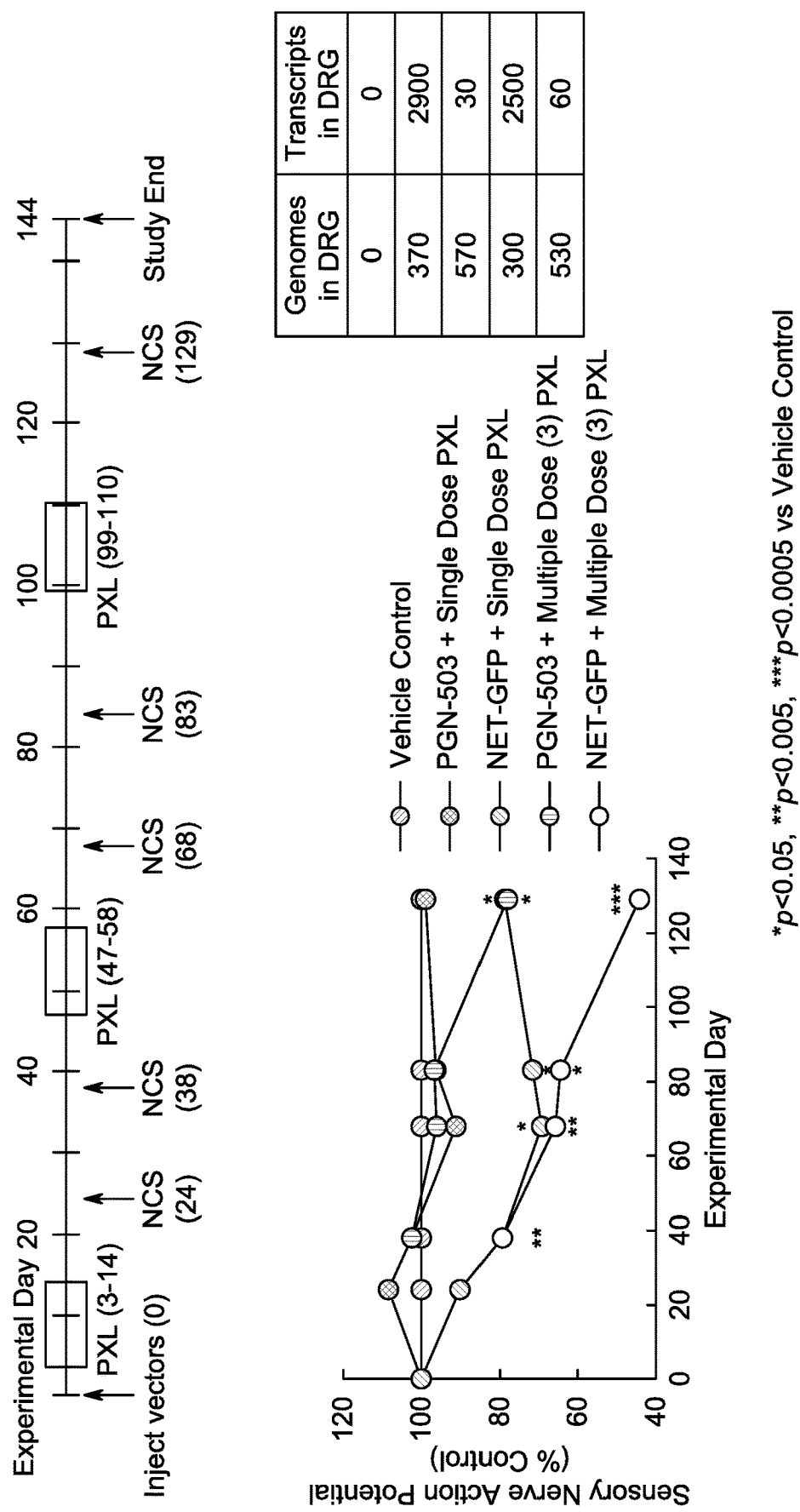
FIG. 32 depicts an exemplary graph showing effects on SNAPs in animals injected with an HSV vector expressing NT3 or an HSV vector expressing GFP prior to receiving three dosing regimens of paclitaxel as compared to vehicle.

As shown in FIG. 15, mice treated with bortezomib developed a peripheral neuropathy characterized by a reduction in the evoked sensory nerve amplitude potential (SNAPs) and a reduction in sensory nerve conduction velocity (SNCV) compared to untreated control mice A single application of PGN-503 prior to bortezomib dosing reduced the severity and duration of peripheral neuropathy.

Example 9: HSV McKrae Strain Vector Expressing NT3 (NET-NT3) Clinical Trial

A Phase I/II randomized, double-blind, placebo-controlled clinical trial of NET-NT3 is performed. NET-NT3 is a replication defective HSV vector expressing human NT-3 for the prevention or treatment of chemotherapy induced peripheral neuropathy (CIPN). The population for the proposed clinical trial is composed of breast cancer patients who are scheduled to receive 12 weekly doses of adjuvant paclitaxel treatment.

The clinical trial includes an escalating dose, randomized, double-blind, placebo-controlled experiment evaluating the safety and efficacy of intradermal administration of NET-NT3 to prevent chemotherapy-induced peripheral neuropathy in patients treated with paclitaxel in the adjuvant setting for breast cancer.

Within 28 days following a screening visit, subjects that meet all inclusion and exclusion criteria will be scheduled to receive NET-NT3 or placebo delivered as a series of approximately 10 intradermal injections on one leg below the knee and 10 injections below the elbow and on the back of the hand for the Phase I/II study on Day 0. NET-NT3 dosing will be scheduled to occur 3-14 days before initiation of chemotherapy. After 2 hours of observation in the clinical research center following dosing, after Day 0 post-dosing assessments, subjects will be discharged. Subjects that receive adjuvant paclitaxel (weekly for 12 weeks) will be followed every two weeks for 16 weeks and then a safety follow up visit at 28 weeks post dosing.

Primary objectives include:
(1) Evaluation of the safety of NET-NT3 delivered intradermally in three escalating dose cohorts, $2 \times 10^8$, $2 \times 10^9$, and $2 \times 10^{10}$ plaque forming units (PFU), in subjects scheduled to receive adjuvant paclitaxel for breast cancer; and
(2) Determination of the efficacy of CIPN prevention of NET-NT3 vs. placebo in subjects scheduled to receive adjuvant paclitaxel for breast cancer. Efficacy measurements will include sensory nerve action potential and nerve conduction velocities, clinical total neuropathy score (TNSc), and EORTC-CIPN20.

A primary efficacy variable is a change in sensory nerve action potential (sural and ulnar) between baseline and end of adjuvant paclitaxel treatment visit on week 12.

Secondary objectives include:
(1) Evaluation of improvement in general and disease-related quality of life (NCI-CTC and ECOG) scores of NET-NT3 vs. placebo; and
(2) Evaluation of the total dose of paclitaxel received in subjects that received NET-NT3 vs. placebo.

Secondary efficacy variables include:
(1) EORTC CIPN20 between baseline each biweekly visit up to week 12;
(2) Changes in the average EORTC CIPN20 at the 4 weeks post chemotherapy dosing visit. Paclitaxel: 16 weeks;
(3) Changes in the average EORTC CIPN20 at the safety follow-up visit. Paclitaxel: 28 weeks;
(4) Differences in the average development of neuropathy, as measured by the Total Neuropathy Score (TNS) from baseline compared to week 12 for paclitaxel subjects;
(5) Change in sural and ulnar nerve conduction velocity between baseline and end of chemotherapy treatment at week 12 for paclitaxel subjects;
(6) Changes in the average TNS at the 4 weeks post chemotherapy dosing visit. Paclitaxel: 16 weeks;
(7) Changes in the average TNS at the safety follow-up visit. Paclitaxel: 28 weeks;
(8) Changes in the National Cancer Institute-Common Toxicity Criteria (NCI-CTC) in subjects that received NET-NT3 vs. placebo at each visit;
(9) Eastern Cooperative Oncology Group (ECOG) scores in subjects that received NET-NT3 vs. placebo at each visit; and
(10) Cumulative total dose of chemotherapy for paclitaxel subjects between Day 0 and the 16 week visit.

Safety variables include:
(1) Physical examination including a neurological exam (sharp, warm, and vibratory sensations, and deep tendon reflexes);
(2) Adverse events (AEs);
(3) Serious Adverse Events (SAEs);
(4) Vital signs; and
(5) Clinical laboratory results.

Dosage and Administration:
NET-NT3 will be delivered at doses of $2 \times 10^8$ PFU, $2 \times 10^9$ PFU, and $2 \times 10^{10}$ PFU (total dose per subject) in 2.0 milliliters. The drug will be injected intradermally into approximately 20 sites made up of 10 sites distributed over the skin surface below one knee and 10 sites on the back of the ipsilateral hand. If all of the first three doses show a similar level of efficacy a fourth dose cohort will be added ($2 \times 10^7$ PFU) with the same number of patients and study performance.

The study is designed to dose three subjects at each dose level in order to assess safety. After one month of safety data has been collected for each patient within the dose cohort it will be determined if the study should advance to the next dose level. Once a dose level has been approved an additional 23 subjects will be recruited at that dose level. Of the 23 subjects 17 will be administered the same dose as the safety cohort and six subject will receive placebo. This dosing regimen will be completed for the three dose levels unless a dose level is not approved for advancement.

The order of dosing will begin with three subjects in the $2\times10^8$ cohort that will comprise the first dose and will advance until either the maximum tolerated dose (MTD) or the highest dose level ($2\times10^{10}$ PFU) is attained. There will be a one month review period after each cohort is filled in order to assess safety before a DSMB will be asked to approve escalation to the next dose level. In order to confirm that the dose chosen for the Phase II is the minimum effective dose an extra 17 subjects will be dosed at each dosing level after the one month safety review is complete for that dose. Precedence for treatment in the study will be given to the three subjects in each dose group before the extra 17 subjects are dosed. Assuming a DLT does not occur the dosing of the three subject safety cohorts and the expansion cohorts will be performed as follows.

1. At the start of the study three subjects will be dosed with $2\times10^8$ PFU and no further treatment will be administered until those three subjects have completed one month post-dosing.

2. Once the DSMB has reviewed the safety data and given an approval to advance to the next dose three subjects will be dosed with $2\times10^9$ PFU. While the one month follow-up period for the $2\times10^9$ PFU cohort is underway additional subjects will be treated with $2\times10^8$ PFU until the DSMB has reviewed the $2\times10^9$ PFU cohort data.

3. Once the DSMB has given approval to advance three subjects will be dosed at $2\times10^{10}$ PFU for the final cohort. While the one month follow-up period for the $2\times10^{10}$ PFU is underway additional subjects will be treated with $2\times10^8$ PFU until the expansion cohort is filled and then additional subjects will be treated with $2\times10^9$ until that cohort is filled.

4. After the safety follow-up period for the three subject $2\times10^{10}$ PFU cohort is completed any remaining subjects that are needed to complete the 17 subject expansion group for the $2\times10^8$, $2\times10^9$, or $2\times10^{10}$ PFU dose level will be recruited.

In the event that all doses are equally effective in preventing CIPN a fourth dose cohort of $2\times10^7$ PFU will be added and study performance for the fourth cohort will be the same as the previous three cohorts.

| Dose | Safety Cohort | Expansion Cohort |
|---|---|---|
| $2\times10^8$ PFU total ($1\times10^8$ on one hand, $1\times10^8$ on one foot) | 3 subjects | 17 subjects |
| $2\times10^9$ PFU total ($1\times10^9$ on one hand, $1\times10^9$ on one foot) | 3 subjects | 17 subjects |
| $2\times10^{10}$ PFU total ($1\times10^{11}$ on one hand, $1\times10^{10}$ on one foot) | 3 subjects | 17 subjects |

Rules for Dose Escalation in Three Safety Subjects:

There will be a minimum one-month observation period from the end of dosing in one dose cohort before initiation of dosing in a subsequent cohort. Dosing will advance until either the maximum tolerated dose (MTD) is attained or the highest dose is reached. The MTD is defined as the highest dose with $\leq\frac{1}{3}$ NET-NT3 treated subjects having dose limiting toxicity (DLT). A DLT is defined as a probable or definite active NET-NT3 treatment-related grade 2 or higher adverse event. With respect to the three subjects in each cohort that will be assessed to allow advancement to the next higher dose the following rules shall apply.

Dose escalation to the next higher dose, de-escalation to the previous lower dose, or additional testing at the current dose will be based upon the following rules:

1. If 0 of the 3 NET-NT3 treated subjects in the cohort have a DLT, escalate to the next higher dose cohort of 3 active NET-NT3 subjects.
2. If 1 or more of the 3 subjects have DLTs, enroll 3 more subjects at the same dose:
   a. If <2 of the 6 NET-NT3 treated subjects in the dosing cohort have DLTs, escalate to the next higher dose;
   b. If >2 of the 6 NET-NT3 treated subjects have DLTs, de-escalate to previous dose;
3. If de-escalation is indicated at the lowest dose level, the study will be discontinued and a new protocol will be submitted to test a lower dose range.

Subjects who drop out prior to the Day 28 visit for reasons other than toxicity will be replaced.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A variant of herpes simplex virus (HSV) McKrae strain whose genome contains an alteration such that the variant fails to express one or more immediate early genes, wherein the genome comprises a nucleic acid molecule encoding a neurotrophin 3 polypeptide.

2. The variant of herpes simplex virus (HSV) McKrae strain according to claim 1, wherein the variant fails to express a functional protein characterized by SEQ ID NO: 2.

3. The variant of herpes simplex virus (HSV) McKrae strain according to claim 1, wherein the variant fails to express a functional protein characterized by SEQ ID NO: 16.

4. A composition comprising:
a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide; and
a pharmaceutically acceptable carrier.

5. The composition according to claim 4, wherein, the variant fails to express a functional protein characterized by SEQ ID NO: 2.

6. The composition according to claim 4 wherein, the variant fails to express a functional protein characterized by SEQ ID NO: 16.

7. The composition of claim 4, wherein the vector further comprises a promoter operatively linked to a sequence encoding neurotrophin 3.

8. The composition of claim 7 wherein the vector further comprises an enhancer upstream of the promoter.

9. The composition of claim 8, wherein the promoter is tissue specific.

10. The composition of claim 8, wherein the promoter is neuron specific.

11. The composition of claim 7 wherein the promoter is a human cytomegalovirus (HCMV) promoter.

12. The composition of claim 7 wherein the promoter is a calcitonin gene-related peptide (CGRP) promoter.

13. The composition of claim 4, wherein the vector comprises a bovine growth hormone (BGH) polyadenylation signal.

14. The composition of claim 4, wherein the carrier is a polyol.

15. The composition of claim 4, wherein the carrier is glycerol.

16. The composition of claim 4, wherein the nucleic acid molecule encoding a neurotrophin 3 polypeptide is codon optimized.

17. A method of inhibiting the development or progression of neuropathy in a subject, the method comprising administering to the subject a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide.

18. The method according to claim 17, wherein the variant fails to express a functional protein characterized by SEQ ID NO: 2.

19. The method according to claim 17, wherein the variant fails to express a functional protein characterized by SEQ ID NO: 16.

20. A method of treating neuropathy in a subject, the method comprising administering to the subject a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide.

21. The method of treating neuropathy in a subject according to claim 20, wherein the variant fails to express a functional protein characterized by SEQ ID NO: 2.

22. The method of treating neuropathy in a subject according to claim 20, wherein the variant fails to express a functional protein characterized by SEQ ID NO: 16.

23. The method according to claim 20, wherein the neuropathy is a peripheral neuropathy.

24. The method according to claim 20, wherein the neuropathy is iatrogenic.

25. The method according to claim 20, wherein the neuropathy is a result of a cancer treatment.

26. The method according to claim 20, wherein the neuropathy is a result of chemotherapy.

27. The method according to claim 26, wherein the chemotherapy comprises a platinum based chemotherapeutic.

28. The method according to claim 20, wherein the vector is administered by contact with the skin of a subject.

29. The method according to claim 20, wherein the vector is administered intradermally.

30. In a method of treating a subject having cancer with a chemotherapeutic agent, the improvement comprising administering to the subject a vector comprising a variant of herpes simplex virus (HSV) McKrae strain whose genome contains an alteration such that the variant fails to express one or more immediate early genes, wherein the genome comprises a nucleic acid molecule encoding a neurotrophin 3 polypeptide, wherein the vector is administered to promote tolerance against chemotherapy induced neuropathy.

* * * * *

SEQUENCE LISTING

<160> NUMBER OF SEQ ID NOS: 25

<210> SEQ ID NO 1
<211> LENGTH: 151135
<212> TYPE: DNA
<213> ORGANISM: human herpesvirus 1 strain McKrae
<220> FEATURE:
<221> NAME/KEY: misc_feature
<222> LOCATION: (61968)..(62069)
<223> OTHER INFORMATION: n is a, c, g, or t

<400> SEQUENCE: 1

```
gcagcccggg ccccccgcgc gcggggcggc gcgcaaaaaa ggcgggcggc ggtccgggcg      60
gcgtgcgcgc gcgcggcggg cgtgggggc ggggccgcgg gagcggggga ggagccccac     120
```

```
ccacagacgg ggaggagcgg gggaggagcg ggggaggagc ggggggaggag ccccacccac       180 agacggggag gagcggggga ggagcggcca gaccccaaaa acgggccccc ccgaaacaca       240
ccccccgggg gtcgcgcgcg gcccttttaaa gcgcggcggc gggcagcccg gccccccgc       300 ggccgagact agcgagttag acaggcaagc actactcgcc tctgcacgca catgcttgcc       360
tgtcaaactc taccaccccg gcacgctctc tgtctccatg gcccgccgcc gccgccatcg       420
cggcccccgc cgcccccggc cgccggggcc cacgggcgcc gtcccaaccg cacagtccca       480
ggtaacctcc acgcccaact cggaacccgc ggtcaggagc gcgcccgcgg ccgccccgcc       540
gccgcccccc gccggtgggc ccccgccttc ttgttcgctg ctgctgcgcc agtggctcca       600
cgttcccgag tccgcgtccg acgacgacga tgacgacgac tggccggaca gccccccgcc       660
cgagccggcg ccagaggccc ggccaccgcc cgccgccccc cggccccggt ccccaccgcc       720
cggcgtgggc ccgggggcg gggctgaccc ctcccacccc ccctcgcgcc ccttccgcct       780
tccgccgcgc ctcgccctcc gcctgcgcgt caccgcggag cacctggcgc gcctgcgcct       840
gcgacgcgcg ggcggggagg gggcgccgga gcccccgcg accccgcga ccccgcgac       900 ccccgcgacc cccgcgaccc ccgcgacccc gcgaccccc gcgaccccg cgcgggtgcg       960 cttctcgccc cacgtccggg tgcgccacct ggtggtctgg gcctcggccg cccgcctggc      1020
gcgccgcggc tcgtgggccc gcgagcgggc cgaccgggct cggttccggc gccgggtggc      1080
ggaggccgag gcggtcatcg ggccgtgcct ggggcccgag gccgtgccc gggccctggc      1140 ccgcggagcc ggcccggcga actcggtcta acgttacacc cgaggcgcct gggtcttccg      1200
cggagctccc gggagctccg caccaagccg ctctccggag agacgatggc aggagccgcg      1260
catatatacg ctgggagccg gtccgccccc aaggcgggcc cgcctcgggg gcgggactgg      1320
ccaatcggcg gccgccagcg cggcggggcc cggccaacca gcgtccgccg agtcttcggg      1380
gcccggccca ttgggcggga gttaccgccc aatgggccgg gccgcccact tcccggtatg      1440
gtaattaaaa acttgcaaga ggccttgttc cgcttcccgg tatggtaatt agaaactcat      1500
taatgggcgg ccccggccgc ccttcccgct tccggcaatt cccgcggccc ttaatgggca      1560
accccggtat tccccgcctc ccgcgccgcg cgtaaccact cccctgggt tccgggttat      1620 gctaattgct tttttggcgg aacacacggc ccctcgcgca ttggcccgcg ggtcgctcaa      1680
tgaacccgca ttggtcccct gggggttccgg gtatggtaat gagtttcttc gggaaggcgg      1740
gaagccccgg ggcaccgacg caggccaagc ccctgttgcg tcggcgggag gggcatgcta      1800
atggggttct ttgggggaca ccgggttggt ccccaaatc gggggccggg ccgtgcatgc      1860
taatgatatt cttgggggc gccggggttgg tccccgggga cggggccgcc ccgcggtggg      1920
cctgcctccc ctgggacgcg cggccattgg gggaatcgtc actgccgccc ctttggggag      1980
gggaaaggcg tggggtataa gttagccctg gcccgacggt ctggtcgcat ttgcacctcg      2040
gcactcggag cgagacgcag cagccaggca gactcgggcc gcccctctc cgcatcacca      2100 cagaagcccc gcctacgttg cgaccccag ggaccctccg tccgcgaccc tccagccgca      2160 tacgacccc atggagcccc gcccggagc gagtacccgc cggcctgagg ccgcccca       2220 gcgcgaggtg aggggccggg cgccatgtct ggggcgccat attgggggc gccatgttgg      2280 gggaccccg accccttaccc tggaaccggc ccccatgttg gggacccccc actcatacac      2340
gggagccggg cgccatgttg gggcgccatg ttagggggcg tggaacccg tgacactata      2400 tatacaggga ccggggggcgc catgttaggg ggcgcggaac ccctgaccc tatatataca      2460
```

-continued

```
gggaccgggg tcgccctgtt gggggtcgcc atgtgacccc ctgactttat atatacagac    2520
ccccaacaca tacacatggc cccctttgact cagacgcagg gcccgggtc gccgtgggac    2580 cccctgactc atacacagag acacgccccc acaacaaaca cacagggacc ggggtcgccg    2640
tgttgggggc gtggtcccca ctgactcata cgcaggcccc ccttactcac acgcatctag    2700 ggggggtgggg aggagccgcc cgccatattt ggggacgcc gtgggacccc cgactccggt    2760
gcgtctggag ggcgggagaa gagggaagaa gaggggtcgg gatccaaagg acggacccag    2820
accacctttg gttgcagacc cctttctccc ccctcttccg aggccagcag ggggcagga    2880 ctttgtgagg cgggggggga gaggggaac tcgtgggcgc tgattgacgc gggaaatccc    2940 ccccattct tacccgcccc ccttttttcc ccttagcccg ccccggatgt ctgggtgttt    3000
ccctgcgacc gagacctgcc ggacagcagc gactctgagg cggagaccga agtggggggg    3060
cggggggacg ccgaccacca tgacgacgac tccgcctccg aggcggacag cacggacacg    3120
gaactgttcg agacgggct gctggggccg cagggcgtgg atggggggc ggtctcgggg    3180 gggagccccc ccgcgagga agaccccggc agttgcgggg gcgccccccc tcgagaggac    3240 gggggagcg acgagggcga cgtgtgcgcc gtgtgcacgg atgagatcgc gccccacctg    3300
cgctgcgaca ccttcccgtg catgcaccgc ttctgcatcc cgtgcatgaa aacctggatg    3360
caattgcgca cacctgcccc gctgtgcaac gccaagctgg tgtacctgat agtgggcgtg    3420
acgcccagcg ggtcgttcag caccatcccg atcgtgaacg accccagac ccgcatggag    3480 gccgaggagg ccgtcagggc gggcacggcc gtggactta tctggacggg caatcagcgg    3540
ttcgccccgc ggtacctgac cctggggggg cacacggtga gggccctgtc gcccacccac    3600
ccggagccca ccacggacga ggatgacgac gacctggacg acgtgaggc ggggggcggc    3660 aaggaccctg ggggaggagg aggagggagg aatgggcggg cggcgagga aagggcgggc    3720 cggggagggg gcgtaacctg atcgcgcccc ccgttgtctc ttgcagcaga ctacgtcccg    3780
cccgcccccc gccggacgcc ccgcgccccc ccacgcagag gcaccgccgc gcccccgtg    3840 acgggcgggg cgtctaacgc agcccccag ccggccgcgg ctcggacagc gcccccctcg    3900
gcgcccatcg ggccacacgg cagcagtaac accaacacca ccaccaacag cagcggcggc    3960
ggcggctccc gccagtcgcg agccgcggcg ccgcgggggg cgtctggccc ctccggggg    4020 gttgggggttg gggttgggg tgttgaagcg gaggcgggc ggccgagggg ccggacgggc    4080
ccccttgtca acagacccgc ccccttgca aacaacagag acccatagt gatcagcgac    4140 tccccccgg cctctcccca caggcccccc gcggcgccca tgccaggctc cgccccccgc    4200
cccgggcccc ccgcgtcctc ggccgcgtcg ggacccgcgc gccccgcgc ggccgtggcc    4260 ccgtgcgtgc gagcgccgcc tccggggccc ggccccccgcg ccccgccccc cggggcggag    4320
ccggccgccc gccccgcgga cgcgcgccgt gtgcccagt cgcactcgtc cctggctcag    4380
gccgcgaacc aagaacagag tctgtgccgg gcgcgtgcga cggtggcgcg cggctcgggg    4440
gggccgggcg tggagggtgg gcacgggccc tcccgcggcc gcaccccctc cggcgccgcc    4500
ccgctcccct ccgccgtctc tgtcgagcag gaggcggcgg tgcgtccgag gaagaggcgc    4560
gggtcgggcc aggaaaaccc ctccccccag tccacgcgtc ccccctcgc gccggcaggg    4620 gccaagaggg cggcgacgca ccccccctcc gactcagggc cggggggcg cggccagggt    4680 gggcccggga cccccctgac gtcctcggcg gcctccgcct cttcctcctc tgcctcttcc    4740
tcctcggccc cgaccccgc gggggccgcc tcttccgccg ccggggccgc gtcctcctcc    4800
gcttccgcct cctcgggcgg ggccgtcggt gccctgggag ggagacaaga ggaaacctcc    4860
```

```
ctcggccccc gcgctgcttc tgggccgcgg gggccgagga agtgtgcccg gaagacgcgc    4920
cacgcggaga cttccggggc cgtccccgcg ggcggcctca cgcgctacct gcccatctcg    4980
ggggtctcta gcgtggtcgc cctgtcgcct tacgtgaaca agactatcac gggggactgc    5040
ctgcccatcc tggacatgga gacggggaac atcgggcgt acgtggtcct ggtggaccag     5100
acgggaaaca tggcgacccg gctgcgggcc gcggtccccg gctggagccg ccgcaccctg    5160
ctccccgaga ccgcgggtaa ccacgtgatg ccccccgagt acccgacggc ccccgcgtcg    5220
gagtggaaca gcctctggat gacccccgtg gggaacatgc tgttcgacca gggcacccta    5280
gtgggcgccc tggacttccg cagcctgcgg tctcggcacc cgtggtccgg ggagcagggg    5340
gcgtcgaccc gggacgaggg aaaacaataa gggacgcccc ccgtgtttgt ggggaggggg    5400
gtcgggtgct gggtggtctc tggccgcgcc cactacacca gccaatccgt gtcggggagg    5460
ggaaagtgaa agacacgggc accacacacc agcgggtctt tagtgttggc cctaataaaa    5520
aactcagggg attttttgctg tctattggga aataaaggtt tacttttgta tcttttccct    5580
gtctgtgttg gatggatctt gggggtgcgt gggagtgggg gtgcgtggga gtggggtgc     5640 gtgggagtgg gggtgcgtgg gagtgggggt gcgtgggagt gggggtgcgt gggagtgggg   5700
gtgcgtggga gtggggtgc gtgggagtgg gggtcgtgg gagtgggggt gcgtgggagt      5760 ggggggtgcgt gggagtgggg gtgcgtggga gtggggtgc gtgggagtgg ggtgccatg     5820 ttgggcaggc tctggtgtta accacagagc gcgccccgg gctgcctgac caccgatccc     5880
cgaaagcatc ctgccactgg catggagcca gaaccacagt gggctgggtg tgggtgttaa    5940
gtttccgcga gcgcctgccc gcccggactg acctggcctc tggccgccac aaagggcggg    6000 ggggggtta actacactat agggcaacaa aggacgggag gggtggcggg acggggcgcc     6060
caaaaggggg tcggccacac cacagacgtg ggtgttgggg ggtggggcgg aggggtgggg   6120
gggagacaga aacaggaaca tagttagaaa acaagaatgc ggtgcagcca gagaatcaca    6180
ggagacgagg ggatgggcgt gttggttacc aacccacacc caggcatgct cggtggtatg    6240
aaggaggggg ggcggtgctt cttagagacc gccgggggac gtgggtggg tgtgcaaagg     6300 cacgcgcacc cgcgtcggcc aggtgggccg gtaccccatc cccccctccc ccgaccccttc   6360 ccccccccgcg tgccagagat caccccccgtc ccccggcacc cgccactcct ccatatcctc   6420
gctttaggaa caactttggg gggggggtac acacgcgccg tgcatttcct tccacacccc    6480
ccctcccccg catcccccccc cccaggcagt aagacccaag catagagagc caggcacaaa   6540
aacacaggcg gggtgggaca catgccttct tggagtacgt gggtcattgg cgtggggggt    6600
tacagcgaca ccggccgacc ccctggcggt cttccagccg gcccttagat aaggggggcag   6660 ttggtggtcg gacgggtaag taacagagtc tgactaaggg tggaggggg ggaaaagaac     6720 gggctggtgt gctgtaacac gagcccaccc gcgagtggcg tggccgacct tagcctctgg    6780
ggcgccccct gtcgtttggg tcccccccccc tctattgggg agaagcaggt gtctaaccta   6840
cctggaaacg cggcgtcttt gttgaacgac accggggcgc cctcgacgag tgggataacg    6900
ggggaggaag ggagggagga gggtactggg ggtgaagaag gggggggggga agaagcgaga   6960 acaggaaagg cgacggagcc cggcagaaca ccgaggaaaa aaaaaacaca gcgcatgcgc    7020
cgggccgttg tggggccccg ggccgggggcc ccttgggtcc gccgggggccc cgggccgggc   7080 cgccacgggg gccggccgtt ggcggtaacc ccgattgttt atctcaggcc ccgggccggg    7140
aacccggaaa agcctccggg gggccttttt cgcgtcgcgt gccggcgagc gggcccggac    7200
```

```
ggggcccgga ccgccgcggt cggggcccc  tcgtcccggg ccgtacgcgg ccttcgcccc  7260
gtgaggggcc gaacgaacga aacatcccgg cgacggaacg aaaaacaccc cagacgggtt  7320
taaaaaacag aaaccgtaac ccccccacc  cccgaaacgg ggaaaacaaa aaacagacca  7380
gcggccggcc ggcgcttagg gggaggatgt cgccgacgcc ccttggccgc ccggctgca   7440
gggggcccg  gagagccgcg gcacccggac gcgcccggaa agtctttcgc accacccgcg  7500
atcggcacgg ccgcgccccc gcttttataa aggctcagat gacgcagcaa aaacaggcca  7560
cagcaccacg tgggtaggtg atgtaatttt attttcctcg tctgcggcct aatggatttc  7620
cgggcgcggt gccctgtct  gcagagcact taacggattg atatctcgcg ggcacgcgcg  7680
cccttaatgg accgcgcgg  ggcggggggc cggatacca  cacgggcggg ggggtgtcgc  7740
gggccgtctg ctggcccgcg gccacataaa caatgactcg ggcctttct  gcctctgccg  7800
cttgtgtgtg cgcgcgccgg ctctgcggtg tcggcggcgg ctgcggcggc tgcggcggcc  7860
gccgtgttcg gtctcggtag ccggccggcg ggtggactcg cgggggggccg gagggtggaa  7920
ggcaggggggg tgtaggatgg gtatcaggac ttccacttcc cgtccttcca tccccgttc   7980
ccctcggttg ttcctcgcct cccccaacac cccgccgctt tccgttgggg ttgttattgt   8040
tgtcgggatc gtgcgggccg ggggtcgccg ggcaggggc  ggggcgggg  gtgctcgtcg  8100
atcgaccggg ctcagtgggg gcgtggggtg ggtgggaaaa ggcgaggaga ctggggtggg   8160
gggtgtcggg ggtggctgtt tttttgtggt tgttttttgt gtctgttccc gtccccgtc   8220
accccctcc  ctccgtcccc ccgtcgcggg tgtttgtgtt tgtttattcc gacatcggtt   8280
tatttaaata aacacagccg ttctgcgtgt ctgttcttgc gtgtggctgg gggcttatat   8340
gtggggtccc ggggggcggga tgggttta g cggcgggggg cggcgcgccg gacggggcgc   8400
tggagataac ggccccgggg gaacggggga ccggggctgg gtctcccgcg gtgggtgggt   8460
gggcggcggt ggccgggccg ggccgggccg ggtgggcggg gtttggaaaa acgaggagga   8520
ggagaaggag gaggagggggg ggggagacgg gggggaaagca aggacacggc cccggggggg  8580
ggggagcgcg ggccgggccg cttggcaacc ccctgtttc  ttccggaaac caggcttgtg   8640
gccccacccg acatcacaag ggacctcttg tcgggcctcc cgacgtacgc cgaggctatg   8700
tcggaccacc ccccaaccta agaggggaga ggggagaggg gagaggggag aggggagagg   8760
ggagagggga ggagagggg  tatataaacc aacgaaaagc gcgggaacgg ggatacgggg   8820
cttgtgtggc acgacgtcgt ggttgtgtta ctgggcaaac acttggggac tgtaggtttc   8880
tgtggtgccg accctaggcg ctatggggat tttgggttgg gttgggctta ttgccgttgg   8940
ggttttgtgt gtgcggggggg gcttgccttc aaccgaatat gttattcgga gtcgggtggc   9000
tcgagaggtg ggggatatat taaaggtgcc ttgtgtgccg ctcccgtctg acgatcttga   9060
ttggcgctac gagaccccct cggctataaa ctatgctttg atagacggta tattttgcg   9120
ttatcactgt cccggattgg acacggtctt gtgggatagg cacgcccaga gggcgtattg   9180
ggttaaccc  ttttttgtttg gggcggggttt tttggaggac ttgagtcatc ccgcgtttcc   9240
tgccgacacc caggaaacag aaacgcgctt ggcccttat  aaagagatac gccaggcgct   9300
ggacagtcgc aagcaggccg ccagccacac acctgtgaag gctgggtgtg tgaactttga   9360
ctattcgcgc accccgccgct gtgtagggcg ccaggatttg ggacttacca acagaacgtc   9420
tggacggacc ccggttctgc cgtcggacga tgaagcgggc ctgcagccga agcccctcac   9480
cacgccgtcg cccatcatcg ccacgtcgga ccccacccccg cgacgggacg ccgccacaaa   9540
aagcagacgc cgacgacccc attcccggcg catctaatga tgcctcgacg gaaaaccgtc   9600
```

```
cgggtttggg gggcgaaccg gccgcctgtc gctcgtcagg gccggcgggc gctcctcgcc      9660
gccctagagg ctgtcccgct ggtgtgacgt tttcctcgtc cgcgcccccc gaccctccca      9720
tggatttaac aaacgggggg gtgtcgcctg cggcgacctc ggcgcctctg gactggacca      9780
cgtttcggcg tgtgtttctg atcgacgacg cgtggcggcc cctgttggag cctgagctgg      9840
cgaacccctt aaccgcccac ctcctggccg aatataatcg tcggtgccag accgaagagg      9900
tgctgccgcc gcgggaggat gtgttttcgt ggactcgtta ttgcaccccc gacgaggtgc      9960
gcgtggttat catcggccag gacccatatc accaccccgg ccaggcgcac ggacttgcgt     10020
ttagcgtgcg cgcgaacgtg ccgcctcccc cgagtcttcg gaatgtcttg gcggccgtca     10080
agaactgtta tcccgaggca cggatgagcg gccacggttg cctggaaaag tgggcgcggg     10140
acggcgtcct gttactaaac acgaccctga ccgtcaagcg cggggcggcg gcgtcccact     10200
ctagaatcgg ttgggaccgc ttcgtgggcg gagttatccg ccggttggct gcgcgccgcc     10260
ccggcctggt gtttatgctc tggggcgcac atgcccagaa tgccatcagg ccggaccctc     10320
gggtccattg cgtcctcaag ttttcgcacc cgtcgcccct ctccaaggtt ccgttcggaa     10380
catgccagca tttcctcgtg gcgaatcgat atctcgagac ccggtcgatt tcacccatcg     10440
actggtcggt ttgaaaggca tcgacgtccg gggttttcgt ctgtggggc ttttgggtat     10500 ttccgatgaa taaagacggt taatggttaa acctctggtc tcatacgggt cggtgatgtc     10560
gggcgtcggg ggagagggag ttccctctgc gcttgcgatt ctagcctcgt ggggctggac     10620
gttcgacacg ccaaaccacg agtcagggat atcgccagat acgactcccg cagattccat     10680 tcgggggggcc gctgtggcct cacctgacca acctttacac gggggcccgg aacgggaggc     10740
cacagcgccg tctttctccc caacgcgcgc ggatgacggc ccgccctgta ccgacgggcc     10800
ctacgtgacg tttgatacccc tgtttatggt gtcgtcgatc gacgaattag ggcgtcgcca     10860
gctcacggac accatccgca aggacctgcg gttgtcgctg gccaagttta gcattgcgtg     10920
caccaagacc tcctcgtttt cgggaaacgc cccgcgccac cacagacgcg gggcgttcca     10980
gcgcggcacg cgggcgccgc gcagcaacaa aagccttcag atgtttgtgt tgtgcaaacg     11040
cgcccacgcc gctcgagtgc gagagcagct tcgggtcgtt attcagtccc gcaagccgcg     11100
caagtattac acgcgatctt cggacgggcg gctctgcccc gccgtccccg tgttcgtcca     11160
cgagttcgtc tcgtccgagc caatgcgcct ccaccgagat aacgtcatgc tggcctcggg     11220
ggccgagtaa ccgccccccc cccgcgccac cctcactgcc cgtcgcgcgt gtttgatgtt     11280
aataaataac acataaattt ggctggttgt ttgttgtctt taatgaccg cccgcagggg     11340 gggtggcatt tcagtgtcgg gtgacgagcg cgatccggcc gggatcctag gaccccaaaa     11400
gtttgtctgc gtattccagg gcgggctcca gttgaatctc ccgcagcacc tctaccagca     11460
ggtccgcggt gggctggaga aactcggccg tcccggggca ggcggtcgtc gggagtggag     11520 gcgcggcgc cacccgtgt gccgcgctg gcgtctcctc tgggggcgac ccgtaaatgg     11580
ttgcagtgat gtaaatggtg tccgcggtcc agaccacggt caaaatgccg gccgtggtgc     11640
tccgggcgct ttcgccgcgc gaggagctga cccaggagtc gaacggatac gcgtacatat     11700
gggcgtccca cccgcgttcg agcttctggt cgctgtcccg gcctataaag cggtaggcac     11760
aaaattcggc gcgacagtcg ataatcacca acagcccaat gggggtgtgc tggataacaa     11820
cgcctccgcg cggcaggcgg tcctggcgct cccggccccg taccataatc gcgcgggtgc     11880
cgtactcaaa aacatgcacc acctgcgcgg cgtcgggcag tgcgctggtc agcgaggccc     11940
```

```
tggcgtggca taggctatac gcgatggtcg tctgtggatt ggacatctcg cggtgggtag    12000
tgagtccccc gggccgggtt cggtagaact gtaaggggac ggcgggttaa tagacaatga    12060
ccacgttcgg atcgcgcaga gccgatagta tgtgctcact aatgacgtca tcgcgctcgt    12120
ggcgctcccg gagcggattt aagttcatgc gaaggaattc ggaggaggtg gtgcgggaca    12180
tggccacgta cgcgctgttg aggcgcaggt tgccgggcgt aaagcagatg gcgaccttgt    12240
ccaggctaag gccctgggag cgcgtgatgg tcatggcaag cttggagctg atgccgtagt    12300
cggcgtttat ggccatggcc agctccgtag agtcaatgga ctcgacaaac tcgctgatgt    12360
tggtgttgac gacggacatg aagccgtgtt ggtcccgcaa gaccacgtaa ggcaggggg    12420 cctcttccag taactcggcc acgttggccg tcgcgtgccg cctccgcagc tcgtccgcaa    12480
aggcaaacac ccgtgcgtac gtgtatccca tgagcgtata attgtccgtc tgcagggcga    12540
cggacatcag ccccccgcgc ggcgagccgg tcagcatctc gcagcccggg aagataacgt    12600
tgtccacgta cgtgctaaag ggggcgcctt caaatgcctc cccgaagagc tcttggagga    12660
ttcggaatct cccgaggaag gcccgcttca gcagcgcaaa ctgggtgtga acggcggcgg    12720
tggtctccgg ttccccgggg gtgtagtggc agtaaaacac gtcgagctgt tgttcgtcca    12780
gccccgcgaa aataacgtcg aggtcgtcgt cgggaaaatc gtccgggccc cgtcccgcg    12840 gccccagttg cttaaaatca aacgcacgct cgccggggc gcctgcgtcg gctattaccg    12900
acgcctgcgt cggcgccccc gaagatttgg ggcgcagaga cagaatctcc gccgttagtt    12960
ctcccatgcg ggcgtaggcg agggtcctct gggtcgcatc caggcccggg cgctgcagaa    13020
agttgtaaaa ggagataagc ccgctaaata tgagccgcga caggaacctg taggcaaact    13080
ccaccgaagt ctcccctga gtctttacaa agctgtcgtc acgcaacact gcctcgaagg    13140
cccggaacgt cccactaaac ccaaaaacca gttttcgcag gcgcgcggtc accgcgatct    13200
ggctgttgag gacgtaagtg acgtcgttgc gggccacgac cagctgctgt ttgctgtgca    13260
cctcgcagcg catgtgcccc gcgtcctggt cctggctctg cgagtagttg gtgatgcggc    13320
tggcgttggc cgtgagccac ttttcaatag tcaggccggg ctggtgtgtc agccgtcggt    13380
attcgtcaaa ctccttgacc gacacgaacg taagcacggg gagggtgaac acgacgaact    13440 cccctcacg ggtcaccttc aggtaggcgt ggagcttggc catgtacgcg ctcacctctt    13500
tgtgggagga gaacagccgc gtccagccgg ggaggttggc ggggttggtg atgtagcttt    13560
ccgggacgac gaagcgatcc acgaactgca tgtgctcctc ggtgatgggc aggccgtact    13620
ccagcacctt catgaggtta ccgaactcgt gctcgacgca ccgtttgttg ttaataaaaa    13680
tggcccagct atacgagagg cgggcgtact cgcgcagcgt gcggttgcag atgaggtacg    13740
tgagcacgtt ctcgctctgg cggacggaac accgcagttt ctggtgctcg aaggtcgact    13800
ccagggacgc cgtctgcgtc ggcgagccca cacaccaa cacgggccgc aggcgggccg    13860
catactgggg ggtgtggtac agggcgttaa tcatccacca gcaatacacc acggccgtga    13920
ggaggtgacg cccaaggagc ccggcctcgt ctatgacgat cacgttgctg cgggtaaagg    13980
ccggcagcgc cccgtgggtg gccggggcca accgcgtcag ggcgccctcg gccaacccca    14040
gggtccgttc cagggcggcc agggcgcgaa actcgttccg cgactcctcg cccccggagg    14100
cggccagggc gcgcttcgtg aggtccaaaa tcacctccca gtagtacgtc agatctcgtc    14160
gctgcaggtc ctccagcgag gcgggggttgc tggtcagggt gtacgggtac tgtcccagtt    14220
gggcctggac gtgattcccg cgaaacccaa attcatgaaa gatggtgttg atgggtcggc    14280
tgagaaaggc gcccgagagt ttggcgtaca tgttttgggc cgcaatgcgc gtggcgcccg    14340
```

```
tcaccacaca gtccaagacc tcgttgattg tctgcacgca cgtgctcttt ccggagccag   14400
cgttgccggt gataagatac accgcgaacg gaaactccct gaggggcagg cctgcggggg   14460
actctaaggc cgccacgtcc cggaaccact gcagacgggg cacttgcgct ccgtcgagct   14520
gttgttgcga gagctctcgg atgcgcttaa ggattggctg caccccgtgc atagacgtaa   14580
aatttaaaaa ggcctcggcc ctccctggaa cggctggtcg gtccccgggt tgctgaaggt   14640
gcggcgggcc gggtctctgt ccgtctagct ggcgctcccc gccggccgcc gccatgaccg   14700
caccacgctc gcgggccccc actacgcgtg cgcgggggga cacggaagcg ctgtgctccc   14760
ccgaggacgg ctgggtaaag gttcacccca cccccggtac gatgctgttc cgtgagattc   14820
tccacgggca gctggggtat accgagggcc aggggggtgta caacgtcgtc cggtccagcg   14880
aggcgaccac ccgcagctg caggcggcga tctttcacgc gctcctcaac gccaccactt   14940
accgggacct cgaggcggac tggctcggcc acgtggcggc ccgcggtctg cagccccaac   15000
ggctggttcg ccgtacagg aacgcccggg aggcggatat cgccggggtg gccgagcggg   15060
tgttcgacac gtggcggaac acgcttagga cgacgctgct ggactttgcc cacgggttgg   15120
tcgcctgctt tgcgccgggc ggcccgagcg gcccgtcaag cttccccaaa tatatcgact   15180
ggctgacgtg cctggggctg gtccccatat tacgcaagcg acaagaaggg ggtgtgacgc   15240
agggtctgag ggcgtttctc aagcagcacc cgctgacccg ccagctggcc acggtcgcgg   15300
aggccgcgga gcgcgccggc cccgggtttt ttgagctggc gctggccttc gactccacgc   15360
gcgtggcgga ctacgaccgc gtgtatatct actacaacca ccgccggggc gactggctcg   15420
tgcgagaccc catcagcggg cagcgcggag aatgtctggt gctgtggcct cccttgtgga   15480
ccggggaccg tctggtcttc gattcgcccg tccagcggct gtttcccgag atcgtcgcgt   15540
gtcactccct ccgggaacac gcgcacgtct gccggctgcg caataccgcg tccgtcaagg   15600
tgctgctggg gcgcaagagc gacagcgagc gcggggtggc cggcgccgcg cgggtcgtta   15660
acaaggtgtt gggggaggac gacgagacca aggccgggtc ggccgcctca cgcctcgtgc   15720
ggcttatcat caacatgaag ggcatgcgcc acgtaggcga cattaacgac accgtgcgtg   15780
cctacctcga cgaggccggg gggcacctga tagacgcccc ggccgtcgac ggtaccctcc   15840
ctggattcgg caagggcgga aacagccgcg ggtctgcggg ccaggaccag gggggcggg   15900 cgccgcagct tcgccaggcc ttccgcacgg ccgtggttaa caacatcaac ggcgtgttgg   15960
agggctatat aaataacctg tttggaacca tcgagcgcct gcgcgagacc aacgcgggcc   16020
tggcgaccca attgcaggag cgcgaccgcg agctccggcg cgcaacagcg ggggccctgg   16080
agcgccagca gcgcgcggcc gacctggcgg ccgagtccgt gaccggtgga tgcggcagcc   16140
gccctgcggg ggcggacctg ctccgggccg actatgacat tatcgacgtc agcaagtcca   16200
tggacgacga catgtacgtc gccaacagct ttcagcaccc gtacatccct tcgtacgccc   16260
aggacctgga gcgcctgtcg cgcctctggg agcacgagct ggtgcgctgt tttaaaattc   16320
tgtgtcaccg caacaaccag ggccaagaga cgtcgatctc gtactccagc ggggcgatcg   16380
ccgcattcgt cgcccctac tttgaggcag tgcttcgggc cccccgggta ggcgcgccca   16440
tcacgggctc cgatgtcatc ctgggggagg aggagttatg ggatgcggtg tttaagaaaa   16500
cctgcctgca aacgtacctg acagacatcg cggccctgtt cgtcgcggac gtccagcacg   16560
cagcgctgcc cccgccccc tccccggtcg gcgccgattt ccggcccggc gcgtccccgc   16620
ggggccggtc cagatcgcgg tcgcccggaa gaactgcgcg aggcgcaccg gaccagggcg   16680
```

-continued

```
ggggcatcgg gcaccgggat ggccgccgcg acggccgacg atgagggggtc ggccgtcacc    16740
atcctcaagc aggccatcgc cggggaccgc agcctggtcg aggcggccga ggcgattagc    16800
cagcagacgc tgctccgcct ggcctgcgag gtgcgccagg tcggcgaccg ccagccgcgg    16860
tttaccgcca ccagcatcgc gcgcgtcgac gtcgcgcctg ggtgccggtt gcggttcgtt    16920
ctggacggga gtcccgagga cgcctatgtg acgtcggagg attactttaa gcgctgctgc    16980
ggccagtcca gttatcgcgg cttcgcggtg gcggtcctga cggccaacga ggaccacgtg    17040
cacagcctgg ccgtgccccc cctcgttctg ctgcaccggt tctccctgtt caaccccagg    17100
gacctcctgg actttgagct tgcctgtctg ctgatgtacc tggagaactg ccccgaagc    17160
cacgccaccc cgtcgacctt tgccaaggtt ctggcgtggc tcggggtcgc gggtcgccgc    17220
acgtccccat tcgaacgcgt tcgctgcctt ttcatccgca gttgccactg ggtcctaaac    17280
acactcatgt tcatggtgca cgtaaaaccg ttcgacgacg agttcgtcct gccccactgg    17340
tacatggccc ggtacctgct ggccaacaac ccgccccccg ttctctcggc cctgttctgt    17400
gccacccccga cgagctcctc attccggctg ccgggggccgc cccccgctc cgactgcgtg    17460
gcctataacc ccgccgggat catggggagc tgctgggcgt cggaggaggt gcgcgcgcct    17520
ctggtctatt ggtggctttc ggagaccccca aaacgacaga cgtcgtcgct gttttatcag    17580
ttttgttgaa ttttagtaaa taaacccggt tttgtttcta tggcctcctg acggatcgc    17640
gtgtccttac tccgttttgg tgggtgggtg gctgtgtatg gcgtcccatc tgtgcgggga    17700
gggggcaagt cggcacgtat tcggacagac tcaagcacac acgggggagc gctcttggct    17760
cagggcaatg ttttttattgg tcaaactcag gcaaacagaa acaacatctt gtcgtcaaag    17820
ggatacacaa acttcccccc ctcgcccatt actcccgcca gcaccccggt aaacaccaac    17880
tcaatctcgc gcaggatttc gcgcaggtga tgagcgcagt ccacgggggg gagcacaagg    17940
ggccgcgggt atagatcgac ggggacgccg accgactccc cgcctccggg acagacacgc    18000
acgacgcgcc gccagtagtg ctctgcgtcc aacaaggcgc cgccgcggaa ggcagtgggg    18060
ggcaaggggt cgctggcctc aaaggggggac acccgaacgc tccagtactc cgcgtccaac    18120
cgttattaaa acgcgtccac gataaggcgg tcgcaggcgt cctccataag gccccgggcc    18180
gtgagcgcgt cctcctccgg cacgcctgcc gttgtcaggc ccaggacccg tcgcagcgtg    18240
tcgcgtacga ccccggccgc cgtggtgtac gcgggcccgc ggagaggaaa tcccccaaga    18300
tggtcagtgt tgtcgcggga gttccagaac cacactcccg cttggctcca ggcgacggcg    18360
tgggtgtaga cgccctcgag cgccaggcac agtgggtgcc gcagcggag gccgttggcc    18420
ataagcacgg ctcccacggc cgtctcgatg gcccgccggg cgtcctcgat caccccggaa    18480
gccgcatccg cgtcttgggg gtccacgtta aagacacccc agaacgcacc cccatcgccc    18540
ccgcagaccg cgaacttaac cgagctggcc gtctcctcaa tctgcaggca gacggcggcc    18600
atcaccccgc ccaggagctg ccgcagcgca gggcaggcgt cgcacgtgtc cgggaccagg    18660
cgctccaaga cggcccccggc ccagggctct gagggagcgg ccaccaccag cgcgtccagt    18720
cttgctaggc ccgtccggcc gtggggttcc gccagcccgc tcccccccgag gtcggccagg    18780
gccgccagga gctgggcgcg aagtccgggg aagcaaaacc gcgccgtcca gacgggcccg    18840
acggccgcgg gcgggtctaa cagttggatg atttttagtgg cgggatgcca ccgcgccacc    18900
gcctcccgca ccgcggggcag gaggcatccg gctgccgccg aggccacgcc gggccaggct    18960
cgcgggggga ggacgaccct ggccccccacc gcgggccagg cccccaggag cgcggcgtaa    19020
gcggccgcgg ccccgcgcac caggtcccgt gccgactcgg ccgtggccgg cacggtgaac    19080
```

```
gtgggccaac ccggaaaccc caggacggca aagtacggga cgggtccccc ccggacctca   19140
aactcgggcc ccagaaaggc aaagacgggg gccaggaccc cggggcggc gtggaccgtg    19200 gtatgccact gccggaaaag ggcgacgagc gccggcgcgg agaacttctc gccggcgctt   19260
acaaagtagt cgtaatcgcg gggcagcagc acccgtgccg tgactcgttg cgggtgcccg   19320
cgtggccgca ggcccacctc gcacacctcg accaggtccc cgaacgctcc ctccttcttg   19380
atcggcggaa acgcaagagt ctggtattcg cgcgcaaata gcgcggttcc ggtggtgatg   19440
ttaacggtca gcgaagcggc ggacgcgcac tgggggggtgt cgcgaatggc cgccaggcgc  19500
gcccacgcca gccgcgcgtc gggatgctcg gcaacgcgcg ccgccagggc catagggtcg   19560
atgtcaatgt tggcctccgc gaccaggaga gcggcgcgag gggcggcggg cgggccccac   19620
gacgctctct caactttcac caccagtccc gtgcgtgggt ccgagccgat acgcagcggg   19680
gcgaacaggg ccaccggccc ggtctggcgc tccagggccg ccaggacgca cgcgtacagc   19740
gcccgccaca gagtcgggtt ctccaggggc tccagcgggg aggcggccgg cgtcgtcgcg   19800
gcgcgggcgg ccgccacgac ggcctggacg agacgtccg cggagccgta gaaatcccgc    19860
agctccgtcg cggtgacgga gacctccgca aagcgcgcgc gaccctcccc tgcggcgttg   19920
cgacatacaa aatacaccag ggcgtggaag tactcgcgag cgcggggggg cagccatacc   19980
gcgtaaaggg taatggcgct gacgctctcc tccacccaca cgatatctgc ggtgtccatc   20040
gcacggcccc taaggatcac gggcggtctg tgggtcccat gctgccgtgc ctggccgggc   20100
ccggtgggtc gcggaaaccg gtgacggggg ggggcggttt ttgggggttgg ggtgggggtg   20160 ggaaacggcc cgggtccggg ggccaacttg gccctcggt gcgttccggc aacagcgccg    20220
ccggtccgcg gacgaccacg taccgaacga gtgcggtccc gagacttata gggtgctaaa   20280
gttcaccgcc ccctgcatca tgggccaggc ctcggtgggg agctccgaca gcgccgcctc   20340
caggatgatg tcagcgttgg ggttggcgct ggatgagtgc gtgcgcaaac agcgcccca    20400 cgcgggcacg cgtagcttga agcgcgcgcc cgcaaactcc cgcttgtggg ccataagcag   20460
ggcgtacagc tgcctgtggg tccggcaggc gctgtggtcg atgtggtggg cgtccaacaa   20520
ccccacgatt gtctgtttgg tgaggttttt aacgcgcccc gccccgggaa acgtctgcgt   20580
gcttttggcc atctgcacgc caaacagttc gccccagatt atcttgaaca gcgccaccgc   20640
gtggtccgtc tcgctaacgg acccgcgcgg gggacagccg cttagggcgt cggcgacgcg   20700
cttgacggct tcctccgaga gcagaagtcc gtcggttacg ttacagtggc ccagttcgaa   20760
caccagctgc atgtagcggt cgtagtgggg ggtcagtagg tccagcacgt catcggggcc   20820
gaaggtcctc ccagatcccc cggccgccga gtcccaatgc aggcgcgcgg ccatggtgct   20880
gcacaggcac aacagctccc agacgggggt tacgttcagg gtgggggggca gggccacgag   20940 ctccagctct ccggtgacgt tgatcgtggg gatgacgccc gtggcgtagt ggtcatagat   21000
ccgccgaaat atggcgctgc tgcggtggc catgggaacg cggagacagg cctccagcaa    21060
cgccaggtaa ataaaccgcg tgcgtccat caggctgttg aggttgcgca tgagcgcgac    21120
aatttccgcc ggcgcgacat cggaccggag gtatttttcg acgaaaagac ccacctcctc   21180
cgtctcggcg gcctgggccg gcagcgacgc ctcgggatcc cggcaccgca gctcccgtag   21240
atcgcgctgg gccctgaggg cgtcgaaatg tacgccccgc aaaaacagac agaagtcctt   21300
tggggtcagg gtatcgtcgt gtccccagaa gcgcacgcgt atgcagttta gggtcagcag   21360
catgtgaagg atgttaaggc tgtccgagag acacgccagc gtgcatctct caaagtagtg   21420
```

```
tttgtaacgg aatttgttgt agatgcgcga ccccccgcccc agcgacgtgt cgcatgccga   21480
cgcgtcacag cgcccctttga accggcgaca cagcaggttt gtgacctggg agaactgcgc   21540
gggccactgg ccgcaggaac tgaccacgtg gttcaggagc atgggcgtaa agacgggctc   21600
cgagcgcgcc ccggagccgt ccatgtaaat cagtagctcc cccttgcgga gggtgcgcac   21660
ccgtcccagg gactggtaca cggacaccat gtccggtccg tagttcatgg gtttcacgta   21720
ggcgaacatg ccatcaaagt gcaggggatc gaagctgagg cccacggtta cgaccgtcgt   21780
gtatataacc acgcggtatt ggccccacgt ggtcacgtcc ccgaggggggg tgagcgagtg   21840 aagcaacagc acgcggtccg taaactgacg gcagaaccgg gccacgatct ccgcgaagga   21900
gaccgtcgat gaaaaaatgc agatgttatc gcccccgcca aggcgcgctt ccagctcccc   21960
aaagaacgtg gccccccggg cgtccggaga ggcgtccgga gacgggccgc ttggcggccc   22020
gggcgggcgc agggcagcct gcaggagctc ggtccccaga cgcgggagaa acaggcaccg   22080
gcgcgccgaa aacccgggca tggcgtactc gccgaccacc acatgcacgt ttttttcgcc   22140
ccggagaccg cacaggaagt ccaccaactg cgcgttggcg gttgcgtcca tggcgatgat   22200
ccgaggacag gtgcgcagca ggcgtagcat taacgcatcc acgcggccca gttgctgcat   22260
cgttggcgaa tagagctggc ccagcgtcga cataacctcg tccagaacga ggacgtcgta   22320
gttgttcaga aggttggggc ccacgcgatg aaggctttcc acctggacga taagtcggtg   22380
gaaggggcgg tcgttcataa tgtaattggt ggatgagaag taggtgacaa agtcgaccag   22440
gcctgactca gcgaaccgcg tcgccagggt ctgggtaaaa ctccgacgac aggagacgac   22500
gagcacactc gtgtccggag agtggatcgc ttcccgcagc cagcggatca gcgcggtagt   22560
ttttcccgac cccattggcg cgcggaccac agtcacgcac ctggccgtcg ggcgctcgc   22620 gttggggaag gtgacgggtc cgtgctgctg ccgctcgatc gttgttttcg ggtgaacccg   22680
gggcacccat tcggccaaat ccccccgta caacatccgc gctagcgata cgctcgacgt   22740
gtactgttcg cactcgtcgt ccccaatggg acgcccggcc cccagaggat cccccgactc   22800
cgcgcccccc acgaaaggca tgaccggggc gcggacggcg tggtgggtct ggtgtgtgca   22860
ggtggcgacg tttgtggtct ctgcggtctg cgtcacgggg cttctcgtcc tggcctctgt   22920
gttccgggca cggtttccct gcttttatgc cacggcgagc tcttatgccg gggtgaactc   22980 cacgccgag gtgcgcgggg gtgtagccgt gccctcagg ttggacacgc agagccttgt   23040
gggcacttat gtaatcacgg ccgtgttgtt gttggccgcg gccgtgtatg ccgtggtcgg   23100
cgccgtgacc tccgctacg accgcgccct ggacgcgggc cgccgtctgg ctgcggcccg   23160
catggccatg ccgcacgcca cgctgatcgc cggaaacgtc tgctcttggt tgctgcagat   23220
caccgtcctg ttgctggccc atcgcatcag ccagctggcc cacctggttt acgtcctgca   23280 cttttgcgtgt ctggtgtatt ttgcggccca tttttgcacc aggggggtcc tgagcgggac   23340
gtatctgcgt caggtgcacg gcctgatgga gccggcccg actcatcatc gcgtcgtcgg   23400
cccggctcga gccgtgctga caaacgcctt gctgttgggc gtcttcctgt gcacggccga   23460
cgccgcggta tccctgaata ccatcgccgc gttcaacttt aattttcgg ccccgggcat   23520 gctcatatgc ctgaccgtgc tgttcgccct tctcgtcgta tcgctgttgt tggtggtcga   23580
gggggtgttg tgtcactacg tgcgcgtgtt ggtgggcccc cacctggggg ccgtggccgc   23640
cacgggcatc gtcggcctgg cctgcgagca ctattacacc aacggctact acgttgtgga   23700
gacgcagtgg ccggggggccc agacgggagt ccgcgtcgcc ctcgcctggg tcgccgcctt   23760
tgccctcggc atggccgtgc tccgctgcac ccgcgcctat ctgtatcaca ggcggcacca   23820
```

```
caccaaattt tttatgcgca tgcgcgacac gcgacaccgc gcacattccg ccctcaggcg   23880
cgtacgcagt tccatgcgcg gatcgcgaga cggccgccac aggcccgcac ccggcagccc   23940
gcccgggatt cccgaatatg cggaagaccc ctacgcgatc tcatacggcg gccagctcga   24000
ccggtacgga gattccgacg gggagccgat ttacgacgag gtggctgacg accaaaccga   24060
cgtattgtac gccaagatac aacacccgcg gcacctgccc gacgacgagc ccatctatga   24120
caccgttggg gggtacgacc ccgagcccgc cgaggacccc gtgtacagca ccgtccgccg   24180
ttggtagctg tttggttccg ttttaataaa ccgtttgtgt ttaacccgac cgtggtgtat   24240
gtctggtgtg tggcgtccga tcccgttact atcaccgttt cccccccccc ccctcaacc   24300
ccggcgattg tgggttttt aaaaacgaca cgcgtgcgac cgtatacaga acattgtttt   24360
ggttttatt cgctatcgga catgggggt ggaaactggg tggcggggca ggcgcctccg   24420
ggggtccgcc ggtgagtgtg gcgcgagggg gggtccgacg aacgcaggcg ctgtctcccc   24480
ggggcccgcg taaccacgcg catatccggg ggcacgtaga aattaccttc ctcttcggac   24540
tcgatatcca cgacatcaaa gtcgtgggcg gtcagcgaga cgacctcccc gtcgtcggtg   24600
atgaggacgt tgtttcggca gcagcaggg cgggccccgg agaacgagag gcccatagct   24660
cggcgagcgt gtcgtcgaac gccaggcggc tgcttcgctg gatggcctta tagatctccg   24720
gatcgatgcg gacgggggta atgatcaggg cgatcggaac ggcctggttc gggagaatgg   24780
acgccttgct gggtcctgcg gccccgagag ccccggcgcc gtcctccagg cggaacgtta   24840
cgccctcctc cgcgctggtg cggtgcctgc cgataaacgt caccagatgc gggtgggggg   24900
ggcagtcggg gaagtggctg tcgagcacgt agccctgcac caagatctgc ttaaagttcg   24960
ggtgacgggg gttcgcgaag acgggctcgc ggcggaccag atccccggag ctccaggaca   25020
cgggggagat ggtgtggcgt ccgaggtcgg gggcgccaaa cagaagcacc tccgagacaa   25080
cgccgctatt taactccacc aaggcccgat ccgcggcgga gcaccgcctt ttttcgcccg   25140
aggcgtgggc ctctgaccag gcctggtctt gcgtgacgag agcctcctcc gggccgggga   25200
cgcgcccggg cgcgaagtat cgcacgctgg gcttcgggat cgaccggata aatgcccgga   25260
acgcctccgg ggaccggtgt gtcatcaagt cctcgtacgc ggaggccgtg gggtcgctgg   25320
ggtccatggg gtcgaaagcg tacttggccc ggcatttgac ctcgtaaaag gccagggggg   25380
tcttggggac tggggccagg tagccgtgaa tgtcccgagg acagacgaga atatccaggg   25440
acgccccgac catccccgtg tgaccgtcca tgaggacccc acacgtatgc acgttctctt   25500
cggtgaggtc gctgggttcg tggaagataa agccgccgcgt gtcggcgccg gcctcgccgc   25560
cgtcgtccgc gcggcccacg cagtagcgaa acagcaggct tcgggccgtc ggctcgttca   25620
cccgcccgaa catcaccgcc gaagactgta catccggccg caggctggcg ttgtgcttca   25680
gccactgggg cgagaaacac ggaccctggg ggccccagcg gagggtggat gcggtcgtga   25740
ggccccgccg gagcagggcc catagctggc agtcggcctg gttttgcgtg gccgcctcgt   25800
aaaaccccat gaggggccgg ggcgccacgg cgtccgcggc ggccgggggc ccgcggcgcg   25860
tcaggcgcca taggtgccgg ccgagtccgg ggtccaccat acccgcctcc tcgaggacca   25920
cggccaggga acacagataa tccaggcggg cccagagggg accgatggcc agaggggcgc   25980
ggacgccgcg cagcaacccg cgcaggtggc gctcgaacgt ctcggctagt atatgggagg   26040
gcagcgcgtt ggggatcacc gacgccgacc acatagagtc aaggtccggg gagtcgggat   26100
cggcgtccgg gtcgcgggcg tgggtgcccc caggagatag cggaatgtct ggggtcggag   26160
```

```
gccctgaggc gtcagaaagt gccggcgacg cggcccgggg cttttcgtct gcggtgtcgg    26220
tggcgtgctg atcacgtggg gggttaacgg gcgaatggga gctcgggtcc acagctgacg    26280
tcgtctgggg tggggggggc aggggacgga aggtggttgt cagcggaaga ctgttagggc    26340
gggggcgctt gggggggctg tcggggccac gaggggtgtc ctcggccagg gcccagggac    26400
gcttagtcac ggtgcgtccc ggcggacatg ctgggcctac cgtggactcc atttccgaga    26460
cgacgtgggg gagcggtggt tgagcgcgcc gccgggtgaa cgctgattct cacgacagcg    26520
cgtgccgcgc gcacgggttg gtgtgacaca ggcgggacac cagcaccagg agaggcttaa    26580
gctcgggagg cagcgccacc gacgacagta tcgccttgtg tgtgtgctgg taatttatac    26640
accgatccgt aaacgcgcgc cgaatcttgg gattgcggag gtggcgccgg atgccctctg    26700
gtacgtcata cgccaggccg tgggtgttgg tctcggccga gttgacaaac agggctgggt    26760
gcagcacgca gcgataggcg agcagggcca gggcgaagtc cggcgacagc tggttgttga    26820
aatactggta accgggaaac cgggtcacgg gtacgcccag gctcggggcg acgtacacgc    26880
taaccaccaa ctccagcagc gtctggccaa gggcgtacag gtcaaccgct aacccgacgt    26940
cgtgcttcag gcggtggttg gtaaattcgg cccgttcgtt gttaaggtat ttcaccaaca    27000
gctccggggg ctggttatac ccgtgaccca ccagggtgtg aaagttggct gtggttaggg    27060
cggtgggcat gccaaacatc cggggggact tgaggtccgg ctcctggagg caaaactgcc    27120
cccgggcgat cgtggagttg gagttgaggg tgacgaggct aaagtcggcg aggacggccc    27180
gccggagcga gacggcgtcc gaccgcagca tgacgaggat gttggcgcac ttgatatcca    27240
ggtggctgat cccgcaggtg gtgttttaaaa acacaacggc gcgggccagc tccgtgaagc    27300
actggtggag ggccgtcgag accgaggggt ttgttgtgcg cagggacgcc agttggccga    27360
tatacttacc gaggtccatg tcgtacgcgg ggaacactat ctgtcgttgt tgcagcgaga    27420
acccgagggg cgcgatgaag ccgcggatgt tgtgggtgcg gccggcgcgt agagcgcact    27480
ccccgaccaa cagggtcgcg atgagctcaa cggcaaacca ctccttttcc tttatggtct    27540
taacggcaag cttatgttcg cgaatcagtt ggacgtcgcc gtatccccca gacccccga    27600 agcttcgggc cccggggatc tcgagggtcg tgtagtgtag ggcggggttg atggcgaaca    27660
cggggctgca tagcttgcgg atgcgcgtga gggtaaggat gtgcgagggg gacgaggggg    27720
gtgcggttaa cgccgcctgg gatctgcgca ggggcgggcg gttcagtttg gccgccgtac    27780
cgggcgtctc gggggacgcg cggcgatgag acgagcggct cattcgccat cgggatagtc    27840
ccgcgcgaag ccgctcgcgg aggccggatc ggtggcggga cccgtgggag gagcgggagc    27900
cggcggcgtc ctggagagag gggccgctgg ggcgcccgga ggccccgtgt gggttggagt    27960
gtatgtagga tgcgagccaa tccttgaagg accgttggcg tgcaccttgg gggctgaggt    28020
tagctgccac atgaccagca ggtcgctgtc tgcgggactc atccatcctt cggccaggtc    28080
gccgtctccc cacagagaag cgttggtcgc tgcttcctcg agttgctcct cctggtccgc    28140
aagacgatcg tccacggcgt ccaggcgctc accaagcgcc ggatcgaggt accgtcggtg    28200
tgcggttaga aagtcacgac gcgccgcttg ctcctccacg cgaattttaa cacaggtcgc    28260
gcgctgtcgc atcatctcta agcgcgcgcg ggactttagc cgcgcctcca attccaagtg    28320
ggccgccttt gcagccataa aggcgccaac aaaccgagga tcttgggtgc tgacgccctc    28380
ccggtgcagc tgcagggtct ggtccttgta atctcggct cggaggtgcg tctcggccag    28440
gcgtcggcgc agggccgcgt gggcggcatc tcggtccatt ccgccaccct gcgggcgacc    28500 cgggggggtgc tctgatagtc tcgcgtgccc aaggcccgtg atcggggtac ttcgccgccg    28560
```

```
cgacccgcca cccggtgtgc gcgatgtttg gtcagcagct ggcgtccgac gtccagcagt  28620
acctggagcg cctcgagaaa cagaggcaac ttaaggtggg cgcggacgag cgtcggcgg   28680
gcctcacaat gggcggcgat gccctacgag tgccctttt agatttcgcg accgcgaccc   28740
ccaagcgcca ccagaccgtg gtcccgggcg tcgggacgct ccacgactgc tgcgagcact  28800
cgccgctctt ctcggccgtg gcgcggcggc tgctgtttaa tagcctggtg ccggcgcaac  28860
taaagggcg tgatttcggg ggcgaccaca cggccaagct ggaattcctg gccccgagt    28920
tggtacgggc ggtggcgcga ctgcggttta aggagtgcgc gccggcggac gtggtgcctc  28980
agcgtaacgc ctactatagc gttctgaaca cgtttcaggc cctccaccgc tccgaagcct  29040
ttcgccagct ggtgcacttt gtgcgggact ttgcccagct gcttaaaacc tcttccggg   29100
cctccagcct cacggagacc acgggccccc ccaaaaaacg ggccaaggtg gacgtggcca  29160
cccacggccg gacgtacggc acgctggagc tgttccaaaa aatgatcctt atgcacgcca  29220
cctactttct ggccgccgtg ctcctcgggg accacgcgga gcaggtcaac acgttcctgc  29280
gtctcgtgtt tgagatcccc ctgtttagcg acgcggccgt gcgccacttc cgccagcgcg  29340
ccaccgtgtt tctcgtcccc cggcgccacg gcaagacctg gtttctagtg cccctcatcg  29400
cgctgtcact ggcctccttt cgggggatca agatcggcta cacggcgcac atccgcaagg  29460
cgaccgagcc ggtgtttgag gagatcgacg cctgcctgcg gggctggttc ggttcggccc  29520
gagtggacca cgttaaaggg gaaaccatct ccttctcgtt tccggacggg tcgcgcagta  29580
ccatcgtgtt tgcctccagc cacaacacaa acgtaagtcc tcttttcttt cgcatggctc  29640
tcccaagggg cccgggtcg acccgaccca cacccacccc cccacccaca tacacacaca   29700
accagacgcg ggaggaaagt ctgccccgtg ggcactgatt tttattcggg atcgcttgag  29760
gaggcccggg caacggcccg ggcaacggtg gggcaactcg tagcaaatag gcgactgatg  29820
tacgaagaga agacacacag gcgccacccg gcgctggtcg gggggatgtt gtccgcgccg  29880
caccgtcccc cgacgacctc ttgcagacgg tccgtgatgc aaggacggcg gggggcctgc  29940
agcagggtga ccgtatccac gggatggcca aagagaagcg gacacaggct agcatccccc  30000
tggaccgcca gggtacactg gccatcttg gcccacagac acggggcgac gcagggacag   30060
gactccgtta cgacggagga gagccacagt gcgttggcgg aatcgatgtg gggcggcggg  30120
gcgcaggact cgcagccccc cggtggttg gtgatcctgg ccaggagcca tcccagatgc   30180
cgggccctgc ttcccggtgg acagagcgac cccaggtcgc tgtccatggc ccagcagtag  30240
atctggccgc tggggaggtg ccaccaggcc cccgggccca aggcgcagca cgcgcccggc  30300
tccggggggg tcttcgcggg gaccagatac gcgccatcca gctcgccgac cactggctcc  30360
tccgcgagct gttcggtggt tgggtcgggg gtttcctccg ggggggtggc cgcccgtatg  30420
cgggcgaacg tgagggtgca caggagcggg gtcaggggt gcgtcacgct ccggaggtgg   30480
acgatcgcg agtagcggcg ctcgcggtta aagaaaaga gggcaaagaa ggtgttcggg    30540
ggcaaccgca gcgccttggg gcgcgtcaga tacagaaaaa tctcgcagaa gagggcgcgc  30600
ccggggtctg ggttaggaag ggccaccga cacagaggct cggtgaggac cgttagacac   30660
cgaaagatct tgagccgctc gtccgcccga acgacgcgcc acacaaagac ggagttgaca  30720
atgcgcgcga tagagtcgac gtccgtcccc aggtcgtcga ctctgtcgcg cgtgccgcga  30780
gctccggccc gggaatccgg ccggggcaag gtccccgggg gaccaggcgg cgccaggggc  30840
cgccggggtc ccagctgcgc catgccgggg gcggggggag ggcaaacccc agaggcgggg  30900
```

```
gccaacggcg cggggaggag tgggtgggcg aggtggccgg gggaaggcgc ccgctagcga   30960
gaacggccgt tcccggacga caccttgcga caaaacctaa ggacagcggc ccgcgcgacg   31020
gggtccgaga ggctaaggta ggccgcgatg ttaatggtga acgcaaagcc gccgggaaag   31080
acaactatgc cacagaggcg gcgattaaac cccaggcaga ggtaggcgta gctttccccg   31140
ggcaggtatt gctcgcagac cctgcgtggg gctgtggagg ggacggcctc catgaagcga   31200
catttactct gctcgcgttt actgacgtca ccatccatcg ccacggcgat tggacgattg   31260
ttaagccgca gcgtgtctcc gcttgtgctg tagtagtcaa aaacgtaatg gccgtcggag   31320
tcggcaaagc gggccgggag gtcgtcgccg agcgggacga cccgccgccc cgaccgccc    31380
cgtccccca ggtgtgccag gacggccagg gcatacgcgg tgtgaaaaaa ggagtcgggg    31440
gcggtcccct cgacgcgcca catcaggttc tcgaggagaa tggggaagcg cctggtcacc   31500
tccccaacc acgcgcgttg gtcggggcca aagtcatagc gcaggcgctg tgagattcgc    31560
gggccgccct gaagcgcggc ccggatggcc tgcccaggg cccggaggca cgccagatgt    31620
atgcgcgcgg taaaggcgac ctcggcgcg atgtcaaagg cggcaggac ggggcgcggg     31680
tggcgcaggg gcacctcgag cgcgggaaag cgtagcagca gctccgcctg cccagcggga   31740
gacagctggt gggggcgcac gacgcgttct gcggcgcagg cctcggtcag ggccgtggcc   31800
agcgccgagg acagcagcgg agggcgggcg cgtcgcccgc ccacgccac ggagttctcg    31860
taggagacga cgacgaagcg ctgcttggtt ccgtagtggt ggcgcaggac cacggagata   31920
gaacgacggc tccacagcca gtccggccgg tcgccgccgg ccagggcttc ccatccgcga   31980
tccaaccact cgaccagcga ccgcggcttt gcggtaccag gggtcagggt tagaacgtcg   32040
ttcaggatgt cctcgccccc gggcccgtgg ggcacggggg ccacaaagcg gcccccgcct   32100
gggggctcca gacccgccaa caccgcatct gcgtcagccg ccccatggc gccccgctg     32160
acggcctggt gaaccagggc gccctggcgg agccccgatg caacgccaca ggccgcacgc   32220
ccggtccgag cgcggaccgg gtggcggcgg gtgacgtcct gcactgcccg ctgaaccaac   32280
gcgaggatct cctcgttctc ctgcgcgatg acacgtcct gggccgcggt cgtgtcgccg    32340
ccggggccg tcagctgctc ctccggggag atggggggt cggacgcccc gacgatgggc     32400
gggtctgcgg gcgcccccgc gtggggccgg gccaagggct gcggacgcgg ggacgcgctt   32460
tcccccagac ccatggacag gtgggccgca gcctccttcg cggccggcgg ggcggcggc    32520
ccaagcagag cgacgtagcg gcacaaatgc cgacagacgc gcatgatgcg cgtgctgtcg   32580
gccgcgtagc gcgtgttggg ggggacgagc tcgtcgtaac taaacagaat cacgcgggca   32640
cagctcgccc ccgagcccca cgcaaggcgc agcgccgcca cggcgtacgg gtcatagacg   32700
ccctgcgcgt tacacaccac gggcaggag acgaacaacc ccccggcgct ggacgcacgc    32760
ggaaggaggc cagggtgtgc cggcacgacg ggggccagaa gctcccccac cgcatccgcg   32820
ggcacgtagg cggcaaacgc cgtgcaccac ggggtacagt cgccggtggc atgagcccga   32880
gtctggattt cgacctggaa gtttgcggcc gtcccgagtc cggggtggcc gcgcatcagg   32940
gcggccagag ggattcccgc ggccgccagg cactcgctgg atatgatgac gtgaaccaaa   33000
gacgagggcc gacccgggcc gtggccgaga tcgtactgga cctcgttggc caagtgcgcg   33060
ttcatggttc gggggtgggt gtgggtgtgt aggcgatgcg ggtccccga gtccgcggga    33120
agggcgtggg tttggcgcgc gtatgcgtat tcgccaacgg aggcgtgcgt gcttatcgcg   33180
ggcgcgtttc ttctgtctct agggaatccg aggccaggac tttaacctgc tctttgtcga   33240
cgaggccaac tttattcgcc cggatgcggt ccagacgatt atgggctttc tcaaccaggc   33300
```

```
caactgcaag attatcttcg tgtcgtccac caacaccggg aaggccagta cgagcttttt    33360
gtacaacctc cgcggggccg cagacgagct tctcaacgtg gtgacctata tatgcgatga    33420
tcacatgccg agggtggtga cgcacacaaa cgccacggcc tgttcttgtt atatcctcaa    33480
caagcccgtt ttcatcacga tggacggggc ggttcgccgg accgccgatt tgtttctggc    33540
cgattccttc atgcaggaga tcatcggggg ccaggccagg gagaccggcg acgaccggcc    33600
cgttctgacc aagtctgcgg gggagcggtt tctgttgtac cgcccctcga ccaccaccaa    33660
cagcggcctc atggcccccg atttgtacgt gtacgtggat cccgcgttca cggccaacac    33720
ccgagcctcc gggaccggcg tcgctgtcgt cgggcggtac cgcgacgatt atatcatctt    33780
cgccctggag cactttttc tccgcgcgct cacgggctcg cccccgccg acatcgcccg       33840
ctgcgtcgtc cacagtctga cgcaggtcct ggccctgcat cccggggcgt ttcgcggcgt    33900
ccgggtggcg gtcgagggaa atagcagcca ggactcggcc gtcgccatcg ccacgcacgt    33960
gcacacagag atgcaccgcc tactggcctc ggaggggggcc gacgcgggct cgggccccga   34020
gcttctcttc taccactgcg agcctcccgg gagcgcggtg ctgtacccct ttttcctgct    34080
caacaaacag aagacgcccg cctttgaaca ctttattaaa aagtttaact ccgggggcgt    34140
catggcctcc caggagatcg tttccgcgac ggtgcgcctg cagaccgacc cggtcgagta    34200
tctgctcgag cagctaaata acctcaccga aaccgtctcc cccaacactg acgtccgtac    34260
gtattccgga aaacggaacg cgcctcgga tgaccttatg gtcgccgtca ttatggccat     34320
ctacctcgcg gcccaggccg gacctccgca cacattcgct cctatcacac gcgtcttgtg    34380
agcgcccaat aaacacaccc aggtatgcta cgcacgacca cggtgtcgtc tgttaagggg    34440
ggggggaagg gggtgttggc gggaagcgtg ggaacacggg ggattctctc acgaccggca    34500
ccagtaccac ccccctgtga acacagaaac cccaacccaa atcccataaa catacgacac    34560
acaggcatat tttggaattt cttaggtttt tatttattta ggtatgctgg ggtttctccc    34620
tggatgccca cccccacccc cccgtgggtc tagccgggcc ttagggatag cgtataacgg    34680
gggccatgtc tccggaccgc acaacggccg cgccgtcaaa ggtgcacacc cgaaccacgg    34740
gagccagggc caaggtgtct cctagttggc ccgcgtgggt cagccaggcg acgagcgcct    34800
cgtaaagcgg cagccttcgc tctccatcct gcatcagggc cggggcttcg gggtgaatga    34860
gctgggcggc ctcccgcgtg acactctgca tctgcaggag agcgttcacg tacccgtcct    34920
gggcacttag cgcaaagagc cggggatta gcgtaaggat gatggtggtt ccctccgtga    34980
tcgagtaaac catgttaagg accagcgatc gcagctcggc gtttacggga ccgagttgtt    35040
ggacgtccgc cagcagcgag aggcgactcc cgttgtagta cagcacgttg aggtctggca    35100
gccctccggg gttctggggg ctggggttca ggtcccggat gccctggcc acgagccgcg     35160
ccacgatttc gcgcgccagg ggcgatggaa gcggaacggg aaaccgcaac gtgaggtcca    35220
gcgaatccag gcgcacgtcc gtcgcttggc cctcgaacac gggcgggacg aggctgatgg    35280
ggtccccgtt acagagatct acggggagg tgttgcgaag gttaacggtg ccggcgtggg     35340
tgaggcccac gtccagggg caggcgacga ttcgcgtggg aagcaccggg gtgatgaccg     35400
cggggaagcg ccttcggtac gccagcaaca accccaacgt gtcgggactg acgcctccgg    35460
agacgaagga ttcgtgcgcc acgtcggcca gcgtcagttg ccgcggatg gtcggcagga     35520
ataccacccg cccttcgcag cgctgcagcg ccgccgcatc ggggcgcgag atgcccgagg    35580
gtatcgcgat gtcagtttca aagccgtccg ccagcatggc gccgatccac gcggcaggga    35640
```

```
gtgcagtggt gggtcgggtg gcgggaggag cgcggtgggg gtcagcggcg tagcagagac   35700
gggcgaccaa cctcgcatag gacgggggt gggtcttagg gggttgggag gcgacaggga   35760
ccccagagca tgcgcgggga ggtctgtcgg gcccagacgc accgagagcg aatccgtccg   35820
cggagtcccg gcttgggttt tatggggccc ggccctcgga atcgcggctt gtcggcgggg   35880 acaaagggg cggggctagg ggcttgcgga aacagaagac gcgtgggata aaagaatcgc   35940
actaccccaa ggaagggcgg ggcggtttat tacagagcca gtcccttgag cggggatgcg   36000
tcatagacga gatactgcgc gaagtgggtc tcccgcgcgt gggcttcccc gttgcgggcg   36060
ctgcggagga gggcggggtc gctggcgcag gtgagcgggt aggcctcctg aaacaggcca   36120
cacgggtcct ccacgagttc gcggcacccc ggggggcgct taaactgtac gtcgctggcg   36180
gcggtggccg tggacaccgc cgaacccgtc tccacgatca ggcgctccag gcagcgatgt   36240
ttggcggcga tgtcggccga cgtaaagaac ttaaagcagg ggctgagcac cggcgaggcc   36300
ccgttgaggt ggtaggcccc gttatagagc aggtccccgt acgaaaatcg ctgcgacgcc   36360
cacgggttgg ccgtggccgc gaaggcccgg gacgggtcg tctggccgtg gtcgtacatg   36420
agggcggtga catccccctc cttgtccccc gcgtaaacgc cccggcggc gcgtccccgg   36480 gggttgcagg gccggcggaa gtagttgacg tcggtcgaca cggggggtggc gataaactca   36540 cacacggcgt cctggccgtg gtccatccct gcgcgccgcg gcacctgggc gcacccgaac   36600
acggggacgg gctgggccgg ccccaggcgg tttcccgcca cgaccgcgtt ccgcaggtac   36660
acggctgccg cgttgtccag gagagggga gccccgcggc ccaggtaaaa gttttgggga   36720
aggttgccca tgtcggtgac ggggttgcgg acggttgccg tggccacgac ggcggtgtag   36780
cccacgccca ggtccacgtt cccgcgcggc tgggtgagcg tgaagtttac ccccccgcca   36840
gtttcgtgcc gggccacctg gagctggccc aggaagtacg cctccgacgc gcgctccgag   36900
aacagcacgt tctcagtcac aaagcggtcc tgtcggacga cggtgaaccc aaacccggga   36960 tggaggccc tcttgagctg atgatgcaag gccacgggac tgatcttgaa gtaccccgcc   37020
atgagcgcgt aggtcagcgc gttctccccg gccgcgctct cgcggacgtg ctgcacgacg   37080
ggctgtcgga tcgacgaaaa gtagttggcc cccagagccg gggggaccag ggggacctgc   37140
cgcgacaggt cgcgcagggc cggggggaaa ttgggcgcgt tcgccacgtg gtcggccccg   37200
gcgaacagcg cgtggacggg gaggggtaa aaatagtcgc cattttggat ggtatggtcc   37260
agatgctggg gggccatcag caggattccg gcgtgcaacg ccccgtcgaa tatgcgcatg   37320
ttggtggtgg acgcggtgtt ggcgcccgcg tcgggcgccg ccgagcagag cagcgccgtt   37380
gtgcgttcgg ccatgttgtg ggccagcacc tgcagcgtga gcatggcggg cccgtccact   37440
accacgcgcc cgttgtgaaa catggcgttg accgtgttgg ccaccagatt ggccgggtgc   37500 aggggggtgcg cggggtccgt cacggggtcg ctggggcact cctcgccggg ggcgatctcc   37560 ggaccacca tgttctgcag ggtggcgtat acgcggtcga agcgaacccc cgcggtgcag   37620
cagcggcccc gcgagaaggc gggcaccatc acgtagtagt aaatcttgtg gtgcacggtc   37680
cagtccgccc cccggtgcgg ccggtcatcc gcggcgtccg cggctcgggc ctgggtgttg   37740
tgcagcagct ggccgtcgtt gcggttgaag tccgcggtcg ccacgttaca tgccgccgcg   37800
tacacggggt cgtggccccc cgcgctaacc cggcagtcgc gatggcggtc cagggccgcg   37860
cgccgcatca gggcgtcaca gtcccacacg aggggtggca gcagcgccgg gtctcgcatt   37920
aggtgattca gctcggcttg cgcctgcccg cccagctccg ggccggtcag ggtaaagtca   37980
tcaaccagct gggccagggc ctcgacgtgc gccaccaggt cccggtacac ggccatgcac   38040
```

```
tcctcgggaa ggtctccccc gaggtaggtc acgacgtacg agaccagcga gtagtcgttc   38100
acgaacgccg cgcaccgcgt gttgttccag tagctggtga tgcactggac cacgagccgg   38160
gccagggcgc agaagacgtg ctcgctgccg tgtatggcgg cctgcagcag gtaaaacacc   38220
gccgggtagt tgcggtcgtc gaacgccccg cgaacggcgg cgatggtggc gggggccatg   38280
gcgtggcgtc ccaccccag ctccaggccc cgggcgtccc ggaacgccgc cggacatagc    38340
gccaggggca agttgccgtt caccacgcgc caggtggcct ggatctcccc cgggccggcc   38400
gggggaacgt ccccccccgg cagctccacg tcggccaccc ccacaaagaa gtcgaacgcg   38460
gggtgcagct caagagccag gttggcgttg tcgggctgca taaactgctc cggggtcatc   38520
tggccttccg cgacccatcg gacccgcccg tgggccaggc gctgccccca ggcgttcaaa   38580
aacagctgct gcatgtctgc ggcggggccg gccggggccg ccacgtacgc cccgtacgga   38640
ttggcggctt cgacggggtc gcggttaagg cccccgaccg ccgcgtcaac gttcatcagc   38700
gaagggtggc acacggtccc gatcgcgtgt tccagagaca ggcgcagcac ctggcggtcc   38760
ttcccccaaa aaaacagctg gcggggcggg aaggcgcggg gatccgggtg gccggggcg    38820 gggactaggt ccccggcgtg cgcggcaaac cgttccatga ccggattgaa caggcccagg   38880
ggcaggacga acgtcaggtc catggcgccc accagggggt agggaacgtt ggtggcggcg   38940
tagatgcgct tctccagggc ctccagaaag accagcttct cgccgatgga caccagatcc   39000
gcgcgcacgc gcgtcgtctg gggggcgctc tcgagctcgt ccagcgtctg ccggttcagg   39060
tcgagctgct cctcctgcat ctccagcagg tggcggccca cgtcgtccag acttcgcacg   39120
gccttgccca tcacgagcgc cgtgaccagg ttggcccgt tcaggaccat ctcgccgtac    39180
gtcaccggca cgtcggcttc ggtgtcctcc gctttcagga aggactgcag gaggcgctgt   39240
ttgatcgggg cggtggtgac gagcaccccg tcgaccggcc gccgcgcgt gtcggcatgc    39300 gtcagacggg gcacggccac ggagggctgc gtggccgtgg tgaggtccac gagccaggcc   39360
tcgacggcct cccggcggtg gcccgccttg cccaggaaaa agctcgtctc gcagaagctt   39420
cgctttagct cggcgaccag ggtcgcccgg gccaccctgg tggccaggcg gccgttgtcc   39480
aggtatcgtt gcatcggcaa caacaaagcc aggggcggcg ccttttccag cagcacgtgc   39540
agcatctggt cggccgtgcc gcgctcaaac gccccgagga cggcctggac gttgcgagcg   39600
agctgttgga tggcgcgcaa ctggcgatgc gcgccgatac ccgtcccgtc cagggcctcc   39660
cccgtgagca gggcgatggc ctcggtggcc aggctgaagg cggcgttcag ggcccggcgg   39720
tcgataatct tggtcatgta attgtgtgtg ggttgctcga tggggtgcgg gccgtcgcgg   39780
gcaatcagcg gctggtggac ctcgaactgt acgcgccct cgttcatgta ggccagctcc    39840
ggaaacttgg tacacacgca cgccaccgac aacccgagct ccagaaagcg cacgagcgac   39900
agggtgttgc aatacgaccc cagcagggcg tcgaactcga cgtcgtacag gctgtttgca   39960
tcggagcgca cgcggaaaa aaaatcgaac aggcgtcgat gcgacgccac ctcgatcgtg    40020
ctaaggaggg acccggtcgg caccatggcc gcggcatacc ggtatcccgg agggtcgcgg   40080
ttgggagctg ccatggggtc gcgtggagat cggctggatc tagcgatatt tgcccgggga   40140
ggctaagatc caccccaacg cccggccacc cgtgtacgtg cccgacggcc caaggtccac   40200
cgaaagacac gacgggcccg gacccaaaaa ggcgggggat gctgtgtgag gggccgggtg   40260
tcggtcgggg gggaaaggca ccgggagaag gctgcggcct cgttccagga gaacccagtg   40320
tccccaacag acccggggac gtgggatccc aggccttata taccccccccc gccccacccc   40380
```

```
cgttagaacg cgacgggtgc attcaagatg gccctggtcc aaaagcgtgc caggaagaaa    40440
ttggcagagg cggcaaagct gtccgccgcc gccacccaca tcgaggcccc ggccgcgcag    40500
gctatcccca gggcccgtgt gcgcagggga tcggtgggcg gcagcatttg gttggtggcg    40560
ataaagtgga aaagcccgtc cggactgaag gtctcgtggg cggcggcgaa caaggcacac    40620
agggccgtgc ctcccaaaaa cacggacatc ccccaaaaca ctggcgccga caacggcaga    40680
cgatccctct tgatgttaac gtacaggagg agcgcccgca ccgccacgt aacgtagtag    40740 ccgacgatgg cggccaggat acaggccggc gccaccaccc ttccggtcag cccgtaatac    40800
atgcccgctg ccaccatctc caacggcttc aggaccaaaa acgaccaaag gaacagaatc    40860
acgcgctttg aaaagaccgg ctgggtatgg ggcggaagac gcgagtatgc cgaactgaca    40920
aaaaaatcag aggtgccgta cgaggacaat gaaaactgtt cctccagcgg cagttctccc    40980 tcctccccc cgaaggcggc ctcgtcgacc agatctcgat ccaccagagg aaggtcatcc    41040
cgcatggtca tggggtgtgc ggtggaggtg gggagaccga aaccgcaaag ggtcgcttac    41100
gtcagcagga tcccgagatc aaagacaccc gggttcttgc acaaacacca cccggggttgc   41160 atccgcggag gcgagtgttt tgataaggcc gttccgcgcc ttgatataac ctttgatgtt    41220
gaccacaaaa cccggaattt acgcctacgc cccaatgccc acgcaagatg aggtaggtaa    41280 ccccccgtg ggtgtgacgt tgcgtttagt tcattggagg ccaaggggaa aaatgggtg     41340 gggaggaaac ggaaaaccca gtaggccgtg tcgggaacac gcccggggtt gtcctcaaaa    41400
ggcagggtcc atactacgga agccgtcgtt gtattcgaga cctgcctgtg cgacgcacgt    41460
cggggttgcc tgtgtccggt tcggccccca ccgcgtgcgg cacgcacgag gacgagtccg    41520
cgtgctttat tggcgttcca agcgttgccc tccagtttct gttgtcggtg ttcccccata    41580
cccacgccca catccaccgt agggggcctc tgggccgtgt tacgtcgccg cccgcgatgg    41640
agcttagcta cgccaccacc atgcactacc gggacgttgt gttttacgtc acaacggacc    41700
gaaaccgggc ctactttgtg tgcgggggt gtgtttattc cgtggggcgg ccgtgtgcct     41760
cgcagcccgg ggagattgcc aagtttggtc tggtcgttcg agggacaggc ccagacgacc    41820
gcgtggtcgc caactatgta cgaagcgagc tccgacaacg cggcctgcag gacgtgcgtc    41880
ccattgggga ggacgaggtg tttctggaca gcgtgtgtct tctaaacccg aacgtgagct    41940
ccgagctgga tgtgattaac acgaacgacg tggaagtgct ggacgaatgt ctggccgagt    42000
actgcacctc gctgcgaacc agcccgggtg tgctaatatc cgggctgcgc gtgcgggcgc    42060
aggacagaat catcgagttg tttgaacacc caacgatagt caacgttttcc tcgcactttg    42120 tgtataccccc gtccccatac gtgttcgccc tggccccaggc gcacctcccc cggctcccga   42180
gctcgctgga ggccctggtg agcggcctgt ttgacggcat ccccgcccca cgccagccac    42240
ttgacgccca caacccgcgc acggatgtgg ttatcacggg ccgccgcgcc ccacgaccca    42300
tcgccgggtc gggggcgggg tcggggggcg cgggcgccaa gcgggccacc gtcagcgagt    42360
tcgtgcaagt caaacacatt gaccgcgtgg gcccgctgg cgtttcgccg gcgcctccgc     42420
caaacaacac cgactcgagt tccctggtgc ccggggccca ggattccgcc ccgcccggcc    42480
ccacgctaag ggagctgtgg tggtgtttt atgccgcaga ccgggcgctg gaggagcccc     42540
gcgccgactc tggcctcacc cgcgaggagg tacgtgccgt acgtgggttc cgggagcagg    42600
cgtggaaact gtttggctcc gcgggggccc cgcgggcgtt tatcggggcc gcgttgggcc    42660 tgagcccct ccaaaagctg gccgtttact actatatcat ccaccgagag aggcgcctgt    42720 ccccccttccc cgcgctagtc cggctcgtag gccggtacac acagcgccac ggcctgtacg    42780
```

```
tccctcggcc cgacgaccca gtcttggccg atgccatcaa cgggctggtt cgcgacgcgc   42840
tggcggccgg aaccacagcc gagcagctcc tcatgttcga ccttctcccc ccaaaggacg   42900
tgccggtggg aagcgacgtg caggccgaca gcaccgctct gctgcgcttt atagaatcgc   42960
aacgtctcgc cgtccccggg ggggtgatct cccccgagca cgtcgcgtac cttggtgcgt   43020
tcctgagcgt gctgtacgct ggccgcgggc gcatgtccgc agccacgcac accgcgcggc   43080
tgacaggggt gacctccctg gtgctagcgg tgggtgacgt ggaccgtctt tccgcgtttg   43140
accgcggagc ggcgggcgcg gccagccgca cgcgggccgc cgggtacctg gatgtgcttc   43200
ttaccgttcg tctcgctcgc tcccaacacg gacagtctgt gtaaaagacc ccaataaacg   43260
tatgtcgcta ctacacccct tgtgtgtcaat ggacgcctct ccggggggggg aagggaaag   43320
caaagagggg ctgggggagc ggcaccaccg gggcctgaac aaacaaacca cagacacggt   43380
tacagtttat tcggtcgggc ggagaaacgg ccgaagccac gcccacttta ttcgcgtctc   43440
caaaaaaacg ggacacttgt ccggagaacc tttaggatgc cagccagggc ggcggtaatc   43500
ataaccacgc ccagcgcaga ggcggccaga aacccgggcg caattgcggc cacgggctgc   43560
gtgtcaaagg ctagcaaatg aatgacggtt ccgtttggaa atagcaacaa ggccgtggac   43620
ggcacgtcgc tcgaaaacac gcttggggcg ccctccgtcg gcccggcggc gatttgctgc   43680
tgtgtgttgt ccgtatccac cagcaacaca gacatgacct ccccgccggg ggtgtagcgc   43740
ataaacacgg ccccacgag ccccaggtcg cgctggtttt gggtgcgcac cagccgcttg   43800
gactcgatat cccgggtgga gccttcgcat gtcgcggtga ggtaggttag gaacagtggg   43860
cgtcggacgt cgacgccggt gagcttgtag ccgatccccc ggggcagagg ggagtgggtg   43920
acgacgtagc tggcgctgtg ggtgatgggt accaggatcc gtggctcgac gttggcagac   43980
tgccccccgc accgatgtga ggcctcaggg acgaaggcgc ggatcagggc gttgtagtgt   44040
gcccaacgcg tcagggtcga ggcgaggccg tgggtctgct gggccaggac ttcgaccggg   44100
gtctcggatc gggtggcttg agccagcgcg tccaggataa acacgctctc gtctagatca   44160
aagcgcaggg aggccgcgca tggcgaaaag tggccggaa gccaaaagag ggttttctgg   44220
tggtcggccc gggccagcgc ggtccggagg tcgcgttgg tcgctgcggc gacgtcggac   44280
gtacacaggg ccgaggctat cagaaggctc cggcgggcgc gttcccgctg caccgccgag   44340
gggacgccag ccaagaacgg ctgccggagg acagccgagg cgtaaaatag cgcccggtgg   44400
acgaccgggg tggtcagcac gcggcccct agaaactcgg catacagggc gtcgatgaga   44460
tgggctgcgc tgggcgccac tgcgtcgtac gccgaggggc tatccagcac gaaggccagc   44520
tgatagccca gcgcgtgtaa tgccaagctc tgttcgcgct ccagaatctc ggccaccagg   44580
tgctggagcc gagcctctag ctgcaggcgg ccgtgggat ccaagactga cacattaaaa   44640
aacacagaat ccgcggcaca gcccgcggcc ccgcgggcgg ccaacccggc aagcgcgcgc   44700
gagtgggcca aaaagcctag caggtcggag aggcagaccg cgccgtttgc gtgggcggcg   44760
ttcacgaaag caaacccga cgtcgcgagc agcccgtta ggcgccagaa gagagggggg   44820
cgcgggccct gctcggcgcc cgcgtccccc gagaaaaact ccgcgtatgc ccgcgacagg   44880
aactgggcgt agttcgtgcc ctcctccggg tagccgccca cgcggcggag ggcgtccagc   44940
gcggagccgt tgtcggcccg cgtcagggac cctaggacaa agacccgata ccggggggccg   45000
cccgggggcc cggaagagc ccccgggggg ttttcgtccg cggggtcccc gacccgatct   45060
agcgtctggc ccgcggggac caccatcact tccaccggag ggctgtcgtg catggatatc   45120
```

```
acgagcccca tgaattcccg cccgtagcgc gcgcgcacca gcgcggcatc gcacccgagc   45180
accagctccc ccgtcgtcca gatgcccacg ggccacgtcg aggccgacgg ggagaaatac   45240
acgtacctac ctggggatct caacaggccc cgggtggcca accaggtcgt ggacgcgttg   45300
tgcaggtgcg tgatgtccag ctccgtcgtc gggtgccgcc gggccccaac cggcggtcgg   45360
gggggcggtg tatcacgcgg cccgctcggg tggctcgccg tcgccacgtt gtctccccgc   45420
gggaacgtca gggcctcggg gtcagggacg gccgaaaacg ttacccaggc ccgggaacgc   45480
agcaacacgg aggcggctgg attgtgcaag agacccttaa ggggggcgac cgagggggga   45540
ggctgggcgg tcggctcgac cgtggtgggg cgggcaggc tcgcgttcgg gggcggccg    45600 agcaggtagg tcttcgggat gtaaagcagc tggccggggt cccgcggaaa ctcggccgtg   45660
gtgaccaata caaacaaaa gcgctcctcg taccagcgaa gaaggggcag agatgccgta   45720
gtcaggttta gttcgtccgg cggcgccaga aatccgcgcg gtggttttttg ggggtcgggg  45780 gtgtttggca gccacagacg cccggtgttc gtgtcgcgcc agtacatgcg gtccatgccc   45840
aggccatcca aaaccatgg gtctgtctgc tcagtccagt cgtggacctg accccacgca    45900
acgcccaaaa taataacccc cacgaaccat aaaccattcc ccatggggga ccccgtccct   45960
aacccacggg gccgtggct atggcagggc ttgccgcccc gacgttggct gcgagccctg    46020
ggccttcacc cgaacttggg gggtggggtg gggaaaagga agaaacgcgg gcgtattggc   46080
cccaatgggg tctcggtggg gtatcgacag agtgccagcc ctgggaccga accccgcgtt   46140
tatgaacaaa cgacccaaca cccgtgcgtt ttattctgtc tttttattgc cgtcatagcg   46200
cgggttactt ccgtattgt ctccttccgt gtttcagtta gcctccccca tctcccgggc    46260
aaacgtgcgc gccaggtcgc agatcgtcgg tatggagccg ggggtggtga cgtgggtctg   46320
gaccatcccg gaggtaagtt gcagcagggc gtcccggcag ccggcgggcg attggtcgta   46380
atccaggata aagacgtgca tgggacggag gcgtttggcc aagacgtcca aggcccaggc   46440
aaacacgtta tacaggtcgc cgttgggggc cagcaactcg ggggcccgaa acagggtaaa   46500
taacgtgtcc ccgatatggg gttgtgggcc cgcgttgctc tggggctcgg caccctgggg   46560
cggcacggcc gtccccgaaa gctgtcccca atcctcccgc cacgaccgc cgccctgcag    46620 ataccgcacc gtattggcaa gcagctcgta aacgcggcga atcgcggcca acatagccag   46680
gtcaagccgc tcgccgggc gctggcgttt ggccaggcgg tcgatgtgtc tgtcctccgg    46740
aagggccccc aacacgatgt tgtgccgggg caaggtcggc gggatgaggg ccacgaacgc   46800
cagcacggcc tgggggtca tgctgcccat aaggtatcgc gcggccgggt aacacaggag   46860
ggcggcgatg ggatggcggt cgaagatgag ggtgagggcc ggggcgggg catgtgagct   46920 cccagcctcc ccccgatat gaggagccag aacggcgtcg gtcacggcat aaggcatgcc    46980
cattgttatc tgggcgcttg tcattaccac cgccgcgtcc ccggccgata tctcaccctg   47040
gtcgaggcgg tgttgtgtgg tgtagatgtt cgcgattgtc tcggaagccc caacacccg    47100 ccagtaagtc atcggctcgg gtacgtagac gatatcgtcg cgcgaaccca gggccaccag   47160
cagttgcgtg gtggtggttt tccccatccc gtggggaccg tctatataaa cccgcagtag   47220
cgtgggcatt ttctgctcca ggcggacttc cgtggctttt tgctgccggc gagggcgcaa   47280
cgccgtacgt cggttgttat ggccgcgaga acgcgcagcc tggtcgaacg cagacgcgtg   47340
ttgatggcag gggtacgaag ccatacgcgc ttctacaagg cgctggccga agaggtgcgg   47400
gagtttcacg ccaccaagat ctgcggcacg ctgttgacgc tgttaagcgg gtcgctgcag   47460
ggtcgctcgg tattcgaggc cacacgcgtc accttaatat gcgaagtgga cctgggaccg   47520
```

```
cgccgccccg actgcatctg cgtgttcgaa ttcgccaatg acaagacgct gggcggggtt   47580
tgtgtcatca tagaactaaa gacatgcaaa tatatttctt ccggggacac cgccagcaaa   47640
cgcgagcaac gggccacggg gatgaagcag ctgcgccact ccctgaagct cctgcagtcc   47700
ctcgcgcctc cgggtgacaa gatagtgtac ctgtgccccg tcctggtgtt tgtcgcccaa   47760
cggacgctcc gcgtcagccg cgtgacccgg ctcgtcccgc agaaggtctc cggtaatatc   47820
accgcagtcg tgcggatgct ccagagcctg tccacgtata cggtccccat tgagcctagg   47880
acccagcgag cccgtcgccg ccgcggcggc gccgcccggg ggtctgcgag cagaccgaaa   47940
aggtcacact ctggggcgcg cgacccgccc gagtcagcgg cccgccagtt accacccgcc   48000
gaccaaaccc ccgcctccac ggagggcggg ggggtgctta agaggatcgc ggcgctcttc   48060
tgcgtgcccg tggccaccaa gaccaaaccc cgagccgcct ccgaatgaga gtgtttcgtt   48120 ccttcccccct ccccccgcgt cagacaaacc ctaaccaccg cttaagcggc cccgcgagg   48180 tccgaagact catttggatc cggcgggagc cacccgacaa cagccccggg gttttcccac   48240
gccagacgcc ggtccgctgt gccatcgcgc cccctcatcc cacccccat cttgtcccca    48300 aataaaacaa ggtctggtag ttaggacaac gaccgcagtt ctcgtgtgtt attttcgctc   48360
tccgcctctc gcagatggac ccgtactgcc catttgacgc tctggacgtc tgggaacaca   48420
ggcgcttcat agtcgccgat tcccgaaact tcatcacccc cgagttcccc cgggacttt    48480 ggatgtcgcc cgtctttaac ctccccgggg agacggcggc ggagcaggtg gtcgtcctac    48540
aggcccagcg cacagcggct gccgctgccc tggagaacgc cgccatgcag gcggccgagc   48600
tccccgtcga tatcgagcgc cggttacgcc cgatcgaacg gaacgtgcac gagatcgcag    48660
gcgccctgga ggcgctggag acggcggcgg ccgccgccga agaggcggat gccgcgcgcg   48720
gggatgagcc ggcgggtggg ggcgacgggg gggcgccccc gggtctggcc gtcgcggaga   48780
tggaggtcca gatcgtgcgc aacgaccgcg cgctacgata cgacaccaac ctccccgtgg   48840
atctgctaca catggtgtac gcgggccgcg gggcgaccgg ctcgtcgggg gtggtgttcg   48900
ggacctggta ccgcactatc caggaccgca ccatcacgga cttcccctg accacccgca    48960 gtgccgactt tcgggacggc cggatgtcca agaccttcat gacggcgctg gtcctgtccc   49020
tgcagtcgtg cggccggctg tatgtgggcc agcgccacta ttccgccttc gagtgcgccg   49080
tgttgtgtct ctacctgctg taccgaaaca cgcacggggc cgccgacgat agcgaccgcg   49140
ctccggtcac gttcggggat ctgctgggcc ggctgccccg ctacctggcg tgcctggccg   49200
cggtgatcgg gaccgagggc ggccggccac agtaccgcta ccgcgacgac aagctcccca   49260
agacgcagtt cgcggccggc gggggccgct acgaacacgg agcgctggcg tcgcacatcg   49320
tgatcgccac gctgatgcac cacggggtgc tccggcggc cccgggggac gtccccgggg   49380
acgcgagtac ccacgttaac cccgacggcg tggcgcacca cgacgacata aaccgcgccg   49440
ccgccgcgtt cctcagccgg ggccacaacc tattcctgtg ggaggaccag actctgctgc   49500
gggcaaccgc gaacaccata acggccctgg gcgttatcca gcggctcctc gcgaacggca   49560
acgtgtacgc ggaccgcctc aacaaccgcc tgcagctggg catgctgatc cccggagccg   49620
tcccttcgga ggccatcgcc cgtggggcct ccgggtccga ctcggggggcc atcaagagcg   49680 gagacaacaa tctggaggcg ctatgtgcca attacgtgct tccgctgtac cgggccgacc   49740
cggcggtcga gctgacccag ctgtttcccg gcctggccgc cctgtgtctt gacgccagg    49800 cggggcggcc ggtcgggtcg acgcggcggg tggtggatat gtcatcgggg gccgccagg    49860
```

```
cggcgctggt gcgcctcacc gccctggaac tcatcaaccg cacccgcaca aaccccaccc    49920 ccgtgggga  ggttatccac gcccacgacg ccctggcgat ccaatacgaa cagggcttg     49980 gcctgctggc gcagcaggca cgcattggct tgggctccaa caccaagcgt ttctccgcgt    50040
tcaacgttag cagcgactac gacatgttgt acttttatg  tctggggttc attccacagt    50100
acctgtcggc ggtttagtgg gtggtgggcg aggggggagg gggcattagg gagaaagaac    50160
aagagcctcc gttgggtttt ctttgtgcct gtactcaaaa ggtcataccc cgtaaacggc    50220
gggctccagt cccggcccgg tggttggcgt gaacgcaacg gcgggagctg ggttagcgtt    50280
tagtttagca ttcgctctcg cctttccgcc cgcccccga  ccgttgcgcc ttttttttcg    50340
tccaccaaag tctctgtggg tgcgcgcatg gcagccgatg ccccgggaga ccggatggag    50400
gagcccctgc ccgacagggc cgtgcccatt tacgtggctg ggttttggc  cctgtatgac    50460 agcggggact cgggcgagtt ggcattggat ccggatacgt gcgggcggc  cctgcctccg    50520 gataacccac tcccgattaa cgtggaccac cgcgctggct gcgaggtggg gcgggtgctg    50580
gccgtggtcg acgaccccg  cgggccgttt tttgtggggc tgatcgcctg cgtgcagctg    50640
gagcgcgtcc tcgagacggc cgccagcgct gcgattttcg agcgccgcgg gccgccgctc    50700
tcccgggagg agcgcctgtt gtacctgatc accaactacc tgccctcggt ctccctggcc    50760
acaaaacgcc tgggggcga  ggcgcacccc gatcgcacgc tgttcgcgca cgtcgcgctg    50820
tgcgcgatcg gcggcgcct  cggcactatc gtcacctacg acaccggtct cgacgccgcc    50880
atcgcgccct ttcgccacct gtcgccggcg tctcgcgagg gggcgcggcg actggccgcc    50940
gaggccgaga tcgcgctgtc cgggcgcacc tgggcgcccg gcgtggaggc gctgacccac    51000
acgctgcttt ccaccgccgt taacaacatg atgctgcggg accgctggag cctggtggcc    51060
gagcggcggc ggcaggccgg gatcgccgga cacacctacc tccaggcgag cgaaaaattc    51120
aaaatgtggg gggcggagcc tgtttccgcg ccggcgcgcg ggtataagaa cggggccccg    51180
gagtccacgg acataccgcc cggctcgatc gctgccgcgc cgcagggtga ccggtgccca    51240
atcgtccgtc agcgcggggt cgccttgtcc ccggtactgc cccccatgaa ccccgttccg    51300
acatcgggca ccccggcccc cgcgccgccc ggcgacggga gctacctgtg gatcccggcc    51360
tcccattaca accagctcgt cgccggccat gccgcgcccc aaccccagcc gcattccgcg    51420
tttggtttcc cggctgcggc ggggccgtg  gcctatgggc ctcacggcgc gggtcttcc    51480 cagcattacc ctccccacgt cgcccatcag tatcccgggg tgctgttctc gggacccagc    51540
ccactcgagg cgcagatagc cgcgttggtg ggggccatag ccgcggaccg ccaggcgggc    51600
ggtcagccgg ccgcgggaga ccctgggtc  cgggggtcgg gaaagcgtcg ccggtacgag    51660
gcggggccgt cggagtccta ctgcgaccag gacgaaccgg acgcggacta cccgtactac    51720
cccggggagg ctcgaggcgg gccgcgcggg gtcgactctc ggcgcgcggc ccgccagtct    51780
cccgggacca acgagaccat cacgcgcgctg atggggcgg  tgacgtcttt gcagcaggaa    51840
ctggcgcaca tgcgggctag gaccagcgcc cctatggga  tgtacacgcc ggtggcgcac    51900
tatcgccctc aggtggggga gccggaacca acaacgaccc acccggccct ttgtccccg    51960 gaggccgtgt atcgccccc  accacacagc gcccctacg  gtcctcccca gggtccggcg    52020
tcccatgccc ccactccccc gtatgcccca gctgcctgcc cgccaggccc gccaccgccc    52080
ccatgtcctt ccacccagac gcgcccccct ctaccgacgg agcccgcgtt ccccccgcc    52140 gccaccggat cccaaccgga ggcatccaac gcggaggccg gggccctgt  caacgccagc    52200 agcgcagcac acgtggacgt tgacacggcc cgcgccgccg atttgttcgt ctctcagatg    52260
```

```
atgggggccc gctgattcgc cccggtctttt ggtaccatgg gatgtcttac tgtatatctt   52320
tttaaataaa ccaggtaata ccaaagaaga cccattggtg tatgttcttt ttttattggg   52380
aggcgcgggt aggcgggtag ctttacaatg caaaagcctt cgacgtggag gaaggcgtgg   52440
gggggaatcg gcactgacca aggggtccg ttttgtcacg ggaaaggaaa gaggaaacag   52500
gccgcggaca cccggggag tttatgtgtt ccctttctct tcttcccaca cacacaaaag   52560
gcgtaccaaa caaacaaacc aaaagatgca catgcggttt aacacccgtg gttttattt   52620 acaacaaacc ccccgtcaca ggtcgtcctc gtcggcgtca ccgtctttgt tgggaacttg   52680
ggtgtagttg gtgttgcggc gcttgcgcat gaccatgtcg gtgaccttgg cgctgagcag   52740
cgcgctcgtg cccttcttct tggccttgtg ttccgtgcgc tccatggcag acaccagggc   52800
catgtaccgt atcatctccc gggcctcggc tagcttggcc tcgtcaaagt cgccgccctc   52860
ctcgccctcc ccggacgcgt ccgggttggt ggggttcttg agctccttgg tggttagcgg   52920
gtacagggcc ttcatggggt tgctctgcag ccgcatgacg tagcgaaagg cgaagaaggc   52980
cgccgccagg ccggccagga ccaacagacc cacggccagc gccccaaagg ggttggacat   53040
gaaggaggac acgcccgaca cggccgatac cacgccgccc acgatgccca tcaccacctt   53100
gccgaccgcg cgccccaggt cgcccatccc ctcgaagaac gcgcccaggc ccgcaaacat   53160
ggcggcgttg gcgtcggcgt ggatgaccgt gtcgatgtcg gcgaagcgca ggtcgtgcag   53220
ctggttgcgg cgctggacct ccgtgtagtc cagcaggccg ctgtccttga tctcgtggcg   53280
ggtgtacacc tccaggggga caaactcgtg atcctccagc atggtgatgt tgaggtcgat   53340
gaaggtgctg acggtggtga tgtcggcgcg gctcagctgg tgggagtacg cgtactcctc   53400
gaagtacacg tagcccccac cgaaggtgaa gtagcgccgg tgtcccacgg tacacggctc   53460
gatcgcatcg cgcgtcagcc gcagctcgtt gttctccccc agctgcccct cgaccaacgg   53520
gccctggtct tcgtaccgaa agctgaccag ggggcggctg tagcaggccc cgggccgcga   53580
gctgatgcgc atcgagtttt ggacgatcac gttgtccgcg gcgaccggca cgcacgtgga   53640
gacggccatc acgtcgccga gcatccgcgc gctcacccgc cggcccacgg tggccgaggc   53700
gatggcgttg gggttcagct tgcgggcctc gttccacagg gtcagctcgt gattctgcag   53760
ctcgcaccac gcgatggcaa cgcggcccaa catatcgttg acatggcgct gtatgtggtt   53820
gtacgtaaac tgcagcctgg cgaactcgat ggaggaggtg tcttgatgc gctccacgga   53880 cgcgttggcg ctggccccgg gcggcggggg cgtggggttt ggggcttgc ggctctgctc   53940 tcggaggtgt tcccgcacgt acagctccgc gagcgtgttc ctgagaaggg gctggtacgg   54000
gatcagaaag cccccattgg ccaggtagta ctgcggctgg cccaccttga tgtgcgtcgc   54060
gttgtacctg cgggcgaaga tgcggtccat ggcgtcgcgg gcgtccttgc cgatgcagtc   54120
ccccaggtcc acgcgcgaga gcgggtactc ggtcaggttg gtggtgaagg tggtggatat   54180
ggcgtcggag gagaatcgga aggagccgcc gtactcggag cgcagcatct cgtccacctc   54240
ctgccacttg gtcatggtgc agaccgacgg gcgctttggc acccagtccc aggccacggt   54300
gaacttgggg gtcgtgagca ggttccgggt ggtcggcgcc gtggcccggg ccttggtggt   54360
gaggtcgcgc gcgtagaagc cgtcgacctg cttgaagcgg tcggcggcgt agctggtgtg   54420
ttcggtgtgc gaccctcc ggtagccgta aaacgggac atgtacacaa agtcgccagt   54480
cgccagcaca aactcgtcgt acgggtacac cgagcgcgcg tccacctcct cgacgatgca   54540
gtttaccgtc gtcccgtacc ggtggaacgc ctccacccgc gaggggttgt acttgaggtc   54600
```

```
ggtggtgtgc cagccccggc tcgtgcgggt cgcggcgttg gccggtttca gctccatgtc    54660
ggtctcgtgg tcgtcccggt gaaacgcggt ggtctccagg ttgttgcgca cgtacttggc    54720
cgtggaccga cagaccccct tggcgttgat cttgtcgatc acctcctcga aggggacggg    54780
ggcgcggtcc tcaaagatcc ccataaactg ggagtagcgg tggccgaacc acacctgcga    54840
aacggtgacg tctttgtagt acatggtggc cttgaacttg tacggggcga tgttctcctt    54900
gaagaccacc gcgatgccct ccgtgtagtt ctgaccctcg ggccgggtcg ggcagcggcg    54960
cggctgctcg aactgcacca ccgtggcgcc cgtgggggt gggcacacgt aaaagtttgc    55020
atcggtgttc tccgccttga tgtcccgcag gtgctcgcgc agggtggcgt ggcccgcggc    55080
gacggtcgcg ttgtcgccgg cggggcgcgg cggctttggg ggtttcggtt ttttgttctt    55140
cttcggtttc gggtccccg ttggggggc gccaggggcg ggcggcgccg gagtggcagg    55200
gcccccgttc gccgcctggg tcgcggccgc gaccccaggc gtgccggggg aactcggagc    55260
cgccgacacc accaggaccc ccagcgtcaa ccccaagagc gcccatacga cgaaccaccg    55320
gcgcccccgc gcgggggcgc cctggcgcat ggcgggacta cggggccgcg tcgtgccccc    55380
cgtcaggtag cctgggggcg aggtgctgga ggaccgagta gaggatcgag aaaacgtctc    55440
ggtcgtagac cacgaccgac cggggccga tacagccgtc gggggcgctc tcgacgatgg    55500
ccaccagcgg acagtcggag tcgtacgtga gatatacgcc gggcgggtaa cggtaacgac    55560
cttcggaggt cgggcggctg cagtccggcc ggcgcaactc gagctccccg caccggtaga    55620
ccgaggcaaa gagtgtggtg gcgataatca gctcgcgaat atatcgccag gcggcgcgct    55680
gagtgggcgt tattccggaa atgccgtcaa aacagtaaaa cctctgaaat tcgctgacgg    55740
cccaatcagc acccgagccc cccgccccca tgatgaaccg ggcgagctcc tccttcaggt    55800
gcggcaggag ccccacgttc tcgacgctgt aatacagcgc ggtgttgggg ggctgggcga    55860
agctgtgggt ggagtgatca agagggggcc cgttgacgag ctcgaagaag cgatgggtga    55920
tgctggggag cagggccggg tccacctggt gtcgcaggag agacgctcgc atgaaccggt    55980
gcgcgtcgaa cacgcccggc gccgagcggt tgtcgatgac cgtgcccgcg cccgccgtca    56040
gggcgcagaa gcgcgcgcgc gccgcaaagc cgttggcgac cgcggcgaac gtcgcgggca    56100
gcacctcgcc gtggacgctg acccgcagca tcttctcgag ctccccgcgc tgctcgcgga    56160
cgcagcgccc caggctggcc aacgaccgct tcgtcaggcg gtccgcgtac agccgccgtc    56220
gctcccgcac gtccgcggcc gcttgcgtgg cgatgtcccc ccacgtctcg ggcccctgcc    56280
ccccgggccc gcggcgacgg tcttcgtcct cgccccgcc cccgggagct cccaaccccc    56340
gtgccccttc ctctacggcg acacggtccc cgtcgtcgtc ggggcccgcg ccgcccttgg    56400
gcgcgtccgc cgcgccccc gccccatgc gcgccagcac gcgacgcagc gcctcctcgt    56460
cgcactgttc ggggctgacg aggcgccgca agagcggcgt cgtcaggtgg tggtcgtagc    56520
acgcgcggat gagcgcctcg atctgatcgt cgggtgacgt ggcctgaccg ccgattatta    56580
gggcgtccac catatccagc gccgccaggt ggctcccgaa cgcgcgatcg aaatgctccg    56640
cccgccgccc gaacagcgcc agttccacgg ccaccgcggc ggtctcctgc tgcaactcgc    56700
gccgcgccag cgcggtcagg ttgctggcaa acgcgtccat ggtggtctgg ccggcgcggt    56760
cgccggacgc gagccagaat cgcaattcgc tgatggcgta caggccgggc gtggtggcct    56820
gaaacacgtc gtgcgcctcc agcagggcgt cggcctcctt gcggaccgag tcattctcgg    56880
gcgacgggtg gggctgcccg tcgccccccg cggtccgggc cagcgcatgg tccaacacgg    56940
agagcgcccg cgcgcggtcg gcgtccgaca gcccggcggc gtggggcagg taccgccgca    57000
```

```
gctcgttggc gtccagccgc acctgcgcct gctgggtgac gtggttacag atacggtccg    57060
ccaggcggcg ggcgatcgtc gcccctggt tcgccgtcac acacagttcc tcgaaacaga     57120
ccgcgcaggg gtgggacggg tcgctaagct ccggggggac gataaggccc gaccccaccg    57180
cccccaccat aaactcccga acgcgctcca gcgcggcggt ggcgccgcgc gaggggtga    57240 tgaggtggca gtagtttagc tgctttagaa agttctcgac gtcgtgcagg aaacacagct    57300
ccatatggac ggtcccgcca tacgtatcca gcctgacccg ttggtgatac ggacagggtc    57360
gggccaggcc catggtctcg gtgaaaaacg ccgcgacgtc tcccgcggtc gcgaacgtct    57420
ccaggctgcc caggagccgc tcgccctcgc gccacgcgta ctctagcagc aactccaggg    57480
tgaccgacag cggggtgaga aaggccccgg cctgggcctc caggcccggc ctcagacgac    57540
gccgcagcgc ccgcacctga agcgcgttca gcttcagttg ggggagcttc ccccgtccga    57600
tgtgggggtc gcaccgccgg agcagctcta tctgaaacac ataggtctgc acctgcccga    57660
gcagggctaa caacttttga cgggccacgg tgggctcgga caccggggcg ccatctcgc    57720 ggcgccgatc tgtaccgcgg ccggagtatg cggtggaccg aggcggtccg tacgctaccc    57780
ggcgtctggc tgagccccgg ggtccccctc ttcggggcgg cctccgcgg gcccgccgac    57840 cggcaagccg ggagtcggcg gcgcgtgcgt ttctgctcta ttcccagaca ccgcggagag    57900
gaatcacggc ccgcccagag atatagacac ggaacacaaa caagcacgga tgtcgtagca    57960
ataatttatt ttacacacat tccccgcccc gccctaggtt ccccccacccc caacccctca   58020 cagcatatcc aacgtcaggt ctcccttttt gtcgggggc ccctcccaa acgggtcatc     58080 cccgtggaac gccgtttgc ggccggcaaa tgccggtccc ggggccccg ggccgccgaa     58140 cggcgtcgcg ttgtcgtcct cgcagccaaa atccccaaag ttaaacacct ccccggcgtt    58200
gccgagttgg ctgactaggg cctcggcctc gtgcgccacc tccagggccg cgtccgtcga    58260
ccactcgccg ttgccgcgct ccagggcacg cgcggtcagc tccatcatct cctcgcttag    58320
gtactcgtcc tccaggagcg ccagccagtc ctcgatctgc agctgctggg tgcggggccc    58380
caggcttttc acggtcacca cgaacacgct actggcgacg gccgcccgc cctcggagat     58440 aatgccccgg agctgctcgc acagcgagct ttcgtgcgct ccgccgccga ggctcgaggc    58500
cgcgcacaca aacccggccc ggggacaggc caggacgaac ttgcgggtgc ggtcaaaaat    58560
aaggagcggg cacgcgtttt tgccgcccat caggctggcc cagttcccgg cctgaaacac    58620
acggtcgttg ccggccatgc cgtagtactt gctgatgctc aaccccaaca cgaccatggg    58680
gcgcgccgcc atgacgggcc gcagcaggtt gcagctggcg aacatggacg tccacgcgcc    58740
cggatgcgcg tccacggcgt ccatcagcgc gcgggccccg gcctccaggc ccgccccgcc    58800
ctgcgcggac cacgcggccg cagcctgcac gctgggggga cggcgggacc ccgcgatgat    58860
ggccgtaagg gtgttgatga agtacgtcga gtgatcgcag taccgcagaa tctggtttgc    58920
catgtagtac atcgccagct cgctcacgtt gttggggggcc aggttaataa agtttatcgc    58980
gccgtagtcc agggaaaact ttttaatgaa cgcgatggtc tcgatgtcct cgcgcgacag    59040
gagccgggcg ggaagctggt tgcgttggag ggccgtccag aaccactgcg ggttcggctg    59100
gttggacccc gggggcttgc cgttgggaa gatggccgcg tggaactgct tcagcagaaa     59160
gcccagcggt ccgaggagga tgtccacgcg cttgtcgggc ttctggtagg cgctctggag    59220
gctggcgacc cgcgccttgg cggcctcgga gcgttggcg ctcgcgcccg cgaacaaacac    59280 gcggctcttg acgcgcagct ccttgggaaa ccccagggtc acgcgggcaa cgtcgccctc    59340
```

```
gaagctgctc tcggcggggg ccgtctggcc ggccgttagg ctgggggcgc agatagccgc    59400
cccctccgag agcgcgaccg tcagcgtttt ggccgacaga aacccgttgt taaacatgtc    59460
catcacgcgc cgccgcagca ccggttggaa ttgattgcga aagttgcgcc cctcgaccga    59520
ctgcccggcg aacaccccgt ggcactggct cagggccagg tcctgataca cggcgaggtt    59580
ggatcgccgc ccgagaagct gaagcagggg gcatggcccg cacgcgtacg ggtccagcgt    59640
cagggacatg gcgtggttgg cctcgcccag accgtcgcga aacttgaagt tcctcccctc    59700
caccaggttg cgcatcagct gctccacctc gcggtccacg acctgcctga cgttgttcac    59760
caccgtatgc agggcctcgc ggttggtgat gatggtctcc agccgcccca tggccgtggg    59820
gaccgcctgg tccacgtact gcagggtctc gagttcggcc atgacgcgct cggtcgccgc    59880
gcggtacgtc tcctgcatga tggtccgggc ggtctcggat ccgtccgcgc gcttcagggc    59940
cgagaaggcg gcgtagtttc ccagcacgtc gcagtcgctg tacatgctgt tcatggtccc    60000
gaagacgccg atggctccgc gggcggcgct ggcgaacttg ggatggcgcg cccggaggcg    60060
catgagcgtc gtgtgtacgc aggcgtggcg cgtgtcgaag gtgcacaggt tgcagggcac    60120
gtcggtctgg ttggagtccg cgacgtatcg aaacacgtcc atctcctggc gcccgacgat    60180
cacgccgccg tcgcagcgct ccaggtaaaa cagcatcttg ccagcagcg ccggggaaaa    60240 cccacacagc atggccaggt gctcgccggc aaattcctgg gttccgccga cgaggggcgc    60300
ggtgggccga ccctcgaacc cgggcaccac gtgtccctcg cggtccacct gtgggttggc    60360
cgccacgtgg gtcccgggca cgaggaagaa gcggtaaaag gagggtttgc tgtggtcctt    60420
tgggtccgcc ggaccggcgt cgtccacctc ggtgagatgg agggccgagt tggtgctaaa    60480
taccatggcc cccacgagtc ccgcggcgcg cgccaggtac gccccgacgg cgttggcgcg    60540
ggccgcggcc gtgtcctggc cctcgcacag cggccatgcg gagatgtcgg tgggcggctc    60600
gtcgaagacg gccatcgaca cgatagactc gagggccagg gcggcgtctc cggccatgac    60660
ggaggccagg cgctgttcga acccgcccgc cgggcccttg ccgccgccgt cgcgcccacc    60720
ccgcggggtc ttaccctggc tggcttcgaa ggccgtgaac gtaatgtcgg cggggagggc    60780
ggcgccctcg tggttttcgt caaacgccag gtgggcggcc gcgcgggcca cggcgtccac    60840
gtttcggcat cgcagtgcca cggcggcggg tcccacgacc gcctcgaaca ggaggcggtt    60900
gagggggcgg ttaaaaaacg gaagcgggta ggtaaaattc tccccgatcg atcggtggtt    60960
ggcgttgaac ggctcggcga tgacccggct aaaatccggc atgaacagct gcaacggata    61020
cacgggtatg cggtgcacct ccgccccgcc tatggttacc ttgtccgagc ctcccaggtg    61080
cagaaaggtg ttgttgatgc acacggcctc cttgaagccc tcggtaacga ccagatacag    61140
gagggcgcgg tccgggtcca ggccgaggcg ctcacacagc gcctcccccg tcgtctcgtg    61200
tttgaggtcg ccgggccggg gggtgtagtc cgaaaagcca aaatggcggc gtgcccgctc    61260
gcagagtcgc gtcaggtttg gggcctgggt gttggggtcc aggtgccggc cgccgtgaaa    61320
gacgtacacg gacgagctgt agtgcgatgg cgtcagtttc agggacaccg cggtaccccc    61380
gagccccgtc gtgcgagaac ccacgaccac ggctacgttg gcctcaaagc cgctctccac    61440
ggtcaggccc acgaccaggg gcgccacggc gacgtcggca tcgccgctgc gcgccgacag    61500
taacgccaga agctcgatgc cttcggatgg acacgcgcga gcgtacacgt atcccagggg    61560 cccgggggg accttgatgg tggttgccgt cttgggcttt gtctccatgt cctcctggca    61620
atcggtccgc aaacggaggt aatcccggca cgacgacgga cgcccgacga ggtatgtctc    61680
ccgagcgtca aaatccgggg ggggcggcga cggtcaaggg gagggtggga gaccgggttt    61740
```

```
ggggaatgaa tccctaccct tcaccgacaa cccccgggta accacggggt gccgatgaac   61800
cccggcggct ggcaacgcgg ggtccctgcg agaggcacag atgcttacgg tcaggtgctc   61860
cgggccgggt gcgtctgata tgcggttggt atatgtacac tttacctggg ggcgtgccgg   61920
accgcaccag cccctcccac accccgcgcg tcatcagccg gtgggcgnnn nnnnnnnnnn   61980
nnnnnnnnnn nnnnnnnnnn nnnnnnnnnn nnnnnnnnnn nnnnnnnnnn nnnnnnnnnn   62040
nnnnnnnnnn nnnnnnnnnn nnnnnnnnnt ttttataata gcggccacgc ccaccggcta   62100
cgtcacgctc ctgtcggccg ccggcggtcc ataagcccgg ccggccgggc cgacgcgaat   62160
aaaccgggcc gccggccggg gcgccgcgca gcagctcgcc gcccggatcc gccagacaaa   62220
caaggccctt gcacatgccg gcccgggcga gcctgggggt ccggtaattt tgccatccca   62280
cccaagcggc ttttggggtt tttcctcttc ccccctcccc acctcccccc tctttagggg   62340
ttcgggtggg aacaaccgcg atgttttccg gtggcggcgg cccgctgtcc cccggaggaa   62400
agtcggcggc cagggcggcg tccgggtttt ttgcgcccgc cggccctcgc ggagccggcc   62460
ggggaccccc gccttgtttg aggcaaaact tttacaaccc ctacctcgcc ccagtcggga   62520
cgcaacagaa gccgaccggg ccaacccagc gccatacgta ctatagcgaa tgcgatgaat   62580
ttcgattcat cgcccgcgg gtgctggacg aggatgcccc cccggagaag cgcgccgggg   62640
tgcacgacgg tcacctcaag cgcgccccca aggtgtactg cggggggggac gagcgcgacg   62700 tcctccgcgt cgggtcgggc ggcttctggc cgcggcgctc gcgcctgtgg ggcggcgtgg   62760
accacgcccc ggcggggttc gacccccaccg tcaccgtctt tcacgtgtat gacatcctgg   62820
agaacgtgga gcacgcgtac ggcatgcgcg cggcccagtt ccacgcgcgg tttatggacg   62880
ccatcacacc gacggggacc gtcatcacgc tcctgggcct gactccggaa ggccaccggg   62940
tggccgttca cgtttacggc acgcggcagt acttttacat gaacaaggag gaggttgaca   63000
ggcacctaca atgccgcgcc ccacgagatc tctgcgagcg catggccgcg gccctgcgcg   63060
agtccccggg cgcgtcgttc cgcggcatct ccgcggacca cttcgaggcg gaggtggtgg   63120
agcgcaccga cgtgtactac tacgagacgc gccccgctct gttttaccgc gtctacgtcc   63180
gaagcgggcg cgtgctgtcg tacctgtgcg acaacttctg cccggccatc aagaagtacg   63240
agggtggggt cgacgccacc acccggttca tcctggacaa ccccgggttc gtcaccttcg   63300
gctggtaccg tctcaaaccg ggccggaaca acacgctagc ccagccgcgg gccccgatgg   63360
ccttcgggac atccagcgat gtcgagttta actgtacggc ggacaacctg gccatcgagg   63420
ggggcatgag cgacctaccg gcatacaagc tcatgtgctt cgatatcgaa tgcaaggcgg   63480 gggggggagga cgagctggcc tttccggtgg ccgggcaccc ggaggacctg gtcatccaga   63540
tatcctgtct gctctacgac ctgtccacca ccgccctgga gcacgtcctc ctgttttcgc   63600
tcggttcctg cgacctcccc gaatcccacc tgaacgagct ggcggccagg ggcctgccca   63660
cgcccgtggt tctggaattc gacagcgaat tcgagatgct gttggccttc atgacccttg   63720
tgaaacagta cggccccgag ttcgtgaccg ggtacaacat catcaacttc gactggccct   63780
tcttgctggc caagctgacg gacatttaca aggtccccct ggacgggtac ggccgcatga   63840
acggccgggg cgtgttttcgc gtgtgggaca taggccagag ccacttccag aagcgcagca   63900
agataaaggt gaacggcatg gtgaacatcg acatgtacgg gattataacc gacaagatca   63960
agctctcgag ctacaagctc aacgccgtgg ccgaagccgt cctgaaggac aagaagaagg   64020
acctgagcta tcgcgacatc cccgcctact acgccgccgg gcccgcgcaa cgcggggtga   64080
```

-continued

| | | | | | |
|---|---|---|---|---|---|
| tcggcgagta | ctgcatacag | gattccctgc | tggtgggcca | gctgttttt | aagttttgc | 64140 |
| cccatctgga | gctctcggcc | gtcgcgcgct | tggcgggtat | taacatcacc | cgcaccatct | 64200 |
| acgacggcca | gcagatccgc | gtctttacgt | gcctgctgcg | cctggccgac | cagaagggct | 64260 |
| ttattctgcc | ggacacccag | gggcgattta | ggggcgccgg | gggggaggcg | cccaagcgtc | 64320 |
| cggccgcagc | ccgggaggac | gaggagcggc | cagaggagga | gggggaggac | gagaacgaac | 64380 |
| gcgaggaggg | cgggggcgag | cgggagccgg | agggcgcgcg | ggagaccgcc | ggccggcacg | 64440 |
| tggggtacca | gggggccagg | gtccttgacc | ccacttccgg | gtttcacgtg | aaccccgtgg | 64500 |
| tggtgttcga | ctttgccagc | ctgtacccca | gcatcatcca | ggcccacaac | ctgtgcttca | 64560 |
| gcacgctctc | cctgagggcc | gacgcagtgg | cgcacctgga | ggcgggcaag | gactacctgg | 64620 |
| agatcgagat | ggggggggcga | cggctgttct | tcgtcaaggc | tcacgtgcga | gagagcctcc | 64680 |
| tcagcatcct | cctgcgggac | tggctcgcca | tgcgaaagca | gatccgctcg | cggattcccc | 64740 |
| agagcagccc | cgaggaggcc | gtgctcctgg | acaagcagca | ggccgccatc | aaggtcgtgt | 64800 |
| gtaactcggt | gtacgggttc | acgggagtgc | agcacggact | cctgccgtgc | ctgcatgttg | 64860 |
| ccgcgacggt | gacgaccatc | ggccgcgaga | tgctgctcgc | gacccgcgag | tacgtccacg | 64920 |
| cgcgctgggc | ggccttcgaa | cagctcctgg | ccgatttccc | ggaggcggcc | gacatgcgcg | 64980 |
| cccccgggcc | ctattccatg | cgcatcatct | acgggacac | ggactccata | tttgtgctgt | 65040 |
| gccgcggcct | cacggccgcc | gggctgacgg | ccatgggcga | caagatggcg | agccacatct | 65100 |
| cgcgcgcgct | gtttctgccc | cccatcaaac | tcgagtgcga | aaagacgttc | accaagctgc | 65160 |
| tgctgatcgc | caagaaaaag | tacatcggcg | tcatctacgg | gggtaagatg | ctcatcaagg | 65220 |
| gcgtggatct | ggtgcgcaaa | acaactgcg | cgtttatcaa | ccgcacctcc | agggccctgg | 65280 |
| tcgacctgct | gttttacgac | gataccgtat | ccggagcggc | cgccgcgtta | gccgagcgcc | 65340 |
| ccgcagagga | gtggctggcg | cgaccccctgc | ccgagggact | gcaggcgttc | ggggccgtcc | 65400 |
| tcgtagacgc | ccatcggcgc | atcaccgacc | cggagaggga | catccaggac | tttgtcctca | 65460 |
| ccgccgaact | gagcagacac | ccgcgcgcgt | acaccaacaa | gcgcctggcc | cacctgacgg | 65520 |
| tgtattacaa | gctcatggcc | cgccgcgcgc | aggtcccgtc | catcaaggac | cggatcccgt | 65580 |
| acgtgatcgt | ggcccagacc | cgcgaggtag | aggagacggt | cgcgcggctg | gccgccctcc | 65640 |
| gcgagctaga | cgccgccgcc | caggggacg | agcccgcccc | ccccgcggcc | ctgccctccc | 65700 |
| cggccaagcg | ccccgggag | acgccgtcgc | atgccgaccc | ccgggaggc | gcgtccaagc | 65760 |
| cccgcaagct | gctggtgtcc | gagctggccg | aggatcccgc | atacgccatt | gcccacggcg | 65820 |
| tcgccctgaa | cacggactat | tacttctccc | acctgttggg | ggcggcgtgc | gtgacattca | 65880 |
| aggccctgtt | tgggaataac | gccaagatca | ccgagagtct | gttaaaaagg | tttattcccg | 65940 |
| aagtgtggca | cccccggac | gacgtggccg | cgcggctccg | ggccgcaggg | ttcggggcgg | 66000 |
| tgggtgccgg | cgctacgcg | gaggaaactc | gtcgaatgtt | gcatagagcc | tttgatactc | 66060 |
| tggggtgccgg | cgctacgcg | gaggaaactc | gtcgaatgtt | gcatagagcc | tttgatactc | 66060 |
| tagcatgagc | ccccgtcga | agctgatgtc | cctcatttta | caataaatgt | ctgcggccga | 66120 |
| cacggtcgga | atctccgcgt | ccgtgggttt | ctctgcgttg | cgccggacca | cgagcacaaa | 66180 |
| cgtgctctgc | cacacgtggg | cgacgaacct | gtaccccggg | cacgcggtga | gcatccggtc | 66240 |
| tatgagccgg | tagtgcaggt | gggcggacgt | gccgggaaag | atgacgtaca | gcatgtggcc | 66300 |
| cccgtaagtg | gggtccgggt | aaaacaacag | ccgcgggtcg | cacgcccgc | ctccgcgcag | 66360 |
| gatcgtgtgc | acgaaaaaaa | gctcgggttg | gccaagaatc | ccggccaaga | ggtcctggag | 66420 |
| gggggcgttg | tggcggtcgg | ccaacacgac | caaggaggcc | aggaaggcgc | gatgctcgaa | 66480 |

```
tatcgtgttg atctgctgca cgaaggccag gattagggcc tcgcggctgg tggcggcgaa   66540
ccgcccgtct cccgcgttgc acgcgggaca gcaaccccg atgcctaggt agtagcccat    66600
cccggagagg gtcaggcagt tgtcggccac ggtctggtcc agacagaagg gcagcgacac   66660
gggagtggtc ttcaccaggg gcaccgagag cgagcgcacg atggcgatct cctcggaggg   66720
cgtctgggcg agggcggcga aaaggccccg atagcgctgg cgctcgtgta aacacagctc   66780
ctgtttgcgg gcgtgaggcg gcaggctctt ccgggaggcc cgacgcacca cgcccagagt   66840
cccgccggcc gcagaggagc gcgaccgccg gcgctccttg ccgtgatagg gcccgggccg   66900
ggagccgcgg cgatggggt cggtatcata cataggtaca cagggtgtgc tccagggaca    66960
ggagcgagat cgagtggcgt ctaagcagcg cgcccgcctc acggacaaat gtggcgagcg   67020
cggtgggctt tggtacaaat acctgatacg tcttgaaggt gtagatgagg gcacgcaacg   67080
ctatgcagac acgcccctcg aactcgttcc cgcaggccag cttggccttg tggagcagca   67140
gctcgtcggg atgggtggcg gggggatggc cgaacagaac ccaggggtca acctccatct   67200
ccgtgatggc gcacatgggg tcacagaaca tgtgcttaaa gatggcctcg ggccccgcgg   67260
cccgcagcag gctcacaaac cggccccccgt ccccgggctg cgtctcgggg tccgcctcga   67320
gctggtcgac gacgggtacg atacagtcga agaggctcgt gttgttttcc gagtagcgga   67380
ccacggaggc ccggagtctg cgcagggcca gccagtaagc ccgcaccagt aacaggttac   67440
acagcaggca ttctccgccg gtgcgcccgc gccccggcc gtgtttcagc acggtggcca    67500
tcagagggcc caggtcgagg tcgggctggg catcgggttc ggtaaactgc gcaaagcgcg   67560
gagccacgtc gcgcgtgcgt gccccgcgat gcgcttccca ggactggcgg accgtggcgc   67620
gacgggcctc cgcggcagcg cgcagctggg gccccgactc ccagacgcg gggtgccgg     67680 cgaggagcag caggaccaga tccgcgtacg cccacgtatc cggcgactcc tccggctcgc   67740
ggtccccggc gaccgtctcg aattcccgt tgcgagcggc ggcgcgcgta cagcagctgt    67800 ccccgcccc gcgccgaccc tccgtgcagt ccaggagacg ggcgcaatcc ttccagttca    67860
tcagtgcggt ggtaagcgac ggctgcgtgc cggataccgc cgccgacccc gcccctcct    67920 cgcccccgga ggccaaggtt ccgatgaggg cccggggtggc agactgcgcc aggaacgagt   67980
agttggagta ctgcacccttg gcggctcccg gggagggcga gggcttgggt tgcttctggg   68040
catgccgccc gggcaccccg ccgtcggtac ggaagcagca gtggagaaaa aagtgccggt   68100
ggatgtcgtt tatggtgagg gcaaagcgtg cgaaggagcc gaccagggtc gccttcttgg   68160
tgcgcagaaa gtggcggtcc atgacgtaca caaactcgaa cgcggccacg aagatgctag   68220
cggcgcagtg gggcgccccc aggcatttgg cacagagaaa cgcgtaatcg gccacccact   68280
gaggcgagag gcggtaggtt tgcttgtaca gctcgatggt gcggcagacc agacagggcc   68340
ggtccagcgc gaaggtgtcg atggccgccg cggaaaaggg cccggtgtcc aaaagcccct   68400
ccccacaggg atccggggc gggttgcggg gtcctccgcg cccgcccgaa cccctccgt     68460 cgcccgcccc cccgcgggcc cttgaggggg cggtgaccac gtcggcggcg acgtcctcgt   68520
cgagcgtacc gacgggcggc acacctatca cgtgactggc cgtcaggagc tcggcgcaga   68580
gagcctcgtt aagagccagg aggctgggat cgaaggccac atacgcgcgc tcgaacgccc   68640
ccgccttcca gctgctgccg ggggactctt cgcacaccgc gacgctcgcc aggaccccgg   68700
ggggcgaagt tgccatggct gggcgggagg ggcgcacgcg ccagcgaact ttacgggaca   68760
caatccccga ctgcgcgctg cggtcccaga ccctggagag tctagacgcg cgctacgtct   68820
```

```
cgcgagacgg cgcgcatgac gcggccgtct ggttcgagga tatgaccccc gccgagctgg    68880
aggttgtctt cccgactacg gacgccaagc taaaactacct gtcgcggacg cagcggctgg    68940
cctccctcct gacgtacgcc gggcctataa aagcgcccga cgacgccgcc gccccgcaga    69000
ccccggacac cgcgtgtgtg cacggcgagc tgctcgcccg caagcgggaa agattcgcgg    69060
cggtcattaa ccggttcctg gacctgcacc agattctgcg gggctgacgc gcgcgctgtt    69120
gggcgggacg gttcgcgaac cctttggtgg gtttacgcgg gcacgcacgc tcccatcgcg    69180
ggcgccatgg cgggactggg caagccctac accggccacc caggtgacgc cttcgagggt    69240
ctcgttcagc gaattcggct tatcgtccca tctacgttgc ggggcgggga cggggaggcg    69300
ggcccctact ctccctccag cctcccctcc aggtgcgcct ttcagtttca tggccatgac    69360
gggtccgacg agtcgtttcc catcgagtat gtactgcggc ttatgaacga ctgggccgag    69420
gtcccgtgca acccttacct gcgcatacag aacaccggcg tgtcggtgct gtttcagggg    69480 tttttttcatc gcccacacaa cgcccccggg ggcgcgatta cgccagagcg gaccaatgtg    69540
atcctggggt ccaccgagac gacggggttg tccctcggcg acctggacac catcaagggg    69600
cggctcggcc tggatgcccg gccgatgatg gccagcatgt ggatcagctg ctttgtgcgc    69660
atgccccgcg tgcagctcgc gtttcggttc atgggcccg aagatgccgg acggacgaga    69720
cggatcctgt gccgcgccgc cgagcaggct attacccgtc gccgcgaac ccggcggtcc    69780 cgggaggcgt acggggccga ggccgggctg ggggtggccg gaacgggttt ccgggccagg    69840
ggggacggtt ttggcccgct ccccttgtta acccaagggc cctcccgccc gtggcaccag    69900
gccctgcggg gtcttaagca cctacggatt ggccccccg cgctcgtttt ggcggcggga    69960
ctcgtcctgg gggccgctat ttggtgggtg gttggtgctg gcgcgcgcct ataaaaaagg    70020
acgcaccgcc gccctaatcg ccagtgcgtt ccggacgcct tcgccccaca cagccctccc    70080
gaccgacacc cccatatcgc tccccgacct ccggtcccga tggccgtccc gcaatttcac    70140
cgccccagca ccgttaccac cgatagcgtc cgggcgcttg gcatgcgcgg gctcgtcttg    70200
gccaccaata actctcagtt tatcatggat aacaaccacc cacaccccca gggcacccaa    70260
ggggccgtgc gggagtttct ccgcggtcag gcggcggcac tgacggacct tggtctggcc    70320
cacgcaaaca acacgtttac cccgcagcct atgttcgcgg gcgacgcacc ggccgcctgg    70380
ttgcggcccg cgtttggcct gcggcgcacc tattcaccctt ttgtcgttcg agaaccttcg    70440
acgcccggga ccccgtgagg cccagggagt tccttctggg gtgttttaat caataaaaga    70500
ccacaccaac gcacgagcct tgcgtttaat gtcgtgttta ttcaagggag tgggataggg    70560
ttcgacggtt cgaaacttaa cacaccaaat aatcgagcgc gtctagccca gtaacatgcg    70620
cacgtgatgt aggctggtca gcacggcgtc gctgtgatga agcagcgccc ggcgggtccg    70680
ctgtaactgc tgttgtaggc ggtaacaggc gcggatcagc accgccaggg cgctacgacc    70740
ggtgcgttgc acgtagcgtc gcgacagaac tgcgtttgcc gatacgggcg ggggccgaa    70800 ttgtaagcgc gtcacctctt gggagtcatc ggcgtataac gcactgaatg gttcgttggt    70860
tatgggggag tgtggttccc cagggagtgg gtcgagcgcc tcggcctcgg aatccgagag    70920
gaacaacgag gtgcgtcgg agtcttcgtc gtcagagaca tacagggtct gaagcagcga    70980
cacgggcgtg ggggtagcgt cgatgtgtag cgcgagggag gatgcccacg aagacacccc    71040
agacaaggag ctgcccgtgc gtggatttgt ggaagacgcg gaagccggga cggatgggcg    71100
gttttgcggt gcccggaacc gaaccgccgg atactccccg ggtgctacat gcccgttttg    71160
gggctggggt tggggctggg gcgcggacag gcggctgacg gtcaaatgcc cccggggggcg    71220
```

```
cgcagatgtg gcgggcgtgg ccaccggctg ccgtgtagtg gggcggcggg aaaccgggcc    71280
tccgggcgta acaccgccct ccagcgtcaa gtatgtgggg ggcgggcctg acgtcggggg    71340
cggggtgacg ggttggaccg cgggaggcgg gggagaggga cctgcgggag aggatgaggt    71400
cggctcggcc gggttgcggc ctaaaacagg ggccgtgggg tcggcggggt cccagggtga    71460
agggagggat tcccgcgatt cggacagcga cgcgacagcg gggcgcgtaa ggcgccgctg    71520
cggcccgcct acgggaaccc tgggggggt tggcgcggga cccgaggtta gcggggggcg    71580
gcggttttcg cccccgggca aaaccgtgcc ggttgcgacc gggggcggaa cgggatcgat    71640
agggagagcg ggagaagcct ggccggcgga ctggggaccg agcgggaggg gcacaccaga    71700
caccaaagcg tggggcgctg gctctggggg tttgggaggg gccggggggc gcgcgaaatc    71760
ggtaaccggg gcgaccgtgt cggggagggc aggcggccgc caaccctggg tggtcgcgga    71820
agcctgggtg gcgcgcgcca gggagcgtgc ccggcggtgt cggcgcgcgc gcgacccgga    71880
cgaagaagcg gcagaagcgc gggaggaggc ggggggggcgg ggggcggtgg catcgggggg    71940
cgccggggaa ctttgggggg acggcaagcg ccggacgtcg tcgcggggc ccacgggcgc    72000 cggccgcgtg ctttcggccg ggacgcccgg tcgtgcttcg cgagccgtga ctgccggccc    72060 aggggggccgc ggtgcacact gggatgtggg gacggactga tcggcggtgg gcgaaagggg    72120
gtccggggca aggaggggcg cggggccgcc ggagtcgtca gacgcgagct cctccaggcc    72180
gtgaatccat gcccacatgc gagggggggac gggctcgccg ggggtggcgt cggtgaatag    72240
cgtgggggcc aggcttccgg gccccaacga gccctccgtc ccaacaaggt ccgccgggcc    72300
gggggtcggg ttcgggaccg aggggctctg gtcgtcgggg gcgcgctggt acaccggatg    72360
ccccgggaat agctcccccg acaggaggga ggcgtcgaac ggccgcccga ggatagctcg    72420
tgcgaggaag gggtcctcgt cggtggcgct ggcggcgagg acgtcctcgc cgcccgccac    72480
aaacgggagc tcctcggtgg cctcgctgcc aacaaaccgc acgtcggggg ggccgggggg    72540
tccgggtttt cccacaacac cgcgaccggg gtcatggaga tgtccacgag caccagacac    72600
ggcgggcccc gggcgagggg ccgctcggcg atgagcgcgg acaggcgcgg gagctgtgcc    72660
gccagacacg cgttttcgat cgggttcagg tcggcgtgca ggaggcggac ggcccacgtc    72720
tcgatgtcgg acgacacggc atcgcgcaag gcggcgtccg gcccgcgagc gcgtgagtca    72780
aacagcgtga ggcacagctc cagctccgac tcgcgggaaa aggccgtggt gttgcggagc    72840
gccacgacga cgggcgcgcc caggagcact gccgccagca ccaggtccat ggccgtaacg    72900
cgcgccgcgc gggtgcggtg ggtggcggcg ccggcacgg cgacgtgctg gcccgtgggc    72960
cggtagaggg cgttgggggg agcggggggt gacgcctcgc gcccccccga ggggctcagc    73020
gtctgcccag attccagacg cgcggtcaga agggcgtcga aactgtcata ctctgtgtag    73080
tcgtccggaa acatgcaggt ccaaagagcg gccagcgcgg tgcttgggag acacatgcgc    73140
ccgaggacgc tcaccgccgc cagcgcctgg gcgggactca gctttcccag cgcggcgccg    73200
cgctcggttc ccagctcggg gaccgagcgc cagggcgcca ggggtcggt ttcggacaac    73260 ttgccgcggc gccagtctgc cagccgcgtg ccgaacatga gccccgggt cggagggcct    73320 ccggccgaaa acgctggcag cacgcggatg cgggcgtctg gatgcgggt caggcgctgc    73380 acgaatagca tggaatctgc tgcgttctga aacgcacggg ggagggtgag atgcatgtac    73440
tcgtgttggc ggaccagatc caggcgccaa aaggtgtaaa tgtgttccgg ggagctggcc    73500
accagcgcca ccagcacgtc gttctcgtta aaggaaacgc ggtgcctagt ggagctctgg    73560
```

```
ggtccgagcg gcggccccgg ggccgccgcg tcaccccccc attccagctg ggcccagcga   73620
cacccaaact cgcgcgtgag agtggtcgcg acgagggcga cgtagagctc ggccgccgca   73680
tccatcgagg cccccatct cgcctggcgg tggcgcacaa agcgtccgaa gagctgaaag    73740
ttggcggcct gggcgtcgct gagggccagc tgaagccggt tgatgacggt gaggacgtac   73800
atggccgtga cggtcgaggc cgactccagg gtgtccgtcg aagcgggggg gcgaatgcat   73860
gccgcctcgg gacacatcag cagcgcgccg agcttgtcgg tcacggccgg gaagcagagc   73920
gcgtactgca gtggcgttcc atccgggacc aaaaagctgg gggcgaacgg ccgatccagc   73980
gtactggtgg cctcgcgcag caccagggggc cccgggcctc cgctcactcg caggtacgcc   74040
tcgccccggc ggcgcagcat ctgcgggtcg gcctcttggc cgggtggggc ggacgcccgg   74100
gcgcgggcgt ctagggcgcg aagatccacg agcaggggcg cgggcgcggc ggccgcgccc   74160
gcgcccgtct ggcctgtggc cttggcgtac gcgctatata agcccatgcg gcgttggatg   74220
agctcccgcg cgccccggaa ctcctccatc gcccatgggg ccaggtcccc ggccaccgcg   74280
tcgaattccg ccaacaggcc ccccaggggta tcaaagttca tctcccaggc cacccttggc   74340
accacctcgt cccgcagccg ggcgctcagg tcggcgtgtt gggccacgcg ccccccgagc   74400
tcctccacgg ccccggcccg ctcggcgctc ttggcgccca ggacgccctg gtacttggcg   74460
ggaaggcgct cgtagtcccg ctgggctcgc agccccgaca cagtgttggt ggtgtcctgc   74520
agggcgcgaa gctgctcgca tgccgcgcga atccctcgg gcgatttcca ggccccccg    74580
cgaacgcggc cgaagcgacc ccatacctcg tcccactccg cctcggcctc ctcgagagac   74640
ctccgcaggg cctcgacgcg cgacgggtg tcgaagagcg cctgcaggcg cgcgccctgt    74700
cgcgtcagga ggcccgggcc gtcgctgctg gccgcgctta gcgggtgcgt ctcaaaggta   74760
cgctgggcat gttccaacca ggcgaccgcc tgcacgtcga gctcgcgcgc cttctccgtc   74820
tggtccaaca gaatttcgac ctgatccgcg atctcctccg ccgagcgcgc ctggtccagc   74880
gtcttggcca cggtcgccgg gacggcgacc accttcagca gggtcttcag attggccaga   74940
ccctcggcct cgagctgggc ccggcgctcg cgcgcggcca gcacatcccg cagccccgcc   75000
gtgacccgct cggtggcttc ggcgcgctgc tgtttggcgc gcaccacggc gtccttggta   75060
tcggccaggt cctgtcgggt cacgaatgcg acgtagtcgg agtacgccgt gtccttcacg   75120
gggctctggt ccacgcgctc cagcgccgcc acgcacgcca ccagcgcgtc ctcgctcggg   75180
cagggcaggg tgacccctgc ccggacaagc tcggcggccg ccgccgggtc gttgcgcacc   75240
gcggatatct cctccgcggc ggcggccagg tccagcgcca cgcttccgat cgcgcgccgc   75300
gcgtcggccc ggagggcgtc caggcgatcg cggatatcca cgtactcggc gtagcccttt   75360
tgaaaaaacg gcacgtactg gcgcagggcc ggcacgcccc ccaagtcttc cgacaggtgt   75420
agtacggcct cgtggtagtc gataaacccg tcgttcgcct gggcccgctc cagcagcccc   75480
cccgcgagcc gcagaagccg cgccagggc tcggtgtcca cccgaaacat gtcggcgtac    75540
gtgtcggccg cggccccaaa ggccgcgctc cagtcgatgc ggtgaatggc tgcgagcggg   75600
gggagcatgg ggtggcgctg gttctcgggg gtgtatgggt taaacgcaag ggccgtctcc   75660
agggcaaggt tcaccgcctt ggcgttggtt cccagcgcct gctcggcccg ctttcggaag   75720
tcccggggggt tgtagccgtg cgtgcccgcc agcgcctgca ggcgacggag ctcgaccacg   75780
tcaaactcgg cactgctttc cacgcggtcc agcacggcct ccacgtcggc ggcccagcgc   75840
tcgtggctac tgcgggcgcg ctgggccgcc atcttctctc tgaggtcggc ggtggcggcc   75900
tcaagttcgt cggcgcggcg tcgcgtggcg ccgatgacct ttcccagctc ctgcagggcg   75960
```

```
cgcccgctgg gggagtggtc cccggccgtc ccttcggcgt gcaacaggcc cccgaacctg    76020
ccctcgtggc ccgcgaggct ttcccgcgcg ccggtggtcg cgcgcgtcgc ggcttggatc    76080
agggaggcat gctctcccct cggttggttg gcggcccggc gcacctggac gacaaggtcg    76140
gcggcagccg accctaaggt cgtgagctgg gcgatggccc cccgcgcgtc cagggccaac    76200
cgagtcgcct tgacgtatcc cgcggcgctg tcggccatgg ccgctaggaa ggccaggggg    76260
gaggccgggt cgctggcggc cgcgcccagg ccgtcaccg cgtcgaccag gacgcggtgc    76320
gcccgcacgg ccgcatccac cgtcgacgcg gggtctgccg tcgcgacggc ggcgctgccg    76380
gcgttgatgg cgttcgagac ggcgtgggct atgatcgggg cgtgatcggc gaagaactgc    76440
aagagaaacg gagtctcggg ggcgtcggcg aacaggttct tcagcaccac cacgaagctg    76500
ggatgcaagc cggacagagc cgtcgccgtg tccggagtcg ggtgctccag ggcatctcgg    76560
tactgcccca gcagcccca catgtccgcc cgcagcgccg ccgtaacctc aggggggcgcc   76620 ccccgaacgg cctcggggag gtccgaccag cccgccggca gggaggcccg cagggtcgcc    76680
aggacggccg gacaggcctt tagccccaca aagtcaggga gggggcgcag gaccccctgg    76740
agtttgtgca agaacttctc ccgggcgtcg cgggccacct tcgcccgctc ccgcgctccc    76800
tcgagcattg cctccaggga gcgcgcgcgc tcccgcaaac ggacacgcgc atcggggcg    76860 agctctgccg tcagcttggc ggcatccatg gcccgcgcct gccgcagcgc ttcctcggcc    76920
atgcgcgtgg cctctggcga cagcccgccg tcgtcgggt agggcgacgc gccgggcgca    76980
ggaacaaagg ccgcgtcgct gtccagctgc tgggccaggg ccgcatctag ggcgtcgaag    77040
cgccgcagct cggccagacc cgagctgcgg cgcgcctgct ggtcgttaat gtcgcggatg    77100
ctgcgcgcca gctcgtccag cggcttgcgt tctatcagcc cttggttggc ggcgtccgtc    77160
aggacggaga gccaggccgc caggtcctcg ggggcgtcca gcgtctggcc ccgctgtatc    77220
agatcccgca acaggatggc cgtggggctg gtcgcgatcg ggggcggggc gggaatggcg    77280
gcgcgctgcg cgatgtcccg cgtgtgctgg tcgaagacag gcaggactc gagcagctgg    77340 accacgggca cgacgcggc cgaagccacg tgaaaccggc ggtcgttgtt gtcgctggcc    77400
tgtagagcct tggcgctgta tacggccccc cggtaaaagt actccttaac cgcccctcg    77460 atcgcccgac gggcctgggt ccgcacctcc tccagccgaa cctgaacggc ctcggggccc    77520 aggggggtg ggcgcggagc cccctgcggg gccgccccgg ccggggcggg cattacgccg    77580
aggggcccgg cgtgctgtga accgcgtcg accccgcgag cgaggcgtc gagggcctcg    77640 cgcatctggc gatcctccgc ctccaccctg atctcttcgc cacgggcaaa tttggccaga    77700
gcctggactc tatacagaag cggttctggg tgcgtcgggg tggcggggc aaaaagggtg    77760 tccgggtggg cctgcgagcg ctccagaagc cactcgccga ggcgtgtata cagattggcc    77820
ggcggggccg cgcgaagctg cagctccagg tccgcgagtt ccccgtaaaa ggcgtccgtc    77880
tcccgaatga catccctagc cacaaggatc agcttcgcca gcgccaggcg accgatcaga    77940
gagttttcgt ccagcacgtg ctggacgagg ggcagatggg cggccacgtc ggccaggctc    78000
aggcgcgtgg aggccagaaa gtcccccacg gccgttttcc ggggcagcat gctcagggta    78060
aactccaaca gggcggcggc cgggccggcc accccgcct gggtgtgcgt ccgggccccg    78120
ttctcgatga gaaaggcgag gacgcgttca agaaaaaaa taacacagag ctccagcagc    78180
cccggagaag ccggatacgg cgaccgtaag gcgctgatgg tgagccgcga acacgcggcg    78240
acctcgcggg ccagggcggc ggagcacgcg gtgaacttaa ccgccgtggc ggccacgttt    78300
```

```
gggtgggcct cgaacagctg ggcaaggtct gcgcccgggg gctcgggtga gcggcgagtc    78360
ttcagcgcct cgagggcctg cgaggacgcc ggaaccgtgg gcccgtcgtc ctcgcccgcc    78420
tcggcgaccg gcggcccggc cgggtcgggg ggtgccgagg cgaggacagg ctccggaacg    78480
gaggcgggga ccgcggcccc gacgggggtt ttgccttlgg gggtggattt cttcttggtt    78540
ttggcagggg gggccgagcg tttcgttttc tcccccgaag tcaggtcttc gacgctggaa    78600
ggcggagtcc aggtgggtcg gcggcgcttg ggatggccgg ccgagtagcg tgccggtgc     78660 cgaccaaccg ggacgacgcc catctccagg acccgcatgt cgtcgtcatc ttcttcggcc    78720
gcctctgcgg cgggggggctt ggggggcgag ggaggcggtg gtgggatcgc ggagggtggg    78780
tcggcggagg ggggatccgt gggtggggta cccttcaggg ccaccgccca tacatcgtcg    78840
ggcgcccgat tcgggcgctt ggcctctggt tttgccgacg gaccggccgt cccccgggat    78900
gtctcggagg ccctgtcgtc gcgacgggcc cgggtcggtg gcggcgactg ggcggctgtg    78960
ggcgggtgtg gccccgtgcc ccctacccccc tcccgggggc ccacgccgac gcagggctcc    79020
cccaggcccg cgatctcgcc ccgcaggggg tgcgtgatgg ccacgcgccg ttcgctgaac    79080
gcttcgtcct gcaggtaagt ctcgctggcc ccgtaaagat gcagagccgc ggccgtcaag    79140
tccgcaggag ccgcgggttc cgggcccgac ggcacgaaaa acaccatggc tcccgcccac    79200
cgtacgtccg ggcgatcgcg ggtgtaatac gtcaggtatg gatacatgtc ccccgcccgc    79260
actttggcga tgaacgcggg ggtgccctcc ggaaggccgt gcgggtcaaa aaggtatgcg    79320
gtgtcgccgt ccctgaacag ccccatccct aggggggccaa tggttaggag cgtgtacgac    79380
agggggcgca gggcccacgg gccggcgaag aacgtgtgtg cggggcattg tgtctccagc    79440
aggcccgccg cgggctcccc gaagaagccc acctcgccgt atacgcgcga aagacacag     79500 cgcagtccgc cgcgcgcccc tgggtactcg aggaagttgg ggagctcgac gatcgaacac    79560
atgcgcggcg gcccagggcc cgcggtcgcg cgcgtccact cgcccccctc gaccaaacaa    79620
ccctcgatgg cctccgcgga cagaacgtcg cgagggccca catcaaatat gaggctgaga    79680
aaggacagcg acgagcgcat gcacgatacc gaccccccg gctccaggtc gggcgcgaac     79740
tggttccgag caccggtgac cacgatgtcg cgatccccccc cgcgttccat cgtggagtgc    79800
ggtggggtgc ccgcgatcat atgtgcccta ctggccagag accccggcctg tttatggacc    79860 ggaccccccgg ggttagtgtt gtttccgcca cccatgcccc cgtaccatgg ccccggttcc    79920
cctgattagg ctacgagtcg cggtgatcgc ttcccaaaaa ccgagctgcg tttgtctgtc    79980
ttgatcttcc ccccccccccc cgccgcccg ccgccgcc cgcccgcaca ccataacacc     80040
gagaacaaca cacgggggtg ggcgtaacat aataaagctt tattggtaac tagttaacgg    80100
caagtccgtg ggtggcgcga cggtgtcctc cgggctcatc tcgtcgtcct cgacggggt     80160 gttggaatga ggcgcccct cgcggtccgc ctggcgtggg ccgtgcccat aggcctccgg    80220
cttctgtgcg tccatgggca taggcgcggg gagactgttt ccggcgtcgc ggacctccag    80280
gtccctggga gactccggtc cggctaacgg acgaaacgcg gaagcgcgaa acacgccgtc    80340
ggtgacccgc aggagctcgt tcatcagtaa ccaatccata ctcagcgtaa cggccagccc    80400
ctggcgagac agatccacgg agtccggaac cgcggtcgtc tggcccaggg ggccgaggct    80460
gtagtccccc caggccccta ggtcgcgacg gctcgtaagc acgacgcggt cggccgcggg    80520
gctttgcggg ggggcgtcct cgggcgcatg cgccattacc tctcggatgg ccgcggcgcg    80580
ctggtcggcc gagctgacca agggcgccac gaccacggcg cgctccgtct gcaggcccttt    80640 ccacgtgtcg tggagttcct ggacaaactc ggccacgggc tcgggtcccg cggccgcgcg    80700
```

```
cgcggcttga tagcaggccg agagacgccg ccagcgcgct agaaactgac ccatgaagca   80760
aaacccgggg acctggtctc ccgacagcag cttcgacgcc cgggtgtgaa tgccggacac   80820
aacggacaga aacccgtgaa tttcgcgccg gaccacggcc agcacgttgt cctcgtgcga   80880
cacctgggcc gccagctcgt cgcacacctc caggtgcgcc gtggtttcgg tgatgacgga   80940
acgcaggctc gcgagggacg cgaccagcgc gcgcttggcg tcgtgataca tgctgcagta   81000
ctgactcacc gcgtccccca tggcctcggg gggccagggc cccaggcggt cgggagtgtc   81060
cccgaccacc gcatacaggc ggcgcccgtc gctctcgaac cgacactcga aaaggcgga   81120 gagcgtgcgc atgtgcagcc gcagcagcac gatggcgtcc tccagttggc gaatcagggg   81180
gtctgcgcgc tcggcgaggt cctgcagcac cccccgggcg gccagggcgt acatgctaat   81240
caacaggagg ctggtgccca cctcgggggg cgggggggc tgcagctgga ccaggggccg   81300
cagctgctcg acggcacccc tggagatcac gtacagctcc cggagcagct gctctatgtt   81360
gtcggccatc tgcatagtgg ggccgaggcc gccccgggcg gccggttcga ggagggtaat   81420
cagcgcgccc agtttggtgc gatggccctc gaccgtgggg agatagccca gcccaaagtc   81480
ccgggcccag gccaacacac gcagggcgaa ctcgaccggg cgtggaaggt aggccgcgct   81540
acacgtggcc cccaacgcgt ccccgaccac cagggccaga acgtagggga cgaagcccgg   81600
gtcggcgagg acgttgggt gaatgccctc gagggcgggg aagcggatct gggtcgccgc   81660
ggccaggtgg acagagggg cgtggctggg ctgcccgacg gggagaagcg cggacagcgg   81720
cgtggccggg gtggtggggg tgatgtccca gtgggtctga ccatacacgt cgatccagat   81780
gagcgccgtc tcgcggagaa ggctgggttg accggaacta agcggcgct cggccgtctc   81840 aaactccccc acgagcgccc gccgcaggct cgccagatgt tccgtcggca cggccggacc   81900
catgatacgc gccagtgtct ggctcagaac gccccccgac aggccgaccg cctcgcagag   81960
ccgcccgtgc gtgtgctcgc tggcgccctg gacccgcctg aaagtttta cgtagttggc   82020 atagtacccg tattcccgcg ccagaccaaa cacgttcgac cccgcgaggg caatgcaccc   82080
aaagagctgc tggacttcgc cgagtccgtg gccggcgggc gtccgcgcgg ggacgcccgc   82140
cgccagaaac ccctccaggg ccgaaaggta gtgcgtgcag tgcgagggcg tgaacccagc   82200
gtcgatcagg gtgttgatca ccacggaggg cgaattggta ttctggatca acgtccacgt   82260
ctgctgcagc agagccagca gccgctgctg ggcgccggcg gagggctgct ccccgagctg   82320
cagcaggctg gagacggcag gctggaagac tgccagtgcc gacgaactca ggaacggcac   82380
gtcgggatca aacacggcca cgtccgtccg cacgcgcgcc attagcgtcc ccgggggcgc   82440
acaggccgag cgcgggctga cgcggctgag ggccgtcgac acgcgcacct cctcgcggct   82500
gcgaaccatc ttgttggcct ccagtggcgg aatcattatg gccgggtcga tctcccgcac   82560
ggtgtgctga aactgcgcca acaggggcgg cggaccaca gccccccgct cggggtcgt   82620 caggtactcg tccaccaggg ccaacgtaaa gagggcccgt gtgaggggag tgagggtcgc   82680
gtcgtctatg cgctggaggt gcgccgagaa cagcgtcacc cgattactca ccagggccaa   82740
gaaccggagg ccctcttgca cgaacggggc ggggaagagc aggctgtacg ccggggtggt   82800
aaggttcgcg ctgggctgcc ccaacgggac cggcgccatc ttgagtgacg tctccccaag   82860
ggcctcgatg gaggtccgcg ggctcatggc caagcagctc ttggtgacgg tttgccagcg   82920
gtctatccac tccacggcgc actgcggac gcggaccggc cccagggccg ccgcggtgcg   82980
caggccggcg gaatccagcg catgggacgt gtcggagccg gtgaccgcga ggatggtgtc   83040
```

```
cttgatgacc tccatctccc ggaaggcctg gtcgggggcc tcggggagag ccaccaccaa   83100
gcggtgtacg agcaacccgg ggaggttctc ggccaagagc gccgtctccg gaagcccgtg   83160
ggcccggtgg agcgcgcaca ggtgttccag cagcggccgc cagcatgccc gcgcgtctac   83220
cggggcaatg gccgttcccg acaacagaaa cgccgccatg gcggcgcgca gcttggccgt   83280
ggccagaaac gccgggtcgt ccgccccgtt tgccgtctcg gccgtggggg ttggcggttg   83340
gcgaaggccg gctaggctcg ccaataggcg ctgcataggt ccgtccgagg gcggaccggc   83400
gggtgaggtc gtgacgacgg gggcctcgga cgggagaccg cggtctgcca tgacgcccgg   83460
ctcgcgtggg tgggggacag cgtagaccaa cgacgagatc gggcgggaat gactgtcgtg   83520
cgctgtaggg agcggcgaat tatcgatccc ccgcggccct ccaggaaccc cgcaggcgtt   83580
gcgagtaccc cgcgtcttcg cggggtgtta tacggccact taagtcccgg catcccgttc   83640
gcggacccag gcccggggga ttgtccggat gtgcgggcag cccggacggc gtgggttgcg   83700
gactttctgc ggggcggccc aaatggccct ttaaacgtgt gtatacggac gcgccgggcc   83760
agtcggccaa cacaacccac cggaggcggt agccgcgttt ggctgtgggg tggtggttc    83820 cgccttgcgt gagtgtcctt tcgaccccc tccccgggt tttgttaggt cgcgatctgc    83880
agtcgcaatg aagaccaatc cgctaccgc aaccccttcc gtgtggggcg ggagtaccgt    83940
ggaactcccc cccaccacac gcgataccgc gggacagggc ctgcttcggc gcgtcctgcg   84000 cccccccgatc tctcgccgcg acggcccagt gctccccagg gggtcgggac cccggagggc   84060
ggccagcacg ctgtggttgc ttggcctgga cggcacagac gcgcccctg gggcgctgac    84120 ccccaacgac gataccgaac aggccctgga caagatcctg cggggcacca tgcgcggggg   84180
ggcggccctg atctgctccc cgcgccatca tctaacccgc caagtgatcc tgacggatct   84240
gtgccaaccc aacgcggatc gtgccgggac gctgcttctg gcgctgcggc accccgccga   84300
cctgcctcac ctggcccacc agcgcgcccc gccaggccgg cagaccgagc ggctgggcga   84360
ggcctggggc cagctgatgg aggcgaccgc cctggggtcg gggcgagccg agagcgggtg   84420
cacgcgcgcg ggcctcgtgt cgtttaactt cctggtggcg gcgtgtgccg cctcgtacga   84480
cgcgcgcgac gccgccgatg cggtacgggc ccacgtcacg gccaactacc gcgggacgcg   84540
ggtgggggcg cgcctggatc gttttttcga gtgtctgcgc gccatggttc acacgcacgt   84600
cttcccccac gaggtcatgc ggttttttcg ggggctggtg tcgtgggtca cccaggacga   84660
gctagcgagc gtcaccgccg tgtgcgccgg gccacaggag gcggcgcaca ccggccaccc   84720 gggcggccc cgctcggccg tgatcctccc ggcgtgtgcg ttcgtggacc tggacgccga    84780
gctggggctg gggggcccgg gtgcggcgtt tctgtacctg gtattcactt accgccagcg   84840
ccgggaccag gagctgtgtt gtgtgtacgt gatcaagagc cagctccccc cgcgcgggtt   84900
ggagccggcc ctggagcggc tgtttgggcg cctccggatc accaacacga ttcacggcac   84960
cgaggacatg acgccccggg ccccaaaccg aaacccgac ttcccctcg cgggcctggc    85020 cgccaatccc caaacccgc gttgctcggc tggccaggtc acgaaccccc agttcgccga   85080
caggctgtac cgctggcagc cggacctgcg ggggcgcccc accgcacgca cctgtacgta   85140
cgccgccttt gcagagctcg gcatgatgcc cgaggatagt ccccgctgcc tgcaccgcac   85200
cgagcgcttt ggggcggtca cgtccccgt tgtcatcctg gaaggcgtgg tgtggcgccc   85260
cggcgagtgg cgggcatgcg cgtgagcgta gcaaacgccc cgcccacaca acgctccgcc   85320 cccaaccct tccccgctgt cactcgtggt tcgttgaccc ggacgtccgc caaataaagc   85380
cactgaaacc cgaaacgcga gtgttgtaac gtcctttggg cgggaggaag ccacaaaatg   85440
```

```
caaatgggat acatggaagg aacacacccc cgtgactcag gacatcggcg tgtccttttg    85500
ggtttcactg aaactggccc gcgccccacc cctgcgcgat gtggataaaa agccagcgcg    85560
ggtggtttag ggtaccacag gtgggtgctt tggaaacttg tcggtcgccg tgctcctgtg    85620
agcttgcgtc cctccccggt ttcctttgcg ctcccgcctt ccggacctgc tcttgcctat    85680
cttctttggc tctcggtgcg attcgtcagg cagcggcctt gtcgaatctc gacccccacca   85740 ctcgccggac ccgccgacgt cccctctcga gcccaccgaa accgccgcg tctgttgaaa     85800 tggccagccg cccagccgca tcctctcccg tcgaagcgcg ggccccggtt ggggggacagg   85860 aggcggcgg ccccagcgca gccacccagg gggaggccgc cggggcccct ctcgcccacg     85920
gccaccacgt gtactgccag cgagtcaatg gcgtgatggt gctttccgac aagacgcccg    85980
ggtccgcgtc ctaccgcatc agcgatagca actttgtcca atgtggttcc aactgcacca    86040
tgatcatcga cggagacgtg gtgcgcgggc gccccagga cccggggccc gcggcatccc     86100
ccgctccctt cgttgcggtg acaaacatcg gagccggcag cgacggcggg accgccgtcg    86160
tggcattcgg gggaacccca cgtcgctcgg cggggacgtc taccggtacc cagacggccg    86220
acgtccccac cgaggcccctt gggggccccc ctcctcctcc ccgcttcacc ctgggtggcg   86280
gctgttgttc ctgtcgcgac acacggcgcc gctctgcggt attcgggggg gaggggggatc  86340 cagtcggccc cgcggagttc gtctcggacg accggtcgtc cgattccgac tcggatgact    86400
cggaggacac ggactcggag acgctgtcac acgcctcctc ggacgtgtcc ggcggggcca    86460
cgtacgacga cgcccttgac tccgattcgt catcggatga ctccctgcag atagatggcc    86520
ccgtgtgtcg cccgtggagc aatgacaccg cgccctgga tgtttgcccc gggacccccg     86580
gcccgggcgc cgacgccggt ggtccctcag cggtagaccc acacgcgccg acgccagagg    86640
ccggcgctgg tcttgcggcc gatcccgccg tgcccggga cgacgcggag gggctttcgg     86700 accccccggcc acgtctggga acgggcacgg cctaccccgt ccccctgaa ctcacgcccg     86760 agaacgcgga ggccgtggcg cgcttttctgg gagatgccgt gaaccgcgaa cccgcgctca    86820
tgctggagta cttttgccgg tgcgcccgcg aggaaaccaa gcgtgtcccc ccaggacat     86880 tcggcagccc ccctcgcctc acggaggacg actttgggct tctcaactac gcgctcgtgg    86940
agatgcagcg cctgtgtctg gacgttcctc cggtcccgcc gaacgcatac atgccctatt    87000
atctcaggga gtatgtgacg cggctggtca acgggttcaa gccgctggtg agccggtccg    87060
ctcgccttta ccgcatcctg ggggttctgg tgcacctgcg gatccggacc cgggaggcct    87120
cctttgagga gtggctgcga tccaaggaag tggccctgga ttttggcctg acggaaaggc    87180
ttcgcgagca cgaagcccag ctggtgatcc tggcccaggc tctggaccat tacgactgtc    87240
tgatccacag cacaccacac acgctggtcg agcggggct gcaatcggcc ctgaagtatg     87300 aggagttttta cctaaagcgt tttggcgggc actacatgga gtccgtcttc cagatgtaca   87360
cccgcatcgc cggcttttttg gcctgccggg ccacgcgcgg catgcgccac atcgccctgg   87420
ggcgagaggg gtcgtggtgg gaaatgttca agttctttt ccaccgcctc tacgaccacc      87480
agatcgtacc gtcgacccc gccatgctga acctggggac ccgcaactac tacacctcca     87540
gctgctacct ggtaaacccc caggccacca caaacaaggc gaccctgcgg gccatcacca    87600
gcaacgtcag tgccatcctc gcccgcaacg ggggcatcgg gctatgcgtg caggcgttta    87660
acgactccgg ccccgggacc gccagcgtca tgcccgccct caaggtcctt gactcgctgg    87720
tggcggcgca caacaaagag agcgcgcgtc cgaccggcgc gtgcgtgtac ctggagccgt    87780
```

```
ggcacaccga cgtgcgggcc gtgctccgga tgaaggggggt cctcgccggc gaagaggccc    87840
agcgctgcga caatatcttc agcgccctct ggatgccaga cctgttttc aagcgcctga    87900 ttcgccacct ggacggcgag aagaacgtca catggaccct gttcgaccgg acaccagca    87960 tgtcgctcgc cgactttcac ggggaggagt tcgagaagct ctaccagcac ctcgaggtca    88020
tggggttcgg cgagcagata cccatccagg agctggccta tggcattgtg cgcagcgcgg    88080
ccacgaccgg gagccccttc gtcatgttca aagacgcgt gaaccgccac tacatctacg    88140
acacccaggg ggcggccatc gccggctcca acctctgcac cgagatcgtc catccggcct    88200
ccaagcgatc cagtggggtc tgcaacctgg gaagcgtgaa tctggcccga tgcgtctcca    88260
ggcagacgtt tgactttggg cggctccgcg acgccgtgca ggcgtgcgtg ctgatggtga    88320
acatcatgat cgacagcacg ctacaaccca cgccccagtg cacccgcggc aacgacaacc    88380
tgcggtccat gggaatcggc atgcagggcc tgcacacggc ctgcctgaag ctggggctgg    88440
atctggagtc tgccgaattt caggacctga acaaacacat cgccgaggtg atgctgctgt    88500
cggcgatgaa gaccagcaac gcgctgtgcg ttcgcggggc ccgtcccttc aaccactta    88560 agcgcagcat gtatcgcgcc ggccgctttc actgggagcg cttcccggac gcccggccgc    88620
ggtacgaggg cgagtgggag atgctacgcc agagcatgat gaaacacggc ctgcgcaaca    88680 gccagttgt cgcgctgatg cccaccgccg cctcggcgca gatctcggac gtcagcgagg    88740
gctttgcccc cctgttcacc aacctgttca gcaaggtgac ccgggacggc gagacgctgc    88800
gccccaacac gctcctgcta aaggaactgg aacgcacgtt tagcgggaag cgcctcctgg    88860
aggtgatgga cagtctcgac gccaagcagt ggtccgtggc gcaggcgctc ccgtgcctgg    88920
agcccaccca ccccctccgg cgattcaaga ccgcgtttga ctacgaccag aagttgttga    88980
tcgacctgtg tgcggaccgc gccccctacg tcgaccatag ccaatccatg accctgtatg    89040
tcacggagaa ggcggacggg accctcccag cctccaccct ggtccgcctt ctggtccacg    89100
catataagcg cggactaaaa acagggatgt actactgcaa ggttcgcaag gcgaccaaca    89160
gcggggtctt tggcggcgac gacaacattg tctgcacgag ctgcgcgctg tgaccgacaa    89220 acccctccg cgccaggccc gccgccactg tcgtcgccgt cccacgctct cccctgctgc    89280
catggattcc gcggccccag ccctctcccc cgctctgacg gcccttacgg ccagagcgc    89340 gacggcggac ctggcgatcc agattccaaa gtgccccgac cccagagagg acttctacac    89400
ctcccagtgt cccgacatta accacctgcg ctccctcagc atccttaacc gctggctgga    89460
aaccgagctt gttttcgtgg gggacgagga ggacgtctcc aagctttccg agggcgagct    89520
cagcttttac cgcttcctct tcgctttcct gtcggccgcc gacgacctgg ttacggaaaa    89580
cctgggcggc ctctccggcc tgtttgagca gaaggacatt ctccactact acgtggagca    89640
ggaatgcatc gaagtcgtac actcgcgcgt gtacaacatc atccagctgg tgcttttcca    89700
caacaacgac caggcgcgcc gcgagtacgt ggccggcacc atcaaccacc cggccatccg    89760
cgccaaggtg gactggttgg aagcgcgggt gcgggaatgc gcctccgttc cggaaaagtt    89820
cattctcatg atcctcatcg agggcatctt ttttgccgcc tcgtttgccg ccatcgccta    89880
ccttcgcacc aacaaccttc tgcgggtcac ctgccagtca aacgacctca tcagcccgga    89940
cgaggccgtg cacacgacgg cctcgtgtta catctacaac aactacctcg gcgggcacgc    90000 caagccccccg cccgaccgcg tgtacgggct gttccgccag gcggtcgaga tcgagatcgg    90060
atttatccga tcccaggcgc cgacggacag ccatatcctg agcccggcgg cgctggcggc    90120
catcgaaaac tacgtgcgat tcagcgcgga tcgcctgttg ggccttatcc acatgaagcc    90180
```

```
actgttttcc gccccacccc ccgacgccag ctttccgctg agcctcatgt ccaccgacaa   90240
acacaccaat ttttcgagt gtcgcagcac ctcctacgcc ggggcggtcg tcaacgatct   90300
gtgagtgtcg cggcgcgctt ctacccgtgt ttgcccataa taaacctctg aaccaaactt   90360
tgggtctcat tgtgattctt gtcagggacg cgggggtggg agaggataaa aggcggcgca   90420
aaaagcagta accaggtccg tccagattct gcggcatag aataccataa ttttattggt   90480
gggtcgtttg ttcggggaca agcgcgctcg tctgacgttt gggctactcg tcccagaatt   90540
tggccaggac gtccttgtag aacgcgggtg gggggcctg ggtccgcaac tgctccagaa   90600
acctgtcggc gatatcaggg gccgtgatat gccgggtcac gatagatcgc gccaggtttt   90660
cgtcgcggat gtcctggtag ataggcaggc gtttcagaag agtccacggc ccccgctcct   90720
tggggccgat aagcgatatg acgtacttaa tgtagcggtg ttccaccagc tcggtgatgg   90780
tcatgggatc ggggagccag tccagggact ctggggcgtc gtggatgacg tggcgtcgcc   90840
ggttggccac ataactgcgg tgctcttcca gcagctgcgc gttcgggacc tggacgagct   90900
cgggcgggt gagtatctcc gaggaggacg acctggggcc ggggtggccc ccggtaacgt   90960
cccgggatc caggggagg tcctcgtcgt cttcgtatcc gccggcgatc tgttgggtta   91020
gaatttcggt ccacgagacg cgcgtctcgg tgccgccggc ggccggcggc agagggggcc   91080
tggtttccgt ggagcgcgag ctggtgtgtt cccggcggat ggcccgccgg gtctgagagc   91140
gactcggggg ggtccagtga cattcgcgca gcacatcctc cacggaggcg taggtgttat   91200
tgggatggag gtcggtgtgg cagcggacaa agagggccag gaactggggg tagctcatct   91260
taaagtactt cagtatatcg cgacagttga tcgtgggaat gtagcaggcg ctaatatcca   91320
acacaatatc acagcccatc aacaggaggt cagtgtccgt ggtgtacacg tacgcgaccg   91380
tgttggtgtg atagaggttg gcgcaggcat cgtccgcctc caactgaccc gagttaatgt   91440
aggcgtaccc cagggcccgg agaacgcgaa tacagaacag atgcgccaga cgcagggccg   91500
gcttcgaggg cgcggcggac ggcagcgcgg ctccggaccc ggccgtcccc cgggtccccg   91560
aggccagaga ggtgccgcgt cggcgcatgt tggaaaaggc agagctgggt ctggagtcgg   91620
tgatggggga aggcggtgga gaggcgtcca cgtcactggc ctcctcgtcc gtccggcact   91680
gggccgtcgt gcgggccagg atggccttgg ctccaaacac aaccggctcc atacaattga   91740
ccccgcgatc ggtaacgaag atggggaaaa gggacttttg ggtaaacacc tttaataagc   91800
gacagaggca gtgtagcgta atggcctcgc ggtcgtaact ggggtatcgg cgctgatatt   91860
tgaccaccaa cgtgtacatg acgttccaca ggtccacggc aatgggggtg aagtacccgg   91920
ccggggcccc aaggccccgg cgcttgacca gatggtgtgt gtgggcaaac ttcatcatcc   91980
cgaacaaacc catgtcaggt cgattgtaac tgcggatcgg cctaactaag gcgtggttgg   92040
tgcgacggtc cgggacaccc gagcctgtct ctctgtgtat ggtgacccag acaacaacac   92100
cgacacaaga ggacaataat ccgttagggg acgctcttta taattttcgat ggcccaactc   92160
cacgcggatt ggtgcagcac cctgcatgcg ccggtgcggg ccaaccttcc ccccgctcat   92220
tgcctcttcc aaaagggtgt ggcctaacga gctgggggcg tatttaatca ggctagcgcg   92280
gcgggcctgc cgtagtttct ggctcggtga gcgacggtcc ggttgcttgg gtcccctggc   92340
tgccatcaaa accccacccct cgcagcggca tacgcccccct ccgcgtcccg cacccgagac   92400
cccgccccgg ctgccctcac caccgaagcc cacctcgtca ctgtggggtg ttcccagccc   92460
gcgttgggat gacggattcc cctggcggtg tggccccgc ctcccacgtg gaggacgcgt   92520
```

```
cggacgcgtc cctcgggcag ccggaggagg gggcgccctg ccaggtggtc ctgcagggcg   92580
ccgaacttaa tggaatccta caggcgtttg ccccgctgcg cacgagcctt ctggactcgc   92640
ttctggttat gggcgaccgg ggcatcctta tccataacac gatctttggg gagcaggtgt   92700
tcctgcccct ggaacactcg caattcagtc ggtatcgctg gcgcggaccc acggcggcgt   92760
tcctgtctct cgtggaccag aagcgctccc tcctgagcgt gtttcgcgcc aaccagtacc   92820
cggacctacg tcgggtggag ttggcgatca cgggccaggc cccgtttcgc acgctggttc   92880
agcgcatatg gacgacgacg tccgacggcg aggccgttga gctagccagc gagacgctga   92940
tgaagcgcga actgacgagc tttgtggtgc tggttcccca gggaaccccc gacgttcagt   93000
tgcgcctgac gaggccgcag ctcaccaagg tccttaacgc gaccggggcc gatagtgcca   93060
cgcccaccac gttcgagctc ggggttaacg gcaaaatttc cgtgttcacc acagtacct    93120 gcgtcacatt tgctgcccgc gaggagggcg tgtcgtccag caccagcacc caggtccaga   93180
tcctgtccaa cgcgctcacc aaggcgggcc aggcggccgc caacgccaag acggtgtacg   93240
gggaaaatac ccatcgcacc ttctctgtgg tcgtcgacga ttgcagcatg cgggcggtgc   93300
tccggcgact gcaggtcggc gggggcaccc tcaagttctt cctcacgacc cccgtcccca   93360
gtctgtgcgt caccgccacc ggtcccaacg ctgtatcggc ggtatttctc ctgaaacccc   93420
agaagatttg cctggactgg ctgggtcata gccaggggtc tccttcagcc gggagctcgg   93480
cctcccgggc ctctgggagc gagccaacag acagcaagga ctccgcgtcg gacgcggtca   93540
gccacggcga tccggaagac ctcgatggcg ctgcccgggc gggagaggcg ggggcctcgc   93600
acgcctgtcc gatgccgtcg tcgaccacgc gggtcactcc cacgaccaag cggggcgct    93660 cgggggggcga ggatgcgcgc gcggacacgg ccctaaagaa acctaagacg gggtcgccca   93720
ccgcaccccc gcccgcagat ccagtccccc tggacacgga ggacgactcc gatgcggcgg   93780
acgggacggc ggcccgtccc gccgctccag acgcccggag cggaagccgt tacgcgtgtt   93840
actttcgcga cctcccgacc ggagaagcaa gccccgcgc cttctccgcc ttccgggggg    93900
ggccccaaac cccgtatggt tttggattcc cctgacgggg cggggccttg gcggccgccc   93960
aactctcgca ccatcccggg ttaatgtaaa taaacttggt attgcccaac actctcccgc   94020
gtgtcgcgtg tggttcatgt gtgtgcctgg cgtcccccac cctcgggttc gtgtatttcc   94080 tttcctgtc cttataaaag ccgtatgtgg ggcgctgacg gaaccacccc gcgtgccatc    94140
acggccaagg cgcgggatgc tccgcaacga cagccaccgg gccgcgtccc cggaggacgg   94200
ccagggacgg gtcgacgacg gacggccaca cctcgcgtgc gtgggggccc tggcgcgggg   94260
gttcatgcat atctggcttc aggccgccac gctgggtttt gcgggatcgg tcgttatgtc   94320
gcgcgggccg tacgcgaatg ccgcgtctgg ggcgttcgcc gtcgggtgcg ccgtgctggg   94380
ctttatgcgc gcacccctc ccctcgcgcg gcccaccgcg cggatatacg cctggctcaa    94440
actggcggcc ggtggagcgg cccttgttct gtggagtctc ggggagcccg gcacgcagcc   94500
gggggccccg gccccgggcc cggccaccca gtgcctggcg ctgggcgccg cctatgcggc   94560
gctcctggtg ctcgccgatg acgtctatcc gctctttctc ctcgccccgg ggcccctgtt   94620
cgtcggcacc ctgggatgg tcgtcggcgg gctgacgatc ggaggcagcg cgcgctactg    94680
gtggatcggt gggcccgccg cggccgcctt ggccgcggcg gtgttggcgg gccgggggc    94740 gaccaccgcc agggactgct ctctccaggg c gtgcccgac caccgccgcg tctgcgtcat   94800
cgtcgcaggc gagtctgttt cccgccgccc ccgggaggac ccagagcgac ccggggaccc   94860
cgggccaccg tccccccga caccccaacg atcccagggg ccgccggccg atgaggtcgc    94920
```

```
accggccggg gtagcgcggc ccgaaaacgt ctgggtgccc gtggtcacct ttctggggc    94980 gggcgcgctc gccgtcaaga cggtgcgaga acatgcccgg ggaacgccgg gcccgggcct    95040
gccgctgtgg ccccaggtgt ttctcggagg ccatgtggcg gtggccctga cggagctgtg    95100
tcaggcgctt gcgccctggg accttacgga cccgctgctg tttgttcacg ccggactgca    95160
ggtcatcaac ctcgggttgg tgtttcggtt ttccgaggtt gtcgtgtatg cggcgctagg    95220
gggtgccgtg tggatttcgt tggcgcaggt gctgggctc cggcgtcgcc tgcgcaggaa    95280
ggaccccggg gacggggccc ggttggcggc gacgcttcgg ggcctcttct tctccgtgta    95340
cgcgctgggg tttggggtgg gggcgctgct gtgccctccg gggtcaacgg gcgggcggtc    95400
gggcgattga tatattttc aataaaaggc attagtcccg aagaccgccg gtgtgtgatg    95460
atttcgccat aacacccaaa ccccggatgg ggcccgggta taaattccgg aaggggacac    95520
gggctaccct cactaccgag ggcgcttggt cgggaggccg catcgaacgc acacccccat    95580
ccggtggtcc gtgtggaggt cgttttcagt gccggtctc gctttgccgg gaacgctagc    95640
cgatccctcg cgagggggag gcgtagggca tggcccggg gcgggtgggc cttgccgtgg    95700
tcctgtggag cctgttgtgg ctcggggcgg gggtgtccgg gggctcggaa actgcctcca    95760
ccgggcccac gatcaccgcg ggagcggtga cgaacgcgag cgaggcccc acatcggggt    95820 cccccgggtc agccgccagc ccggaagtca ccccccacatc gacccaaac ccaacaatg    95880 tcacacaaaa caaaccacc cccaccgagc cggccagccc cccaacaacc cccaagccca    95940
cctccacgcc caaaagcccc cccacgtcca cccccgaccc caaacccaag aacaacacca    96000
cccccgccaa gtcgggccgc cccactaaac ccccgggcc cgtgtggtgc gaccgccgcg    96060
acccattggc ccggtacggc tcgcgggtgc agatccgatg ccggtttcgg aattccaccc    96120
gcatggagtt ccgcctccag atatggcgtt actccatggg tccgtccccc ccaatcgctc    96180
cggctcccga cctagaggag gtcctgacga acatcaccgc cccacccggg ggactcctgg    96240
tgtacgacag cgcccccaac ctgacggacc cccacgtgct ctgggcggag ggggccggcc    96300
cgggtgccga ccctccgttg tattctgtca ccgggccgct gccgacccag cggctgatta    96360
tcggcgaggt gacgccgcg acccagggaa tgtattactt ggcctgggc cggatggaca    96420 gcccgcacga gtacgggacg tgggtgcgcg tccgcatgtt ccgccccccg tctctgaccc    96480
tccagcccca cgcggtgatg gagggtcagc cgttcaaggc gacgtgcacg gccgacgcct    96540
actacccgcg taaccccgtg gagttggtct ggttcgagga cgaccgccag gtgtttaacc    96600
cgggccagat cgacacgcag acgcacgagc accccgacgg gttcaccacc gtctctaccg    96660
tgacctccga ggctgtcggc ggccaggtcc ccccgcggac cttcacctgc cagatgacgt    96720
ggcaccgcga ctccgtgaca ttctcgcgac gcaatgccac cgggctggcc ctggtgctgc    96780
cgcggccaac catcaccatg gaatttgggg tccggcatgt ggtctgcacg gccggctgcg    96840
tccccgaggg cgtgacgttt gcctggttcc tggggacga cccctcaccg gcggctaagt    96900
cggccgttac ggcccaggag tcatgcgacc acccccgggct ggctacggtc cggtccaccc    96960
tgcccatttc gtacgactac agcgagtaca tctgtcggtt gaccggatat ccggccggga    97020
ttcccgttct agaacaccac ggcagtcacc agccccacc cagggacccc accgagcggc    97080
aggtgatcga ggcgatcgag tgggtgggga ttggaatcgg ggttctcgcg gcggggggtcc    97140 tggtcgtaac ggcgatcgtg tacgtcgtcc gcacatcaca gtcgcggcag cgtcatcggc    97200
ggtaacgcga gaccccccg ttaccttttt aatatctata tagtttggtc cccctctat    97260
```

```
cccgcccacc gctgggcgct ataaagccgc caccctctct tccctcaggt catccttggt      97320
cgatcccgaa cgacacacgg cgtggagcaa aacgcctccc cctgagccgc tttcctacca      97380
acacaccggc atgcctctgc gggcatcgga acacgcctac cggcccctgg gccccgggac      97440
accccccatg cgggctcggc tccccgccgc ggcctgggtt ggcgtcggga ccatcatcgg      97500
gggagttgtg atcattgccg cgttggtcct cgtgccctcg cgggcctcgt gggcactttc      97560
cccatgcgac agcggatggc acgagttcaa cctcgggtgc atatcctggg atccgacccc      97620
catggagcac gagcaggcgg tcggcggctg tagcgccccg gcgaccctga tccccgcgc       97680 ggctgccaaa cagctggccg ccgtcgcacg cgtccagtcg gcaagatcct cgggctactg      97740
gtgggtgagc ggagacggca ttcgggcctg cctgcggctc gtcgacggcg tcggcggtat      97800
tgaccagttt tgcgaggagc ccgcccttcg catatgctac tatccccgca gtccggggg       97860 ctttgttcag tttgtaactt cgacccgcaa cgcgctgggg ctgccgtgag gcgcgtgtac      97920
tgcggtctgt ctcgtctcct cttctcccct tccctccccc tccgcatccc aggatcacac      97980
cggccaacga gggttggggg gtccggcacg gacccaaaat aataaacaca caatcacgtg      98040
cgataaaaag aacacgcggt cccctgtggt gttttttggtt attttttatta aatctcgtcg    98100 acaaacaggg ggaaggggc gtggtctagc gacggcagca cgggcggagg cgttcaccgg       98160
ctccggcgtc cttcgcgttt aagcttggtc aggagggcgc tcagggcggc gacgttggtc      98220
gggccgtcgt tggtcagggc gttggctcga tggcgggcga ggacgggcga ggggctcaac      98280
ggcgggggcg ggggcccggt gcggcccggg ggggaaaata gggcggatcc ccccagtcg       98340 tacagggggat tttccgcctc aatgtacggg gaggccggcg ctgcattcgc cgtgttcacg     98400
cagacgtttt cgtagacccg catccatggt atttcctcgt agacacgccc cccgtcctcg      98460
cgcaccgtct cgtatattga ctcgtcgtcc tcgtaggggg cgtgccgttc gcgggccgag      98520
gcggcgtggg tggctttgcg gcgggcgtcg tcgtcgtcgt cgtcggccgt cagatacgtg      98580
gcttccatct ggtcgggttc tccctccggg gcgggtcccc acaccgtgg ccgatcgagg       98640 ctccccagag acgcgcgccg gacgaggagg gggcacgtcg ccgccggcgg tcgcctgtcg      98700
ggtcccgcga cgttacgggc cgggaggcgc ggggcacct ccccccatgtg cgtgtaatac      98760 gtggccggct gtgcggccgc agcgggggc tcggcgaccg ggtcgttcgc atccggaagc       98820
gggggccccg cgccgtccgc gcggcgcctc cggaacctcc gggtggacgc gggggtcgag      98880
tgtaggcgag gtcgggggag gggcgggggc tcgttgtcgc gccgcgcccg ctgaatctttt     98940 tcccgacagg tcccacccc cgcgcgatgc cccccgggc cgctggccat gtcgtccggg        99000
ggaggccccg cggaccacgt cgtccggcga gacgccacga gccgcaggat ggactcgtag      99060
tggagcgacg gcgccccgct gcggagcaga tccgcggcca gggcggcccc gaaccaagcc     99120
ttgatgctca actccatccg ggcccagctg ggggcggtca tcgtggggaa caggggggcg     99180
gtggtccgac agaaacgctc ctggctgtcc accgcggccc gcagatactc gttgttcagg     99240
ctgtcggtgg cccagacgcc gtaccggtg agggtcgcgt tgatgatata ctgggcgtgg      99300
tgatggacga tcgacagaac ctccaccgtg gatacgacgg tatccacggt cccgtacgta     99360
ccgccgctcc gcttgccggt ctgccacagg ttggctaggc gcgtcaggtg gcccaggacg     99420
tcgctgaccg ccgccctgag cgccatgcac tgcatggagc cggttgtgcc gctgggaccc     99480
cggtccagat ggcgcgcgaa cgtttccgcg ggcgcctccg ggctgccgcc gagcgggagg     99540
aaccggcgat tggagggact cagccggtga catacgtgct tgtctgtcgt ccacagcatc     99600
caggacgccc accggtacag cacggagacg taggccagga gctcgttgag ccgcagtgcg     99660
```

```
gtgtcggtgc tggggcggct tgggtccgcc gggcgcataa agaacatgta ctgctgaatc    99720
cgatggaggg cgtcgcgcag gccggccacg gtggcggcgt acttggccgc cacggccccg    99780
ctcttgaacg gggtgcgcgc cagcagcttt ggcgccaggg tgggccgcag cagcacgtga    99840
aggctggggt cgcagtcgcc cacggggtcc tcggggacgt ccaggccgct gggcaccacc    99900
gtctgcaggt acttccagta ctgcgtgagg atggcgcggc tcaactggcc gccgggcagc    99960
tccacctcgc ccagcgcctg ggtggcggcc gaagcgtagt gccggatgta ctcgtagtgc   100020
gggtcgctgg cgagcccgtc cacgatcaaa ctctcgggaa ccgtgttgtg ttgccgcgcg   100080
gccaaccgga cgctgcgatc ggtgcaggtc agaaacgccg gctgcgcgtc gtcggagcgc   100140
tgccgcaagg cgcccacggc cgcgctaagg agccctccg gggtggggag cagacacccg    100200
ccgaagatgc gccgctcggg aacgcccgcg ttgtcgccgc ggatcaggtt ggcaggcgtc   100260
aggcaccgcg ccagccgcag ggagctcgcg ccgcgcgtcc ggcgctgcat ggtgacgccc   100320
gttcggtcgg gacccgccgg tcggagttat gccgcgtcca gggccatcgg ggcgcttttt   100380
atcgggagga gcttatgggc gtggcgggcc tcccagcccg gtcgcgcgcc tccccgacac   100440
gtgcgcccgc agggcggcgg cccctcgtc tcccatcagc agtttcctaa actgggacat    100500
gatgtccacc acgcggaccc gcgggcccaa cacggacccg ccgcttacgg gggcgggggg   100560
gaagggctcc aggtccttga gaagaaaggc ggggtctgcc gtcccggaca cggggggcccg   100620 gggcgctgag gaggcgggc gcagatccac gtgctccgcg gccgcgcgga cgtccgccca    100680
gaacttggcg ggggtggtgc gcgcgtacag gggctgggtc gctcggagga cgcacgcgta   100740
gcgcaggggg gtgtacgtgc ccacctcggg ggccgtgaat cccccgtcaa acgcggccag   100800
tgtcacgcac gccaccacgg tgtcggcaaa gcccagcagc cgctgcagga cgagcccggc   100860
ggccagaatg gcgcgcgtgg ccgccgcgtc gtcccggcgc cggtgcgcgt ccccgcacgc   100920
ccgggcgtac tttaaggtca cggtcgccag ggccgtgtgc agcgcgtaca ccgcagcgcc   100980
cagcacggcg ttgagcccgc tgttggcgag cagccggcgc gctgcggtgt cgcccagcgc   101040
ctcgtgctcg gccccacga ccgcggggct tcccaggggc agggcgcgaa acagctcctc    101100
ccgcgccacg tccgcaaagg cggggtggtg cacgtgcggg tgcaggcgcg ccccacgac    101160 caccgagagc cactggaccg tctgctccgc catcaccgcc agcacatcca gcacgcgccc   101220
caggaaggcg gcctccgcg tcaaaacgca ccggacggc tcgggattga agcgggcgag     101280
cagggccccg gtggccaggt acgtcatgcg gccggcatag cgggcggcca cgcgacagtc   101340
gcggtccagc agcgcgcgca cccgggcca gtacagcagg acccagcg agctgcgaa       101400 caccgcggcg tcggggccgg attgggggga cactaacccc ccgcgctca gtaacggcac    101460 ggccgcggcc ccgacgggac gcaacgccgt gaggctcgcg aactgccgcc tcagctcggc   101520
cgccctgtcg tccaggtcag acccgcgcgc ctccgcgtga aggcgcgtcc cgcacaccca   101580
cccgttgatg ccagccgcca cgacggcatc cgccaaaaag ctcatcgcct gggcggggct   101640 ggttttttgtt cgacgatccg tcaggtcaag aatcccatcg cccgtgatat accaggccaa   101700
cgcctcgccc tgctgcaggg tttggcgaa aaacaccgcg ggttgtcgg gggaggcgaa     101760 gtgcatgacc cccacgcgcg ataacccgaa cgcgctatcc ggacacgggt aaacccggc    101820 cggatgcccc agggctaggg cggagcgcac ggactcgtcc cacacggcaa cctgagggc    101880 cagtcgatcc aacgggaatg ccgccgag ctccgggccc ggcacgcgtc cctccagaac     101940
ctccaccttg ggcggggaac gggccccgcc gccgtcctcc ggcccgacgg cttccgggta   102000
```

```
gtcgtcctcc tcgtactgca gctcctctag aacagcggc gacggcgcca cccgcgaacc    102060
gccgacccgc cccaaaatag cccgcgcgtc gacgggaccc aggtatcccc cctgccgggc   102120
ctgcggagga ccgcggggaa cctcatcatc atcgtccagg cgaccgcgca ccgactggct   102180
acgggccgca tcgggcccgg ggcgctgccg ggacgctcgg cgatgggatg tgggcggggc   102240
ttccgacgcg cgccgtcgtc gggctcgcgg gccttcccgt cgacggcgca cgggcggctc   102300
gtcgcccgcc atctcctcca gagcctctag ctcgctgtcg tcatccccgc ggaacaccgc   102360
acgcaggtac cccatgaacc ccaccccatc gcccgctggc tcgtccgcca cgggcgaggc   102420
gcggggggcgg gtggatgcgc gcctcctgcg ccccgcgggt tcgcgagccg acatggtggc  102480
gatagacgcg ggttatcgga tgtccgctac cccccaaaaa agaaaaagac cccacagcgc   102540
ggatggaggc cggggtaggt gccgccgac ccctcgcga tgggaatgga cgggagcgac    102600
ggggccggcg caaaaaaacg cagtatctcc cgcgaaggct acccgccgcc ccagccccg    102660
gccaaatgcg gaaacggtcc cgcgctctcg cctttatacg cgggccgccc tgcgacacaa   102720
tcacccgtcc gtggtttcga atctacacga caggcccgca gacgcggcta acacacacgc   102780
cggcaaccca gacccagtg ggttggttgc gcggtcccgt ctcctggcta gttcttccc    102840
ccaccaccaa ataatcagac gacaaccgca ggttttgtaa tgtatgtgct cgtgtttatt   102900
gtggatacga accggtgacg ggaggggaaa acccagacgg gggatgcggg tccggtcgcg   102960
ccccctaccc accgtactcg tcaattccaa gggcatcggg aaacatctgc tcaaactcga   103020
agtcggccat atccagagcg ccgtaggggg cggagtcgtg gggggtaaat cccggccccg   103080
gggaatcccc gtccccaac atgtccagat cgaaatcgtc tagcgcgtcg gcatgcgcca   103140
tcgccacgtc ctcgccgtct aagtggagct cgtccccag gctgacatcg gtcgggggg    103200
ccgtcgacag tctgcgcgtg tgtcccgcgg ggagaaagga caggcgcgga gccgccagcc   103260
ccgcctcttc gggggcgtcg tcgtccggga gatcgagcag gccctcgatg gtagacccgt   103320
aattgttttt cgtacgcgcg cggctgtacg cgtgttcccg catgaccgcc tcggaggcg    103380
aggtcgtgaa gctggaatac gagtccaact tcgcccgaat caacaccata agtacccag    103440
aggcgcgggc ctgggtgcca tgcagggtgg gagggggtcgt caacggcgcc cctggctcct   103500
ccgtagccgc gctgcgcacc agcgggaggt taaggtgctc gcgaatgtgg tttagctccc   103560
gcagccggcg ggcctcgatt ggcactcccc ggacggtgag cgctccgttg acgaacatga   103620
agggctggaa cagacccgcc aactgacgcc agctctccag gtcgcaacag aggcagtcaa   103680
acaggtcggg ccgcatcatc tgctcggcgt acgcggccca taggatctcg cgggtcaaaa   103740
atagatacaa atgcaaaaac agaacacgcg ccagacgagc ggtctctcgg tagtacctgt   103800
ccgcgatcgt ggcgcgcagc atttctccca ggtcgcgatc gcgtccgcgc atgtgcgcct   103860
ggcggtgcag ctgccggacg ctggcgcgca ggtaccggta cagggccgag cagaagttgg   103920
ccaacacggt tcgatagctc tcctcccgcg cccgtagctc ggcgtggaag aaacgagaga   103980
gcgcttcgta gtagagcccg aggccgtcgc gggtggccgg aagcgtcggg aaggccacgt   104040
cgccgtgggc gcgaatgtcg atttgggcgc gttcggggac gtacgcgtcc ccccattcca   104100
ccacatcgct gggcagcgtt gataggaatt tacactcccg gtacaggtcg gcgttggtcg   104160
gtagcgccga aaacagatcc tcgttccagg tatcgagcat ggtacatagc gcggggcccg   104220
cgctaaagcc caagtcgtcg aggagacggt taaagagggc ggcgggggggg acgggcatgg  104280
gtggggaggg catgagctgg gcctggctca ggcgcccgt tgcgtacagc ggggggggccg    104340
ccggggtgtt tttgggaccc ccggctgggc gggggggcgg tggcgaagcg ccgtccgcgt   104400
```

```
tcatgtcggc aaacagctcg tcgaccaaga ggtccattgg gtggggttga tacgggaaag  104460
acgatatcgg gcttttgatg cgatcgtccc cgcccgccca gagagtgtgg gacgcccgac  104520
ggcgcgggaa gagaaaaacc cccaaacgcg ttagaggacc ggacggacct tatgggggga  104580
agtgggcagc gggaaccccg tccgttcccg aggaatgaca gcccgtggtc gccaccacgc  104640
atttaagcaa cccgcacggg ccgccccgta cctcgtgact tccccccaca ttggctcctg  104700
tcacgtgaag gcgaaccgag ggcggctgtc caacccaccc ccgccaccc agtcccggtc  104760 cccgtcggat tgggaaacaa aggcacgcaa cgccaacacc gaatgaaccc ctgttggtgc  104820
tttattgtct gggtacggaa gttttcactc gacgggccgt ctggggcgag aagcggagcg  104880
ggctggggct cgaggtcgct cggtggggcg cgacgccgca gaacgccctc gagtcgccgt  104940
ggccgcgtcg acgtcctgca ccacgtctgg attcaccaac tcgttggcgc gctgaagcag  105000 gttttgccc tcgcagaccg tcacgcggat ggtggtgatg ccaaggagtt cgttgaggtc  105060
ttcgtctgtg cgcggacgcg acatgtccca gagctggacc gccgccatcc gggcatgcat  105120
ggccgccagg cgcccgaccg cggcgcagaa gacgcgcttg ttaaagccgg ccacccgggg  105180
ggtccatggc gcgtcgggt ttgggggggc ggtgctaaag tgcagctttc tggccagccc  105240
ctgcgcgggt gtcttggatc gggttggcgc cgtcgacgcg ggggcgtctg ggagtgcggc  105300
ggattctggc tgggccgatt tcctgccgcg ggtggtctcc gccgccgggg ccgcgggggc  105360
cttagtcgcc accgctggg ttcgggggc ccgggggcg gtggtgggtg tgcgtccggc  105420
ccctccggac ccagcgggtg gcggaggtgc ccgcgcaggc cccgggccgg acaaaaccgc  105480
cccggaaacg ggacgccgcg tccggggac ctccgggtgt tcgtcgtctt cggatgacga  105540
gcccccgtag agggcataat ccgactcgtc gtactggacg aaacggacct cgcccctctg  105600
gcgcgagcgt gtctgtaggg cgccacggcg ggaggtgtca ggcggactat cgggactcgc  105660
catacctgaa gacggggtgt agtacagatc ctcgtactca tcgcgcggaa cctcccgcgg  105720
acccgacttc acggagcggc gagaggtcat ggttccacga acacgctagg gtcggatgcg  105780
cggacaatta ggcctgggtt cggacggcgg gggtggtgca ggtgtggaga ggtcgagcga  105840
taggggcggc ccgggagaga agagagggtc cgcaaaaccc actggggatg cgtgagtggc  105900
cctctgtggg cggtggggga gagtcttata ggaagtgcat ataaccacaa cccatgggtc  105960
taaccaatcc ccaggggcca agaaacagac acgcccaaa cggtctcggt ttccgcgagg  106020
aaggggaagt cctgggacac cctccacccc cacccctcac cccacacagg gcgggttcag  106080
gcgtgccccg cagccagtag cctctggcag atctgacaga cgtgtgcgat aatacacacg  106140
cccatcgagg ccatgcctac ataaaggggc accagggccc ccggggcaga catttggcca  106200 gtgtttggg tctcgcaccg cgcgccccg atcccatcgc gcccgccctc ctcgccgggc  106260
ggctccccgt gcgggcccgc gtctcccgcc gctaaggcga cgagcaagac aaacaacagg  106320
cccgcccgac agacccttct gggggggccc atcgtcccta acaggaagat gagtcagtgg  106380
ggatccgggg cgatccttgt ccagccggac agcttgggtc gggggtacga tggcgactgg  106440
cacacgcccg tcgctactcg cggggcgga gtcgtgcaac tgaacctggt caacaggcgc  106500
gcggtggctt ttatgccgaa ggttagcggg gactccggat gggccgtcgg gcgcgtctct  106560
ctggacctgc gaatggctat gccggctgac ttttgcgcga ttattcacgc cccgcgcta  106620 gccagccccg gcaccacgt aatactgggt cttatcgact cggggtaccg cggaaccgtt  106680
atggccgtgg tcgtagcgcc taaaaggacg cgggaatttg cccccgggac cctgtgggtc  106740
```

```
gacgtgacgt tcctggacat cctggcgacc cccccggccc tcaccgagcc gatttccctg   106800
cggcagttcc cgcaactggc gccccccct  caaccgggg  ccgggatacg cgaagatcct   106860
tggttggagg gggcgctcgg ggcccaagc  gtgactacgg ccctaccggc gcgacgccga   106920
gggcggtccc tcgtctatgc cggcgagctg acgccggttc agacggaaca cggggacggc   106980
gtacgagaag ccatcgcctt ccttccaaaa cgcgaggagg atgccggttt cgacattgtc   107040
gtccgtcgcc cggtcaccgt cccggcaaac ggcaccacgg tcgtgcagcc atccctccgc   107100
atgctccacg cggacgccgg gcccgcggcc tgctatgtgt tggggcggtc gtcgctcaac   107160
gcccgcggcc tcctggtcgt tcctacgcgc tggctccccg ggcacgtatg tgcgtttgtt   107220
gtttacaacc ttacggggt  tcctgtgacc ctcgaggccg cgccaaggt  cgcccagctc   107280 ctggttgcgg gggcggacgc tcttccttgg atcccccgg  acaactttca cgggaccaaa   107340
gcgcttcgaa actacccag  gggtgttccg gactcaaccg ccgaacccag gaacccgccg   107400
ctcctggtgt ttacgaacga gtttgacgcg gaggccccc  cgagcgagcg cgggaccggg   107460
ggttttggct ctaccggtat ttagcccaca gctttgggtt cgttccgggc aataaaaaac   107520
gtttgtatcg catcttttcct gtgtgtagtt gtttatgttg gatgcctgtg ggtctatcac   107580 acccgccct  ccatcccaca aacacaaaac acacggttg  gatgaaaaca cgcatttatt   107640
gacccaaaac acacggagct gctcgagatg ggccagggcg aggtgcggtt ggggaggctg   107700
taggtctggg aacggacacg cggggacacg attccggttt ggggtccggg agggcgtcgc   107760
cgtttcgggc ggcaggcgcc agcgtaacct ccggggggcgg cgtgtggggg tgccccaagg   107820
agggcgcctc ggtcacccca atccccccg  accgggttcc cccggcaacc ccgaaggcgg   107880
agaggccaag ggcccgttcg gcgatggcca catcctccat gaccacgtca ctctcggcca   107940
tgctccgaat agcctgggag acgagcacat ccgcggactt gtcagccgcc cccacgggaca  108000 tgtacatctg caggatggtg gccatacacg tgtccgccag gcgccgcatc ttgtcctgat   108060
gggccgccac ggccccgtcg atcgtggggg cctcgagccc ggggtggtgg cgcgccagtc   108120
gttctaggtt caccatgcag gcgtggtacg tgcgggccaa ggcgcgggcc ttcacgaggc   108180
gtcgggtgtc gtccagggac cccagggcgt catcgagcgt gatggggggcg ggaagtagcg  108240 cgttaacgac cgccagggcc tcctgcagcc gcggctccgc ctccgagggc ggaacggccg   108300
cgcggatcat ctcatattgt tcctcggggc gcgctcccca gccacatata gccccgaaa   108360 gagaagccat cgcgggcggg tactggccct tgggcgcgcg gacgcaatgg ggcaggaaga   108420
cgggaaccgc ggggagaggc gggcggccgg gactcccgtg gaggtgaccg cgctttatgc   108480
gaccgacggg tgcgttatta cctcttcgat cgccctcctc acaaactctc tactggggc   108540 cgagccggtt tatatattca gctacgacgc atacacgcac gatggccgtg ctgacgggcc   108600
cacggagcaa gacaggttcg aagagagtcg ggcgctctac caagcgtcgg gcgggctaaa   108660
tggcgactcc ttccgagtaa cctttttgttt attggggacg gaagtgggtg gacccacca   108720 ggcccgcggg cgaacccgac ccatgttcgt ctgtcgcttc gagcgagcgg acgacgtcgc   108780
cgcgctacag gacgccctgg cgcacgggac cccgctacaa ccggaccaca tcgccgccac   108840
cctggacgcg gaggccacgt tcgcgctgca tgcgaacatg atcctggctc tcaccgtggc   108900
catcaacaac gccagccccc gcaccggacg cgacgccgcc gcggcgcagt atgatcaggg   108960
cgcgtcccta cgctcgctcg tggggcgcac gtccctggga caacgcgcc  ttaccacgct   109020 atacgtccac cacgaggcgc gcgtgcttgc cgcgtaccgc agggcgtatt atggaagcgc   109080
gcagagtccc ttctggtttc ttagcaaatt cgggccggac gaaaaaagcc tggtgctcac   109140
```

```
cactcggtac tacctgcttc aggcccagcg tctgggggc gcggggggcca cgtacgacct 109200 gcaggccatc aaggacatct gcgccaccta cgcgattccc cacgcccccc gccccgacac 109260
cgtcagcgct gcgtccctga cctcgtttgc cgccatcacg cggttctgtt gcacgagcca 109320
gtacgcccgc ggggccgcgg cggccgggtt tccgctttac gtggagcgcc gtattgcggc 109380
cgacgtccgc gagaccagtg cgctggagaa gttcataacc cacgatcgca gttgcctgcg 109440
cgtgtccgac cgtgaattca ttacgtacat ctacctggcc cattttgagt gtttcagccc 109500
cccgcgccta gccacgcatc ttcgggccgt gacgacccac gaccccaacc ccgcggccag 109560
cacggagcag ccctcgcccc tgggcaggga ggccgtggaa caattttttt gtcacgtgcg 109620
cgcccaactg aatatcgggg agtacgtcaa acacaacgtg acccccgggg agaccgtcct 109680
ggatggcgat acgccaagg cctacctgcg cgctcgcacg tacgcgcccg gggccctgac 109740
gcccgccccc gcgtattgcg gggccgtgga ctccgccacc aaaatgatgg ggcgtttggc 109800
ggacgccgaa aagctcctgg tccccgcgcg gtggcccgcg tttgcgcccg ccagtcccgg 109860
ggaggacacg gcgggcggca cgccgccccc acagacctgc ggaattgtca agcgcctcct 109920
gagactggcc gccacggaac agcagggcac cacaccccg gcgatcgcgg cgcttatccg 109980
taatgcggcg gtgcagactc ccctgcccgt ctaccggata tccatggtcc ccacgggaca 110040
ggcatttgcc gcgctggcct gggacgactg ggcccgcata acgcgggacg ctcgcctggc 110100
cgaagcggtc gtgtccgccg aagcggcggc gcaccccgac cacggcgcgc tgggcaggcg 110160
gctcacggat cgcatccgcg cccagggccc cgtgatgccc cctggcggcc tggatgccga 110220
ggggcagatg tacgtgaatc gcaacgagat attcaacggc gcgctggcaa tcacaaacat 110280
catcctggat ctcgacatcg ccctgaagga gcccgtcccc tttcgccggc tccacgaggc 110340
cctgggccac tttaggcgcg gggctctggc tgcggttcag ctcctgtttc ccgcggcccg 110400
cgtggacccc gacgcatatc cctgttattt tttcaaaagc gcatgtcggc ccggcccggc 110460
gtccgtgggt tccggcagcg gactcggcaa cgacgacgac ggggactggt ttccctgcta 110520
cgacgacgcc ggtgatgagg agtgggcgga ggacccgggc gccatggaca catcccacga 110580
tcccccggac gacgaggttg cctactttga cctgtgccac gaagtcggcc ccacggcgga 110640
acctcgcgaa acggattcgc ccgtgtgttc ctgcaccgac aagatcggac tgcgggtgtg 110700
catgcccgtc cccgccccgt acgtcgtcca cggttctcta acgatgcggg gggtggcacg 110760
ggtcatccag caggcggtgc tgttggaccg agatttttgtg gaggccatcg ggagctacgt 110820
aaaaaacttc ctgttgatcg atacgggagt gtacgcccac ggccacagcc tgcgcttgcc 110880
gtattttgcc aaaatcgccc ccgacgggcc tgcgtgcgga aggctgctgc cagtgtttgt 110940 gatcccccc gcctgcaaag acgttccggc gtttgtcgcc gcgcacgccg acccgcggcg 111000
cttccatttt cacgccccgc ccacctatct cgcttccccc cgggagatcc gtgtcctgca 111060
cagcctgggt ggggactatg tgagcttctt tgaaaggaag gcgtcccgca acgcgctgga 111120
acactttggg cgacgcgaga ccctgacgga ggtcctgggt cggtacaacg tacagccgga 111180
tgcgggaggg accgtcgagg ggttcgcatc ggaactgctg gggcggatag tcgcgtgcat 111240
cgaaacccac tttcccgaac acgccggcga atatcaggcc gtatccgtcc ggcgggccgt 111300
cagtaaggac gactgggtcc tcctacagct agtccccgtt cgcggtaccc tgcagcaaag 111360
cctgtcgtgt ctgcgcttta agcacggccg ggcgagtcgc gccacggcgc ggacattcgt 111420
cgcgctgagc gtcggggcca acaaccgcct gtgcgtgtcc ttgtgtcagc agtgctttgc 111480
```

```
cgccaaatgc gacagcaacc gcctgcacac gctgtttacc attgacgccg gtacgccatg   111540
ctcgccgtcc gttccctgca gcacctctca accgtcgtct tgataacggc gtacggcctc   111600
gtgctcgtgt ggtacaccgt cttcggtgcc agtccgctgc accgatgtat ttacgcggta   111660
cgccccaccg gcaccaacaa cgacaccgcc ctcgtgtgga tgaaaatgaa ccagacccta   111720
ttgtttctgg gggccccgac gcaccccccc aacgggggct ggcgcaacca cgcccatatc   111780
tgctacgcca atcttatcgc gggtagggtc gtgcccttcc aggtcccacc cgacgccatg   111840
aatcgtcgga tcatgaacgt ccacgaggca gttaactgtc tggagaccct atggtacaca   111900
cgggtgcgtc tggtggtcgt agggtggttc ctgtatctgg cgttcgtcgc cctccaccaa   111960
cgccgatgta tgtttggtgt cgtgagtccc gcccacaaga tggtggcccc ggccacctac   112020
ctcttgaact acgcaggccg catcgtatcg agcgtgttcc tgcagtaccc ctacacgaaa   112080
attacccgcc tgctctgcga gctgtcggtc cagcggcaaa acctggttca gttgtttgag   112140
acggacccgg tcaccttctt gtaccaccgc cccgccatcg gggtcatcgt aggctgcgag   112200
ttgatgctac gctttgtggc cgtgggtctc atcgtcggca ccgctttcat atcccggggg   112260
gcatgtgcga tcacataccc cctgtttctg accatcacca cctggtgttt tgtctccacc   112320
atcggcctga cagagctgta ttgtattctg cggcggggcc cggcccccaa gaacgcagac   112380
aaggccgccg ccccggggcg atccaagggg ctgtctggcg tctgcgggcg ctgttgttcc   112440
atcatcctct cgggcatcgc agtgcgattg tgttatatcg ccgtggtggc cggggtggtg   112500
ctcgtggcgc ttcactacga gcaggagatc cagaggcgcc tgtttgatgt atgacgtcac   112560
atccaggccg gcgaaaccg gaacggcata tgcaaattgg aaactgtcct gtcttgggc   112620 ccacccaccc gacgcgtcat atgcaaatga aaatcggtcc cccgaggcca cgtgtagcct   112680
ggatcccaac gaccccgccc atgggtccca attggccgtc ccgttaccaa gaccaaccca   112740
gccagcgtat ccaccccgc ccgggtcccc gcggaagcgg aacggtgtat gtgatatgct   112800
aattaaatac atgccacgta cttatggtgt ctgattggtc cttgtctgtg ccggaggtgg   112860
ggcggggccc ccgcccgggg ggcggaacga ggaggggttt gggagagccg gccccggcac   112920
cacgggtata aggacatcca ccacccggcc ggtggtggtg tgcagccgtg ttccaaccac   112980
ggtcacgctt ctgtgcctct ccccgattcg ggcccggtcg ctcgctaccg gtgcaccacc   113040
accagaggcc atatccgaca ccccagcccc gacggcagcc gacagcccgg tcatggcgac   113100
tgacattgat atgctaattg acctcggcct ggacctctcc gacagcgatc tggacgagga   113160 ccccccgag ccggcggaga gccgccgcga cgacctggca tcggacagca gcggggagtg   113220
ttcctcgtcg gacgaggaca tggaagaccc ccacggagag gacggaccgg agccgatact   113280
cgacgccgct cgcccggcgg tccgcccgtc tcgtccagaa gaccccggcg tacccagcac   113340
ccagacgcct cgtccgacgg agcggcaggg ccccaacgat cctcaaccag cgccccacag   113400
tgtgtggtcg cgcctcgggg cccggcgacc gtcttgctcc cccgagcagc acggggcaa   113460 ggtggcccgc ctccaacccc caccgaccaa agccagcct gccgcggcg gacgccgtgg   113520 gcgtcgcagg ggtcggggtc gcggtggtcc cggggccgcc gatggtttgt cggacccccg   113580
ccggcgtgcc cccagaacca atcgcaaccc ggggggaccc cgccccgggg cggggtggac   113640
ggacggcccc ggcgcccccc atggcgaggc gtggcgcgga agtgagcagc ccgacccacc   113700
cggaggcccg cggacacggg gcgtgcgcca agcacccccc ccgctaatga cgctggcgat   113760
tgcccccccg cccgcggacc cccgcgcccc ggccccggag cgaaaggcgc ccgccgccga   113820
caccatcgac gccaccacgc ggttggtcct gcgctccatc tccgagcgcg cggcggtcga   113880
```

```
ccgcatcagc gagagctttg gccgcagcgc acaggtcatg cacgacccct ttgggggca    113940
gccgtttccc gccgcgaata gccctgggc cccggtgttg gcgggccaag gagggccctt    114000
tgacgccgag accagacggg tctcctggga aaccttggtc gcccacggcc cgagcctcta   114060
tcgcactttt gccggcaatc ctcgggccgc atcgaccgcc aaggccatgc gcgactgcgt   114120
gctgcgccaa gaaaatttca tcgaggcgct ggcctccgcc gacgagacgc tggcgtggtg   114180
caagatgtgc atccaccaca acctgccgct gcgccccag gacccatta tcgggacggc     114240
cgcggctgtg ctggataacc tcgccacgcg cctgcggccc tttctccagt gctacctgaa   114300
ggcgcgaggc ctgtgcggcc tggacgaact gtgttcgcgg cggcgtctgg cggacattaa   114360
ggacattgca tccttcgtgt ttgtcattct ggccaggctc gccaaccgcg tcgagcgtgg   114420
cgtcgcggag atcgactacg cgacccttgg tgtcggggtc ggagagaaga tgcatttcta   114480
cctccccggg gcctgcatgg cgggcctgat cgaaatccta gacacgcacc gccaggagtg   114540
ttcgagtcgt gtctgcgagt tgacggccag tcacatcgtc gccccccgt acgtgcacgg    114600
caaatatttt tattgcaact ccctgtttta ggtacaataa aaacaaaaca tttcaaacaa   114660
atcgccccac gtgttgtcct tctttgctca tggccggcgg ggcgtgggtc acggcagatg   114720
gcggggtgg gcccggcgta cggcctgggt gggcggaggg aactaaccca acgtataaat    114780
ccgtccccgc tccaaggccg gtgtcatagt gcccttagga gcttcccgcc cgggcgcatc   114840
cccccttttg cactatgaca gcgaccccc tcaccaacct gttcttacgg gccccggaca    114900
taacccacgt tgcccccct tactgcctca acgccacctg gcaggccgaa acggccatgc    114960
acaccagcaa aactgactcc gcttgcgtgg ccgtgtggag ttacctggtc cgcgcctcct   115020
gtgagaccag cggcacaatc cactgctttt tctttgtggt atacaaggac acccaccata   115080
cccctccgct gattaccgag ctccgcaact ttgcggacct ggttaaccac ccgccggtcc   115140
tacgcgaact ggaggataag cgcggggtgc ggctgcggtg tgcgcggccg tttagcgtcg   115200
ggacgattaa ggacgtctct gggtccggcg cgtcctcggc gggagagtac acgataaacg   115260
ggatcgtgta ccactgccac tgtcggtatc cgttctcaaa aacatgctgg atgggggcct   115320
ccgcggccct acagcacctg cgctccatca gctccagcgg catggccgcc cgcgcggcag   115380
agcatcgacg cgtcaagatt aaaattaagg cgtgatttcc aaccccccat gaatgtgtgt   115440
aaccccccc aaaaaaataa agagccgtaa cccaaccaaa ccaggcgtgg tgtgagtttg    115500
tggacccaaa gccctcagag acaacgcgac aggccagtat ggaccgtgag acttttattt   115560
attaactcac aggggcgctt accgccacag gaataccaga ataatgacca ccacaatcgc   115620
gaccacccca aatacagcat ggcgccccac cacgccacaa cagccctgtc gccggtatgg   115680
ggcatgatca gacgagccgc gagccgcgcg ttgggccctg tacagctcgc gcgaattgac   115740
cctaggaggc cgccacgcgc ccgagttttg cgttcgtcgc tggtcgtcgg gcaccaaagc   115800
cccggacggc tgttcggtcg aacgaacggc cacgacagtg gcataggttg ggggtggtc    115860
cgacatagcc tcggcgtacg tcgggaggcc cgacaagagg tcccttgtga tgtcgggtgg   115920
ggccacaagc ctggtttccg gaagaaacag ggggttgcc aataaccgc cagggccaaa     115980
actccggccc tggcgcacgt cgttcggcgc ggcgccgggc gcgccgagcg gctcgctggg   116040
cggcttggcg tgagcggccc cgctccgacg cctcgccctc tccggaggag gttggtggaa   116100
ttggcacgga cgacagggc ccagcagagt acggtggagg tgggtccgtg ggggtgtcca    116160
gatcaataac gacaaacggc ccctcgttcc taccagacaa gctatcgtag gggggcgggg   116220
```

```
gatcaacaaa cgcgttcccc gcgctccata gacccgcgtc gggttgcgcc gcctccgaag   116280
ccatggatgc gccccaaagc cacgactccc gcgcgctagg tccttggggt aagggaaaag   116340
gccctactcc ccatccaagc cagccaagtt aacgggctac gccttcgggg atgggactgg   116400
caccccggcg gattttgttg ggctggcatg cgtcgcccaa ccgagggccg cgtccacggg   116460
acgcgccttt tataaccccg ggggtcattc ccaacgatca catgcaatct aactggctcc   116520
cctctcctcc cctctcccct ctccctctc ccctctcccc tctccctct ccctcttag   116580 gttgggggt ggtccgacat agcctcggcg tacgtcggga ggcccgacaa gaggtccctt   116640
gtgatgtcgg gtggggccac aagcctggtt tccggaagaa acagggggt tgccaagcgg   116700 cccggcccgc gctccccccc ccccggggcc gtgtccttgc tttccccccg tctccccccc   116760
cctcctcctc cttctcctcc tcctcgtttt tccaaacccc gcccaccgg cccgcccgg   116820 cccggccacc gccgcccacc cacccaccgc gggagaccca gccccggtcc cccgttcccc   116880
gggggccgtt atctccagcg ccccgtccgg cgcgccgccc ccgccgcta aaccccatcc   116940 cgcccccggg accccacata taagccccca gccacacgca agaacagaca cgcagaacgg   117000
ctgtgtttat ttaaataaac cgatgtcgga ataaacaaac acaaacaccc gcgacggggg   117060
gacggaggga gggggtgac ggggacggg aacagacaca aaaacaaacc acaaaaaaac   117120
agccaccccc gacacccccc accccagtct cctcgccttt tcccaccac cccacgcccc   117180 cactgagccc ggtcgatcga cgagcacccc cgccccccgcc cctgcccccgg cgaccccccgg   117240 cccgcacgat cccgacaaca ataacaaccc caacggaaag cggcggggtg ttgggggagg   117300
cgaggaacaa ccgaggggaa cggggatgg aaggacggga agtggaagtc ctgatacccca   117360 tcctacacccc ccctgccttc caccctccgg ccccccgcga gtccacccgc cggccggcta   117420
ccgagaccga acacgcggc cgccgcagcc gccgcagccg ccgccgacac cgcagagccg   117480
gcgcgcgcac acacaagcgg cagaggcaga aaggcccccga gtcattgttt atgtggccgc   117540
gggccagcag acgcccgcg acacccccccc gcccgtgtgg gtatccggcc ccccgccccg   117600
cgccggtcca ttaagggcgc gcgtgcccgc gagatatcaa tccgttaagt gctctgcaga   117660 cagggggcacc cgcgcccggaa atccattagg ccgcagacga ggaaaataaa attacatcac   117720
ctacccacgt ggtgctgtgg cctgttttttg ctgcgtcatc tgagcctttta taaaagcggg   117780 ggcgcggccc tgccgatcgc gggtggtgcg aaagactttc cggcgcgtc cgggtgccgc   117840 ggctctccgg gcccccctgc agccggggcg gccaaggggc gtcggcgaca tcctcccccct   117900 aagcgccggc cggccgctgg tctgttttttt gttttcccg tttcgggggt ggggggggtt   117960
acggtttctg tttttttaaac ccgtctgggg tgttttcgt tccgtcgccg ggatgtttcg   118020
ttcgttcggc ccctcacggg gcgaaggccg cgtacggccc gggacgaggg gccccccgacc   118080 gcggcggtcc gggcccgtc cgggcccgct cgccggcacg cgacgcgaaa aaggcccccc   118140
ggaggctttt ccgggttccc ggccggggc ctgagataaa caatcggggt taccgccaac   118200
ggccggcccc cgtggcggcc cggccgggg ccccggcgga cccaaggggc ccggcccgg   118260 ggccccacaa cggcccggcg catgcgctgt gttttttttt tcctcggtgt tctgccgggc   118320
tccgtcgcct ttcctgttct cgcttcttcc cccccccctt cttcacccccc agtaccctcc   118380 tccctccctt cctccccgt tatcccactc gtcgagggcg ccccggtgtc gttcaacaaa   118440
gacgccgcgt ttccaggtag gttagacacc tgcttctccc caatagaggg gggggaccc   118500 aaacgacagg gggcgcccca gaggctaagg tcggccacgc cactcgcggg tgggctcgtg   118560
ttacagcaca ccagcccgtt cttttccccc cctcccaccc ttagtcagac tctgttactt   118620
```

```
acccgtccga ccaccaactg cccccttatc taagggccgg ctggaagacc gccaggggt   118680 cggccggtgt cgctgtaacc ccccacgcca atgacccacg tactccaaga aggcatgtgt   118740
cccaccccgc ctgtgttttt gtgcctggct ctctatgctt gggtcttact gcctgggggg   118800
ggggatgcgg gggaggggg gtgtggaagg aaatgcacgg cgcgtgtgta cccccccccc   118860
aaagttgttc ctaaagcgag gatatggagg agtggcgggt gccgggggac ggggtgatc   118920 tctggcacgc gggggggaa gggtcggggg aggggggat ggggtaccgg cccacctggc   118980
cgacgcgggt gcgcgtgcct ttgcacacca accccacgtc ccccggcggt ctctaagaag   119040
caccgccccc cctccttcat accaccgagc atgcctgggt gtgggttggt aaccaacacg   119100
cccatcccct cgtctcctgt gattctctgg ctgcaccgca ttcttgtttt ctaactatgt   119160
tcctgtttct gtctccccc caccctccg ccccaccccc caacacccac gtctgtggtg   119220
tggccgaccc ccttttgggc gccccgtccc gccacccctc ccgtcctttg ttgccctata   119280
gtgtagttaa ccccccccc gcccttttgtg gcggccagag gccaggtcag tccgggcggg   119340
caggcgctcg cggaaactta acacccacac ccagcccact gtggttctgg ctccatgcca   119400
gtggcaggat gctttcgggg atcggtggtc aggcagcccg ggccgcggct ctgtggttaa   119460
caccagagcc tgcccaacat ggcacccca ctcccacgca ccccactcc cacgcaccccc   119520 cactcccacg cacccccact cccacgcacc cccactccca cgcaccccca ctcccacgca   119580
cccccactcc cacgcaccccc cactcccacg caccccact cccacgcacc cccactccca   119640 cgcacccca ctcccacgca ccccactcc cacgcacccc cactcccacg cacccccaag   119700
atccatccaa cacagacagg gaaaagatac aaaagtaaac ctttatttcc caatagacag   119760
caaaaatccc ctgagttttt tattaggcc aacactaaag acccgctggt gtgtggtgcc   119820
cgtgtctttc actttcccct ccccgacacg gattggctgg tgtagtgggc gcggccgag   119880 accacccagc acccgaccc cctccccaca aacacggggg gcgtcccta ttgttttccc   119940 tcgtcccggg tcgacgcccc ctgctccccg gaccacgggt gccgagaccg caggctgcgg   120000
aagtccaggg cgcccactag ggtgcctgg tcgaacagca tgttcccac gggggcatc   120060 cagaggctgt tccactccga cgcggggcc gtcgggtact cggggggcat cacgtggtta   120120
cccgcggtct cggggagcag ggtgcggcg ctccagccgg ggaccgcggc ccgcagccgg   120180
gtcgccatgt ttcccgtctg gtccaccagg accacgtacg ccccgatgtt ccccgtctcc   120240
atgtccagga tgggcaggca gtccccgtg atagtcttgt tcacgtaagg cgacagggcg   120300
accacgctag agaccccga gatgggcagg tagcgcgtga ggccgccgc ggggacggcc   120360 ccggaagtct ccgcgtggcg cgtcttccgg gcacacttcc tcggcccccg cggcccagaa   120420
gcagcgcggg ggccgaggga ggtttcctct tgtctccctc ccagggcacc gacgcccg    120480 cccgaggagg cggaagcgga ggaggacgcg gccccggcgg cggaagaggc ggccccgcg   120540 ggggtcgggg ccgaggagga agaggcagag gaggaagagg cggaggccgc cgaggacgtc   120600
aggggggtcc cgggcccacc ctggccgcgc ccccggcc ctgagtcgga gggggggtgc   120660
gtcgccgccc tcttggcccc tgccggcgcg aggggggac gcgtggactg ggggagggg   120720 ttttcctggc ccgacccgcg cctcttcctc ggacgcaccg ccgcctcctg ctcgacagag   120780
acggcggagg ggagcggggc ggcgccggag ggggtgcggc cgcgggaggg cccgtgccca   120840
ccctccacgc ccgccccc cgagccgcgc gccaccgtcg cacgcgcccg gcacagactc   120900
tgttcttggt tcgcggcctg agccagggac gagtgcgact ggggcacacg gcgcgcgtcc   120960
```

```
gcggggcggg cggccggctc cgccccgggg gccggggcgc ggggccggg ccccggaggc   121020 ggcgctcgca cgcacggggc cacggccgcg cggggggcgcg cgggtcccga cgcggccgag   121080
gacgcggggg gcccggggcg ggggggcggag cctggcatgg gcgccgcggg gggcctgtgg   121140
ggagaggccg gggggggagtc gctgatcact atggggtctc tgttgtttgc aaggggggcg   121200
ggtctgttga caagggggcc cgtccggccc ctcggccgcc ccgcctccgc ttcaacaacc   121260
ccaaccccaa ccccaacccc cccggagggg ccagacgccc ccgcggcgc cgcggctcgc   121320 gactggcggg agccgccgcc gccgctgctg ttggtggtgg tgttggtgtt actgctgccg   121380
tgtggcccga tgggcgccga gggggcgct gtccgagccg cggccggctg ggggctgcg   121440 ttagacgccc cgcccgtcac gggggggcgcg gcggtgcctc tgcgtggggg ggcgcggggc   121500
gtccggcggg gggcgggcgg gacgtagtct gctgcaagag acaacggggg gcgcgatcag   121560
gttacgcccc ctccccggcc cgcccttttcc tcgcccgccc gcccattcct ccctcctcct   121620
cctcccccag ggtccttgcc gcccccgcc tcaccgtcgt ccaggtcgtc gtcatcctcg   121680
tccgtggtgg gctccgggtg ggtggggcgac agggccctca ccgtgtgccc cccagggtc   121740 aggtaccgcg gggcgaaccg ctgattgccc gtccagataa agtccacggc cgtgcccgcc   121800
ctgacggcct cctcggcctc catgcgggtc tgggggtcgt tcacgatcgg gatggtgctg   121860
aacgacccgc tgggcgtcac gcccactatc aggtacacca gcttggcgtt gcacagcggg   121920
caggtgttgc gcaattgcat ccaggttttc atgcacggga tgcagaagcg gtgcatgcac   121980
gggaaggtgt cgcagcgcag gtggggcgcg atctcatccg tgcacacggc gcacacgtcg   122040
ccctcgtcgc tccccccgtc ctctcgaggg ggggcgcccc cgcaactgcc ggggtcttcc   122100 tcgcggggg ggctccccccc cgagaccgcc ccccccatcca cgccctgcgg ccccagcagc   122160
cccgtctcga acagttccgt gtccgtgctg tccgcctcgg aggcggagtc gtcgtcatgg   122220
tggtcggcgt ccccccgccc ccccacttcg gtctccgcct cagagtcgct gctgtccggc   122280
aggtctcggt cgcagggaaa cacccagaca tccggggcgg gctaagggga aaaaggggg   122340 gcgggtaaga atgggggggg atttcccgcg tcaatcagcg cccacgagtt ccccctctcc   122400
ccccccgcct cacaaagtcc tgccccccctg ctggcctcgg aagagggggg agaaaggggt   122460
ctgcaaccaa aggtggtctg ggtccgtcct ttggatcccg accctcttc ttccctcttc   122520 tcccgccctc cagacgcacc ggagtcgggg gtcccacggc gtcccccaaa tatggcgggc   122580
ggctcctccc caccccccta gatgcgtgtg agtaagggg gcctgcgtat gagtcagtgg   122640
ggaccacgcc cccaacacgg cgaccccggt ccctgtgtgt ttgttgtggg ggcgtgtctc   122700
tgtgtatgag tcaggggtc ccacggcgac cccgggccct gcgtctgagt caaagggggcc   122760 atgtgtatgt gttgggggtc tgtatatata aagtcagggg gtcacatggc gaccccaac   122820 agggcgaccc cggtccctgt atatataggg tcaggggtt ccgcgccccc taacatggcg   122880
cccccggtcc ctgtatatat agtgtcacgg ggttccacgc ccctaacat ggcgccccaa   122940 catggcgccc ggctcccgtg tatgagtggg ggtccccaa catgggggcc ggttccaggg   123000
taagggtcgg gggtccccca acatggcgcc ccccaatatg gcgccccaga catggcgccc   123060
ggcccctcac ctcgcgctgg gggcggccct caggccggcg ggtactcgct ccggggcggg   123120
gctccatggg ggtcgtatgc ggctggaggg tcgcggacgg agggtccctg ggggtcgcaa   123180
cgtaggcggg gcttctgtgg tgatgcggag aggggggcggc ccgagtctgc ctggctgctg   123240
cgtctcgctc cgagtgccga ggtgcaaatg cgaccagacc gtcgggccag ggctaactta   123300
taccccacgc ctttcccctc cccaaagggg cggcagtgac gattcccca atggccgcgc   123360
```

```
gtcccagggg aggcaggccc accgcggggc ggccccgtcc ccggggacca accccggcgcc   123420 cccaaagaat atcattagca tgcacggccc ggccccccgat ttgggggacc aacccggtgt   123480
cccccaaaga accccattag catgccccctc ccgccgacgc aacagggggct tggcctgcgt   123540 cggtgccccg gggcttcccg ccttcccgaa gaaactcatt accatacccg gaaccccagg   123600
ggaccaatgc gggttcattg agcgacccgc gggccaatgc gcgaggggcc gtgtgttccg   123660
ccaaaaaagc aattagcata acccggaacc ccagggggagt ggttacgcgc ggcgcgggag   123720
gcggggaata ccggggttgc ccattaaggg ccgcgggaat tgccggaagc gggaagggcg   123780
gccggggccg cccattaatg agtttctaat taccataccg ggaagcggaa caaggcctct   123840
tgcaagtttt taattaccat accgggaagt gggcggcccg gcccattggg cggtaactcc   123900
cgcccaatgg gccgggcccc gaagactcgg cggacgctgg ttggccgggc ccgccgcgc   123960 tggcggccgc cgattggcca gtcccgccccc cgaggcgggc ccgccttggg ggcggaccgg   124020
ctcccagcgt atatatgcgc ggctcctgcc atcgtctctc cggagagcgg cttggtgcgg   124080
agctcccggg agctccgcgg aagacccagg cgcctcgggt gtaacgttag accgagttcg   124140 ccgggccgg tccgcgggcc agggcccggg cacgggcctc ggggccccagg cacgcccga   124200 tgaccgcctc ggcctccgcc acccggcgcc ggaaccgagc ccggtcggcc cgctcgcggg   124260
cccacgagcc gcgcgcgcc aggcgggcgg ccgaggccca gaccaccagg tggcgcaccc   124320
ggacgtgggg cgagaagcgc accgcgcgg gggtcgcggg ggtcgcgggg gtcgcggggg   124380
tcgcgggggt cgcgggggtc gcggggggtcg cggggggtcgc ggggggctcc ggcgccccct   124440
ccccgcccgc gcgtcgcagg cgcaggcgcg ccaggtgctc cgcggtgacg cgcaggcgga   124500
gggcgaggcg cggcggaagg cggaagggggc gcgaggggggg gtgggagggg tcagccccgc   124560
cccccgggcc cacgccgggc ggtggggacc ggggccgggg ggcggcggcg gtgggccggg   124620
cctctggcgc cggctcgggc gggggctgt ccggccagtc gtcgtcatcg tcgtcgtcgg   124680
acgcggactc gggaacgtgg agccactggc gcagcagcag cgaacaagaa ggcgggggcc   124740
caccggcggg gggcggcggc ggggcggccg cgggcgcgct cctgaccgcg ggttccgagt   124800
tgggcgtgga ggttacctgg gactgtgcgg ttggacggc gcccgtgggc ccgggcgcc   124860 gggggcggcg gggccgcga tggcggcggc ggcgggccat ggagacagag agcgtgccgg   124920
ggtggtagag tttgacaggc aagcatgtgc gtgcagaggc gagtagtgct tgcctgtcta   124980
actcgctagt ctcggccgcg gggggcccgg gctgcccgcc gccgcgcttt aaagggccgc   125040
gcgcgacccc cggggggtgt gtttcggggg ggcccgtttt tggggtctgg ccgctcctcc   125100
cccgctcctc cccgtctgtg ggtggggctc ctccccgct cctccccgc tcctcccccg   125160 ctcctcccccg tctgtgggtg gggctcctcc cccgctcccg cggccccgcc cccacgccc   125220 gccgcgcgcg cgcacgccgc ccggaccgcc gcccgccttt tttgcgcgcc gccccgcgcg   125280
cggggggccc gggctgccac aggtgtaaca acaccaacag aacaccaaca gcacggcgca   125340
ccggcgactc cggttcctca tccacacgtc acgtcatcca acacacctgc ccaacaacac   125400
aactcacagc gacaactcac cgcgcaacaa ctcctgttcc tcatccacac gtcaccgcgc   125460
accccccgct cctccagacg tccccagcg caacacgccg ctcctgtcac acaccacagc   125520
cccagccctc cccagcccca gcctccccca gccccagccc tccccagccc cagccctccc   125580
cagccccagc cctccccagc cccagccctc ccagcccca gccctcccca gccccagccc   125640
tccccagccc cagccctccc cagccccagc cctccccagc ccagccctc ccagccccca   125700
```

```
gccctcccca gccgcgtccc gcgctccctc gggggggttc gggcatctct acctcagtgc   125760
cgccaatctc aggtcagaga tccaaaccct ccggggcgc ccgcgcacca ccaccgcccc    125820 tcgcccccte cegeccetcg ccccctcccg ccctcgccc cctcccgccc ctcgcccect   125880 cccgcccctc gccccctccc gccctcgcc cctcccgcc cctcgccccc tcccgccect   125940 cgccccctcc cgcccctcga ataaacaacg ctactgcaaa acttaatcag gtcgttgccg   126000
tttattgcgt cttcgggttt cacaagcgcc ccgcccgtc ccggcccgtt acagcacccc    126060
gtccccctcg aacgcgccgc cgtcgtcttc gtcccaggcg ccttcccagt ccacaacgtc   126120
ccgtcgcggg ggcgtggcca agcccgcctc cgcccccagc acctccacgg ccccgccgc    126180 cgccagcacg gtgccgctgc ggcccgtggc cgaggcccag cgaatcccgg gcggcgccgg   126240
cggcagggcc cccgggccgt cgtcgtcgcc gcgcagcacc agcgggggg cgtcgtcgtc    126300 gggctccagc agggcgcggg cgcaaaagtc cctccgcggc ccgcgccacc gggccgggcc    126360
ggcgcgcacc gcctcgcgcc ccagcgccac gtacacgggc cgcagcggcg cgcccaggcc   126420
ccagcgcgcg caggcgcggt gcgagtgggc ctcctcctcg cagaagtccg gcgcgccggg   126480
cgccatggcg tcggtggtcc ccgaggccgc cgcccggccg tccagcgccg gcagcacggg   126540
ccggcggtac tcgcgcgggg acatgggcac cggcgtgtcc gggccgaagc gcgtgcgcac   126600
gcggtagcgc acgttgccgc cgcggcacag gcgcagcggc ggcgcgtcgg ggtacaggcg   126660
cgcgtgcgcg gcctccacgc gcgcgaagac ccccgggccg aacacgcggc ccgaggccag   126720
caccgtgcgg cgcaggtcgc gcgccgccgg ccagcgcacg gcgcactgca cggcgggcag   126780
caggtcgcac gccaggtagg cgtgctgccg cgacaccgcg ggcccgtcgg cgggccagtc   126840
gcaggcgcgc acggtgttga ccacgatgag ccgccggtcg ccgcgctgg cgagcagccc    126900 cagaaactcc acgcccccgg cgaaggccag gtcccgcgtg gacagcagca gcacgccctg   126960
cgcgcccagc gccgacacgt cggggcgcc ggtccagttg cccgcccagg cggccgtgtc    127020
cggcccgcac agccggttgg ccagggccgc cagcaggcag gacagcccgc cgcgctcggc   127080
ggaccactcc ggcggccccc ccgaggcccc gccgcggcc aggtcctcgc ccggcagcgg    127140
cgagtacagc accaccacgc gcacgtcctc ggggtcgggg atctggcgca tccaggccgc   127200
catgcggcgc agcgggcccg aggcgcgcag ggggccaaag aggcggcccc cggcggcccc   127260 gtggggtgg gggttctcgt cgtcgtcgcc gccgccgcac gcggcctggg cggcggggc    127320 gggcccggcg caccgcgcgg cgatcgaggc cagggcccgc gggtcaaaca tgagggccgg   127380
tcgccagggg acgggaaca gcgggtggtc cgtgagctcg gccacggcgc gcggggagca    127440
gtaggcctcc agggcggcgg ccgcgggcgc cgccgtgtgg ctgggccccg ggggctgccg   127500
ccgccagccg cccaggggt cggggccctc ggcgggccgg cgcgacagcg ccacggggcg    127560
cgggcgggcc tgcgccgcgg cggcccgggg cgccgcgggc tgggcggggg cgggctcggg    127620
ccccgggggc gtggagggg gcgcgggcgc ggggaggggg gcgcgggcgt ccgagccggg   127680
ggcgtccgcg ccgctcttct tcgtcttcgg gggtcgcggg ccgccgcctc cgggcggccg   127740
ggccgggccg ggactcttgc gcttgcgccc ctcccgcggc gcggcggagg cggcggccgc    127800 gaccccgaa gacgaagaag agcggcgcgg accgccgcc agcaggggc gcaggctctg     127860 gttctcaaac agcaggtccg cggcggcggc ggccgcggag ctcggcaggc gcgggtcccg   127920
cggcagcgcg ggaccccaggg cccccggcgac caggctcacg gcgcgcacgg cggccacggg   127980
ggcctcgctg ccgccggcca cgcgcaggtc ccgcgcaggg cgcatgagca ccagcgcgtc   128040
gcgcacgaac cgcagctcgc gcagccacgc gcgcaggcgg ggcgcgtcgg cgtgcggcgg   128100
```

-continued

```
cggcggggaa gcggggcccg cgggtccctc cggccgcggg gggctggcgg gccgggcccc    128160
ggccagcccc gggacggccg ccaggtcgcc gtcgaagccc tcggccagcg cctccaggat    128220
cccgcggcag gcggccaggc actccacggc cacgcggccg gcctgggcgc ggcgcccggc    128280
gtcgtcgtcg gcgtcggcgt ggcgggcggc gtcggggtcg tcgcccccg cggggaggc     128340 gggcgcggcg gacagccgcc ccagggcggc gaggatcccc gcggcgccgt acccggcggg   128400
caccgcgcgc tcgcccggtg cggcggcggc ggcgacgacg gcggcggcga ccccctcgtc    128460
atctgcgccg gcgccggggc tccccgcggc ccccgtcagc gccgcgttct cgcgcgccaa    128520
caggggcgcg taggcgcggc gcaggctggt cagcaggaag cccttctgcg cgcggtcgta    128580
tcggcggctc atggccacgg cggccgccgc gtgcgccagg cccagccga agcggccggc     128640 cgccatggcg tagcccaggt ggggcacggc ccgcgccacg ctgccggtga tgaaggagct    128700
gctgttgcgc gcggcgcccg agatccggaa gcaggcctgg tccagcgcca cgtccccggg    128760
gaccacgcgc gggttctgga gccacccat ggcctccgcg tccggggtgt acagcagccg    128820
cgtgatcagg gcgtactgct gcgcggcgtc gcccagctcg ggcgcccaca cggccgccgg    128880
ggcgcccgag gcctcgaacc ggcgtcgcgc ctcctccgcc tcgggcgccc ccagaggcc     128940 cgggcggctg tcgcccaggc cgccgtacag cacccgcccc ggggcgggg gcccggcgcc    129000 gggccacggc tccccgctga cgtacccgtc gcgatagcgc gcgtagaagg cgccggaggc    129060
cgcgtcggcg tccagctcga cccgccgggg ctgcccggcc gtgaagcggc ccgtggcgtc    129120
gcggccggcc accgccgcgc gggcccggcg gcgctcgatg cggccgcgg aggccgcggg    129180 ggtcctcgcc gccgcccggg gcttgggcgc ggcctcggag agggggggtg gcccgggcgg    129240
gggcggcgtc cgcccggggg cttccggcgc cgcgctcgac ggaccccgcc cgacggcccg    129300
cgcctcgcgt gcgtggtcgg ccgcgtcgtt gccgtcgtcg tcctcgtcct cgtcggacga    129360
cgaggacgaa gaggatgcgg acgacgagga cgaggacccg gagtccgacg aggtcgatga    129420
cgccgatggc cgccgccggc cgtgacgacg tctctgcggc ggctgggccg gcgggcgcgg    129480
cgacaggcgg tccgtggggt ccggatacgc gccgcgtagc ggggcctccc gtgcgcggcc    129540
ccgggccggg gcccggtcgc cggcggcgtc ggctgcgtcg tcgtactcgt ccccgtcatc    129600
gtcgtcggct cgaaaggcgg gggtccgggg cggcgaggcc gcggggtcgg gcgtcgggat    129660
cgtccggacg gcctcctcta ccatggaggc cagcaggggc agctgtcgcg gcgagacggc    129720
gtccccggcg tcctcgccgg cgtcggtgcc cgccgcgggg gccctcccgt ccgccgggc    129780 gtcgtcgagg tcgtgggggt ggtcggggtc gtggtcgggg tcgtccccgc cctcctccgt    129840
ctccgcgccc caccccgaggg ccccccgctc gtcgcggtct gggctcgggg tgggcggcgg   129900
cccgtcggtg gggcccgggg agccggggcg ctgcttgttc tccgacgcca tgccgatgc    129960 ggggcgatcc tccggggata cgactgcgac ggcggacgta gcacggtagg tcacctacgg    130020
actctcgatg gggaggggc gagacccacg gaccccgacg accccgccg tcgacgcgga     130080 actagcgcgg accggtcgat gcttgggtgg gaaaaaggac agggacggcc gatcccctc    130140 ccgcgcttcg tccgcgtatc ggcgtccccg cgcggcgagc gtctgacggt ctgtctctgg    130200
cggtcccgcg tcgggtcgtg gatccgtgtc ggcagccgcg ctccgtgtgg acgatcgggg    130260
cgtcctcggg ctcatatagt cccagggcc ggcgggaagg aggagcagcg gaggccgccg    130320
gccccccgcc cccacggcgg gccgcccccg aacggaattc cattatgcac gaccccgccc    130380
cgacgccggc acgccggggg cccgtggccg cggcccgttg gtcgaacccc cggccccgcc    130440
```

```
catccgcgcc atctgccatg ggcggggcgc tagggcgggt gggcccgcgc ccgccccgc   130500
atggcatctc attaccgccc gatccggcgg tttccgcttc cgttccgcat gctaacgagg  130560
aacgggcagg gggcggggcc cgggccccga cttcccggtt cggcggtaat gagatacgag  130620
ccccgcgcgc ccgttggccg tccccgggcc cccggtcccg cccgccggac gccgggacca  130680
acgggacggc gggcggccca agggccgccc gccttgccgc cccccattg gccggcgggc   130740
ggaccgccc caaggggcg gggccgccgg gtaaaagaag tgagaacgcg aagcgttcgc    130800
acttcgtccc aatatatata tattattagg gcgaagtgcg agcactggcg ccgtgcccga  130860
ctccgcgccg gccccggggg cgggcccggg cggcggggg cgggtctctc cggcgcacat   130920
aaaggcccgg cgcgaccgac gcccgcagac ggcgccggcc acgaacgacg ggagctgctg  130980
cggagcacgc ggaccgggag cgggactcgc agagggccgt cggagcggac ggcgtcggca  131040
tcgcgacgcc ccggctcggg atcgggatcg catcggaaag ggacacgcgg aaagacccac  131100
ccaccccacc cacgaaacac aggggacgca ccccgggggc ctccgacgac agaaaccac   131160
cggtccgcct ttttgcacgg gtaagcacct tgggtgggcg gaggagggcg gaggaggggg  131220
gacgcggggg cggaggaggg gggacgcggg ggcggaggag gggggacgcg ggggcggagg  131280
aggggggacg cggggggcgga ggaggggct caccgcgtt cgtgccttcc cgcaggagga  131340
acgtcctcgt cgaggcgacc ggcggcgacc gttgcgtgga ccgcttcctg ctcgtcgggg  131400
cgaccggcgg cgaccgttgc gtggaccgct tcctgctcgt cggggcgacc ggcggcgacc  131460
gttgcgtgga ccgcttcctg ctcgtcgggg gggggggggg gaagccactg tggtcctccg  131520
ggacgttttc tggatggccg acatttcccc aggcgctttt gcgccttgtg taaaagcgcg  131580
gcgtcccgct ctccgatccc cgccctgggg cacgcgcaag cgcaagcgcc ctgcccgccc  131640
cctctcatcg gagtctgagg tcgaaaccga tacagcttg gagtctgagg tcgaatccga   131700
gacagcatcg gattcgaccg agtctgggga ccaggaggaa gcccccgca tcggtggccg   131760
tagggccccc cggaggcttg gggggcggtt ttttctggac atgtcggcgg aatccaccac  131820
ggggacggaa acggatacgg cggtgtcgga cgaccccgac gacacgtccg actggtctta  131880
tgacgacatt ccccacgac ccaagcgggc ccgggtaaac ctgcggctca cgagctctcc   131940
cgatcggcgg gatggggtta tttttcctaa gatggggcgg gtccggtcta cccgggaaac  132000
gcagccccgg gccccaaccc cgtcggcccc aagcccaaat gcaatgctac ggcgctcggt  132060
gcgccaggcc cagaggcgga gcagcgcacg atggacccc gacctgggct acatgcgcca   132120
gtgtatcaat cagctgtttc gggtcctgcg ggtcgcccgg gaccccacg gcagtgccaa   132180
ccgcctgcgc cacctgatac gcgactgtta cctgatggga tactgccgag cccgtctggc  132240
cccgcgcacg tggtgccgct tgctgcaggt gtccggcgga acctggggca tgcacctgcg  132300
caacaccata cgggaggtgg aggctcgatt cgacgccacc gcggaacccg tgtgcaaact   132360
tccttgtttg gaggccagac ggtacggccc ggagtgtgat cttagtaatc tcgagattca   132420
tctcagcgcg acaagcgatg atgaaatctc cgatgccacc gatctggagg ccgccggttc  132480
ggaccacacg ctcgcgtccc agtccgacac ggaggatgcc cctccccg ttacgctgga    132540
aaccccagaa ccccgcgggt ccctcgctgt cgtctggag gatgagtttg gggagtttga   132600
ctggaccccc caggagggct cccagccctg gctgtctgcg gtcgtggccg ataccagctc  132660
cgtggaacgc ccgggcccat ccgattctgg ggcgggtcgc gccgcagaag accgcaagtg  132720
tctgacggg tgccggaaaa tgcgcttctc caccgcctgc ccctatccgt gtagcgacac   132780
gtttctccgg ccgtgagtcc ggtcgccccg acccctttgt atgtcaccaa aataaaagac  132840
```

```
caaaatcaaa gcgtttgtcc cagcgtctta atggcgggaa gggcggagag aaacagacca   132900
cgcggacatg gggggtgttt gggggtttat tggcaccggg ggctaaaggg tggtaaccgg   132960
atagcagatg tgaggaagtc ggggccgttc gccgcgaacg gcgatcagag ggtcagtttc   133020
ttgcggacca cggcccggcg atgtgggttg ctcgtctggg acctcgggca tgcccataca   133080
cgcacaacac ggacgccgca ccggatggga cgtcgtaagg gggcctgggg tagctgggtg   133140
gggtttgtgc agagcaatca gggaccgcag ccagcgcata caatcgcgct cccgtccgtt   133200
tgtcccgggc agtaccacgc cgtactggta ttcgtaccgg ctgagcaggg tctccagggg   133260
gtggttgggg gccgcgggga acggggtcca cgccacggtc cactcgggca aaaccgagt   133320 cggcacggcc cacggttctc ccacccacgc gtctggggtc ttgatggcga taaatcttac   133380
cccgagccgg attttttggg cgtattcgag aaacggcaca cacagatccg ccgcgcctac   133440
cacccacaag tggtagatgc gagggggggct gggttggtct cggtgcagca gtcggaagca   133500
cgccacggcc tccacgacct cggtgctctc caaggggctg tcctccgcaa acaggccgt    133560 ggtggtgttt gggggcagc gacaggacct agtgcgcacg atcggcgggg tgggtttggg   133620
taagtccatc agcggctcgg ccaaccgtcg aaggttggcc ggacgaacga cgaccggggt   133680
acccaggggt tctgatgcca aaatgcggca ctgcctaagc aggaagctcc acagggccgg   133740
gcttgcgtcg acggaagtcc ggggcagggc gttgttctgg tcaaggaggg tcattacgtt   133800
gacgacaaca acgcccatgt tggtatatta caggcccgtg tccgatttgg ggcacttgca   133860
gatttgtaag gccacgcacg gcggggagac aggccgacgc gggggctgct ctaaaaattt   133920
aagggcccta cggtccacag acccgccttc ccggggggggg ggcccttgga gcgaccggca   133980
gcgtaggcgt ccgggggagg ggagggtgat ttacggggggg gtaggtcagg gggtgggtcg   134040
tcaaactgcc gctccttaaa accccggggc ccgtcgttcg gggtgctcgt tggttggcac   134100
tcacggtgcg gcgaatggcc tgtcgtaagt tttgtcgcgt ttacgggggga cagggcagga   134160 ggaaggagga ggccgtcccg ccggagacaa agccgtcccg ggtgtttcct catggcccct   134220
tttatacccc agccgaggac gcgtgcctgg actccccgcc cccggagacc cccaaacctt   134280
cccacaccac accacccagc gaggccgagc gcctgtttca tctgcaggag atccttgccc   134340
agatgtacgg aaaccaggac tacccccatag aggacgaccc cagcgcggat gccgcggacg   134400
atgtcgacga ggacgcccccg gacgacgtgg cctatccgga ggaatacgca gaggagcttt   134460
ttctgcccgg ggacgcgacc ggtcccctta tcggggccaa cgaccacatc cctccccgt    134520 gtggcgcatc tccccccggt atacgacgac gcagccggga tgagattggg gccacggat    134580 ttaccgcgga agagctggac gccatggaca gggaggcggc tcgagccatc agccgcggcg   134640
gcaagccccc ctcgaccatg gccaagctgg tgactggcat gggctttacg atccacggag   134700
cgctcacccc aggatcggag gggtgtgtct ttgatagcag ccacccagat tacccccaac   134760
gggtaatcgt gaaggcgggg tggtacacga gcacagagcca cgaggcgcga ctgctgaggc   134820
gactggacca ccccgcgatc ctgcccctcc tggacctgca tgtcgtctcc ggggtcacgt   134880
gtctggtcct ccccaagtac caggccgacc tgtataccta tctgagtagg cgcctgaacc   134940
cgctgggacg cccgcagatc gcagcggtct cccggcagct cctaagcgcc gttgactaca   135000
ttcaccgcca gggcattatc caccgcgaca ttaagaccga aaatatttt attaacaccc   135060 ccgaggacat ttgcctgggg gactttggtg ccgcgtgctt cgtgcagggt tcccgatcaa   135120
gccccttccc ctacggaatc gccggaacca tcgacaccaa cgcccccgag gtcctggccg   135180
```

```
gggatccgta taccacgacc gtcgacattt ggagcgccgg tctggtgatc ttcgagactg   135240
ccgtccacaa cgcgtccttg ttctcggccc ccgcggccc caaaaggggc cgtgtgaca    135300
gtcagatcac ccgcatcatc cgacaggccc aggtccacgt tgacgagttt tccccgcatc   135360
cagaatcgcg cctcacctcg cgctaccgct ccgcgcggc cgggaacaat cgcccgcctt   135420
acacccgacc ggcctggacc cgctactaca agatggacat agacgtcgaa tatctggttt   135480
gcaaagccct caccttcgac ggcgcgcttc gccccagcgc cgcagagctg ctttgtttgc   135540
cgctgtttca acagaaatga ccgccccccgg ggggcggtgc tgtttgcggg ttggcacaaa   135600
aagaccccga cccgcgtctg tggtgttttt ggcatcatgt cgccgggcgc catgcgtgcc   135660
gttgttccca ttatcccatt cctttttggtt cttgtcggtg tatcgggggt tcccaccaac   135720
gtctcctcca ccacccaacc ccaactccag accaccggtc gtccctcgca tgaagccccc   135780
aacatgaccc agaccggcac caccgactct cccaccgcca tcagccttac cacgcccgac   135840
cacacaccc ccatgccaag tatcggactg gaggaggagg aggaagagga ggaggggggcc   135900
ggggatggcg aacatcttaa gggggagat ggaccccgtg acaccctacc ccagtccccg   135960
ggtccagccg tcccgttggc cggggatgac gagaaggaca aacccaaccg tcccgtagtc   136020
ccacccccg gtcccaacaa ctcccccgcg cgccccgaga ccagtcgacc gaagacaccc   136080
cccaccagta tcgggccgct ggcaactcga cccacgaccc aactcccctc aaagggggcga   136140
cccttggttc cgacgcctca acatacccg ctgttctcgt tcctcactgc ctccccccgcc   136200
ctggacaccc tcttcgtcgt cagcaccgtc atccacacct tatcgttttt gtgtattggt   136260
gcgatggcga cacacctgtg tggcggttgg tccagacgcg ggcgacgcac acaccctagc   136320
gtgcgttacg tgtgcctgcc gtccgaacgc gggtagggta tggggcgggg gatggggaga   136380
gcccacatgc ggaaagcaag aacaataaag gcggtggtat ctagttgata tgcatctctg   136440
ggtgttttttg gggtgtggcg gacgcggggc ggtcattgga cggggtgcag ttaaatacat   136500
gcccgggacc catgaagcat gcgcgacttc cgggcctcgg aacccacccg aaacggccaa   136560
cggacgtctg agccaggcct ggctatccgg agaaacagca cacgacttgg cgttctgtgt   136620
gtcgcgatgt ctctgcgcgc agtctggcat ctggggcttt tggaagcct cgtgggggct   136680
gttcttgccg ccacccatcg gggacctgcg gccaacacaa cggacccctt aacgcacgcc   136740
ccagtgtccc ctcaccccag cccctgggg ggctttgccg tccccctcgt agtcggtggg   136800
ctgtgcgccg tagtcctggg ggcggcgtgt ctgcttgagc tcctgcgtcg tacgtgccgc   136860
gggtgggggc gttaccatcc ctacatggac ccagttgtcg tataattccc cccccccctt   136920
ctccgcatgg gtgatgtcgg gtccaaactc ccgacaccac cagctggcat ggtataaatc   136980
accggtgcgc cccccaaacc atgtccggca ggggatggg ggggcgaatg cggagggcac   137040
ccaacaacac cgggctaacc aggaaatccg tggccccggc cccaataaa gatcgcggta   137100
gcccggccgt gtgacactat cgtccatacc gaccacaccg acgaatcccc taaggggag   137160
gggccatttt acgaggagga ggggtataac aaagtctgtc tttaaaaagc aggggttagg   137220
gagttgttcg gtcataagct tcagcgcgaa cgaccaacta ccccgatcat cagttatcct   137280
taaggtctct tttgtgtggt gcgttccggt atggggggg ctgccgccag ttggggggcc   137340
gtgattttgt ttgtcgtcat agtgggcctc catgggggtcc gcggcaaata tgccttggcg   137400
gatgcctctc tcaagatggc cgaccccaat cgctttcgcg gcaaagacct tccggtcctg   137460
gaccagctga ccgaccctcc gggggtccgg cgcgtgtacc acatccaggc gggcctaccg   137520
gacccgttcc agcccccccag cctcccgatc acggtttact acgccgtgtt ggagcgcgcc   137580
```

```
tgccgcagcg tgctcctaaa cgcaccgtcg gaggcccccc agattgtccg cggggcctcc   137640
gaagacgtcc ggaaacaacc ctacaacctg accatcgctt ggtttcggat gggaggcaac   137700
tgtgctatcc ccatcacggt catggagtac accgaatgct cctacaacaa gtctctgggg   137760
gcctgtccca tccgaacgca gccccgctgg aactactatg acagcttcag cgccgtcagc   137820
gaggataacc tggggttcct gatgcacgcc cccgcgtttg agaccgccgg cacgtacctg   137880
cggctcgtga agataaacga ctggacggag attacacagt ttatcctgga gcaccgagcc   137940
aagggctcct gtaagtacgc cctcccgctg cgcatccccc cgtcagcctg cctgtccccc   138000
caggcctacc agcaggtggt gacggtggac agcatcggga tgctgccccg cttcatcccc   138060
gagaaccagc gcaccgtcgc cgtatacagc ttgaagatcg ccgggtggca cgggcccaag   138120
gccccataca cgagcaccct gctgcccccg gagctgtccg agaccccaa cgccacgcag   138180 ccagaactcg ccccggaaga ccccgaggat tcggccctct tggaggaccc cgtggggacg   138240
gtggcgccgc aaatcccacc aaactggcac ataccgtcga tccaggacgc cgcgacgcct   138300
taccatcccc cggccacccc gaacaacatg ggcctgatcg ccggcgcggt gggcggcagt   138360
ctcctggcag ccctggtcat ttgcggaatt gtgtactgga tgcgccgccg cactcaaaaa   138420
gccccaaagc gcatacgcct cccccacatc cgggaagacg accagccgtc ctcgcaccag   138480
cccttgtttt actagatacc ccccttaat gggtgcgggg gggtcaggtc tgcggggttg   138540
ggatgggacc ttaactccat ataaagcgag tctggaaggg gggaaaggcg acagtcgat   138600 aagtcggtag cggggacgc gcacctgttc cgcctgtcgc acccacagct ttttttgcga   138660
accgtcccgt tccgggatgc cgtgccgccc gttgcagggc ctggtgctcg tgggcctctg   138720
ggtctgtgcc accagcctgg ttgtccgtgg ccccacggtc agtctggtat caaactcatt   138780
tgtggacgcc ggggccttgg ggcccgacgg cgtagtggag gaagacctgc ttattctcgg   138840
ggagcttcgc tttgtggggg accaggtccc ccacaccacc tactacgatg gggtcgtaga   138900
gctgtggcac taccccatgg gacacaaatg cccacgggtc gtgcatgtcg tcacggtgac   138960
cgcgtgccca cgtcgccccg ccgtggcttt cgccctgtgt cgcgcgaccg acaacactca   139020
cagccccgca tatcccaccc tggagctgaa tctggcccaa cagccgcttt tgcgggtccg   139080
gagggcgacg cgtgactatg ccggggtgta cgtgttacgc gtatgggtcg tggacgcacc   139140
aaacgccagc ctgtttgtcc tggggatggc catagccgcc gaagggactc tggcgtacaa   139200
cggctcggcc catggctcct gcgacccgaa actgcttccg tattcggccc cgcgtctggc   139260
cccggcgagc gtataccaac ccgccccctaa cccggcctcc accccctcga ccaccacctc   139320
caccccctcg accaccacct ccaccccctc gaccaccacc tccacccct cgaccaccac   139380 ctccaccccc tcgaccacca cctccacccc ctcgaccacc acctccaccc cctcgaccac   139440
catccccgct ccccaagcat cgaccacacc cttcccccacg ggagacccaa accccccaacc   139500 tcacggggtc aaccacgaac ccccatcgaa tgccacgcga gcgacccgcg actcgcgata   139560
cgcgctaacg gtgacccaga taatccagat agccatcccc gcgtccatta tagccctggt   139620
gtttctgggg agctgtattt gctttataca cagatgtcaa cgccgctacc gacgctcccg   139680
ccgcccgatt tacaaccccc agatacccac gggcatctca tgcgcggtga acgaagcggc   139740
catggcccgc ctcggagccg agctcaaatc gcatccgagc accccccccca aatcccggcg   139800 ccggtcgtca cgcacgccaa tgccctccct gacggccatc gccgaagagt cggagcccgc   139860
gggggcggct gggcttccga cgccccccgt ggaccccacg acatccaccc caacgcctcc   139920
```

```
cctgttggta taggtccacg gccactggcc gggggcacca cataaccgac cgcagtcact   139980
gagttgggaa taaaccggta ttatttacct atatccgtgt atgtccattt ctttcccccc   140040
cccccccccc cggaaaccca agaaggaag caaagaatgg atgggaggag ttcaggaagc   140100
cggggagagg gcccgcggcg catttaaggc gttgttgtgt tgactttggc tcttctggcg   140160
ggttggtgcg gtgctgtttg ttgggctccc attttacccg aagatcggct gctatccccg   140220
ggacatggat cgcggggcgg tggtgggggtt tcttctcggt gtttgtgttg tatcgtgctt   140280
ggcgggaatg cccaaaacgt cctggagacg ggtgagtgtc ggcgaggacg tttcgttgct   140340
tccagctccg gggcctacgg ggcgcggccc gacccagaaa ctactatggg ccgtggaacc   140400
cctggatggg tgcggcccct tacacccgtc gtgggtctcg ctgatgcccc ccaagcaggt   140460
gcccgagacg gtcgtggatg cggcgtgcat cgcgctccg gtcccgctgg cgatggcgta   140520
cgcccccccg gccccatctg cgaccggggg tctacgaacg gacttcgtgt ggcaggagcg   140580
cgcggccgtg gttaaccgga gtctggttat tcacggggtc cgagagacgg acagcggcct   140640
gtataccctg tccgtgggcg acataaagga cccggctcgc caagtggcct cggtggtcct   140700
ggtggtgcaa ccggccccag ttccgacccc acccccgacc ccagccgatt acgacgagga   140760
tgacaatgac gagggcgagg gcgaggacga aagtctagcc ggcactcccg ccagcgggac   140820 ccccccggctc ccgcctcccc ccgcccccc gaggtcttgg cccagcgccc ccgaagtctc   140880
acacgtgcgt ggggtgaccg tgcgtatgga gactccggaa gctatcctgt tttccccccg   140940
ggaggcgttt agcacgaacg tctccatcca tgccatcgcc cacgacgacc agacctacac   141000 catgacgtc gtctggttga ggttcgacgt gccgacctcg tgtgccgaga tgcgaatata   141060
cgaatcgtgt ctgtatcacc cgcagctccc agagtgtctg tccccggccg acgctccgtg   141120
cgccgcgagt acgtggacgt ctcgcctggc cgtccgcagc tacgcggggt gttccagaac   141180
aaaccccccg ccgcgctgtt cggccgaggc tcacatggag cccttcccgg ggctggcgtg   141240
gcaggcggcc tccgtcaatc tggagttccg ggacgcgtcc ccacaacact ccggcctgta   141300
tctgtgcgtg gtgtacgtca acgaccatat tcacgcatgg ggccacatta ccatcagcac   141360
cgcggcgcag taccggaacg cggtggtgga acagcccctc ccacagcgcg cgcggattt   141420 ggccgagccc acccacccgc acgtcggggc ccctccccac gcgcccccaa cccacggcgc   141480
cctgcggtta ggggcggtga tgggggccgc cctgctgctg tctgcgctgg ggttgtcggt   141540
gtgggcgtgt atgacctgtt ggcgcaggcg tgcctggcgg gcggttaaaa gcagggcctc   141600
gggtaagggg cccacgtaca ttcgcgtggc cgacagcgag ctgtacgcgg actgagctc   141660 ggacagcgag ggagaacgcg accaggtccc gtggctggcc cccccggaga gacccgactc   141720
tccctccacc aatggatccg gctttgagat cttatcacca acggctccgt ctgtatcccc   141780
ccgtagcgat gggcatcaat ctcgccgcca gctcacaacc tttggatccg gaaggcccga   141840
tcgccgttac tccaggcct ccgattcgtc cgtcttctgg taaggcgccc catcccgagg   141900
ccccacgtcg gtcgccgaac tgggcgaccg ccggcgaggt ggacgtcgga gacgagctaa   141960
tcgcgatttc cgacgaacgc ggaccccccc gacatgaccg cccgcccctc gccacgtcga   142020
ccgcgccctc gccacacccg cgaccccgg gctacacggc cgttgtctcc ccgatggccc   142080
tccaggctgt cgacgccccc tccctgttg tcgcctggct ggccgctcgg tggctccggg   142140
gggcttccgg cctgggggcc gtcttgtgtg ggattgcgtg gtatgtgacg tcaattgccc   142200
gaggcgcata aagggccggt ggtccgccta gccgcagcaa attaaaaatc gtgagtcact   142260
gcgaccgcaa cttcccaccc ggagctttct tccggcctcg atgacgtccc ggctctccga   142320
```

```
tcccaactcc tcagcgcgat ccgacatgtc cgtgccgctt tatcccacgg cctcgccagt   142380
ttcggtcgaa gcctactact cggaaagcga agacgaggcg gccaacgact tcctcgtacg   142440
catgggccgc caacagtcgg tattaaggcg tcgacgcaga cgcacccgct gcgtcggcat   142500
ggtgatcgcc tgtctcctcg tggccgttct gtcgggcgga tttggggcgc tcctgatgtg   142560
gctgctccgc taaaagaccg catcgacacg cgcgtccttc ttgtcgtctc tcttccccccc  142620 atcaccccgc aatttgcacc cagcctttaa ctacattaaa ttgggttcga ttggcaatgt   142680
tgtctcccgg ttgatttttg ggtgggtggg gagtgggtgg gtggggagtg ggtgggtggg   142740
gagtgggtgg gtggggagtg ggtgggtggg gagtgggtgg gtggggagtg ggtgggtggg   142800
gagtgggtgg gtggggagtg ggtgggtggg gagtgggtgg gtggggagtg ggtgggtggg   142860
gagtgggtgg gtggggagtg ggtgggtggg gagtgggtgg gtggggagtg ggtgggtggg   142920
gagtgggtgg gtggggagtg gcaaggaaga aacaagcccg accaccagac agaaaatgta   142980
accataccca aaccgactct gggggctgtt tgtggggtcg gaaccatagg atgaacaaac   143040
caccccgtac ctcccgcacc cttgggtgcg ggtggctcat cggcatctgt ccggtatggg   143100
ttgttcccca cccactcgcg ttcggacgtc ttagaatcat ggcggtttct atgccgacat   143160
cggtttctcc cccgcaataa gacacgatgc gataaaatct gtttgtgaaa tttattaagg   143220
gtacaaattg ccctagcaca ggggtggggt tagggccggg tccccacacc caaacgcacc   143280
aaacagatgc aggcagtggg tcgagtacag ccccgcgtac gaacacgtcg atgcgtgtgt   143340
cagacagcac cagaaagcac aggccatcaa caggtcgtgc atgtgtcggt gggtttggac   143400
gcggggggcc atggtgggtg ataaagttaa tggccgccgt ccgccagggc cacaggggcg   143460
acgtctcttg gttggcccgg agccactggg tgtggaccag ccgcgcgtgg cggcccaaca   143520
tggcccctgt agccgggggc gggggatcgc gcacgtttgc agcgcacatg cgagacacct   143580
cgaccacggt tcggaagaag gcccggtggt ccgcgggcaa catcaccagg tgcgcaagcg   143640
cccgggcgtc cagagggtag agccctgagt catccgaggt tggctcatcg cccgggtcat   143700
gccgcaagtg cgtgtgggtt gggcttccgg tgggcgggac gcgaaccgcg gtgtggagcc   143760
cgacgcgggc ccgagcgtac gctccatctt gtggggagaa ggggtctggg ctcgccaggg   143820
gggcatactt gcccgggcta tacagacccg cgagccgtac gtggttcgcg ggggtgcgt   143880 ggggtccggg gctcccgggg aggccgggc tcccgggtt gtcgtggatc cctggggtca   143940
cgcggtaccc tggggtctct gggagctcgc ggtactctgg gttccctagg ttctcggggt   144000
ggtcgcggaa cccggggctc ccggggaaca cgcggtgtcc tggggattgt tggcggtcgg   144060
acggcttcag atggcttcga gatcgtagtg tccgcaccga ctcgtagtag acccgaatct   144120
ccacattgcc ctgccgcttg atcattatca ccccgttgcg ggggtccgga gatcatcgc   144180 gggtgtcctc gaggtgcgtg aacacctctg gggtgcatgc cggcggacgg cacgcctttt   144240
aagtaaacat ctgggtcgcc cggcccaact ggggccgggg gttgggtctg gctcatctcg   144300
agagccacgg ggggaaccac cctccgccca gaaacttggg cgatggtcgt acccgggact   144360
caacgggtta ccggattacg gggactgtcg gtcacggtcc cgccggttct tcgatgtgcc   144420
acacccaagg atgcgttggg ggcgattttg ggcagcagcc cggagagcg cagcaggaga   144480 cgctccgggt cgtgcacggc ggttctggcc gcctccggt cctcacgccc cctttattg    144540 atctcatcgc gtacgtcggc gtacgtcctg ggccaacccc gcatgttgtc caggaaggtg   144600
tccgccattt ccagggccca cgacatgctc ccccccccc ccccgacgag caggaagcgg    144660
```

```
tccacgcaac ggtcgccgcc ggtcgccccg acgagcagga agcggtccac gcaacggtcg   144720
ccgccggtcg ccccgacgag caggaagcgg tccacgcaac ggtcgccgcc ggtcgcctcg   144780
acgaggacgt tcctcctgcg ggaaggcacg aacgcgggtg agccccctcc tccgccccg    144840 cgtcccccct cctccgcccc cgcgtccccc ctcctccgcc cccgcgtccc cctcctccg    144900 cccccgcgtc ccccctcctc cgccctcctc cgcccaccca aggtgcttac ccgtgcaaaa   144960
aggcggaccg gtgggtttct gtcgtcggag gccccgggg tgcgtcccct gtgtttcgtg    145020
ggtggggtgg gtgggtcttt ccgcgtgtcc ctttccgatg cgatcccgat cccgagccgg   145080
ggcgtcgcga tgccgacgcc gtccgctccg acggccctct gcgagtcccg ctcccggtcc   145140
gcgtgctccg cagcagctcc cgtcgttcgt ggccggcgcc gtctgcgggc gtcggtcgcg   145200
ccgggccttt atgtgcgccg gagagacccg ccccccgccg cccggcccg ccccggggc     145260 cggcgcggag tcgggcacgg cgccagtgct cgcacttcgc cctaataata tatatatatt   145320
gggacgaagt gcgaacgctt cgcgttctca cttcttttac ccggcggccc cgccccttg    145380 gggcggtccc gcccgccggc caatgggggg gcggcaaggc gggcggccct tgggccgccc   145440
gccgtcccgt tggtcccggc gtccggcggg cgggaccggg ggcccgggga cggccaacgg   145500
gcgcgcgggg ctcgtatctc attaccgccg aaccgggaag tcggggcccg ggccccgccc   145560
cctgcccgtt cctcgttagc atgcggaacg gaagcgaaaa ccgccggatc gggcggtaat   145620
gagatgccat gcggggcggg gcgcgggccc accgcccta gcgcccccgcc catggcagat    145680 ggcgcggatg ggcggggccg ggggttcgac caacgggccg cggccacggg ccccccggcgt   145740 gccggcgtcg gggcggggtc gtgcataatg gaattccgtt cggggcgggc ccgccgtggg   145800 ggcgggggc cggcggcctc cgctgctcct ccttcccgcc ggccctggg actatatgag     145860 cccgaggacg ccccgatcgt ccacacggag cgcggctgcc gacacggatc cacgacccga   145920
cgcgggaccg ccagagacag accgtcagac gctcgccgcg ccgggacgcc gatacgcgga   145980
cgaagcgcgg gaggggatc ggccgtccct gtccttttc ccacccaagc atcgaccggt     146040
ccgcgctagt tccgcgtcga cggcgggggt cgtcgggtc cgtgggtctc gccccctccc    146100
catcgagagt ccgtaggtga cctaccgtgc tacgtccgcc gtcgcagtcg tatccccgga   146160
ggatcgcccc gcatcggcga tggcgtcgga gaacaagcag cgccccggct ccccgggccc   146220
caccgacggg ccgccgccca ccccgagccc agaccgcgac gagcgggggg ccctcgggtg   146280
gggcgcggag acggaggagg gcggggacga ccccgaccac gaccccgacc accccacga    146340 cctcgacgac gcccggcggg acgggagggc ccccgcggcg ggcaccgacg ccggcgagga   146400
cgccggggac gccgtctcgc cgcgacagct ggccctgctg gcctccatgg tagaggaggc   146460
cgtccggacg atcccgacgc ccgaccccgc ggcctcgccg ccccggaccc ccgcctttcg   146520
agccgacgac gatgacgggg acgagtacga cgacgcagcc gacgccgccg gcgaccgggc   146580
cccgccccgg ggccgcgcac gggaggcccc gctacgcggc gcgtatccgg accccacgga   146640
ccgcctgtcg ccgcgcccgc cggccagcc gccgcagaga cgtcgtcacg gccggcggcg    146700
gccatcggcg tcatcgacct cgtcggactc cgggtcctcg tcctcgtcgt ccgcatcctc   146760
ttcgtcctcg tcgtccgacg aggacgagga cgacgacgc aacgacgcgg ccgaccacgc     146820
acgcgaggcg cgggccgtcg ggcggggtcc gtcgagcgcg gcgccggaag ccccgggcg     146880 gacgccgccc ccgcccgggc caccccccct ctccgaggcc gcgccaagc ccgggcggc     146940 ggcgaggacc cccgcggcct ccgcgggccg catgagcgc cgccgggccc gcggcggt      147000 ggccggccgc gacgccacgg gccgcttcac ggccgggcag ccccggcggg tcgagctgga   147060
```

```
cgccgacgcg gcctccggcg ccttctacgc gcgctatcgc gacgggtacg tcagcgggga   147120
gccgtggccc ggcgccgggc ccccgccccc ggggcgggtg ctgtacggcg gcctgggcga   147180
cagccgcccg ggcctctggg gggcgcccga ggcggaggag gcgcgacgcc ggttcgaggc   147240
ctcgggcgcc ccggcggccg tgtgggcgcc cgagctgggc gacgccgcgc agcagtacgc   147300
cctgatcacg cggctgctgt acaccccgga cgcggaggcc atggggtggc tccagaaccc   147360
gcgcgtggtc cccggggacg tggcgctgga ccaggcctgc ttccggatct cgggcgccgc   147420
gcgcaacagc agctccttca tcaccggcag cgtggcgcgg gccgtgcccc acctgggcta   147480
cgccatggcg gccggccgct tcggctgggg cctggcgcac gcggcggccg ccgtggccat   147540
gagccgccga tacgaccgcg cgcagaaggg cttcctgctg accagcctgc gccgcgccta   147600
cgcgcccctg ttggcgcgcg agaacgcggc gctgacgggg gccgcgggga gccccggcgc   147660
cggcgcagat gacgaggggg tcgccgccgc cgtcgtcgcc gccgccgccg caccgggcga   147720
gcgcgcggtg cccgccgggt acggcgccgc ggggatcctc gccgccctgg ggcggctgtc   147780
cgccgcgccc gcctccccccg cgggggggcga cgaccccgac gccgcccgcc acgccgacgc   147840
cgacgacgac gccgggcgcc gcgcccaggc cggccgcgtg gccgtggagt gcctggccgc   147900
ctgccgcggg atcctggagg cgctggccga gggcttcgac ggcgacctgg cggccgtccc   147960
ggggctggcc ggggccccggc ccgccagccc ccgcggccg gagggacccg cgggccccgc   148020
ttccccgccg ccgccgcacg ccgacgcgcc ccgcctgcgc gcgtggctgc gcgagctgcg   148080
gttcgtgcgc gacgcgctgg tgctcatgcg cctgcgcggg gacctgcgcg tggcggcgg   148140 cagcgaggcc gccgtggccg ccgtgcgcgc cgtgagcctg gtcgccgggg ccctgggtcc   148200
cgcgctgccg cgggacccgc gcctgccgag ctccgcggcc gccgccgccg cggacctgct   148260
gtttgagaac cagagcctgc gccccctgct ggcggcgggt ccgcgccgct cttcttcgtc   148320 ttcggggtc gcggccgccg cctccgccgc gccgcgggag gggcgcaagc gcaagagtcc   148380
cggcccggcc cggccgcccg gaggcggcgg cccgcgaccc ccgaagacga agaagagcgg   148440
cgcggacgcc cccggctcgg acgcccgcgc cccccctcccc gcgccgcgc ccccctccac   148500 gcccccgggg cccgagcccg cccccgccca gcccgcggcg ccccggggccg ccgcggcgca   148560 ggcccgcccg cgccccgtgg cgctgtcgcg ccggcccgcc gagggcccg accccctggg   148620 cggctggcgg cggcagcccc cggggcccag ccacacggcg gcgcccgcgg ccgccgccct   148680
ggaggcctac tgctccccgc gcgccgtggc cgagctcacg gaccacccgc tgttccccgt   148740
cccctggcga ccgccccctca tgtttgaccc gcggggccctg gcctcgatcg ccgcgcggtg   148800
cgccgggccc gccccgcccg cccaggccgc gtgcggcggc ggcgacgacg acgagaaccc   148860
ccacccccac ggggccgccg ggggccgcct ctttggcccc ctgcgcgcct cgggccgct   148920 gcgccgcatg gcggcctgga tgcgccagat ccccgacccc gaggacgtgc gcgtggtggt   148980
gctgtactcg ccgctgccgg gcgaggacct ggccggcggc ggggcctcgg gggggccgcc   149040
ggagtggtcc gccgagcgcg gcgggctgtc ctgcctgctg gcggccctgg ccaaccggct   149100
gtgcgggccg gacacggccg cctgggcggg caactggacc ggcgccccg acgtgtcggc   149160 gctgggcgca cagggcgtgc tgctgctgtc cacgcgggac ctggccttcg ccggggccgt   149220
ggagtttctg gggctgctcg ccagcgccgg cgaccggcgg ctcatcgtgg tcaacaccgt   149280
gcgcgcctgc gactgccccg ccgacgggcc gcggtgtcg cggcagcacg cctacctggc   149340
gtgcgacctg ctgcccgccg tgcagtgcgc cgtgcgctgg ccggcggcgc gcgacctgcg   149400
```

-continued

```
ccgcacggtg ctggcctcgg gccgcgtgtt cggcccgggg gtcttcgcgc gcgtggaggc 149460
cgcgcacgcg cgcctgtacc ccgacgcgcc gccgctgcgc ctgtgccgcg gcggcaacgt 149520
gcgctaccgc gtgcgcacgc gcttcggccc ggacacgccg gtgcccatgt ccccgcgcga 149580
gtaccgccgg gccgtgctgc cggcgctgga cggccgggcg gcggcctcgg ggaccaccga 149640
cgccatggcg cccggcgcgc cggacttctg cgaggaggag gcccactcgc accgcgcctg 149700
cgcgcgctgg ggcctgggcg cgccgctgcg gcccgtgtac gtggcgctgg ggcgcgaggc 149760
ggtgcgcgcc ggcccggccc ggtggcgcgg gccgcggagg gacttttgcg cccgcgccct 149820
gctggagccc gacgacgacg ccccccccgct ggtgctgcgc ggcgacgacg acggcccggg 149880
ggccctgccg ccggcgccgc ccgggattcg ctgggcctcg gccacgggcc gcagcggcac 149940
cgtgctggcg gcggcggggg ccgtggaggt gctgggggcg gaggcgggct tggccacgcc 150000
cccgcgacgg gacgttgtgg actgggaagg cgcctgggac gaagacgacg gcggcgcgtt 150060
cgagggggac ggggtgctgt aacgggccgg gacggggcgg ggcgcttgtg aaacccgaag 150120
acgcaataaa cggcaacgac ctgattaagt tttgcagtag cgttgtttat tcgagggcg 150180
ggagggggcg aggggcggga ggggcgcagg ggcgggaggg ggcgaggggc gggaggggc 150240
gagggcggg aggggcgag gggcgggagg gggcgagggg cgggaggggg cgaggggcgg 150300
gaggggcga ggggcggtgg tggtgcgcgg gcgcccccgg agggttttgga tctctgacct 150360
gagattggcg gcactgaggt agagatgccc gaacccccc gagggagcgc gggacgcggc 150420
tggggagggc tggggctggg gagggctggg gctgggggag gctgggggctg gggagggctg 150480
gggctgggga gggctggggc tggggagggc tgggggctggg gagggctggg gctggggagg 150540
gctgggggctg gggagggctg gggctgggga gggctggggc tggggagggc tggggctggg 150600
gagggctggg gctgtggtgt gtgacaggag cggcgtgttg cgctggggga cgtctggagg 150660
agcggggggt gcgcggtgac gtgtggatga ggaacaggag ttgttgcgcg gtgagttgtc 150720
gctgtgagtt gtgttgttgg gcaggtgtgt tggatgacgt gacgtgtgga tgaggaaccg 150780
gagtcgccgg tgcgccgtgc tgttggtgtt ctgttggtgt tgttacacct gtggcagccc 150840
gggccccccg cgcgcgggc ggcgcgcaaa aaaggcgggc ggcggtccgg gcggcgtgcg 150900
cgcgcgcggc gggcgtgggg ggcggggccg cgggagcggg ggaggagccc cacccacaga 150960
cggggaggag cggggggagga gcgggggagg agcgggggag gagcccccacc cacagacggg 151020
gaggagcggg ggaggagcgg ccagacccca aaaacgggcc ccccgaaaac acacccccg 151080
ggggtcgcgc gcggcccttt aaagcgcggc ggcgggcagc ccgggccccc cgcgg     151135
```

<210> SEQ ID NO 2
<211> LENGTH: 1300
<212> TYPE: PRT
<213> ORGANISM: human herpesvirus 1 strain McKrae ICP4

<400> SEQUENCE: 2

Met Ala Ser Glu Asn Lys Gln Arg Pro Gly Ser Pro Gly Pro Thr Asp
1               5                   10                  15

Gly Pro Pro Pro Thr Pro Ser Pro Asp Arg Asp Glu Arg Gly Ala Leu
            20                  25                  30

Gly Trp Gly Ala Glu Thr Glu Glu Gly Gly Asp Asp Pro Asp His Asp
        35                  40                  45

Pro Asp His Pro His Asp Leu Asp Asp Ala Arg Arg Asp Gly Arg Ala
    50                  55                  60

Pro Ala Ala Gly Thr Asp Ala Gly Glu Asp Ala Gly Asp Ala Val Ser

-continued

```
                65                  70                  75                  80
Pro Arg Gln Leu Ala Leu Leu Ala Ser Met Val Glu Ala Val Arg
                    85                  90                  95
Thr Ile Pro Thr Pro Asp Pro Ala Ala Ser Pro Pro Arg Thr Pro Ala
                100                 105                 110
Phe Arg Ala Asp Asp Asp Asp Gly Asp Glu Tyr Asp Asp Ala Ala Asp
                115                 120                 125
Ala Ala Gly Asp Arg Ala Pro Ala Arg Gly Arg Ala Arg Glu Ala Pro
            130                 135                 140
Leu Arg Gly Ala Tyr Pro Asp Pro Thr Asp Arg Leu Ser Pro Arg Pro
145                 150                 155                 160
Pro Ala Gln Pro Pro Gln Arg Arg His Gly Arg Arg Pro Ser
                    165                 170                 175
Ala Ser Ser Thr Ser Ser Asp Ser Gly Ser Ser Ser Ser Ser Ala
                180                 185                 190
Ser Ser Ser Ser Ser Ser Ser Asp Glu Asp Glu Asp Asp Gly Asn
            195                 200                 205
Asp Ala Ala Asp His Ala Arg Glu Ala Arg Ala Val Gly Arg Gly Pro
        210                 215                 220
Ser Ser Ala Ala Pro Glu Ala Pro Gly Arg Thr Pro Pro Pro Gly
225                 230                 235                 240
Pro Pro Pro Leu Ser Glu Ala Ala Pro Lys Pro Arg Ala Ala Ala Arg
                    245                 250                 255
Thr Pro Ala Ala Ser Ala Gly Arg Ile Glu Arg Arg Ala Arg Ala
                260                 265                 270
Ala Val Ala Gly Arg Asp Ala Thr Gly Arg Phe Thr Ala Gly Gln Pro
    275                 280                 285
Arg Arg Val Glu Leu Asp Ala Asp Ala Ala Ser Gly Ala Phe Tyr Ala
290                 295                 300
Arg Tyr Arg Asp Gly Tyr Val Ser Gly Glu Pro Trp Pro Gly Ala Gly
305                 310                 315                 320
Pro Pro Pro Pro Gly Arg Val Leu Tyr Gly Gly Leu Gly Asp Ser Arg
                    325                 330                 335
Pro Gly Leu Trp Gly Ala Pro Glu Ala Glu Glu Ala Arg Arg Arg Phe
            340                 345                 350
Glu Ala Ser Gly Ala Pro Ala Ala Val Trp Pro Glu Leu Gly Asp
        355                 360                 365
Ala Ala Gln Gln Tyr Ala Leu Ile Thr Arg Leu Leu Tyr Thr Pro Asp
    370                 375                 380
Ala Glu Ala Met Gly Trp Leu Gln Asn Pro Arg Val Val Pro Gly Asp
385                 390                 395                 400
Val Ala Leu Asp Gln Ala Cys Phe Arg Ile Ser Gly Ala Ala Arg Asn
                    405                 410                 415
Ser Ser Ser Phe Ile Thr Gly Ser Val Ala Arg Ala Val Pro His Leu
                420                 425                 430
Gly Tyr Ala Met Ala Ala Gly Arg Phe Gly Trp Gly Leu Ala His Ala
            435                 440                 445
Ala Ala Ala Val Ala Met Ser Arg Arg Tyr Asp Arg Ala Gln Lys Gly
        450                 455                 460
Phe Leu Leu Thr Ser Leu Arg Arg Ala Tyr Ala Pro Leu Leu Ala Arg
465                 470                 475                 480
Glu Asn Ala Ala Leu Thr Gly Ala Ala Gly Ser Pro Gly Ala Gly Ala
                    485                 490                 495
```

-continued

```
Asp Asp Glu Gly Val Ala Ala Val Val Ala Ala Ala Pro
            500                 505             510
Gly Glu Arg Ala Val Pro Ala Tyr Gly Ala Ala Gly Ile Leu Ala
            515                 520             525
Ala Leu Gly Arg Leu Ser Ala Ala Pro Ala Ser Pro Ala Gly Gly Asp
            530                 535             540
Asp Pro Asp Ala Ala Arg His Ala Asp Ala Asp Asp Asp Ala Gly Arg
545                 550                 555             560
Arg Ala Gln Ala Gly Arg Val Ala Val Glu Cys Leu Ala Ala Cys Arg
                565                 570             575
Gly Ile Leu Glu Ala Leu Ala Glu Gly Phe Asp Gly Asp Leu Ala Ala
            580                 585             590
Val Pro Gly Leu Ala Gly Ala Arg Pro Ala Ser Pro Pro Arg Pro Glu
            595                 600             605
Gly Pro Ala Gly Pro Ala Ser Pro Pro Pro His Ala Asp Ala Pro
            610                 615             620
Arg Leu Arg Ala Trp Leu Arg Glu Leu Arg Phe Val Arg Asp Ala Leu
625                 630                 635             640
Val Leu Met Arg Leu Arg Gly Asp Leu Arg Val Ala Gly Gly Ser Glu
                645                 650             655
Ala Ala Val Ala Ala Val Arg Ala Val Ser Leu Val Ala Gly Ala Leu
                660                 665             670
Gly Pro Ala Leu Pro Arg Asp Pro Arg Leu Pro Ser Ser Ala Ala Ala
            675                 680             685
Ala Ala Ala Asp Leu Leu Phe Glu Asn Gln Ser Leu Arg Pro Leu Leu
            690                 695             700
Ala Ala Gly Pro Arg Arg Ser Ser Ser Ser Gly Val Ala Ala Ala
705                 710                 715             720
Ala Ser Ala Ala Pro Arg Glu Gly Arg Lys Arg Lys Ser Pro Gly Pro
                725                 730             735
Ala Arg Pro Pro Gly Gly Gly Pro Arg Pro Pro Lys Thr Lys Lys
            740                 745             750
Ser Gly Ala Asp Ala Pro Gly Ser Asp Ala Arg Ala Pro Leu Pro Ala
            755                 760             765
Pro Ala Pro Pro Ser Thr Pro Pro Gly Pro Glu Pro Ala Pro Ala Gln
770                 775                 780
Pro Ala Ala Pro Arg Ala Ala Ala Gln Ala Arg Pro Arg Pro Val
785                 790                 795             800
Ala Leu Ser Arg Arg Pro Ala Glu Gly Pro Asp Pro Leu Gly Gly Trp
            805                 810             815
Arg Arg Gln Pro Pro Gly Pro Ser His Thr Ala Ala Pro Ala Ala Ala
            820                 825             830
Ala Leu Glu Ala Tyr Cys Ser Pro Arg Ala Val Ala Glu Leu Thr Asp
            835                 840             845
His Pro Leu Phe Pro Val Pro Trp Arg Pro Ala Leu Met Phe Asp Pro
            850                 855             860
Arg Ala Leu Ala Ser Ile Ala Ala Arg Cys Ala Gly Pro Ala Pro Ala
865                 870                 875             880
Ala Gln Ala Ala Cys Gly Gly Asp Asp Asp Glu Asn Pro His Pro
                885                 890             895
His Gly Ala Ala Gly Gly Arg Leu Phe Gly Pro Leu Arg Ala Ser Gly
            900                 905             910
```

```
Pro Leu Arg Arg Met Ala Ala Trp Met Arg Gln Ile Pro Asp Pro Glu
        915                 920                 925

Asp Val Arg Val Val Leu Tyr Ser Pro Leu Pro Gly Glu Asp Leu
    930                 935                 940

Ala Gly Gly Gly Ala Ser Gly Gly Pro Pro Glu Trp Ser Ala Glu Arg
945                 950                 955                 960

Gly Gly Leu Ser Cys Leu Leu Ala Ala Leu Ala Asn Arg Leu Cys Gly
            965                 970                 975

Pro Asp Thr Ala Ala Trp Ala Gly Asn Trp Thr Gly Ala Pro Asp Val
        980                 985                 990

Ser Ala Leu Gly Ala Gln Gly Val Leu Leu Leu Ser Thr Arg Asp Leu
    995                 1000                1005

Ala Phe Ala Gly Ala Val Glu Phe Leu Gly Leu Leu Ala Ser Ala
    1010                1015                1020

Gly Asp Arg Arg Leu Ile Val Val Asn Thr Val Arg Ala Cys Asp
    1025                1030                1035

Trp Pro Ala Asp Gly Pro Ala Val Ser Arg Gln His Ala Tyr Leu
    1040                1045                1050

Ala Cys Asp Leu Leu Pro Ala Val Gln Cys Ala Val Arg Trp Pro
    1055                1060                1065

Ala Ala Arg Asp Leu Arg Arg Thr Val Leu Ala Ser Gly Arg Val
    1070                1075                1080

Phe Gly Pro Gly Val Phe Ala Arg Val Glu Ala Ala His Ala Arg
    1085                1090                1095

Leu Tyr Pro Asp Ala Pro Pro Leu Arg Leu Cys Arg Gly Gly Asn
    1100                1105                1110

Val Arg Tyr Arg Val Arg Thr Arg Phe Gly Pro Asp Thr Pro Val
    1115                1120                1125

Pro Met Ser Pro Arg Glu Tyr Arg Arg Ala Val Leu Pro Ala Leu
    1130                1135                1140

Asp Gly Arg Ala Ala Ala Ser Gly Thr Thr Asp Ala Met Ala Pro
    1145                1150                1155

Gly Ala Pro Asp Phe Cys Glu Glu Glu Ala His Ser His Arg Ala
    1160                1165                1170

Cys Ala Arg Trp Gly Leu Gly Ala Pro Leu Arg Pro Val Tyr Val
    1175                1180                1185

Ala Leu Gly Arg Glu Ala Val Arg Ala Gly Pro Ala Arg Trp Arg
    1190                1195                1200

Gly Pro Arg Arg Asp Phe Cys Ala Arg Ala Leu Leu Glu Pro Asp
    1205                1210                1215

Asp Asp Ala Pro Pro Leu Val Leu Arg Gly Asp Asp Asp Gly Pro
    1220                1225                1230

Gly Ala Leu Pro Pro Ala Pro Pro Gly Ile Arg Trp Ala Ser Ala
    1235                1240                1245

Thr Gly Arg Ser Gly Thr Val Leu Ala Ala Ala Gly Ala Val Glu
    1250                1255                1260

Val Leu Gly Ala Glu Ala Gly Leu Ala Thr Pro Pro Arg Arg Asp
    1265                1270                1275

Val Val Asp Trp Glu Gly Ala Trp Asp Glu Asp Asp Gly Gly Ala
    1280                1285                1290

Phe Glu Gly Asp Gly Val Leu
    1295                1300
```

```
<210> SEQ ID NO 3
<211> LENGTH: 420
<212> TYPE: PRT
<213> ORGANISM: human herpesvirus 1 strain McKrae ICP22

<400> SEQUENCE: 3
```

Met Ala Asp Ile Ser Pro Gly Ala Phe Ala Pro Cys Val Lys Ala Arg
1               5                   10                  15

Arg Pro Ala Leu Arg Ser Pro Leu Gly Thr Arg Lys Arg Lys Arg
            20                  25                  30

Pro Ala Arg Pro Leu Ser Ser Glu Ser Glu Val Glu Thr Asp Thr Ala
            35                  40                  45

Leu Glu Ser Glu Val Glu Ser Glu Thr Ala Ser Asp Ser Thr Glu Ser
 50                  55                  60

Gly Asp Gln Glu Glu Ala Pro Arg Ile Gly Gly Arg Arg Ala Pro Arg
 65                  70                  75                  80

Arg Leu Gly Gly Arg Phe Phe Leu Asp Met Ser Ala Glu Ser Thr Thr
                85                  90                  95

Gly Thr Glu Thr Asp Thr Ala Val Ser Asp Asp Pro Asp Asp Thr Ser
            100                 105                 110

Asp Trp Ser Tyr Asp Asp Ile Pro Pro Arg Pro Lys Arg Ala Arg Val
            115                 120                 125

Asn Leu Arg Leu Thr Ser Ser Pro Asp Arg Arg Asp Gly Val Ile Phe
130                 135                 140

Pro Lys Met Gly Arg Val Arg Ser Thr Arg Glu Thr Gln Pro Arg Ala
145                 150                 155                 160

Pro Thr Pro Ser Ala Pro Ser Pro Asn Ala Met Leu Arg Arg Ser Val
                165                 170                 175

Arg Gln Ala Gln Arg Arg Ser Ser Ala Arg Trp Thr Pro Asp Leu Gly
            180                 185                 190

Tyr Met Arg Gln Cys Ile Asn Gln Leu Phe Arg Val Leu Arg Val Ala
            195                 200                 205

Arg Asp Pro His Gly Ser Ala Asn Arg Leu Arg His Leu Ile Arg Asp
210                 215                 220

Cys Tyr Leu Met Gly Tyr Cys Arg Ala Arg Leu Ala Pro Arg Thr Trp
225                 230                 235                 240

Cys Arg Leu Leu Gln Val Ser Gly Gly Thr Trp Gly Met His Leu Arg
                245                 250                 255

Asn Thr Ile Arg Glu Val Glu Ala Arg Phe Asp Ala Thr Ala Glu Pro
            260                 265                 270

Val Cys Lys Leu Pro Cys Leu Glu Ala Arg Arg Tyr Gly Pro Glu Cys
            275                 280                 285

Asp Leu Ser Asn Leu Glu Ile His Leu Ser Ala Thr Ser Asp Asp Glu
290                 295                 300

Ile Ser Asp Ala Thr Asp Leu Glu Ala Ala Gly Ser Asp His Thr Leu
305                 310                 315                 320

Ala Ser Gln Ser Asp Thr Glu Asp Ala Pro Ser Val Thr Leu Glu
                325                 330                 335

Thr Pro Glu Pro Arg Gly Ser Leu Ala Val Arg Leu Glu Asp Glu Phe
            340                 345                 350

Gly Glu Phe Asp Trp Thr Pro Gln Glu Gly Ser Gln Pro Trp Leu Ser
            355                 360                 365

Ala Val Val Ala Asp Thr Ser Ser Val Glu Arg Pro Gly Pro Ser Asp
370                 375                 380

```
Ser Gly Ala Gly Arg Ala Ala Glu Asp Arg Lys Cys Leu Asp Gly Cys
385                 390                 395                 400

Arg Lys Met Arg Phe Ser Thr Ala Cys Pro Tyr Pro Cys Ser Asp Thr
                405                 410                 415

Phe Leu Arg Pro
            420

<210> SEQ ID NO 4
<211> LENGTH: 88
<212> TYPE: PRT
<213> ORGANISM: human herpesvirus 1 strain McKrae ICP47

<400> SEQUENCE: 4

Met Ser Trp Ala Leu Glu Met Ala Asp Thr Phe Leu Asp Asn Met Arg
1               5                   10                  15

Val Gly Pro Arg Thr Tyr Ala Asp Val Arg Asp Glu Ile Asn Lys Arg
            20                  25                  30

Gly Arg Glu Asp Arg Glu Ala Ala Arg Thr Ala Val His Asp Pro Glu
        35                  40                  45

Arg Pro Leu Leu Arg Ser Pro Gly Leu Leu Pro Lys Ile Ala Pro Asn
    50                  55                  60

Ala Ser Leu Gly Val Ala His Arg Arg Thr Gly Gly Thr Val Thr Asp
65                  70                  75                  80

Ser Pro Arg Asn Pro Val Thr Arg
                85

<210> SEQ ID NO 5
<211> LENGTH: 4020
<212> TYPE: DNA
<213> ORGANISM: human herpesvirus 1 strain McKrae ICP4

<400> SEQUENCE: 5
tttattgcgt cttcgggttt cacaagcgcc ccgccccgtc ccggcccgtt acagcacccc      60 gtcccccteg aacgcgccgc cgtcgtcttc gtcccaggcg ccttcccagt ccacaacgtc     120
ccgtcgcggg ggcgtggcca agcccgcctc cgcccccagc acctccacgg ccccccgccgc    180 cgccagcacg gtgccgctgc ggcccgtggc cgaggcccag cgaatcccgg gcggcgccgg    240
cggcagggcc cccgggccgt cgtcgtcgcc gcgcagcacc agcggggggg cgtcgtcgtc    300
gggctccagc agggcgcggg cgcaaaagtc cctccgcggc ccgcgccacc gggccgggcc    360
ggcgcgcacc gcctcgcgcc ccagcgccac gtacacgggc cgcagcggcg cgcccaggcc    420
ccagcgcgcg caggcgcggt gcgagtgggc ctcctcctcg cagaagtccg gcgcgccggg    480
cgccatggcg tcggtggtcc ccgaggccgc cgcccggccg tccagcgccg gcagcacggc    540
ccggcggtac tcgcgcgggg acatgggcac cggcgtgtcc gggccgaagc gcgtgcgcac    600
gcggtagcgc acgttgccgc cgcggcacag gcgcagcggc ggcgcgtcgg ggtacaggcg    660
cgcgtgcgcg gcctccacgc gcgcgaagac ccccgggccg aacacgcggc ccgaggccag    720
caccgtgcgg cgcaggtcgc gcgccgccgg ccagcgcacg gcgcactgca cggcgggcag    780
caggtcgcac gccaggtagg cgtgctgccg cgacaccgcg ggcccgtcgg cgggccagtc    840
gcaggcgcgc acgtgttga ccacgatgag ccgccggtcg ccggcgctgg cgagcagccc    900
cagaaactcc acggcccccgg cgaaggccag gtcccgcgtg acagcagca gcacgccctg    960 cgcgcccagc gccgacacgt cggggggcgcc ggtccagttg cccgcccagg cggccgtgtc   1020
cggcccgcac agccggttgg ccaggccgcc cagcaggcag gacagcccgc cgcgctcggc   1080
```

```
ggaccactcc ggcggccccc ccgaggcccc gccgccggcc aggtcctcgc ccggcagcgg   1140
cgagtacagc accaccacgc gcacgtcctc ggggtcgggg atctggcgca tccaggccgc   1200
catgcggcgc agcgggcccg aggcgcgcag ggggccaaag aggcggcccc cggcggcccc   1260
gtggggtgg gggttctcgt cgtcgtcgcc gccgccgcac gcggcctggg cggcgggggc   1320
gggcccggcg caccgcgcgg cgatcgaggc cagggcccgc gggtcaaaca tgagggccgg   1380
tcgccagggg acgggaaca gcgggtggtc cgtgagctcg gccacggcgc gcggggagca   1440
gtaggcctcc agggcggcgg ccgcgggcgc cgccgtgtgg ctgggccccg ggggctgccg   1500
ccgccagccg cccaggggggt cggggccctc ggcgggccgg cgcgacagcg ccacggggcg   1560
cgggcgggcc tgccgccgcg cggcccgggg cgccgcgggc tgggcggggg cgggctcggg   1620
ccccgggggc gtggagggg gcgcgggcgc ggggagggggg gcgcgggcgt ccgagccggg   1680
ggcgtccgcg ccgctcttct tcgtcttcgg gggtcgcggg ccgccgcctc cgggcggccg   1740
ggccgggccg ggactcttgc gcttgcgccc ctcccgcggc gcggcggagg cggcggccgc   1800
gaccccgaa gacgaagaag agcggcgcgg accgccgcc agcaggggggc gcaggctctg   1860
gttctcaaac agcaggtccg cggcggcggc ggccgcggag ctcggcaggc gcgggtcccg   1920
cggcagcgcg ggacccaggg ccccggcgac caggctcacg gcgcgcacgg cggccacggc   1980
ggcctcgctg ccgccggcca cgcgcaggtc cccgcgcagg cgcatgagca ccagcgcgtc   2040
gcgcacgaac cgcagctcgc gcagccacgc gcgcaggcgg ggcgcgtcgg cgtgcggcgg   2100
cggcggggaa gcggggcccg cgggtccctc cggccgcggg gggctggcgg gccgggcccc   2160
ggccagcccc gggacggccg ccaggtcgcc gtcgaagccc tcggcagcg cctccaggat   2220
cccgcggcag gcggccaggc actccacggc cacgcggccg gcctgggcgc ggcgcccggc   2280
gtcgtcgtcg gcgtcggcgt ggcggccggc gtcggggtcg tcgcccccg cggggggaggc   2340
gggcgcggcg gacagccgcc ccagggcggc gaggatcccc gcggcgccgt acccggcggg   2400
caccgcgcgc tcgcccggtg cggcggcggc ggcgacgacg gcggcggcga cccctcgtc   2460
atctgcgccg gcgccggggc tccccgcggc ccccgtcagc gccgcgttct cgcgcgccaa   2520
cagggggcgcg taggcgcggc gcaggctggt cagcaggaag cccttctgcg cgcggtcgta   2580
tcggcggctc atggccacgg cggccgccgc gtgcgccagg cccccagccga agcggccggc   2640
cgccatggcg tagcccaggt ggggcacggc ccgcgcacg ctgccggtga tgaaggagct   2700
gctgttgcgc gcggcgcccg agatccggaa gcaggcctgg tccagcgcca cgtccccggg   2760
gaccacgcgc gggttctgga gccaccccat ggcctccgcg tccggggtgt acagcagccg   2820
cgtgatcagg gcgtactgct gcgcggcgtc gcccagctcg ggcgcccaca cggccgccgg   2880
ggcgcccgag gcctcgaacc ggcgtcgcgc ctcctccgcc tcgggcgccc cccagaggcc   2940
cgggcggctg tcgcccaggc cgccgtacag caccccgcccc ggggcgggg gcccggcgcc   3000
gggcacggc tccccgctga cgtacccgtc gcgatagcgc gctagaagc cgccggaggc   3060
cgcgtcggcg tccagctcga cccgccgggg ctgcccggcc gtgaagcggc ccgtggcgtc   3120
gcggccggcc accgccgcgc gggcccggcg cgctcgatg cggcccgcgg aggccgcggg   3180
ggtcctcgcc gccgccgggg gcttgggcgc ggcctcggag aggggggtg gcccgggcgg   3240
gggcggcgtc cgccggggg cttccggcgc cgcgctcgac ggaccccgcc cgacggcccg   3300
cgcctcgcgt gcgtggtcgg ccgcgtcgtt gccgtcgtcg tcctcgtcct cgtcggacga   3360
cgaggacgaa gaggatgcgg acgacgagga cgaggacccg gagtccgacg aggtcgatga   3420
cgccgatggc cgccgccggc cgtgacgacg tctctgcggc ggctgggccg gcgggcgcgg   3480
```

```
cgacaggcgg tccgtggggt ccggatacgc gccgcgtagc gggcctccc gtgcgcggcc    3540 ccgggccggg gcccggtcgc cggcggcgtc ggctgcgtcg tcgtactcgt ccccgtcatc    3600
gtcgtcggct cgaaaggcgg gggtccgggg cggcgaggcc gcggggtcgg gcgtcgggat    3660
cgtccggacg gcctcctcta ccatggaggc cagcagggcc agctgtcgcg gcgagacggc    3720
gtccccggcg tcctcgccgg cgtcggtgcc cgccgcgggg gccctcccgt ccgccgggc    3780 gtcgtcgagg tcgtgggggt ggtcgggtc gtggtcgggg tcgtcccgc cctcctccgt    3840 ctccgcgccc cacccgaggg cccccgctc gtcgcggtct gggctcgggg tgggcggcgg    3900
cccgtcggtg gggcccgggg agccggggcg ctgcttgttc ccgacgcca tcgccgatgc    3960 ggggcgatcc tccggggata cgactgcgac ggcggacgta gcacggtagg tcacctacgg    4020

<210> SEQ ID NO 6
<211> LENGTH: 1320
<212> TYPE: DNA
<213> ORGANISM: human herpesvirus 1 strain McKrae ICP22

<400> SEQUENCE: 6
ggtcctccgg gacgttttct ggatggccga catttcccca ggcgcttttg tgccttgtgt      60
aaaagcgcgg cgtcccgctc tccgatcccc gcccctgggc acgcgcaagc gcaagcgccc    120
tgcccgcccc ctctcatcgg agtctgaggt cgaatccgag acagccttgg agtctgaggt    180
cgaatccgag acagcatcgg attcgaccga gtctggggac caggaggaag ccccccgcat    240
cggtggccgt agggcccccc ggaggcttgg ggggcggttt tttctggaca tgtcggcgga    300
atccaccacg gggacggaaa cggatgcgtc ggtgtcggac gaccccgacg acacgtccga    360
ctggtcttgt gacgacattc ccccacgacc caagcgggcc cggtaaacc tgcggctcac    420 tagctctccc gatcggcggg atggggttat ttttcctaag atggggcggg tccggtctac    480
ccgggaaacg cagccccggg ccccccaccc gtcggcccca gcccaaatg caatgctccg    540 gcgctcggtg cgccaggccc agaggcggag cagcgcacga tggaccccg acctgggcta    600 catgcgccag tgtatcaatc agctgttttcg ggtcctgcgg gtcgcccggg accccccacgg    660 cagtgccaac cgcctgcgcc acctgatacg cgactgttac ctgatgggat actgccgagc    720
ccgtctggcc ccgcgcacgt ggtgccgctt gctgcaggtg tccggcggaa cctggggcat    780
gcacctgcgc aacaccatac gggaggtgga ggctcgattc gacgccaccg cagaaccgt    840 gtgcaagctt ccttgtttgg aggccagacg gtacggcccg gagtgtgatc ttagtaatct    900
cgagattcat ctcagcgcga caagcgatga tgaaatctcc gatgccaccg atctggaggc    960
cgccggttcg gaccacacgc tcgcgtccca gtccgacacg gaggatgccc cctccccgt    1020 tacgctggaa accccagaac cccgcgggtc cctcgctgtg cgtctggagg atgagttttgg    1080 ggagtttgac tggaccccc aggagggctc ccagccctgg ctgtctgcgg tcgtggccga    1140
taccagctcc gtgaacgcc cgggcccatc cgattctggg gcgggtcgcg cagcagaaga    1200
ccgcaagtgt ctgacggct gccggaaaat gcgcttctcc accgcctgcc cctatccgtg    1260
cagcgacacg tttctccggc cgtgagtccg gtcgcccga cccccttgta tgtccccaaa    1320

<210> SEQ ID NO 7
<211> LENGTH: 360
<212> TYPE: DNA
<213> ORGANISM: human herpesvirus 1 strain McKrae ICP47

<400> SEQUENCE: 7
```

```
tccgcccaga gactcgggtg atggtcgtac ccgggactca acgggttacc ggattacggg      60
gactgtcggt cacggtcccg ccggttcttc gatgtgccac acccaaggat gcgttggggg     120
cgatttcggg cagcagcccg ggagagcgca gcaggggacg ctccgggtcg tgcacggcgg     180
ttctggccgc ctcccggtcc tcacgccccc ttttattgat ctcatcgcgt acgtcggcgt     240
acgtcctggg cccaacccgc atgttgtcca ggaaggtgtc cgccatttcc agggcccacg     300
acatgctttt cccccgacg agcaggaagc ggtccacgca acggtcgccg ccggtcgcct      360

<210> SEQ ID NO 8
<211> LENGTH: 523
<212> TYPE: DNA
<213> ORGANISM: Human cytomegalovirus

<400> SEQUENCE: 8
gaagatcttt ggttatatag cataaatcaa tattggctat tggccattgc atacgttgta     60
tccatatcat aatatgtaca tttatattgg ctcatgtcca acattaccgc catgttgaca    120
ttgattattg actagttatt aatagtaatc aattacgggg tcattagttc atagcccata    180
tatggagttc cgcgttacat aacttacggt aaatggcccg cctggctgac cgcccaacga    240
cccccgccca ttgacgtcaa taatgacgta tgttcccata gtaacgccaa tagggacttt    300
ccattgacgt caatgggtgg agtatttacg gtaaactgcc cacttggcag tacatcaagt    360
gtatcatatg ccaagtacgc ccctattga cgtcaatgac ggtaaatggc ccgcctggca    420
ttatgcccag tacatgacct tatgggactt tcctacttgg cagtacatct acgtattagt    480
catcgctatt accatggtga tgcggttttg gcagtacatc aat                       523

<210> SEQ ID NO 9
<211> LENGTH: 1199
<212> TYPE: DNA
<213> ORGANISM: Homo sapiens

<400> SEQUENCE: 9
aatgggtttg ggtgtgtgta aatgagtgtg accggaagcg agtgtgagct tgatctaggc     60
agggaccaca cagcactgtc acacctgcct gctctttagt agaggactga agtgcggggg    120
tgggggtacg gggccggaat agaatgtctc tgggacatct tggcaaacag cagccggaag    180
caaaggggca gctgtgcaaa cggctcaggc aggtgatgga tggcagggta ggaaggggga    240
ggtccagagg tctggatgga ggcttccgca tctgtacctt gcaactcacc cctcaggccc    300
agcaggtcat cggccccctc ctcacacatg taatgacgta gaagagtacc ccgggacagt    360
ccggggagat ggagattcgg aaagtatcca tggagctctt acagaatccc ctgtgcggac    420
caggaaactc ttgtagatcc ctgcctatct gaggcccagg cgctgggctg tttctcacaa    480
tattccttca agatgagatt gtggtcccca tttcaaagat gagtacactg agcctctgtg    540
aagttacttg cccatgatca cacaaccagg aattgggcca actgtaattg aactcctgtc    600
taacaaagtt cttgctccca gctccgtctc ttgtttccca cgagccctgg ccctctgtgg    660
gtaataccag ctactggagt cagatttctt gggcccagaa cccacccta ggggcattaa     720 cctttaaaat ctcacttggg cagggtctg ggatcagagt tggaagagtc cctacaatcc    780 tggaccettt ccgccaaatc gtgaaaccag gggtggagtg gggcgagggt tcaaaaccag    840
gccggactga gaggtgaaat tcaccatgac gtcaaactgc cctcaaattc ccgctcactt    900
taagggcgtt acttgttggt gcccccacca tcccccacca tttccatcaa tgacctcaat    960
gcaaatacaa gtgggacggt cctgctgacg cctccaggtt ctggaagcat gagggtgacg   1020
```

```
cacccagggg caaaggaccc ctccgcccat tggttgctgt gcactggcgg aactttcccg    1080
acccacagcg gcgggaataa gagcagtcgc tggcgctggg aggcatcaga gacactgccc    1140
agcccaagtg tcgccgccgc ttccacaggg ctctggctgg acgccgccgc cgccgctgc    1199

<210> SEQ ID NO 10
<211> LENGTH: 225
<212> TYPE: DNA
<213> ORGANISM: Artificial Sequence
<220> FEATURE:
<223> OTHER INFORMATION: bovine growth hormone polyadenylation signal

<400> SEQUENCE: 10
ggatcccgac tgtgccttct agttgccagc catctgttgt ttgcccctcc cccgtgcctt    60
ccttgaccct ggaaggtgcc actcccactg tcctttccta ataaaatgag gaaattgcat    120
cgcattgtct gagtaggtgt cattctattc tggggggtgg ggtggggcag gacagcaagg    180
gggaggattg ggaagacaat agcaggcatg ctggggaaga tcttc                    225

<210> SEQ ID NO 11
<211> LENGTH: 7
<212> TYPE: PRT
<213> ORGANISM: human herpesvirus 1 strain McKrae

<400> SEQUENCE: 11

Ser Thr Pro Ser Thr Thr Thr
1               5

<210> SEQ ID NO 12
<211> LENGTH: 16
<212> TYPE: DNA
<213> ORGANISM: human herpesvirus 1 strain McKrae

<400> SEQUENCE: 12 gcaccccac tcccac                                                     16

<210> SEQ ID NO 13
<211> LENGTH: 16
<212> TYPE: DNA
<213> ORGANISM: human herpesvirus 1 strain McKrae

<400> SEQUENCE: 13
ccccagccct ccccag                                                    16

<210> SEQ ID NO 14
<211> LENGTH: 17
<212> TYPE: DNA
<213> ORGANISM: human herpesvirus 1 strain McKrae

<400> SEQUENCE: 14 ccctcgccc cctcccg                                                    17

<210> SEQ ID NO 15
<211> LENGTH: 14
<212> TYPE: PRT
<213> ORGANISM: human herpesvirus 1 strain KOS

<400> SEQUENCE: 15

Ala Ala Ser Ala Pro Asp Ala Ala Asp Ala Leu Ala Ala Ala
1               5                   10

<210> SEQ ID NO 16
```

```
<211> LENGTH: 13
<212> TYPE: PRT
<213> ORGANISM: human herpesvirus 1 strain McKrae

<400> SEQUENCE: 16

Gly Pro Arg Arg Ser Ser Ser Ser Gly Val Ala Ala
1               5                   10

<210> SEQ ID NO 17

<400> SEQUENCE: 17

000

<210> SEQ ID NO 18

<400> SEQUENCE: 18

000

<210> SEQ ID NO 19
<211> LENGTH: 9
<212> TYPE: PRT
<213> ORGANISM: human herpesvirus 1

<400> SEQUENCE: 19

Thr Ala Ala Thr Gly Ala Arg Ala Thr
1               5

<210> SEQ ID NO 20
<211> LENGTH: 257
<212> TYPE: PRT
<213> ORGANISM: Homo sapiens

<400> SEQUENCE: 20

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
    130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
```

```
                195                 200                 205
Asp Asp Lys His Trp Asn Ser Gln Cys Lys Thr Ser Gln Thr Tyr Val
        210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 21
<211> LENGTH: 1020
<212> TYPE: DNA
<213> ORGANISM: Homo sapiens

<400> SEQUENCE: 21
taacacagac tcagctgcca gagcctgctc ttaacacctg tgtttccttt tcagatctta      60
caggtgaaca aggtgatgtc catcttgttt tatgtgatat ttctcgctta tctccgtggc     120
atccaaggta caacatggat caaaggagtt ttgccagaag actcgctcaa ttccctcatt     180
attaagctga tccaggcaga tatttttgaaa aacaagctct ccaagcagat ggtggacgtt    240
aaggaaaatt accagagcac cctgcccaaa gctgaggctc cccgagagcc ggagcgggga    300
gggcccgcca gtcagcatt ccagccggtg attgcaatgg acaccgaact gctgcgacaa     360
cagagacgct acaactcacc gcgggtcctg ctgagcgaca gcacccccctt ggagcccccg    420 cccttgtatc tcatggagga ttacgtgggc agccccgtgg tggcgaacag aacatcacgg    480
cggaaacggt acgcggagca taagagtcac cgaggggagt actcggtatg tgacagtgag    540
agtctgtggg tgaccgacaa gtcatcggcc atcgacattc ggggacacca ggtcacggtg    600
ctgggggaga tcaaaacggg caactctccc gtcaaacaat atttttatga aacgcgatgt    660
aaggaagcca ggccggtcaa aaacggttgc aggggtattg atgataaaca ctggaactct    720
cagtgcaaaa catcccaaac ctacgtccga gcactgactt cagagaacaa taaactcgtg    780
ggctggcggt ggatacggat agacacgtcc tgtgtgtgtg ccttgtcgag aaaaatcgga    840
agaacatgaa ttggcatctc tccccatata taaattatta ctttaaatta tatgatatgc    900
atgtagcata taaatgttta tattgttttt atatattata agttgacctt tatttattaa    960
acttcagcaa ccctacagta tataagcttt tttctcaata aaatcagtgt gcttgccttc   1020

<210> SEQ ID NO 22
<211> LENGTH: 6
<212> TYPE: DNA
<213> ORGANISM: Artificial Sequence
<220> FEATURE:
<223> OTHER INFORMATION: BamHI restriction site

<400> SEQUENCE: 22 ggatcc                                                                 6

<210> SEQ ID NO 23
<211> LENGTH: 837
<212> TYPE: DNA
<213> ORGANISM: Artificial Sequence
<220> FEATURE:
<223> OTHER INFORMATION: codon optimized sequence encoding NT3

<400> SEQUENCE: 23
ggatccatgg tcactttcgc aactattctg caggtcaaca aggtcatgtc tattctgttc     60
```

```
tatgtcatct ttctggctta tctgagaggc attcagggga caatatggac ccagagaagc      120
ctgccagaag attccctgaa ctctctgatc attaagctga tccaggcaga cattctgaag      180
aacaaactgt caaagcagat ggtggatgtc aaagaaaatt accagagcac actgccaaag      240
gcagaggctc cacgagagcc tgaacgagga ggaccagcaa aatccgcctt ccagcccgtg      300
atcgctatgg acacagagct gctgcggcag cagcggagat ataactctcc tagagtgctg      360
ctgtctgaca gtactccact ggaacccccct ccactgtacc tgatggagga ttatgtgggc      420
tctcctgtgg tcgctaatcg caccagtagg cgcaagcgat acgcagagca caaaagccat      480 cgagggaat attccgtgtg cgattcagag agcctgtggg tcacagacaa gagctccgcc      540
atcgatattc gcggacacca agtgactgtc ctggggaaaa tcaagaccgg aaatagtccc      600
gtgaaacagt acttttatga gactagatgc aaggaagcca ggcctgtcaa aaacggatgt      660
cggggcattg acgataagca ttggaatagt cagtgtaaaa cctcacagac atacgtgagg      720
gctctgacca gcgagaacaa caagctggtc ggctggcgct ggattagaat tgacactagc      780
tgcgtctgcg ccctgagtag gaagattgga agaacttaaa ttggcatctc tggatcc      837

<210> SEQ ID NO 24
<211> LENGTH: 43
<212> TYPE: DNA
<213> ORGANISM: Artificial Sequence
<220> FEATURE:
<223> OTHER INFORMATION: leader sequence

<400> SEQUENCE: 24
gcggaggact ctggacagta gaggccccgg gacgaccgag ctg                        43

<210> SEQ ID NO 25
<211> LENGTH: 887
<212> TYPE: DNA
<213> ORGANISM: Artificial Sequence
<220> FEATURE:
<223> OTHER INFORMATION: codon optimized sequence encoding NT3

<400> SEQUENCE: 25
cgcggatccg cggaggactc tggacagtag aggccccggg acgaccgagc tgatggtcac       60
ctttgccacc atcctgcaag tgaacaaagt gatgagcatc ctgttctacg tgatcttcct      120
ggcctacctg cggggcatcc agggcaacaa catggaccag agaagcctgc ccgaggacag      180
cctgaactcc ctgatcatca gctgatcca ggccgacatc ctgaagaaca agctgagcaa      240
gcagatggtg gacgtgaaag agaactacca gagcaccctg cccaaggccg aggcccctag      300
agaacctgaa agaggcggcc ctgccaagag cgccttccag cctgtgatcg ccatggatac      360
cgagctgctg agacagcagc ggcggtacaa cagccccaga gtgctgctga gcgacagcac      420
ccctctggaa cctccccccc tgtacctgat ggaagattac gtgggcagcc ccgtggtggc      480
caaccggacc agcagaagaa agagatacgc gagcacaag agccaccggg cgagtacag       540 cgtgtgcgat agcgagagcc tgtgggtcac cgacaagagc agcgccatcg acatcagagg      600
ccaccaagtg accgtgctgg gcgagatcaa gaccggcaac tccccccgtga agcagtactt      660 ctacgagaca cggtgcaaag aggccagacc cgtgaagaac ggctgccggg gcatcgacga      720
caagcactgg aacagccagt gcaagaccag ccagacctac gtgcgggccc tgaccagcga      780
gaacaacaag ctcgtgggct ggcggtggat cagaatcgac accagctgcg tgtgcgccct      840
gagccggaag atcggcagaa cataagttta aaccgcggga tccgcgc                    887
```